(12) United States Patent
Lazzari et al.

(10) Patent No.: US 9,181,196 B2
(45) Date of Patent: Nov. 10, 2015

(54) PHARMACEUTICAL COMPOUNDS

(71) Applicant: KEMOTECH S.r.l., Pula (Cagliari) (IT)

(72) Inventors: Paolo Lazzari, Pula (IT); Matteo Zanda, Gandino (IT); Monica Sani, Corsico (IT)

(73) Assignee: KEMOTECH S.r.l., Pula (Cagliari) (IT)

( * ) Notice: Subject to any disclaimer, the term of this patent is extended or adjusted under 35 U.S.C. 154(b) by 0 days.

(21) Appl. No.: 14/250,052

(22) Filed: Apr. 10, 2014

(65) Prior Publication Data
US 2014/0343294 A1 Nov. 20, 2014

(30) Foreign Application Priority Data

Apr. 12, 2013 (IT) .............................. MI2013A0602
Feb. 27, 2014 (IT) .............................. MI2014A0297

(51) Int. Cl.
| | | |
|---|---|---|
| *C07D 487/14* | (2006.01) | |
| *C07D 231/54* | (2006.01) | |
| *C07D 519/00* | (2006.01) | |
| *C07D 491/044* | (2006.01) | |
| *C07D 491/048* | (2006.01) | |
| *C07D 495/04* | (2006.01) | |

(52) U.S. Cl.
CPC ............ *C07D 231/54* (2013.01); *C07D 487/14* (2013.01); *C07D 491/044* (2013.01); *C07D 491/048* (2013.01); *C07D 495/04* (2013.01); *C07D 519/00* (2013.01)

(58) Field of Classification Search
None
See application file for complete search history.

(56) References Cited

U.S. PATENT DOCUMENTS

| | | |
|---|---|---|
| 5,547,975 A | 8/1996 | Talley et al. |
| 6,028,084 A | 2/2000 | Barth et al. |
| 6,916,838 B1 | 7/2005 | Barth et al. |
| 7,384,960 B2 | 6/2008 | Barth et al. |
| 7,485,730 B2 | 2/2009 | Lazzari et al. |
| 2003/0152635 A1 | 8/2003 | Heurtault et al. |
| 2004/0131692 A1 | 7/2004 | Kreuter et al. |
| 2010/0215741 A1 | 8/2010 | Lazzari et al. |
| 2010/0215759 A1 | 8/2010 | Lazzari et al. |
| 2013/0030171 A1 | 1/2013 | Bold et al. |

FOREIGN PATENT DOCUMENTS

| | | |
|---|---|---|
| WO | WO 03/070236 A2 | 8/2003 |
| WO | WO 2004/011468 A1 | 2/2004 |
| WO | WO 2005/028476 A1 | 3/2005 |
| WO | WO 2005/100338 A1 | 10/2005 |

OTHER PUBLICATIONS

Belotti et al., "The rnicrotubule-affecting drug paclitaxel has antiangiogenic activity," Clinical Cancer Research, vol. 2, Nov. 1996, pp. 1843-1849.

Colombo et al., "Non-peptidic Thrombospondin-1 Mimics as Fibroblast Growth Factor-2 Inhibitors," Journal of Biological Chemistry, vol. 285, No. 12, Mar. 19, 2010, pp. 8733-8742.

Costantino et al., "Peptide-derivatized biodegradable nanoparticles able to cross the blood-brain barrier," Journal of Controlled Release, vol. 108, 2005, pp. 84-96.

D'Amato et al., "Thalidomide is an inhibitor of angiogenesis," Proc. Natl. Acad. Sci., vol. 91, Apr. 1994, pp. 4082-4085.

Garcia-Garcia et al., "Collodial carriers and blood-brain barrier (BBB) translocation: A way to deliver drugs to the brain?,"International Journal of Pharmaceutics, vol. 298, 2005, pp. 274-292.

Jang et al., "Bioinspired application of dendrimers: From bio-mimicry to biomedical applications," Progress in Polymer Science, vol. 34, 2009, pp. 1-23.

Kreuter et al., "Nanoparticulate systems for brain delivery of drugs," Advanced Drug Delivery Reviews, vol. 47, 2001, pp. 65-81.

Kusaka et al., "Cytostatic inhibition of endothelial cell growth by the angiogenesis inhibitor TNP-470 (AGM-1470)," Br. J. Cancer, vol. 69, 1994, pp. 212-216.

McNamee et al., "Physicochemical Characterization of PEG1500-12-acyloxy-stearate Micelles and Liquid Crystalline Phases," American Society, vol. 21, 2005, pp. 8146-8154.

Mitra et al., "Physiochemical investigations of microemulsification of eucalyptus oil and water using mixed surfactants (AOT + Brij-35) abd butanol," Journal of Colloid and Interface Sciences, vol. 283, 2005, pp. 565-577.

Montalbetti et al., "Amide bond formation and peptide coupling," Tetrahedron, vol. 61, 2005, pp. 10827-10852.

Peracchia et al., "Synthesis of a Novel Poly (MePEG cyanoacrylate-co-alkyl cyanoacrylate) Amphiphilic Copolymer for Nanoparticle Technology," Macromolecules, vol. 30, 1997, pp. 846-851.

Pinna et al., "Chromophore-modified bis-benzo[g]indole carboxamides: synthesis and antiproliferative activity of bis-benzo[g]indazole-3-carboxamides and related dimers," Il Farmaco, vol. 58, 2003, pp. 749-763.

(Continued)

*Primary Examiner* — Samantha Shterengarts
(74) *Attorney, Agent, or Firm* — Arent Fox LLP

(57) ABSTRACT

Compounds of formula (I):

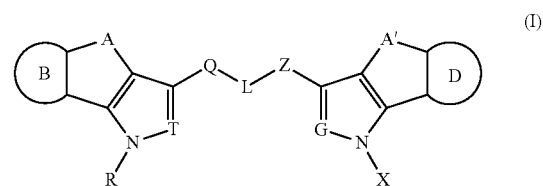

wherein:
A, R, T, Q, L, Z, G, X and A' are as defined in the description.
B and D, equal to or different from each other, are selected between heteroaryl and aryl, wherein at least one of the hydrogen atoms of said heteroaryl and aryl are substituted with groups selected from $SO_3^-$, $SO_3H$, $COO^-$, $COOH$, and one or more of the other hydrogen atoms of said heteroaryl and aryl are optionally substituted as reported in the description.

21 Claims, 1 Drawing Sheet

(56) References Cited

OTHER PUBLICATIONS

Remington, "The Science and Practice of Pharmacy," vol. 2, 1995, p. 1457.
Schluep et al., "Polymeric Tubulysin-Peptide Nanoparticles with Potent Antitumor Activity," Clin. Cancer Res., vol. 15(1), Jan. 1, 2009, pp. 181-189.
Search Report issued in Italian Patent Application No. MI20130602, dated Jul. 16, 2013, 1page.
Simovic et al., "Dry Hybrid Lipid-Silica Microcapsules Engineered from Submicron Lipid Droplets and Nanoparticies as a Novel Delivery System for Poorly Soluble Drugs," Molecular Pharmaceutics, vol. 6., No. 3, pp. 861-872.
Stein, "Suramin: A Novel Antineoplastic Agent with Multiple Potential Mechanisms of Action," Cancer Res, vol. 53, 1993, pp. 2239-2248.
Stella et al., "Design of Folic Acid-Conjugated Nanoparticles for Drug Targeting," Journal of Pharmaceutical Sciences, vol. 89, No. 11, 2000, pp. 1452-1464.
Talbot, "Experimental and Clinical Studies on the Use of Matrix Metalloproteinase Inhibitors for the Treatment of Cancer," European Journal of Cancer, vol. 32A, No. 14, 1996, pp. 2528-2533.
Volpert et al., "Captopril Inhibits Angiogenesis and Slows the Growth of Experimental Tumors in Rats," J. Clin. Invest, vol. 98, No. 3, 1996, pp. 671-679.
Wuts et al., "Greene's Protective Groups in Organic Synthesis," Fourth Edition, Wiley-Interscience, 1112 pages.
European Search Report, date Aug. 22, 2014, corresponding to European Patent Applicatio No. 14 16 3522.

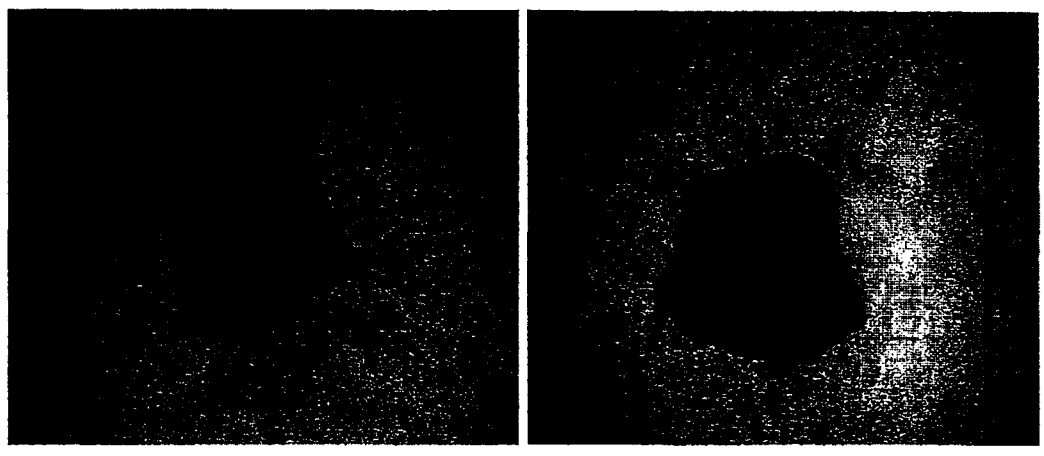
(a)            (b)

PHARMACEUTICAL COMPOUNDS

CROSS-REFERENCE TO RELATED APPLICATIONS

This application claims priority to Italian Patent Applications No. MI2013A000602, filed Apr. 12, 2013 and MI2014A000297, filed Feb. 27, 2014. The disclosures of the prior applications are hereby incorporated in their entirety by reference.

The present invention relates to condensed tricyclic compounds, a process for preparing them, their pharmaceutical compositions and their pharmaceutical use.

Specifically the invention refers to condensed tricyclic compounds dimmers having an inhibitory activity towards angiogenesis, to a process for their preparation, to their pharmaceutical compositions and to their use in the treatment of angiogenesis-related diseases, such as for example tumours, with particular reference to solid tumours, and of some eye pathologies.

As well known, angiogenesis is a process leading to the development of new blood vessels starting from other preexisting vessels of the tissue of origin and has a role of primary importance in many pathologic and physiological processes. More specifically, the role of angiogenesis in physiological processes relates for example to the embryonal development, ovulation, cicatrization of wounds and placental development. In non pathological conditions, angiogenesis is a quiescent phenomenon and it manifests only in the cicatrization of wounds and in neo-vascularization of the endometrium in the menstruation period. The physiopathological angiogenesis relates to inflammatory processes, repair of wounds and ischemia. The pathological angiogenesis is instead involved in several pathologies, such as for example: neoplasias, atherosclerosis, psoriasis, arthritis, rheumatoid arthritis, diabetic retinopathy, age-related macular degeneration (in abbreviated form AMD), gastric ulcer, endometriosis, Crohn syndrome, sclerodermia, cancer, in particular solid tumours. See for example US patent application 2013/0030171.

The identification of the angiogenesis role in several physiological and pathological processes has addressed various researches towards the synthesis of new compounds having a pro-angiogenic or anti-angiogenic activity. Compounds with anti-angiogenic activity have been in particular developed and successfully used in the antitumoral therapy, with particular reference to the treatment of solid tumours, also in association with other oncological therapies, such as for example radiotherapy, chemotherapy and immunotherapy. Recently the antitumoural activity induced by the treatment of solid tumours with compounds having antiangiogenic activity in association with antitumoural therapies based on the use of viruses, such as for example oncolytic herpes virus, has also been reported. A necessary condition to create a microenvironment favouring the tumoural growth is an abnormal stimulation of tumour induced neovascularization, that is the development of new blood vessels deriving from preexisting vessels of the tissue of origin.

The development of anti-angiogenic therapies for the treatment in particular of solid tumours has allowed to overcome some limits of efficacy observed in the case of therapies based on the use of chemotherapeutics (cytotoxic drugs) in treating the same tumours. The cytotoxic drugs have proved indeed effective only in few patients with solid tumours and, in most cases, the chemotherapy efficacy in these tumours has been partial and transitory. The main causes of the above mentioned limits are mainly due to the secondary acquired pharmacological resistance, to the genetic instability of the neoplastic cells, to their heterogeneity and to the high mutational index.

The control of the angiogenesis is a complex process and represents the result of a balance operated by peptides stimulating the angiogenesis and by endogenous factors inhibiting it. Peptides stimulating angiogenesis are for example Vascular Endothelial Growth Factor (VEGF), Fibroblastic Growth Factor (FGF), Interleukin 4, Interleukin 8. Factors inhibiting the angiogenesis are for example Trombospondine (TSP), Angiostatine, Endostatine. The therapeutical strategies based on an anti-angiogenesis effect are therefore addressed to restore the balance between angiogenic factors and inhibitors of the angiogenic factors, so to bring the vascularization in a physiological quiescent condition. Anti-angiogenic pharmacological strategies based on the VEGF inhibition are for example those using VEGF inhibitors such as for example Sunitinib and Sorafenib. Anti-angiogenic activity has been furthermore found in drugs already used for other therapeutical applications, such as for example thalidomide and captopril. See for example the following publications: R. J. D'Amato et al. "Thalidomide is an inhibitor of angiogenesis" Proc. Natl. Acad. Sci., 91 (1994) 4082-4088; O. V. Volpert et al. "Captopril inhibits angiogenesis and slows the growth of experimental tumors in rats" J. Clin. Invest. 98 (1996) 671-679. Some antitumoural drugs having a high cytotoxicity and used in oncology as chemotherapeutics, as for example paclitaxel, have also been shown effective in angiogenesis. See for example the article by D. Belotti et al. "The microtubule-affecting drug paclitaxel has anti-angiogenic activity" Clin. Cancer Res., 2 (1996) 1843-1849.

As examples of compounds specifically developed as anti-angiogenic drugs the following ones can be mentioned: TNP-470, that inhibits angiogenesis by blocking the inlet of the endothelial cells in the G phase of the cell cycle (M. Kusaka et al. "Cytostatic inhibition of endothelial cell growth by the angiogenesis inhibitor TNP-470 (AGM-1470)" Br. J. Cancer, 69 (1994) 212-216); marimastat, an inhibitor of tissue metalloproteinases (D. C. Talbot et al. "Experimental and clinical studies on the use of matrix metalloproteinase inhibitors for the treatment of cancer" Eur. J. Cancer, 32A (1996) 2523-2533); suramin, having the following chemical structure:

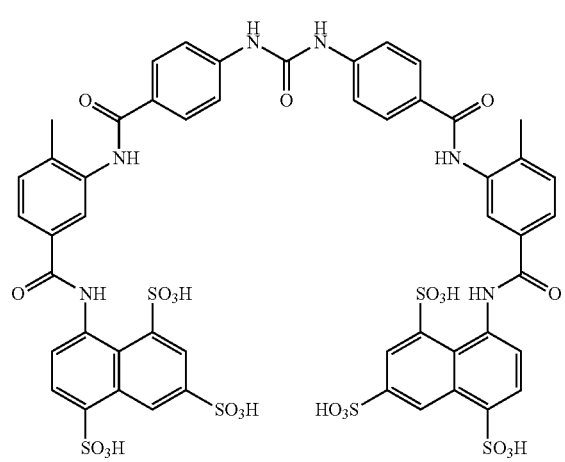

which is used also for the treatment of infections from Tripanosoma and Nematodes, able to block the bond of various tumoural growth factors to the corresponding cell surface receptors (C. A. Stein "Suramin: a novel antineoplastic agent with multiple potential mechanisms of action" Cancer Res, 53 (1993) 2239-2248).

Recently the importance of FGFs as angiogenic factors involved in the development of pathologies correlated to angiogenesis has been emphasized. The development of compounds able to mimic the action of endogenous FGF inhibitors is therefore a valid pharmacological strategy for the treatment of angiogenesis-related pathologies. Through their binding to specific FGF receptors located on the cell walls, FGFs stimulate a remarkable variety of cell functions. In angiogenesis FGF-1 and FGF-2 are particularly important inside the FGF class. FGF-1 stimulates in particular the proliferation and differentiation of all the cellular species needed for the formation of arterial vessels, including the endothelium cells and the smooth muscle cells. FGF-2 promotes angiogenesis, as it is active on the proliferation of the endothelial cells and on their organization. Compounds capable to mimic the action of endogenous inhibitors of FGF and in particular of FGF-2, represent therefore a pharmacological strategy for the treatment of angiogenesis-related pathologies. In the article by G. Colombo et al. "Non-peptidic Thrombospondin-1 mimics as fibroblast growth factor-2 inhibitors", Journal of Biological Chemistry, 285 (2010) 8733-8742, synthesis compounds are described that are able to inhibit the FGF-2 bond to the endothelial cells and the cell proliferation of endothelial cells induced by FGF-2, and angiogenesis induced by FGF-2 in an in vivo test. The compound sm27 (NSC37204), having the structure hereinafter reported, has been shown to be the most effective among the compounds reported in the article by G. Colombo et al. in inhibiting FGF-2-mediated angiogenesis.

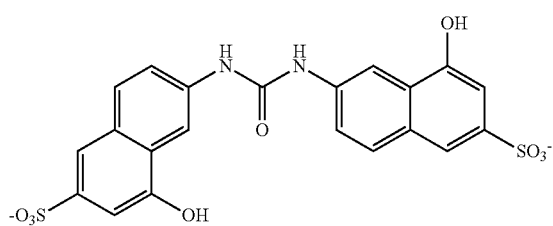

sm27

Also the angiogenic action of Suramine is partly due to a block of the bond between FGF-2 and the corresponding cellular surface receptors. It is however worth noting that the treatment with Suramine has the drawback to cause important systemic side effects such as renal toxicity, peripheral neuropathy and coagulopathy.

The article by G. Pinna "Chromophore-modified bis-benzo [g]indole carboxamides: Synthesis and antiproliferative activity of bis-benzo[g]indazole-3-carboxamides and related dimers" Il Farmaco 58 (2003) 749-763, describes cytotoxic dimers of tricyclic pyrazole compounds comprising linking bridges of the —CONH—$(CH_2)_n$—$N(CH_3)$—$(CH_2)_n$—NHCO— type. These dimers show antiproliferative activity towards various types of cancerous cells and behave as typical agents intercalating DNA. The Applicant has found, see the comparative examples, that these prior art compounds are not active in inhibiting protein FGF-2-mediated angiogenesis.

The need was felt to have available inhibitors of the angiogenesis process, characterized by a high inhibition activity towards protein FGF-2 (Fibroblast Growth Factor-2), combined with reduced side effects, and easily obtainable with chemical synthesis processes with high yields.

Surprisingly and unexpectedly it has been found by the Applicant a new class of synthesis compounds with inhibitory activity towards FGF-2 solving the above mentioned technical problem.

It is an object of the present invention compounds of formula (I), and pharmaceutically acceptable salts thereof:

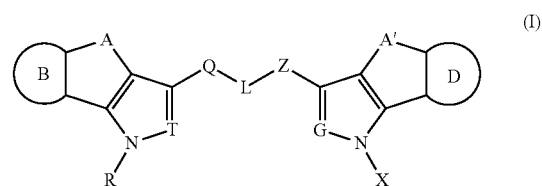

(I)

wherein:
A is selected from: O, $CH_2$, $CH_2$—$CH_2$, $CH$=$CH$, $CH_2$—$CH_2$—$CH_2$, $CH_2$—$CH_2$—$CH_2$—$CH_2$, O—$CH_2$, O—$CH_2$—$CH_2$, or O—$CH_2$—$CH_2$—$CH_2$ wherein when A is selected from O—$CH_2$, O—$CH_2$—$CH_2$, or O—$CH_2$—$CH_2$—$CH_2$, the oxygen atom is linked to the adjacent carbon atom that is shared with ring B, A' has the following meanings:
  A'=A when A=O, $CH_2$, $CH_2$—$CH_2$, $CH$=$CH$, $CH_2$—$CH_2$, or $CH_2$—$CH_2$—$CH_2$—$CH_2$,
  A'=$CH_2$—O when A=O—$CH_2$,
  A'=$CH_2$—$CH_2$—O when A=O—$CH_2$—$CH_2$,
  A'=$CH_2$—$CH_2$—$CH_2$—O when A=O—$CH_2$—$CH_2$—$CH_2$, wherein when A' is selected from $CH_2$—O, $CH_2$—$CH_2$—O or $CH_2$—$CH_2$—$CH_2$—O, the oxygen atom is linked to the adjacent carbon atom that is shared with ring D, T and G, equal to or different from each other, preferably T=G, are selected between N or CH, R and X, equal to or different from each other, preferably R=X, are selected from:
  heteroaryl, etheroarylalkyl, aryl, arylalkyl, arylalkenyl, cycloalkyl, cycloalkylalkyl, heterocycloalkyl, or heterocycloalkylalkyl, wherein one or more hydrogen atoms of said heteroaryl, heteroarylalkyl, aryl, arylalkyl, arylalkenyl, cycloalkyl, cycloalkylalkyl, heterocycloalkyl, heterocycloalkylalkyl are optionally substituted with one or more of the following groups, equal to or different from each other: OH, halogen, linear or when possible branched $C_1$-$C_7$ alkyl, linear or when possible branched $C_2$-$C_7$ alkenyl, linear or when possible branched $C_2$-$C_7$ alkynyl, linear or when possible branched $C_1$-$C_7$ alkylthio, linear or branched when possible $C_1$-$C_7$ alkoxy, linear or when possible branched $C_1$-$C_7$ haloalkyl, linear or when possible branched $C_1$-$C_7$ haloalkoxy, $SO_2NH_2$, $SO_3H$, COOH, cyano, nitro, or $NR_{10}R_{11}$ wherein $R_{10}$ and $R_{11}$, equal to or different from each other, are selected from H, linear or when possible $C_1$-$C_7$ alkyl, or cycloalkyl, $R_{30}$—W wherein $R_{30}$ is a linear or when possible branched bivalent aliphatic $C_1$-$C_{10}$, preferably $C_2$-$C_6$ chain, W is selected from hydrogen, halogen, isothiocyanate, CN, OH, $OCH_3$, $NH_2$, $SO_2NH_2$ or $CH$=$CH_2$, preferably W=$W_a$ selected from hydrogen, halogen, OH, $OCH_3$, $NH_2$, $SO_2NH_2$ or $CH$=$CH_2$, more preferably W=$W_b$ selected from hydrogen and halogen, B and D, equal to or different from each other, preferably B=D, are selected between heteroaryl and aryl, wherein at least one of the hydrogen atoms, preferably from 1 to 2 hydrogen atoms, still more preferably one hydrogen atom, of said heteroaryl and aryl is substituted with a group selected from $SO_3^-$, $SO_3H$, $COO^-$, $COOH$ and one or more of the remaining hydrogen atoms of said heteroaryl and aryl are optionally substituted with G1 groups, equal to or different from each other, selected from OH, halogen, linear or when possible branched $C_1$-$C_{20}$ alkyl, linear or when possible branched $C_2$-$C_{20}$ alkenyl, linear or when possible branched $C_2$-$C_{20}$ alkynyl, linear or when possible branched $C_1$-$C_{20}$ alkylthio, linear or when possible branched $C_1$-$C_{20}$ alkoxy, linear or when possible branched $C_1$-$C_{20}$ haloalkyl, linear or when possible branched $C_1$-$C_{20}$ haloalkoxy, cyano, nitro, $SO_2NH_2$, $COOR_{19}$, or $NR_{20}R_{21}$, wherein $R_{19}$ is a group selected from linear or when possible branched $C_1$-$C_{20}$ alkyl, linear or when possible branched $C_2$-$C_{20}$ alkenyl, linear or when possible branched $C_2$-$C_{20}$ alkynyl, heteroaryl, heteroarylalkyl, aryl, arylalkyl, arylalkenyl, cycloalkyl, cycloalkylalkyl, heterocycloalkyl, or heterocyclo alkylalkyl, $R_{20}$ and $R_{21}$, equal to or different from each other have the meaning of $R_{19}$ or H, Q is a bivalent group selected from the following:

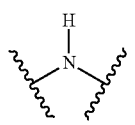
QA

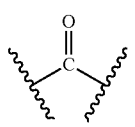
QB

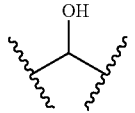
QC

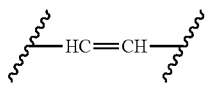
QD

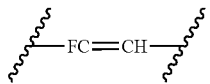
QE

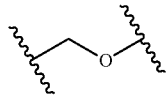
QF

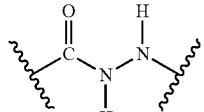
QG

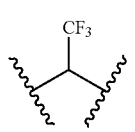
QH

Z is a bivalent group having the following meanings:
Z=Q when Q is selected from QA, QB, QC, QD, or QH,
Z=QE' when Q=QE,

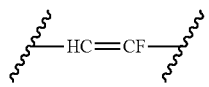
QE'

Z=QF' when Q=QF,

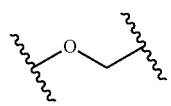
QF'

Z=QG' when Q=QG,

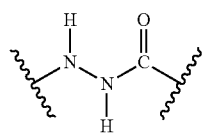
QG'

L is a bivalent group having the following meanings:
L=L1 when Q=Z=QA,

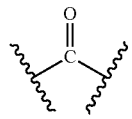
L1

L is selected between L2 or L3 when Q=Z=QB,

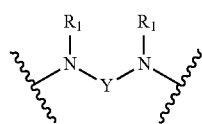
L2

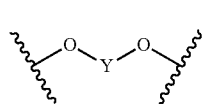
L3 wherein $R_1$ is selected from H, $CH_3$ or $CH_2$—$CH_3$,
L=L4 when Q=Z and Q is selected from QA, QB, QC, QD, or QH, or
  when Q=QF and Z=QF',
  when Q=QE and Z=QE',

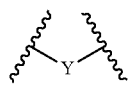
L4

L=L5 when Q=Z and Q=QH,

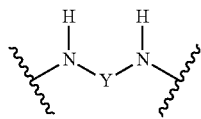
L5

L is selected between L6 or L7 when Q=QG and Z=QG',

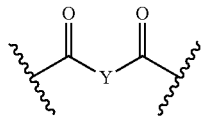
L6

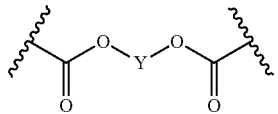
L7 wherein Y is a bivalent group selected from:
linear or when possible branched $C_2$-$C_{20}$ alkylene,
$CH_2$-$A_1$-$CH_2$ wherein $A_1$ is a linear or when possible branched $C_2$-$C_{20}$ alkenylene,
$CH_2$-$A_2$-$CH_2$ wherein $A_2$ is a linear or when possible branched $C_2$-$C_{20}$ alkynylene,
$CH_2$—$CH_2$—$(O$—$CH_2$—$CH_2)_k$—$O$—$CH_2$—$CH_2$
wherein k is an integer comprised between 4 and 30,
or Y is selected from the following groups:

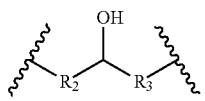
Y1

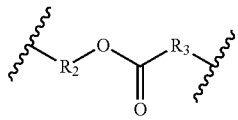
Y2

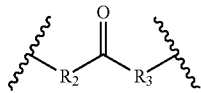
Y3

Y4

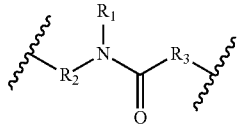
Y5

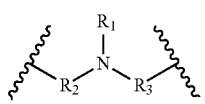
Y6

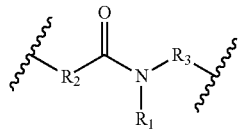
Y7

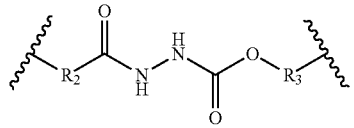
Y8

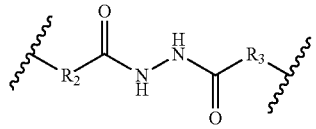
Y9

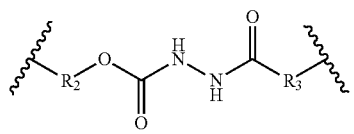
Y10

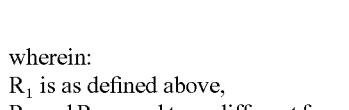
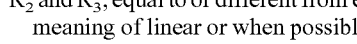

wherein:
$R_1$ is as defined above,
$R_2$ and $R_3$, equal to or different from each other, have the meaning of linear or when possible branched $C_1$-$C_{20}$ alkylene,
$CH_2$-$A_1$-$CH_2$ and $CH_2$-$A_2$-$CH_2$, wherein $A_1$ and $A_2$ are as defined above,
preferably Y=$Y_{100}$ selected from linear or when possible branched $C_2$-$C_{20}$ alkylene, Y1, Y3, Y5, Y6, Y7; more preferably Y=$Y_{50}$ selected from linear or when possible branched $C_2$-$C_{10}$ alkylene and Y6.

In this patent application, where not otherwise specified, the following definitions apply:
by alkyl it is meant a saturated $C_1$-$C_{20}$ hydrocarbon chain, linear, branched when possible, wherein one or more hydrogen atoms can optionally be substituted with halogen atoms. Preferably the hydrocarbon chain is $C_1$-$C_{12}$, more preferably $C_1$-$C_6$, for example methyl, ethyl, n-propyl, isopropyl, n-butyl, isobutyl, sec-butyl, tert-butyl;
by alkylene it is meant a bivalent aliphatic $C_1$-$C_{20}$ chain, linear or when possible branched, having at each end one free valence, wherein one or more hydrogen atoms can optionally be substituted with halogen atoms, preferably the hydrocarbon chain is $C_1$-$C_8$;
by alkenyl it is meant a mono- or poly-unsaturated $C_2$-$C_{20}$ hydrocarbon chain, preferably mono-unsaturated, wherein the unsaturation is a double bond, said chain being a linear or when possible branched chain, wherein one or more hydrogen atoms can optionally be substituted with halogen atoms. Preferably the hydrocarbon chain is $C_2$-$C_{12}$;
by alkenylene it is meant a bivalent mono- or poly-unsaturated $C_2$-$C_{20}$ hydrocarbon chain, wherein the unsaturation is a double bond, linear or when possible branched, having at each end one free valence, wherein one or more hydrogen atoms can optionally be substituted with halogen atoms, preferably the bivalent hydrocarbon chain is $C_2$-$C_8$;
by alkynyl it is meant a mono- or poly-unsaturated $C_2$-$C_{20}$ hydrocarbon chain, preferably mono-unsaturated, wherein the unsaturation is a triple bond, said chain being linear or when possible branched, wherein one or more hydrogen atoms can optionally be substituted with halogen atoms, preferably the hydrocarbon chain is $C_2$-$C_{12}$;

by alkynylene it is meant a bivalent mono- or poly-unsaturated $C_2$-$C_{20}$ hydrocarbon chain, wherein the unsaturation is a triple bond, linear or branched when possible, having at each end one free valence, wherein one or more hydrogen atoms can optionally be substituted with halogen atoms, preferably the bivalent hydrocarbon chain is $C_2$-$C_8$, by halogen it is meant one atom selected from fluorine, chlorine, bromine, iodine;

by haloalkyl it is meant an alkyl as defined above, wherein one or more hydrogen atoms are substituted with halogen atoms. Examples of haloalkyl are trifluoromethyl, 1-bromo-n-butyl, pentachloroethyl, etc.;

by aryl it is meant an aromatic monocyclic radical, or a condensed aromatic polycyclic radical, having from 6 to 20 carbon atoms;

by arylalkyl it is meant an alkyl as defined above, preferably $C_1$-$C_7$, linked to one aryl as defined above. Benzyl can for example be mentioned, by cycloalkyl it is meant:
- an aliphatic monocyclic ring, optionally containing one or more unsaturations but with the proviso that the structure is not aromatic, said ring having from 3 to 10 carbon atoms, preferably from 4 to 9 carbon atoms, or
- a polycyclic structure having from 7 to 19 carbon atoms; by heterocycloalkyl it is meant a cycloalkyl as defined above wherein one or more carbon atoms are substituted with heteroatoms, equal to or different from each other, selected from S, O, N. When the ring is monocyclic, preferably the number of heteroatoms is not higher than 2;

by heteroaryl it is meant an aryl as defined above, but the monocyclic radical is $C_5$-$C_6$ wherein at least one or more carbon atoms are substituted with one or more heteroatoms, equal to or different from each other, selected from S, O, N. When the radical is monocyclic, preferably the number of heteroatoms is not higher than 2. The preferred monocyclic heteroaryls are furan, thiophene, pyrrole, pyridine, pyrazole, imidazole, oxazole, isoxazole, thiazole; thiophene, pyrrole, pyrazole, oxazole are still more preferred;

by heteroarylalkyl it is meant an alkyl as defined above, preferably $C_1$-$C_7$, linked to an heteroaryl as defined above;

by cycloalkylalkyl it is meant an alkyl as defined above, preferably $C_1$-$C_7$, linked to a cycloalkyl as defined above;

by heterocycloalkylalkyl it is meant an alkyl as defined above, preferably $C_1$-$C_7$, linked to an heterocycloalkyl as defined above;

by alkylcycloalkyl it is meant a cycloalkyl as defined above, linked to one alkyl as defined above, by heteroalkylcycloalkyl it is meant a cycloalkyl as defined above, linked to an heteroalkyl as defined above;

by arylene, heteroarylene, cycloalkylene, heterocycloalkylene, arylalkylene, heteroarylalkylene, alkylcycloalkylene and heteroalkylcycloalkylene are respectively meant an aryl, an heteroaryl, a cycloalkyl, an heterocycloalkyl, an arylalkyl, an heteroarylalkyl, an alkylcycloalkyl, an heteroalkylcycloalkyl, as defined above, wherein one hydrogen atom is substituted by a free valence.

In the present invention the preferred compounds of formula (I) are those wherein A, Q, L, Z, and A' are as defined above, T=G, R=X, B=D.

The compounds of formula (I) wherein T and G, equal to each other, are nitrogen, are more preferred.

The compounds of formula (I) are more preferred, wherein T=G, R=X, B and D equal to each other are selected from monocyclic heteroaryl and phenyl, wherein one hydrogen atom of said monocyclic heteroaryl and phenyl is substituted with a group selected from $SO_3^-$, $SO_3H$, $COO^-$, $COOH$ and wherein one or more of the remaining hydrogen atoms of said monocyclic heteroaryl and phenyl are optionally substituted with one or more G1 groups, equal to or different from each other.

The most preferred compounds are those of formula (I) wherein:

A, Q, L, Z, and A' are as defined above, T and G, equal to each other, are nitrogen, R=X, B=D, the bivalent substituent L is as defined above wherein:

$Y=Y_{100}$ as defined above, wherein:

$R_1$ is as defined above, $R_2$ and $R_3$ equal to or different from each other are linear or when possible branched $C_1$-$C_{20}$ alkylene, B and D, equal to each other, are selected between phenyl and monocyclic heteroaryl, wherein one hydrogen atom of said phenyl and monocyclic heteroaryl is substituted with one group selected from $SO_3H$, $SO_3^-$, $COO^-$, $COOH$ and the other hydrogen atoms are optionally substituted with G1 groups, R and X, equal to each other, are selected from the following groups:

GA, having the following meanings: monocyclic heteroaryl, monocyclic heteroarylalkyl, phenyl, monocyclic arylalkyl, monocyclic arylalkenyl, monocyclic cycloalkyl, monocyclic cycloalkylalkyl, monocyclic heterocycloalkyl or monocyclic heterocycloalkylalkyl, wherein one or more hydrogen atoms of said monocyclic heteroaryl, monocyclic heteroarylalkyl, phenyl, monocyclic arylalkyl, monocyclic arylalkenyl, monocyclic cycloalkyl, monocyclic cycloalkylalkyl, monocyclic heterocycloalkyl, monocyclic heterocycloalkylalkyl are optionally substituted with groups, equal to or different from each other, selected from OH, halogen, linear or when possible branched $C_1$-$C_7$ alkyl, linear or when possible branched $C_2$-$C_7$ alkenyl, linear or when possible branched $C_2$-$C_7$ alkynyl, linear or when possible branched $C_1$-$C_7$ alkylthio, linear or when possible branched $C_1$-$C_7$ alkoxy, linear or when possible branched $C_1$-$C_7$ haloalkyl, linear or when possible branched $C_1$-$C_7$ haloalkoxy, $SO_2NH_2$, $SO_3H$, COOH, cyano, nitro, or $NR_{10}R_{11}$ wherein $R_{10}$ and $R_{11}$, equal to or different from each other, are selected from H, linear or when possible branched $C_1$-$C_7$ alkyl, or cycloalkyl, $R_{30}$—W with W=$W_a$, wherein $R_{30}$ and $W_a$ are as defined above.

The compounds of formula (I) are particularly preferred, wherein:

A, Q, Z, and A' are as defined above,

L is as defined above and $Y=Y_{100}$ as defined above,

T and G are nitrogen,

B and D, equal to each other, are selected between phenyl and thiophene, wherein one hydrogen atom of said phenyl and thiophene is substituted with a group selected from $SO_3H$, $SO_2^-$, $COO^-$, $COOH$, R and X, equal to each other, are selected from the groups GA and $R_{30}$—W with W=$W_a$ as defined above.

Examples of the preferred compounds of formula (I) are the following:

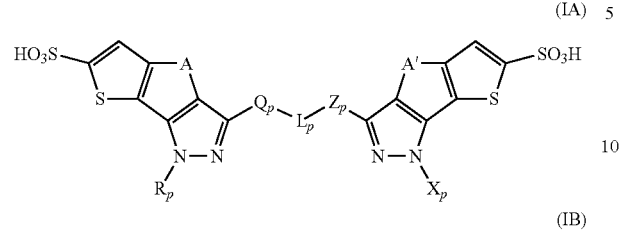
(IA)

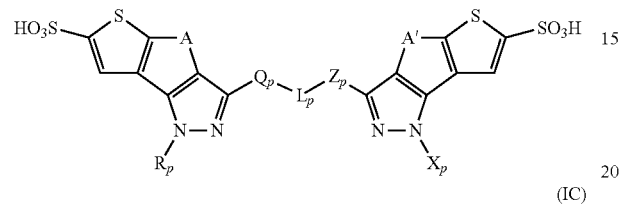
(IB)

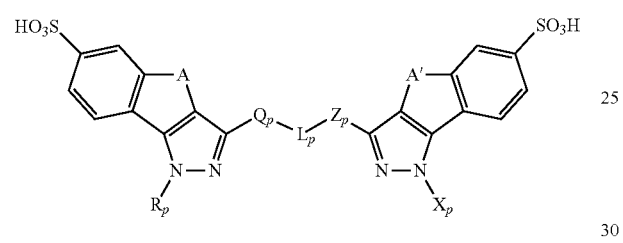
(IC)

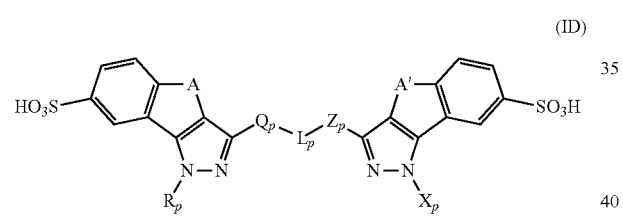
(ID)

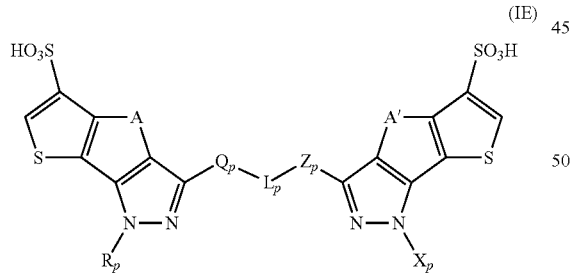
(IE)

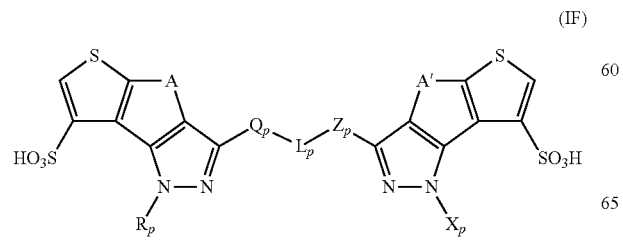
(IF)

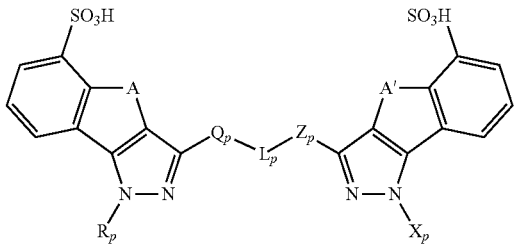
(IG)

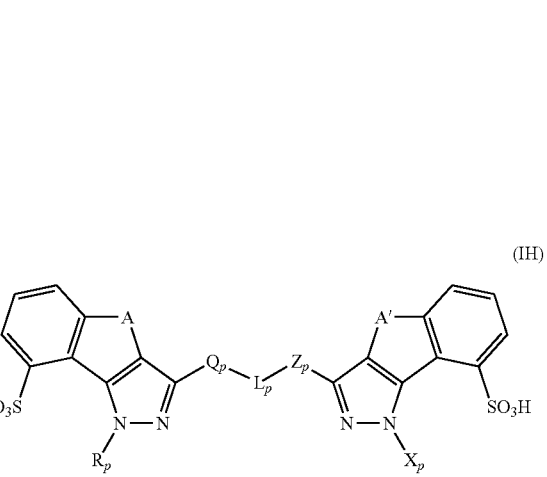
(IH)

wherein:

A and A' are as defined above, $R_p$ and $X_p$, equal to each other, have the following meanings:
phenyl, thiophene, benzyl and cyclohexyl, wherein one or more hydrogen atoms of said phenyl, thiophene, benzyl and cyclohexyl are optionally substituted with groups, equal to or different from each other, selected from halogen, linear or when possible branched $C_1$-$C_7$ alkyl, $SO_2NH_2$, $SO_3H$, COOH, cyano, nitro, or $NR_{10A}R_{11A}$ wherein $R_{10A}$ and $R_{11A}$, equal to or different from each other, are selected between H and linear or when possible branched $C_1$-$C_7$ alkyl, $R_{30}$—W with W=$W_b$, wherein $R_{30}$ and $W_b$ are as defined above, $Q_p$ and $Z_p$, equal to each other, are selected between the bivalent groups QA or QB as defined above, $L_p$ has the following meanings:
$L_p$=L1 when $Q_p$=$Z_p$=QA wherein L1 and QA are as defined above,
$L_p$=L5' when $Q_p$=$Z_p$=QB, wherein QB is as defined above and L5' has the following formula

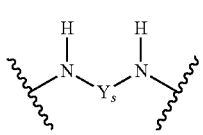
L5' wherein $Y_s$ has the meaning of $Y_{100}$.

Preferably CH=CH is excluded from the meanings of A and A'.

Specific examples of the most preferred compounds of the present invention are the following:
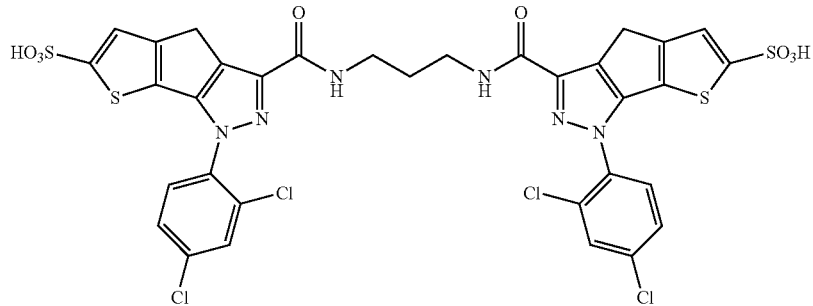
(IAA)
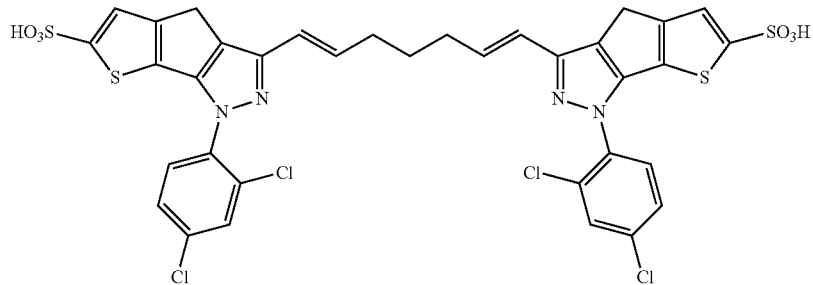
(IAB)
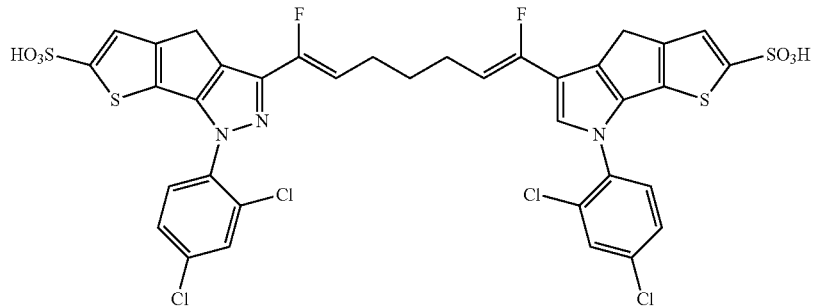
(IAC)
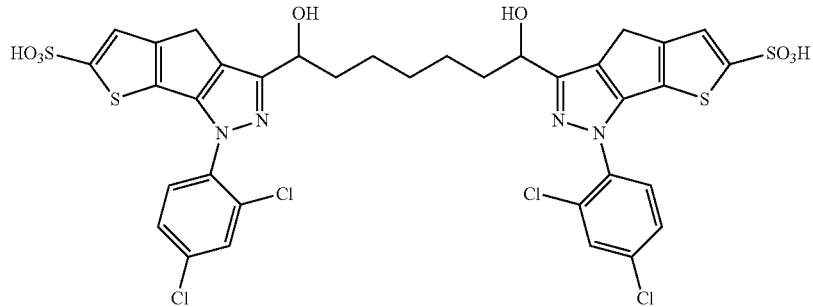
(IAD)
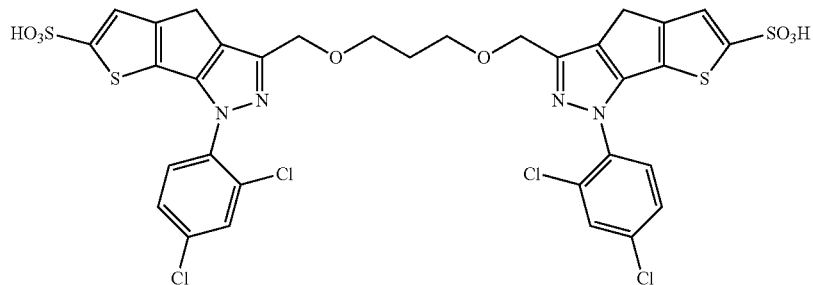
(IAE)

-continued
(IAF)
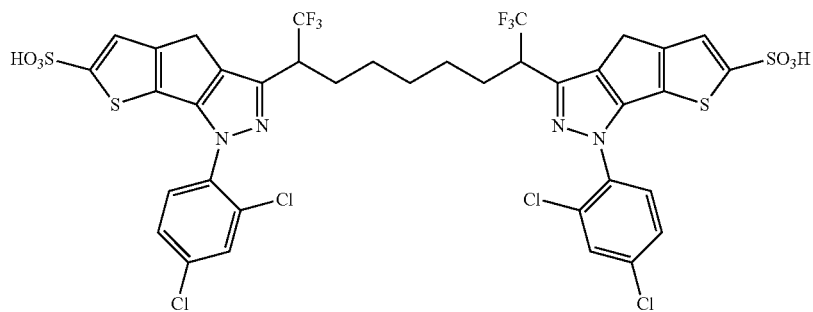
(IAG)
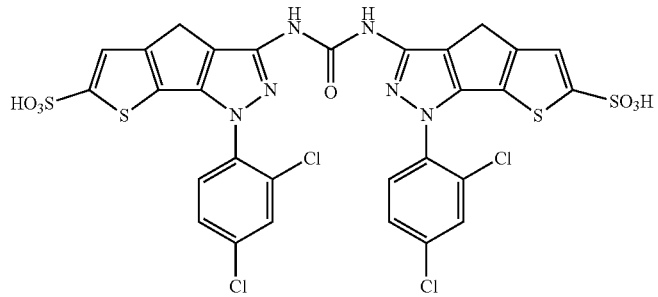
(IBA)
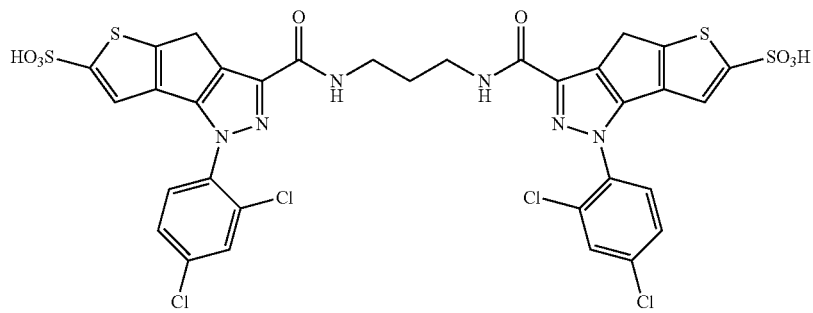
(IBB)
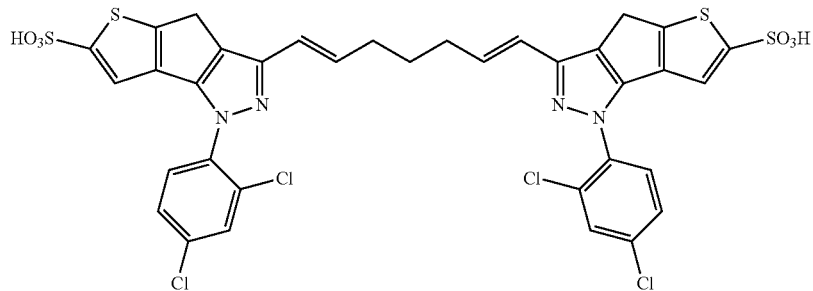
(IBC)
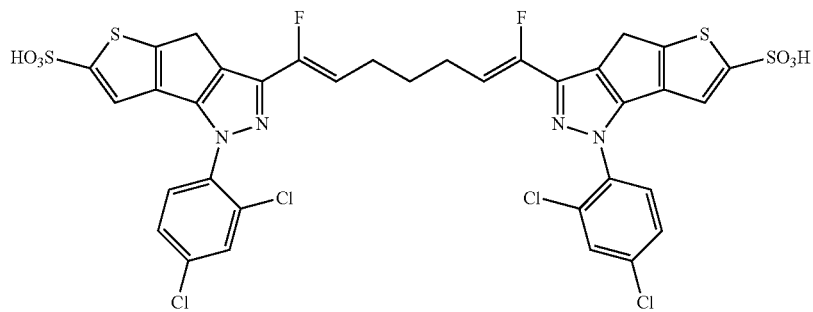

-continued
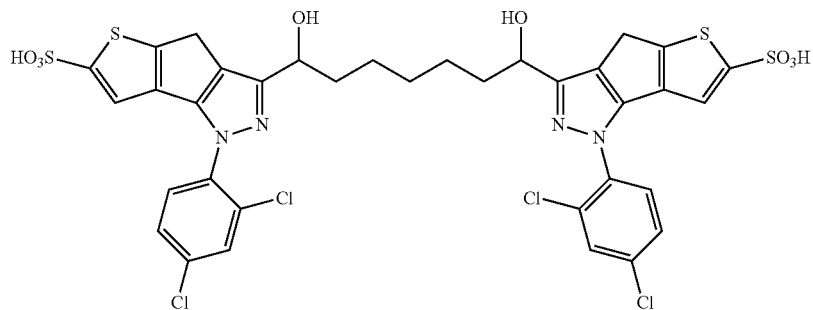
(IBD)
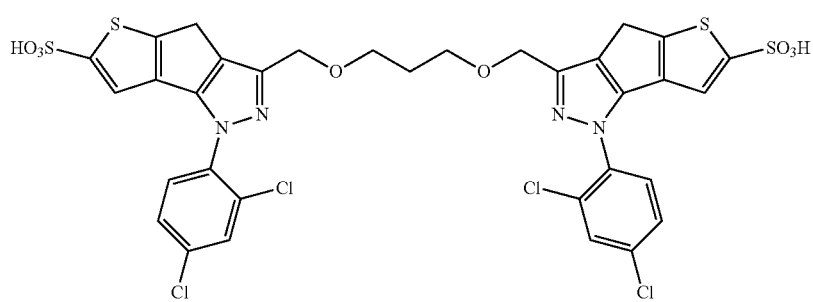
(IBE)
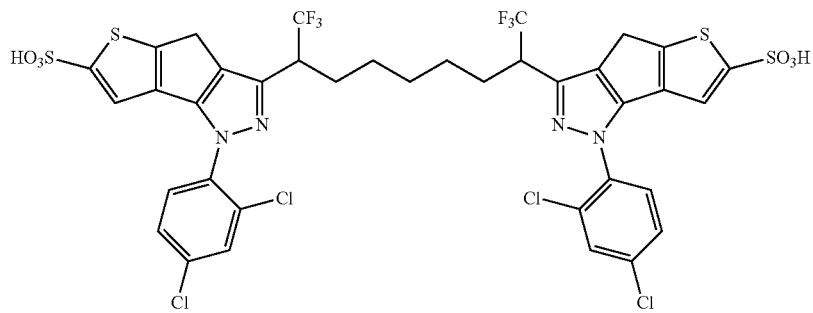
(IBF)
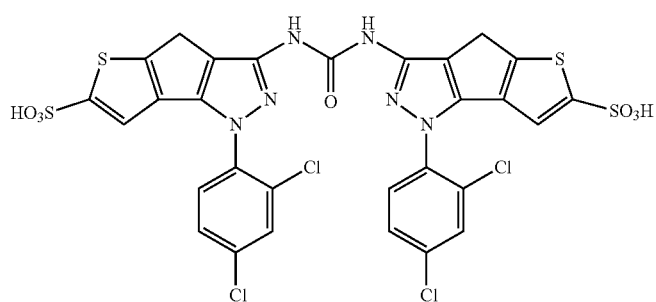
(IBG)
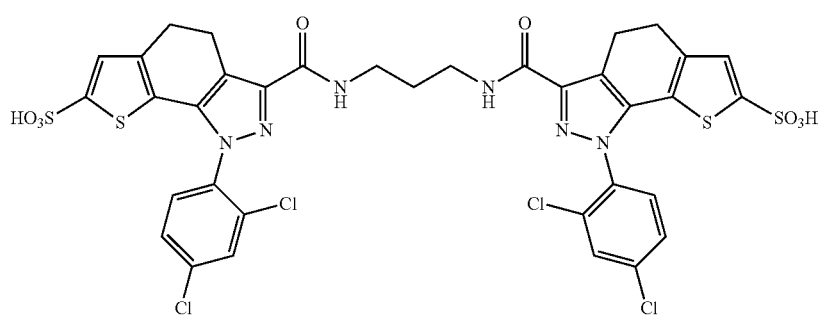
(ICA)

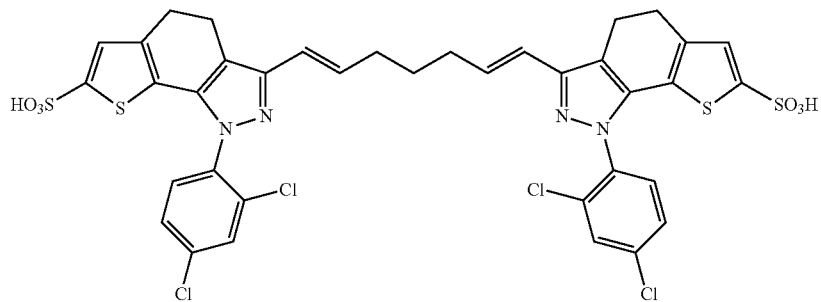
(ICB)
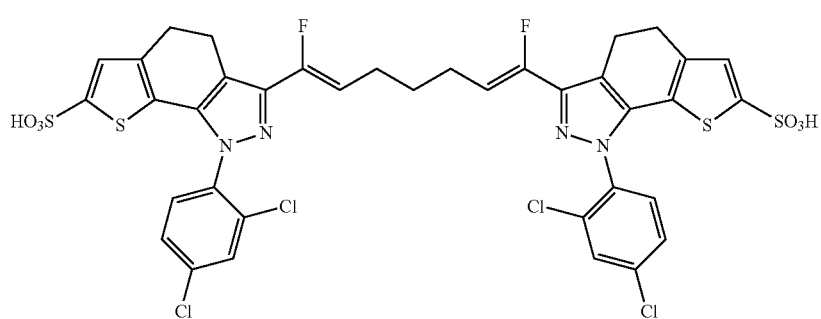
(ICC)
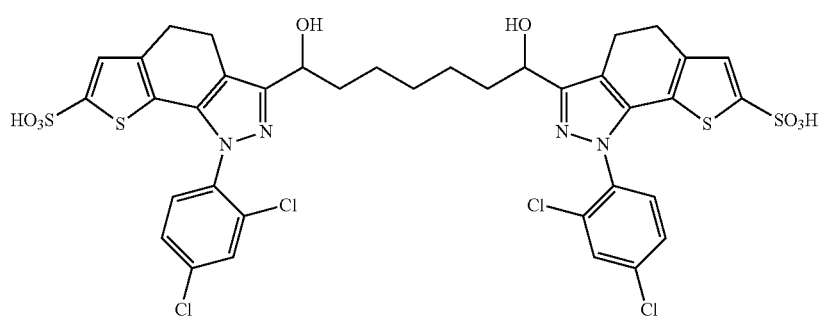
(ICD)
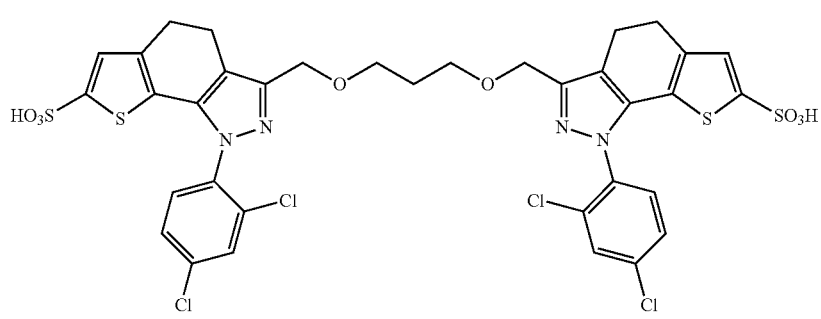
(ICE)
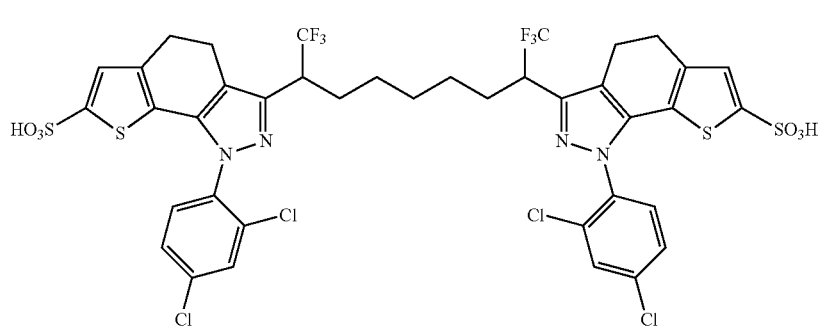
(ICF)

-continued
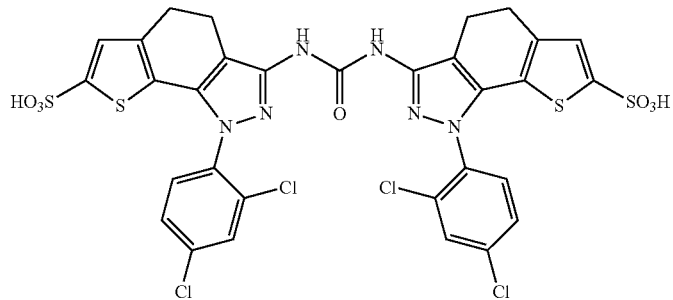
(ICG)
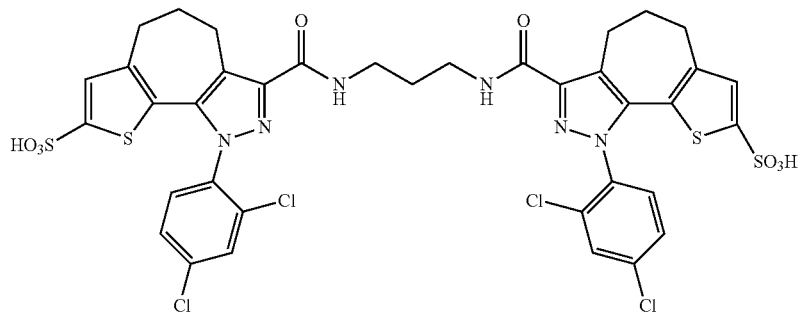
(IDA)
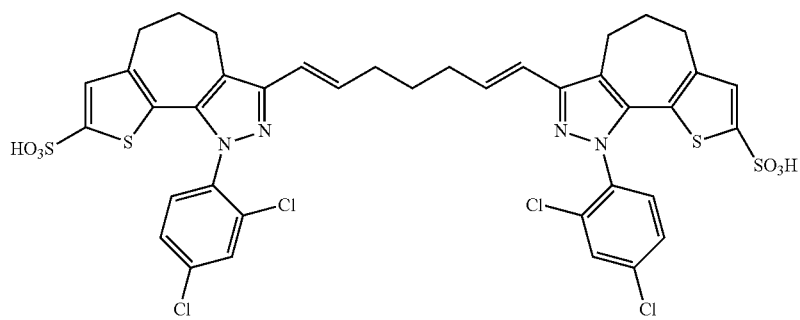
(IDB)
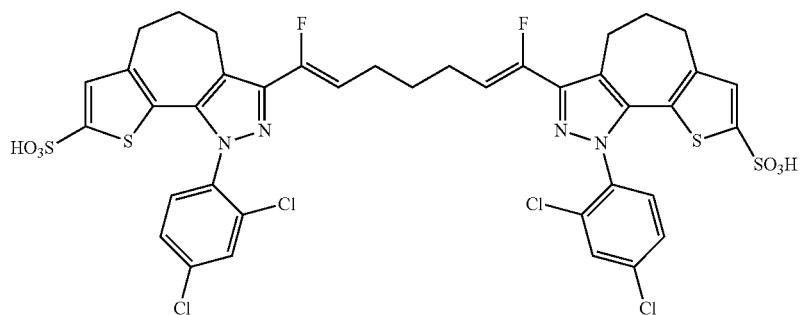
(IDC)
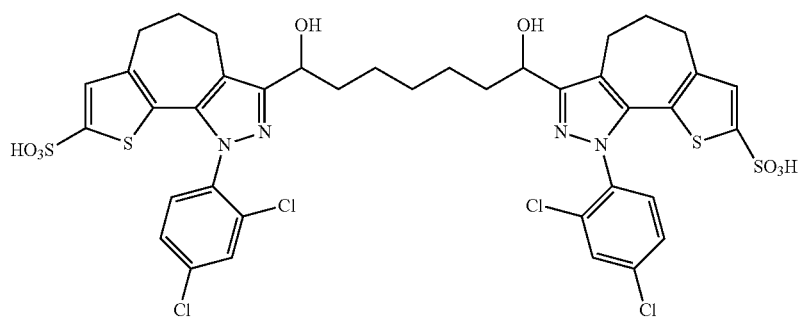
(IDD)

(IDE)
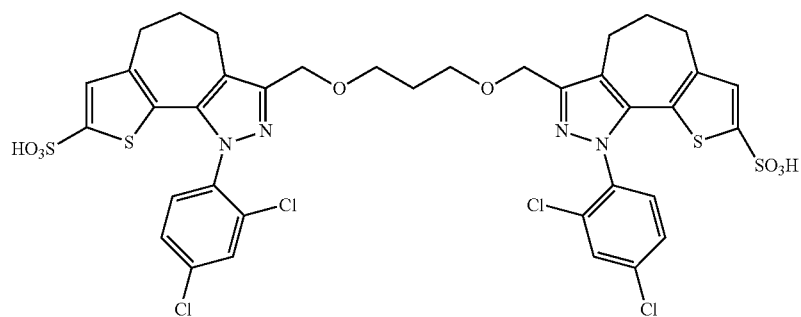
(IDF)
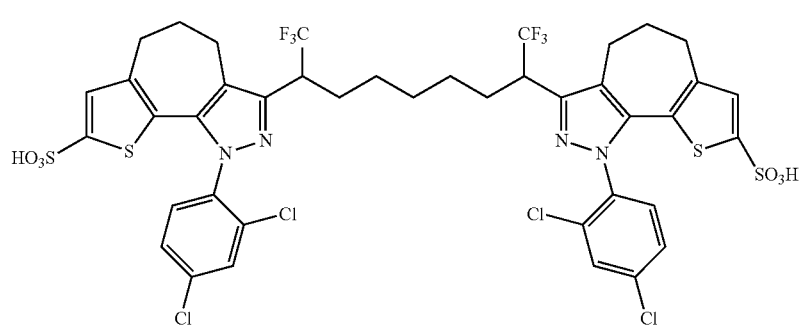
(IDG)
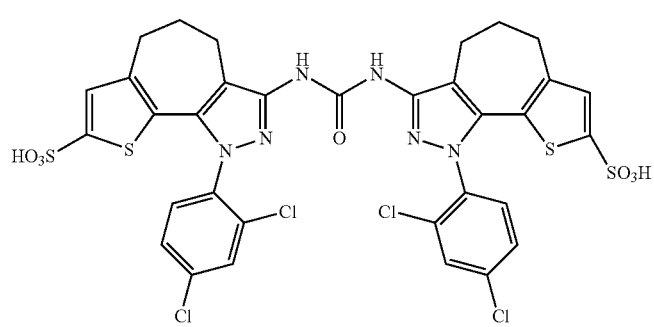
(IEA)
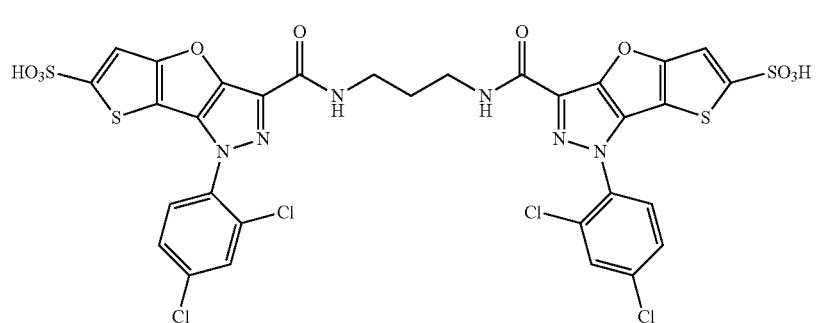
(IEB)
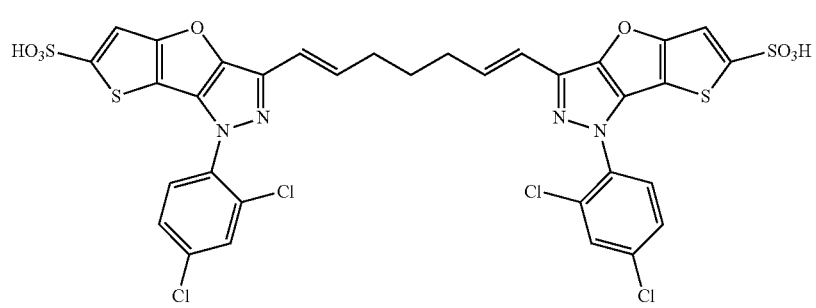

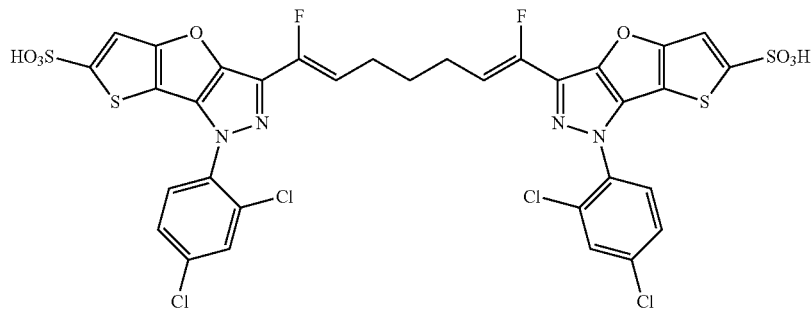
(IEC)
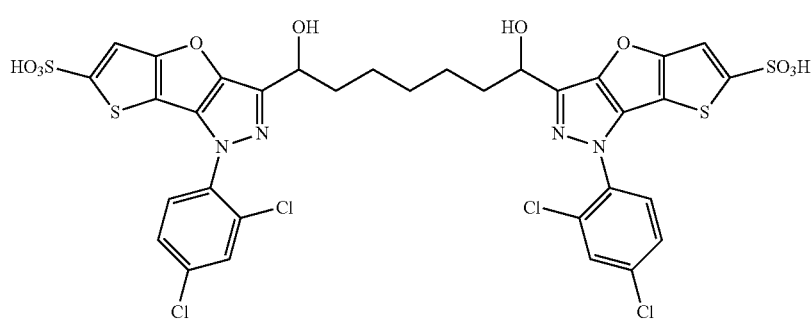
(IED)
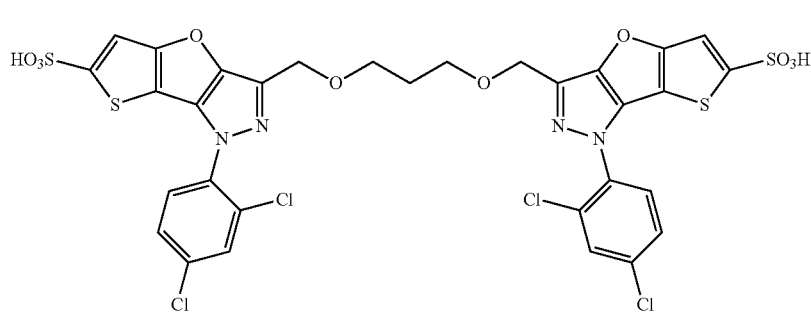
(IEE)
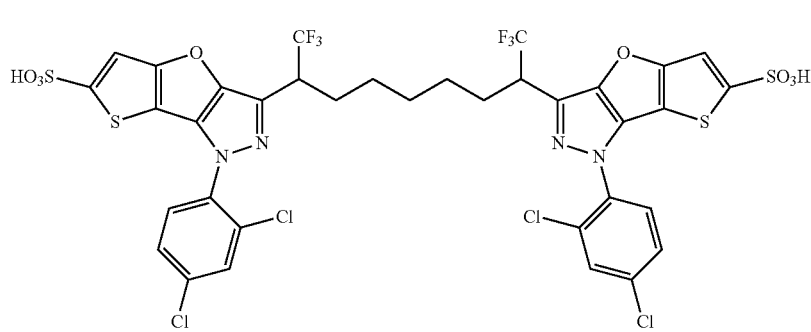
(IEF)
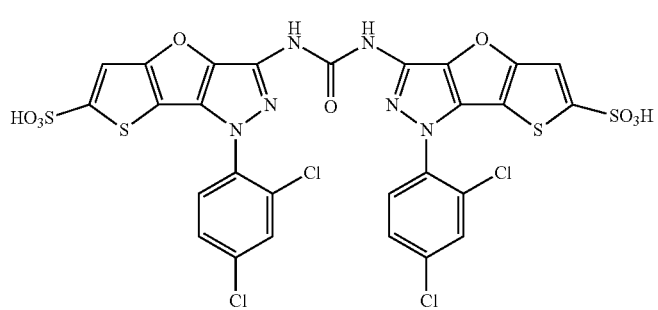
(IEG)

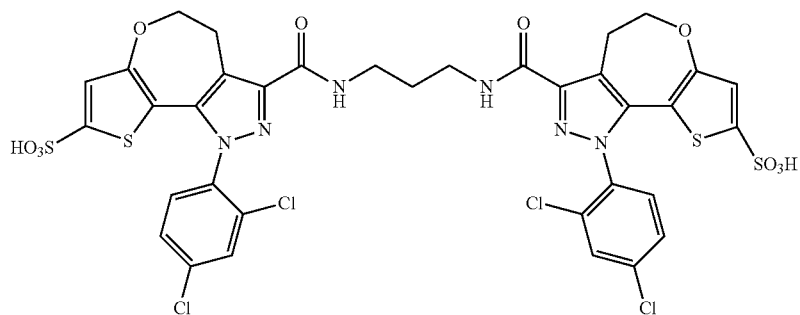
(IFA)

(IFB)
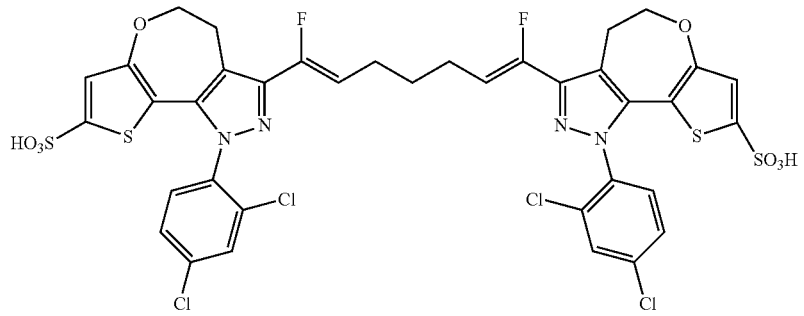
(IFC)
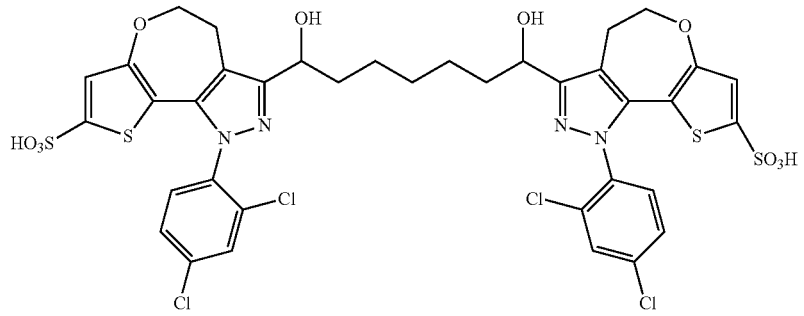
(IFD)
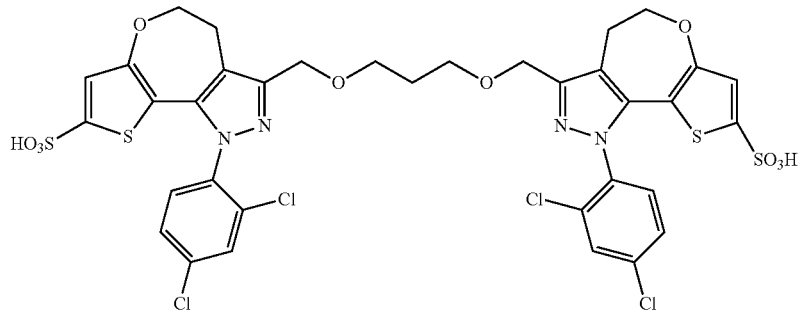
(IFE)

-continued
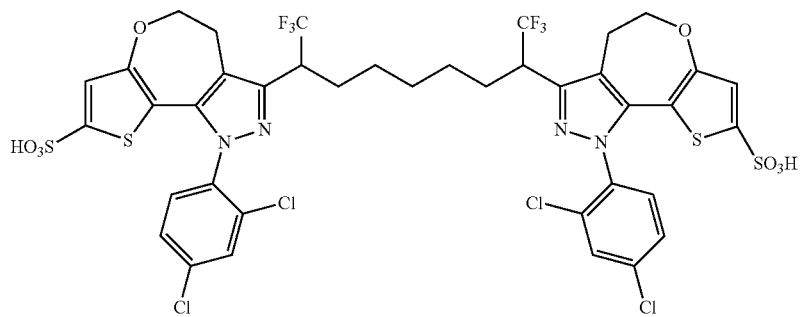
(IFF)
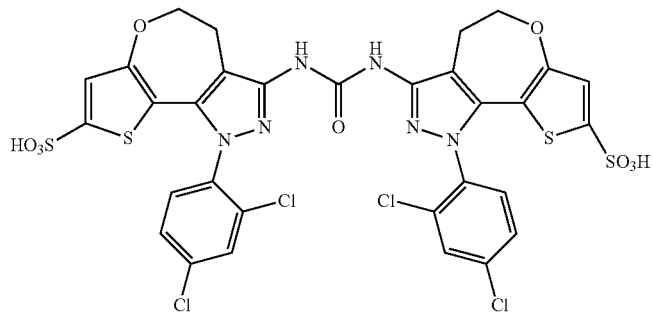
(IFG)
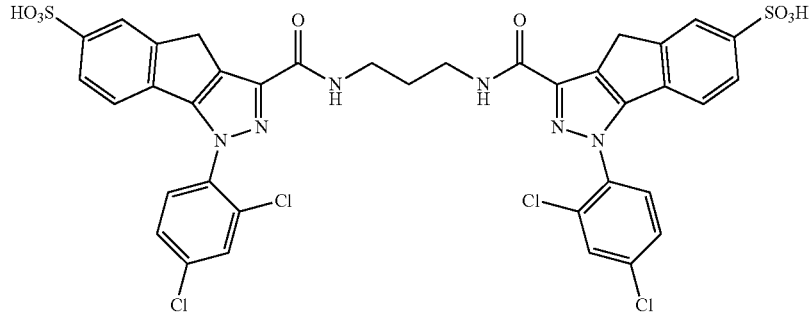
(IGA)
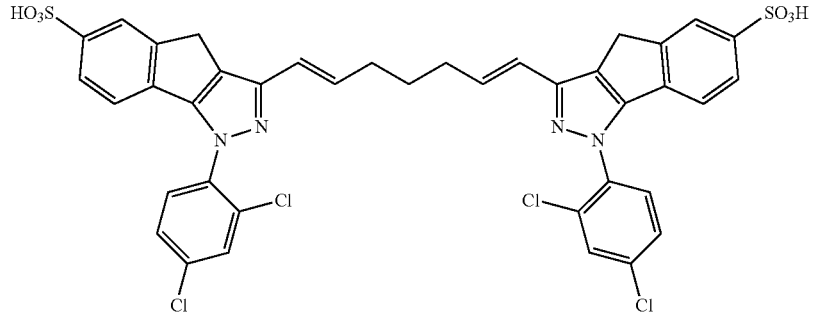
(IGB)
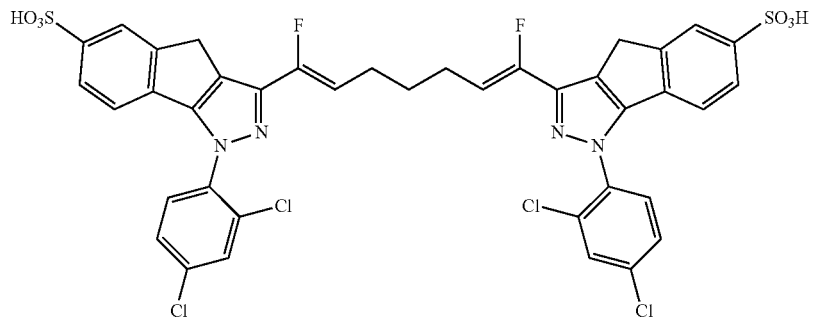
(IGC)

-continued
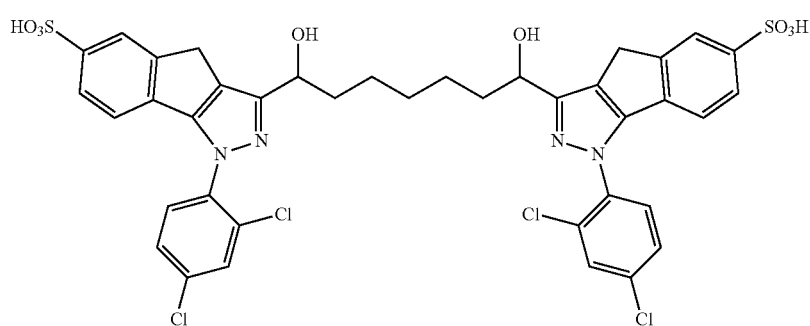
(IGD)
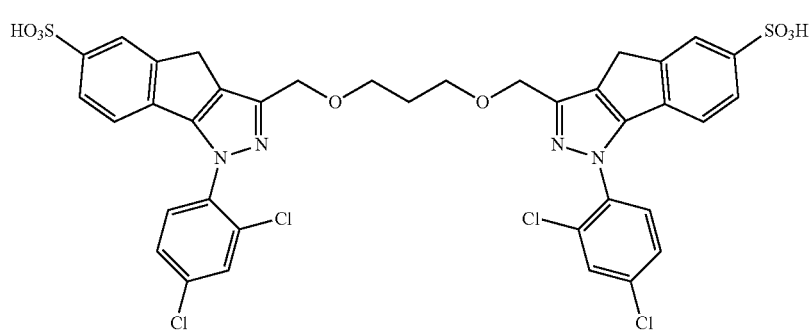
(IGE)
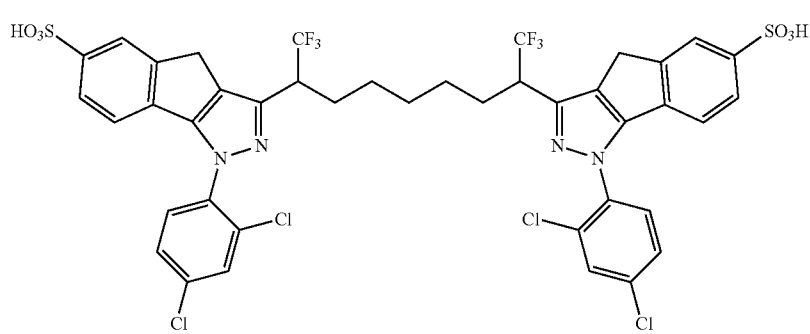
(IGF)
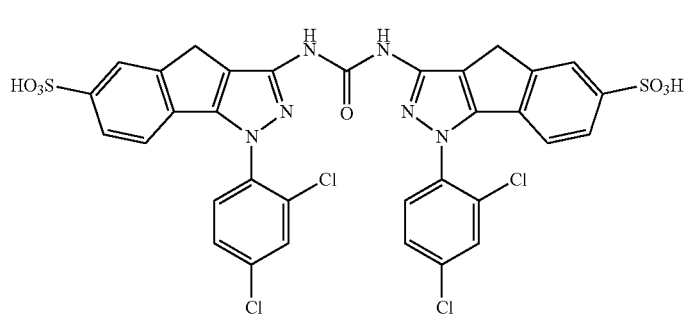
(IGG)
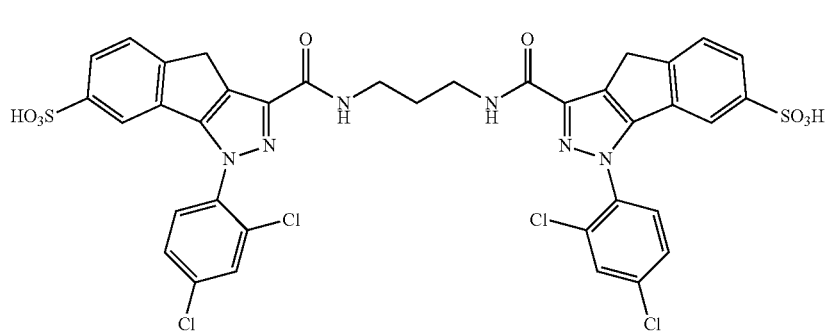
(IHA)

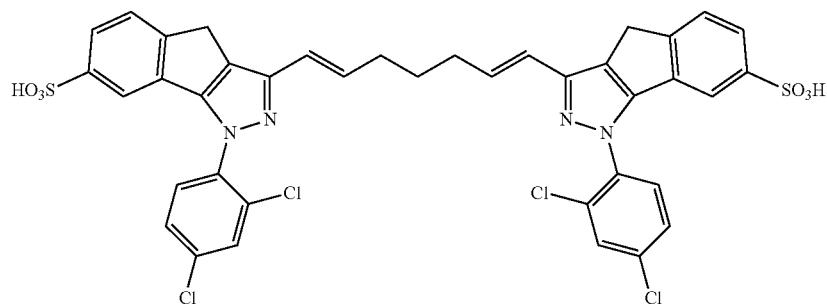
(IHB)
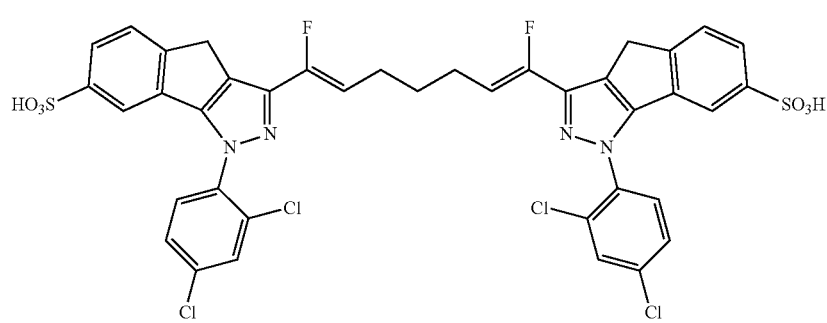
(IHC)
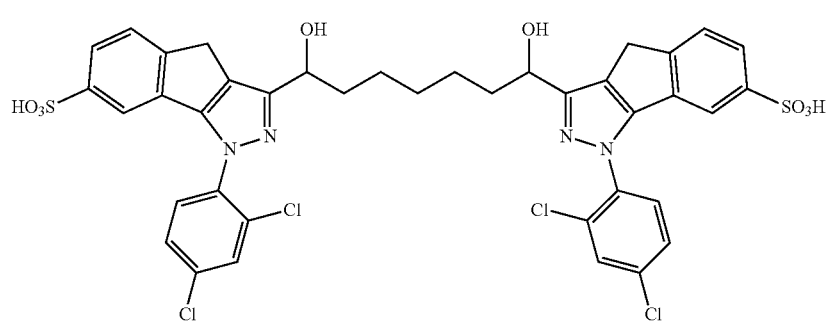
(IHD)
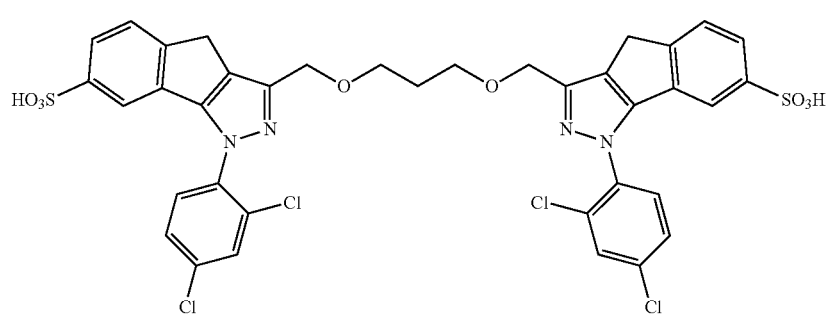
(IHE)
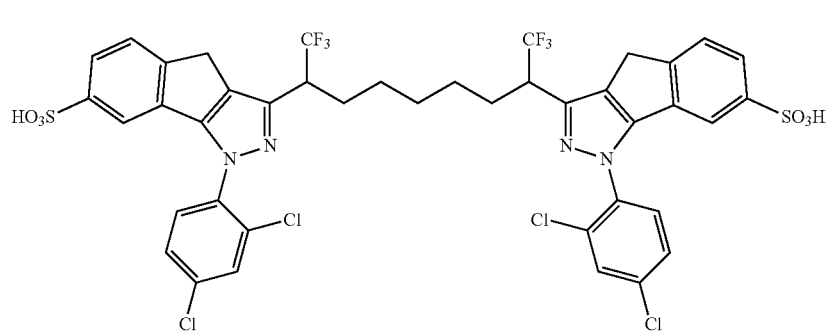
(IHF)

-continued
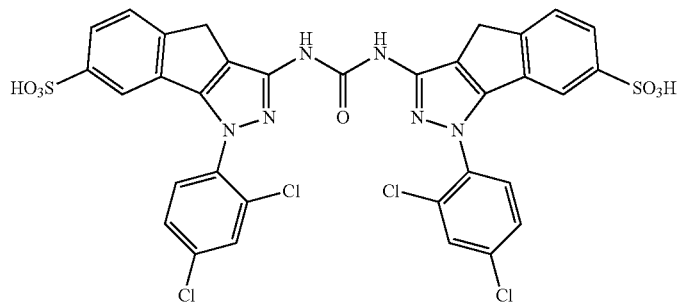
(IHG)
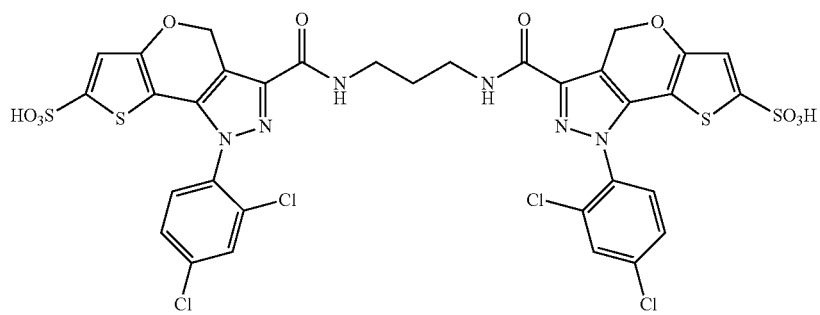
(ILA)
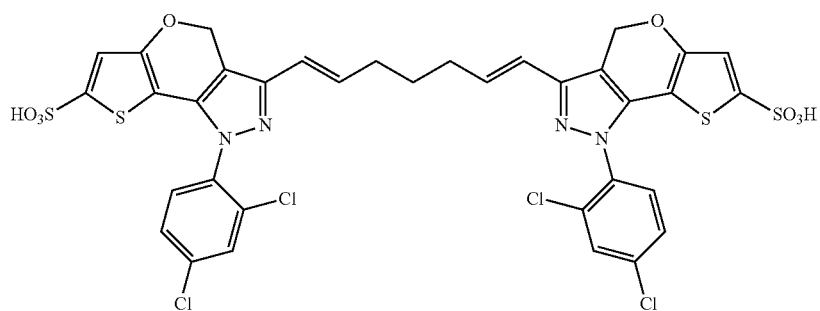
(ILB)
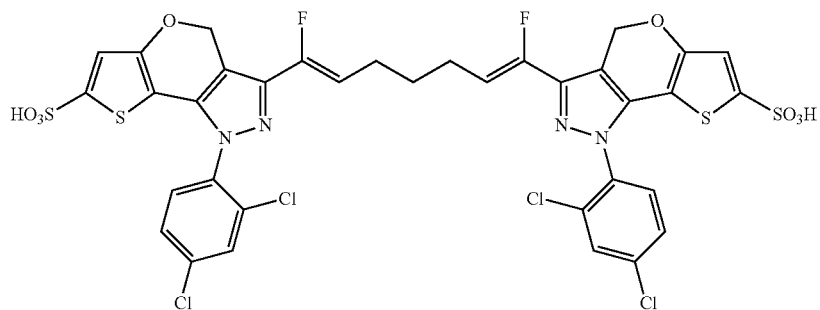
(ILC)
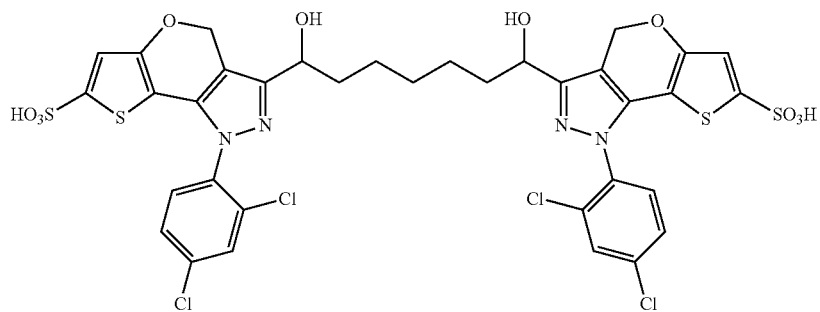
(ILD)

-continued
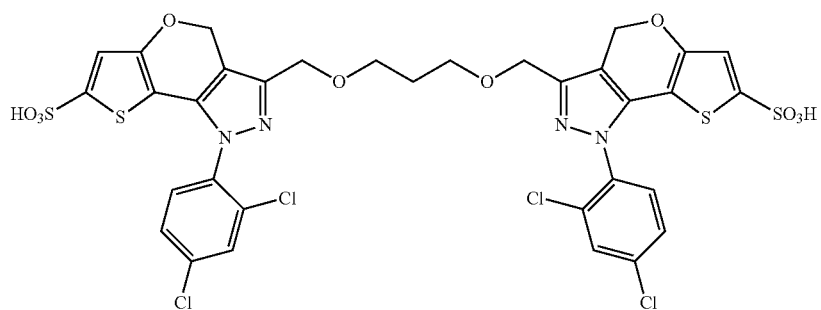
(ILE)
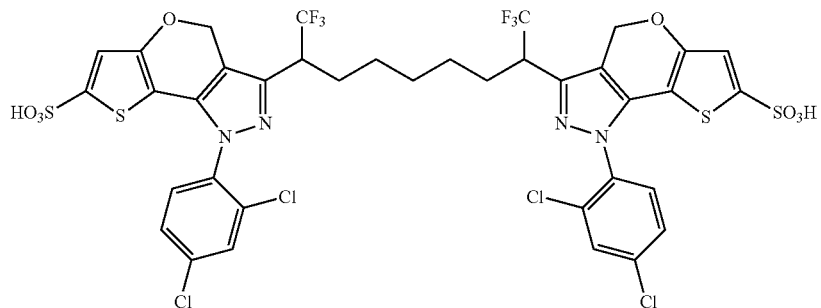
(ILF)
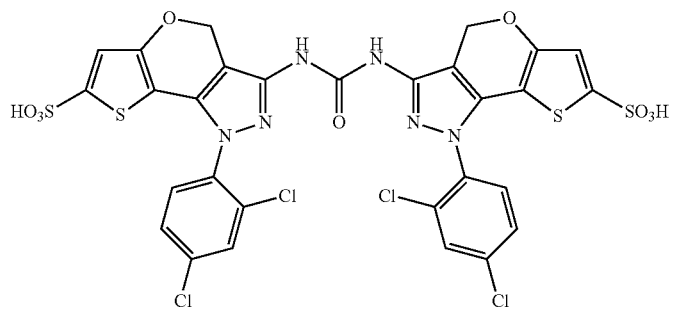
(ILG)
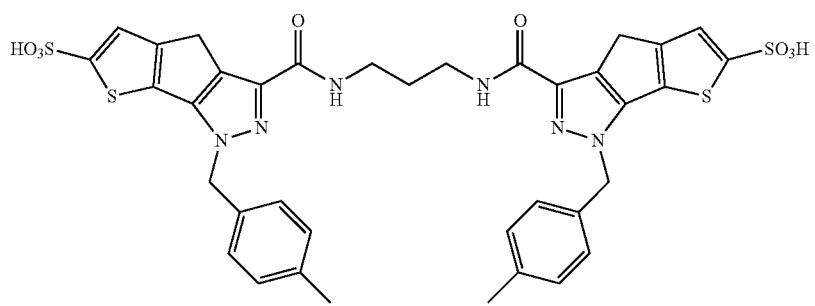
(IIAA)
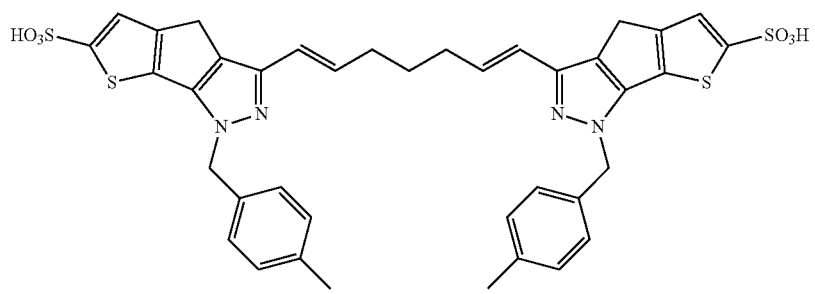
(IIAB)

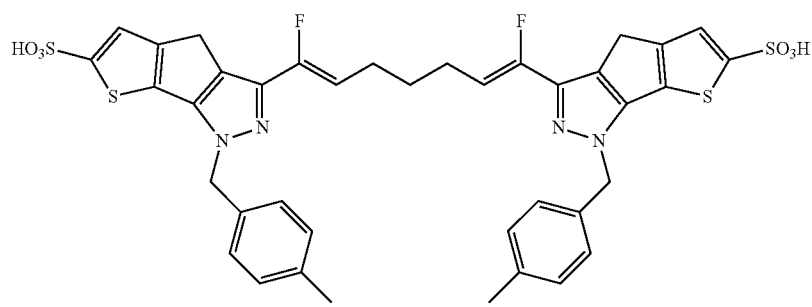
(IIAC)
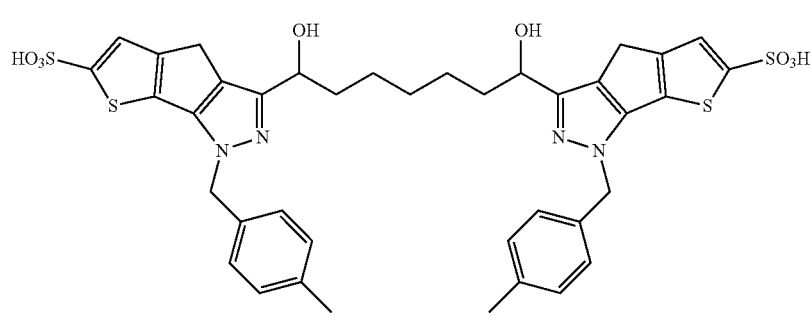
(IIAD)
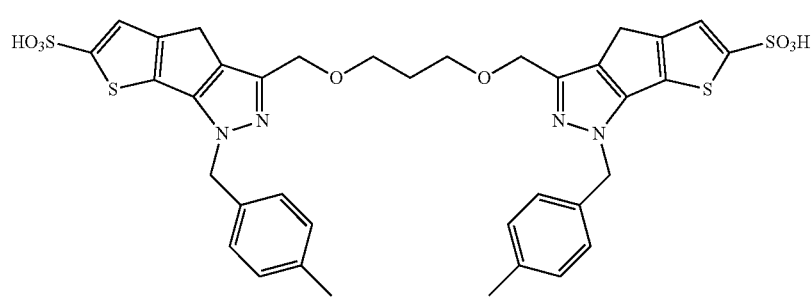
(IIAE)
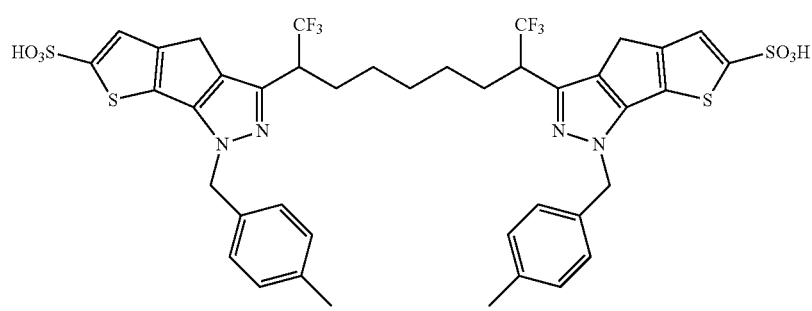
(IIAF)
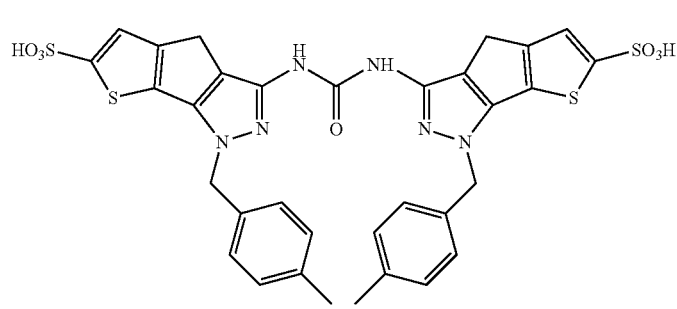
(IIAG)

-continued
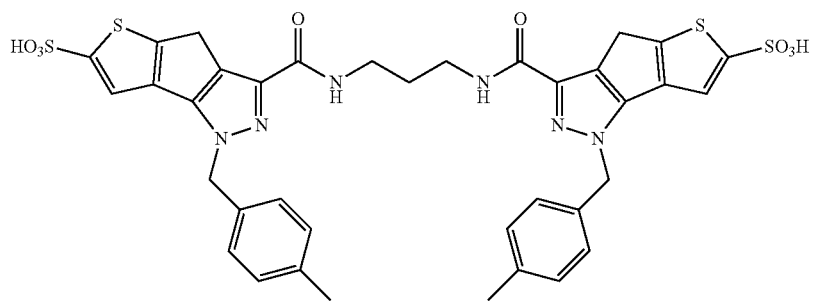
(IIBA)
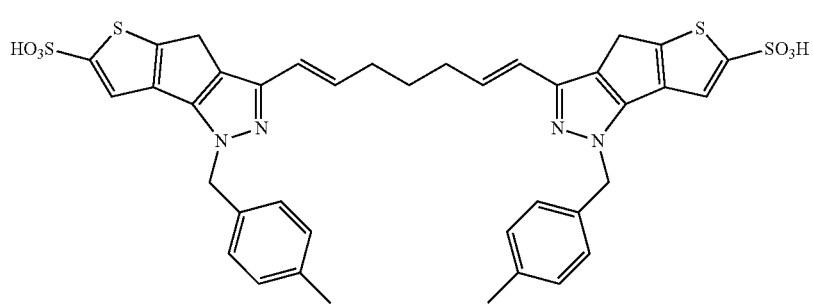
(IIBB)
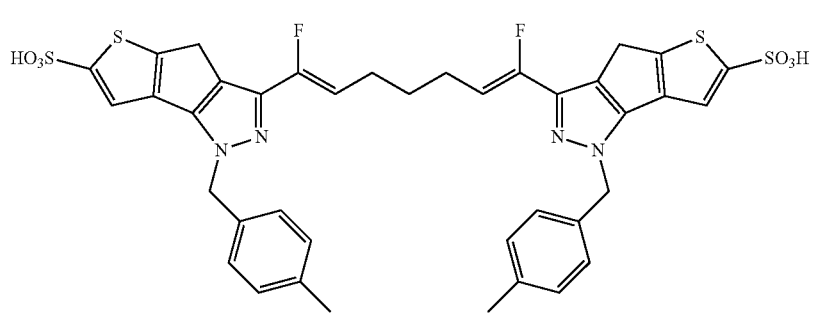
(IIBC)
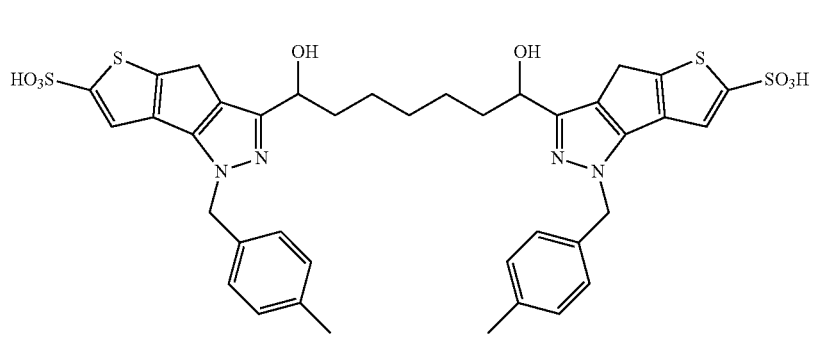
(IIBD)
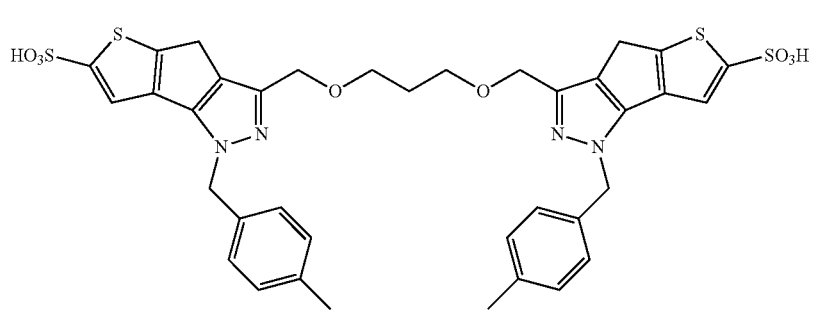
(IIBE)

-continued
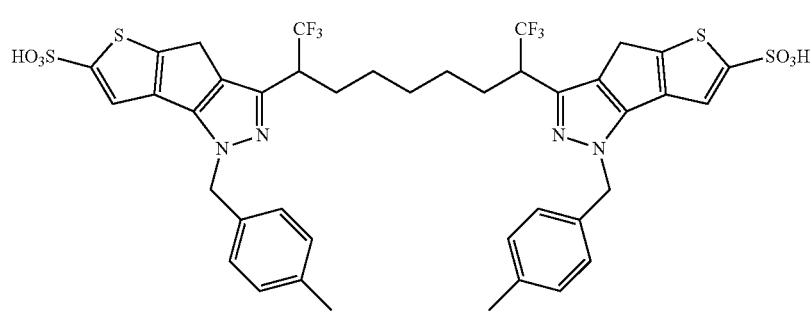
(IIBF)
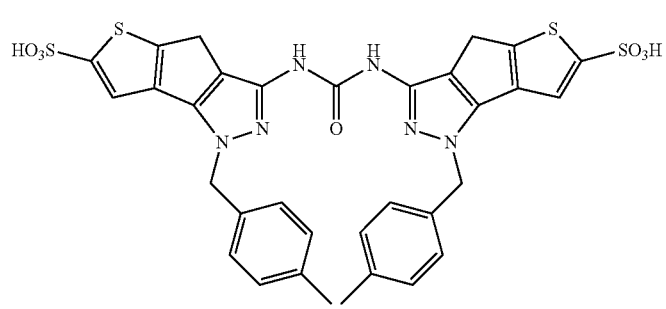
(IIBG)
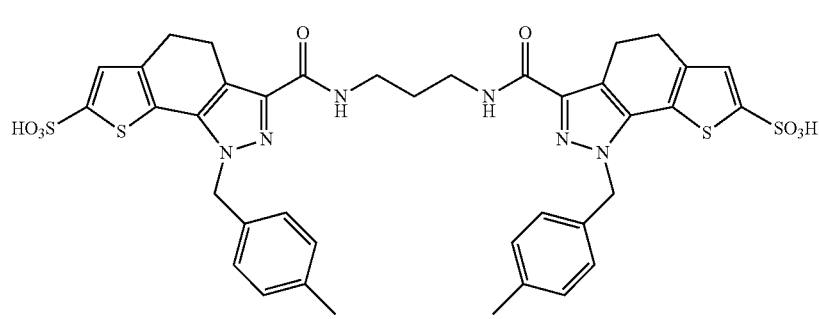
(IICA)
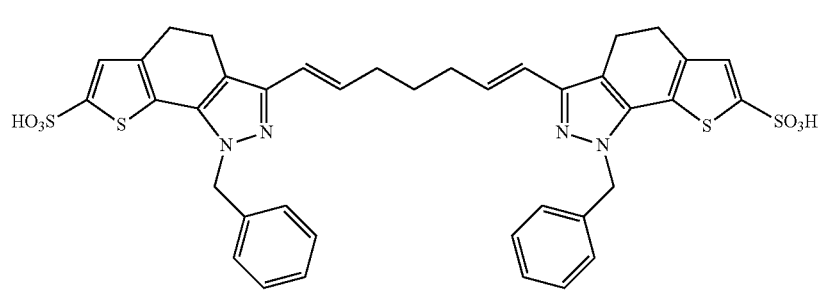
(IICB)
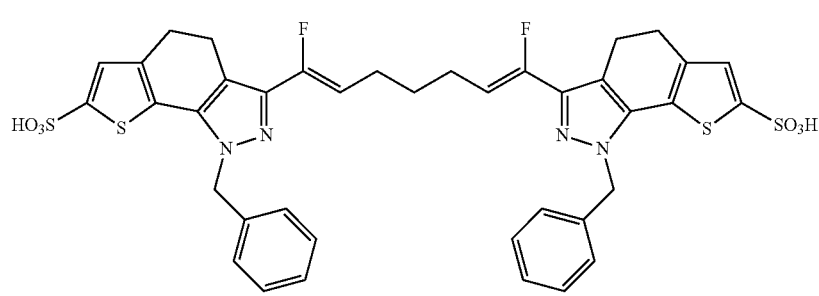
(IICC)

-continued
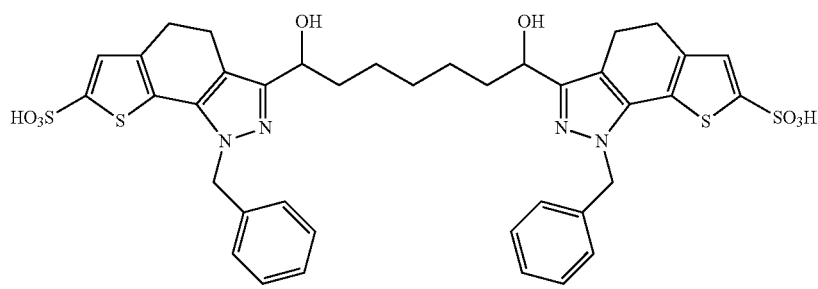
(IICD)
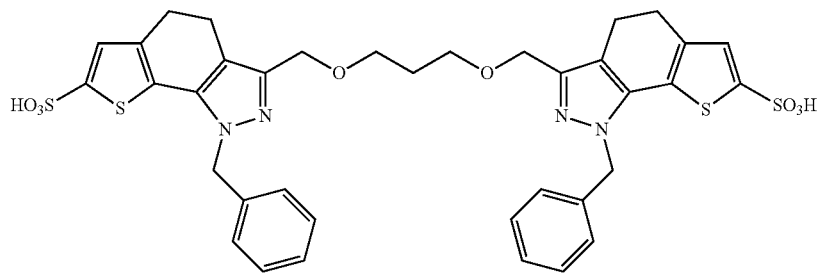
(IICE)
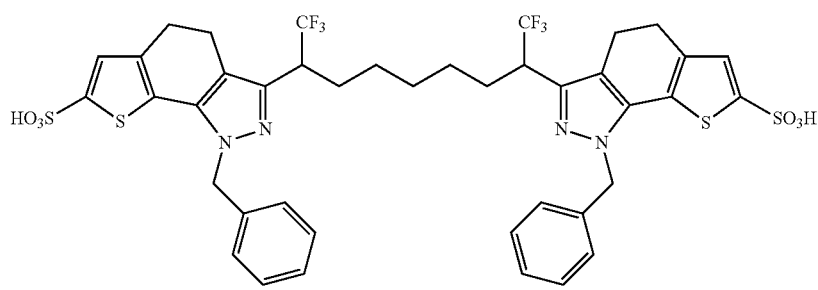
(IICF)
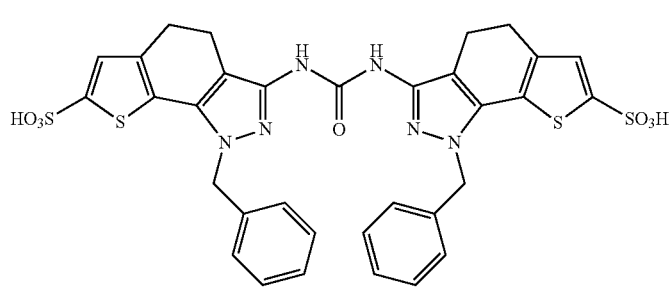
(IICG)
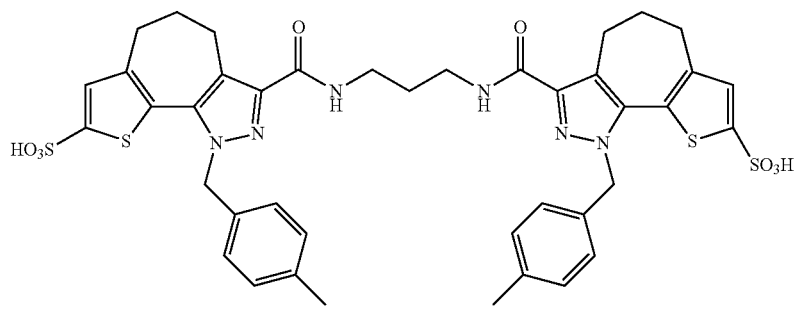
(IIDA)

-continued
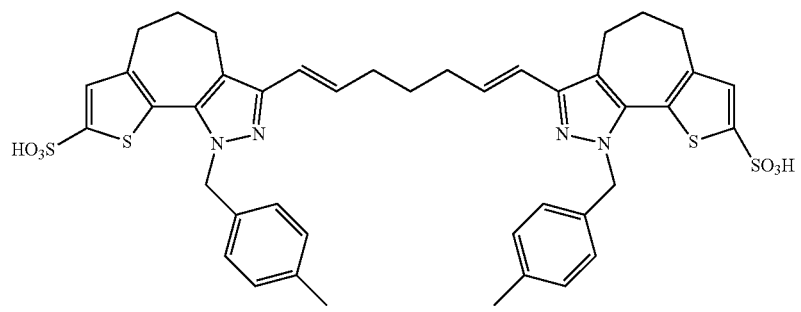
(IIDB)
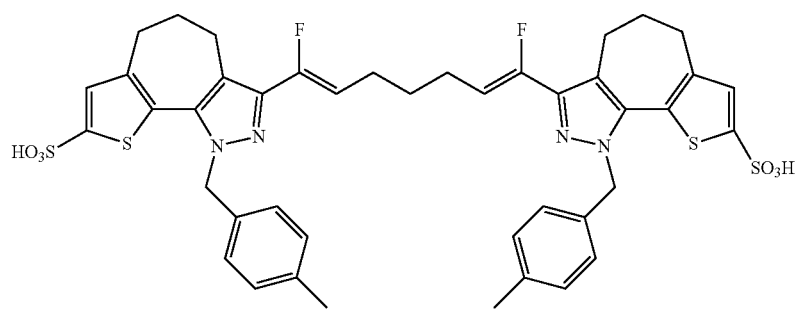
(IIDC)
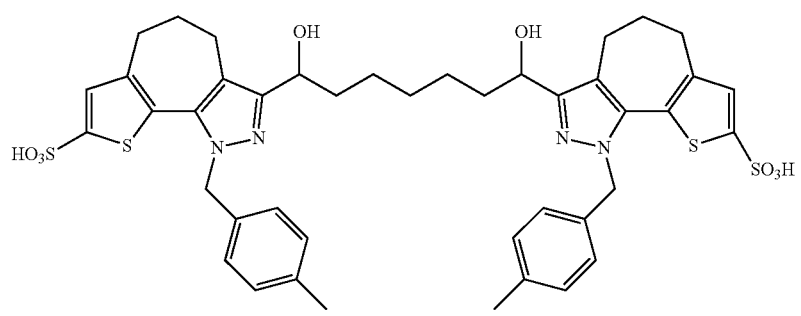
(IIDD)
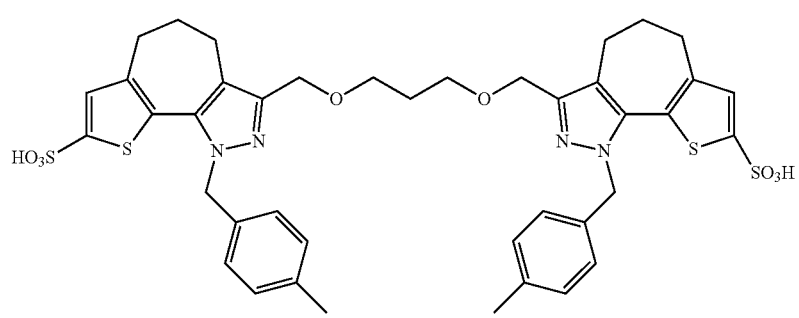
(IIDE)
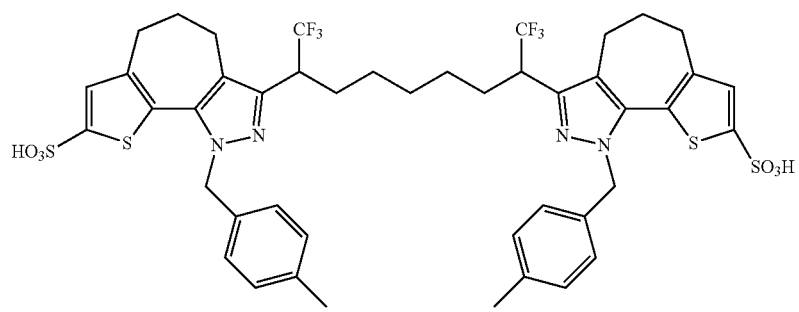
(IIDF)

-continued
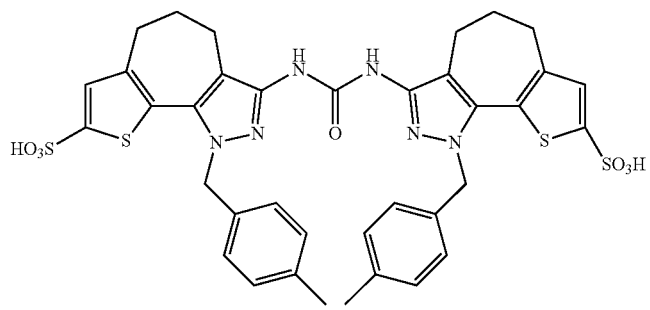
(IIDG)
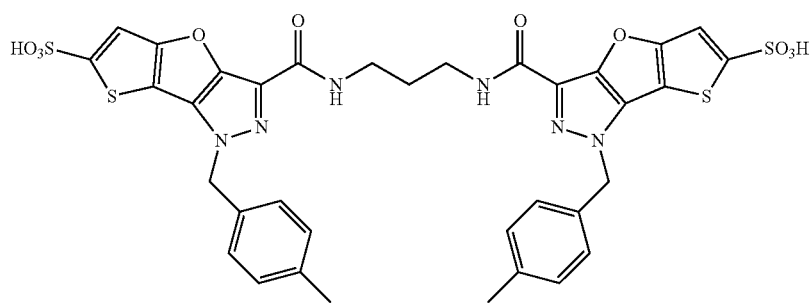
(IIEA)
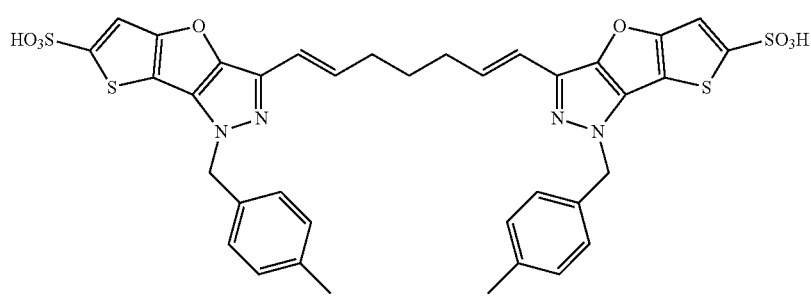
(IIEB)
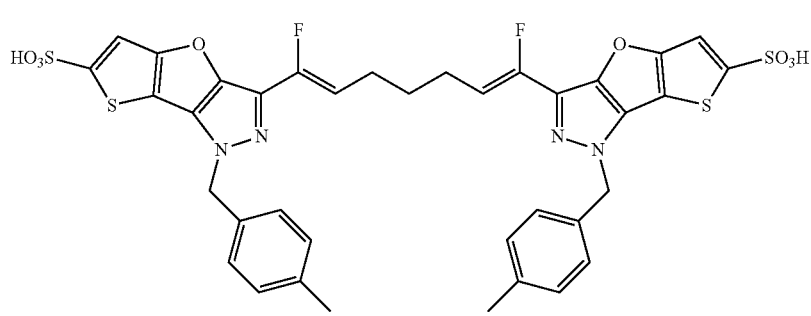
(IIEC)
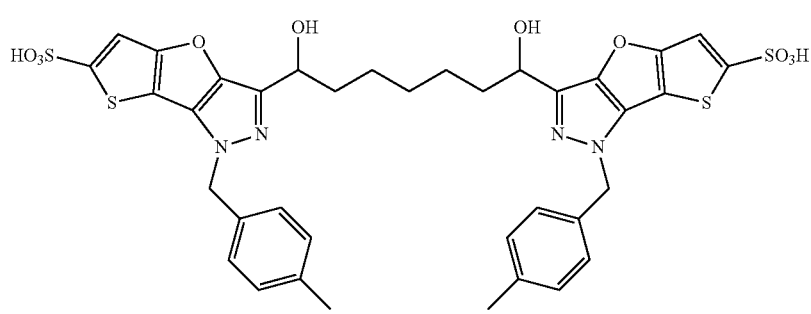
(IIED)

(IIEE)
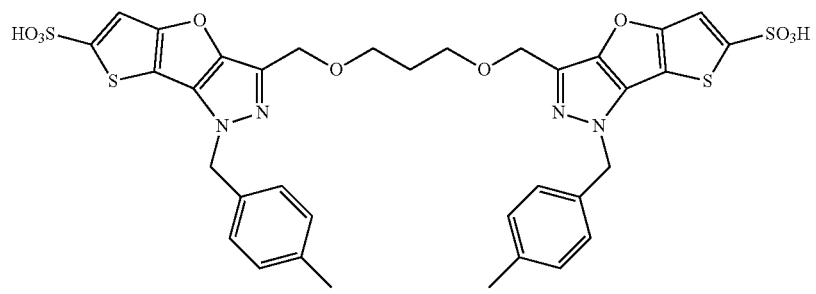
(IIEF)
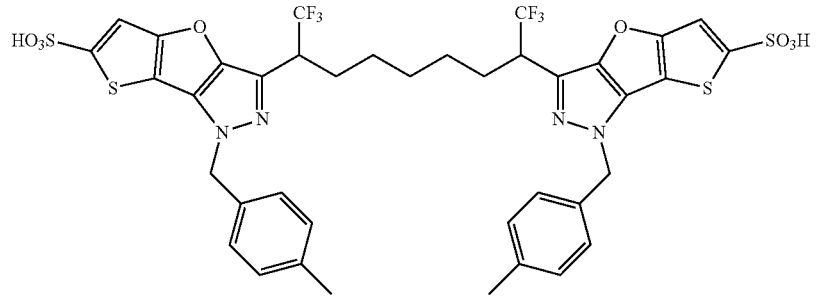
(IIEG)
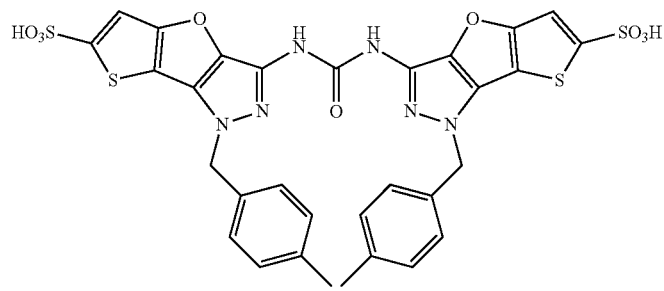
(IIFA)
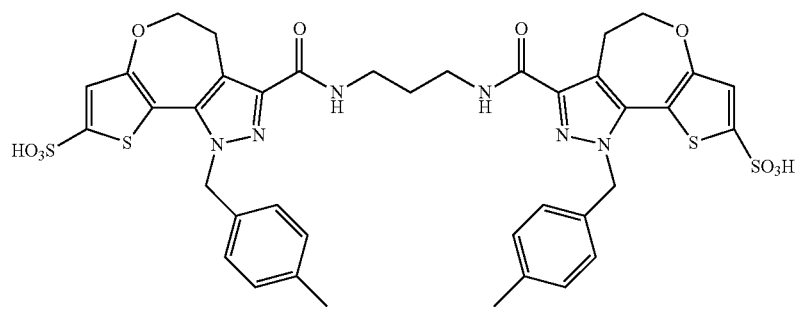
(IIFB)
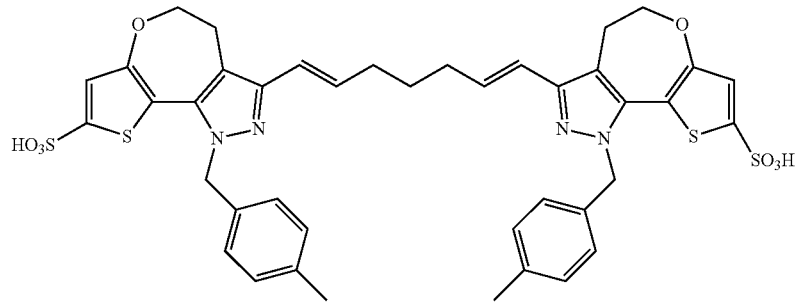

-continued
(IIFC)
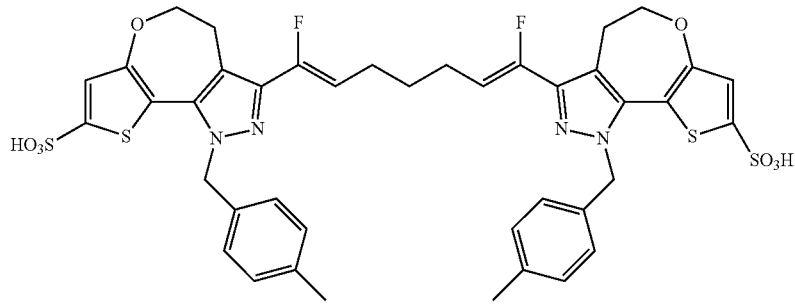
(IIFD)
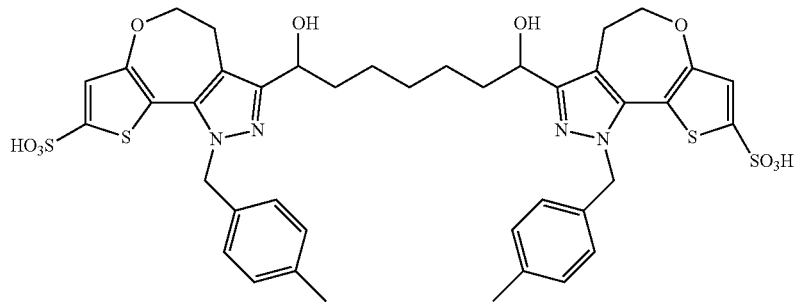
(IIFE)
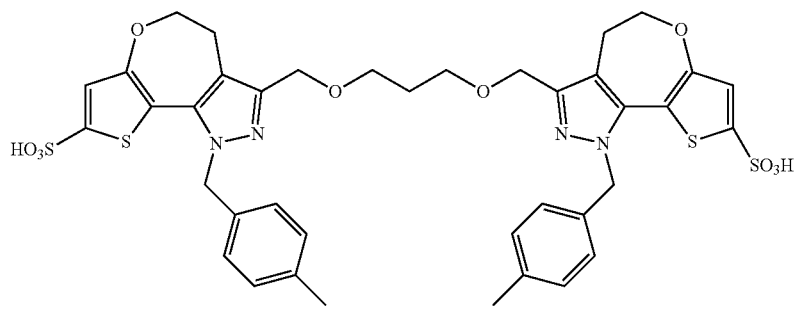
(IIFF)
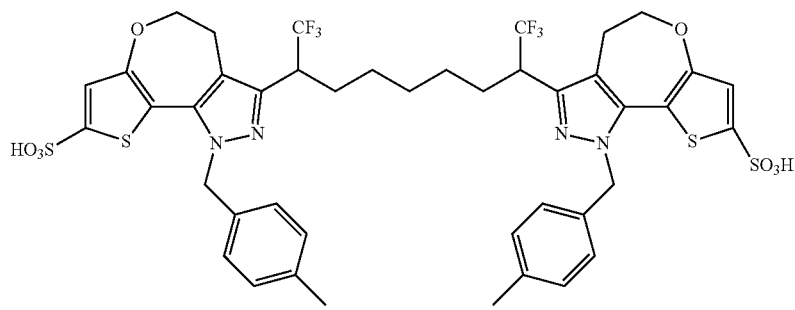
(IIFG)
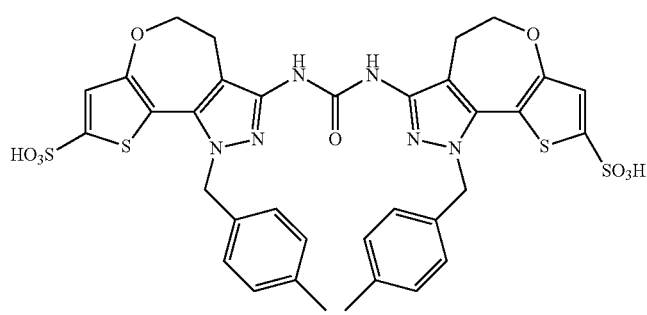

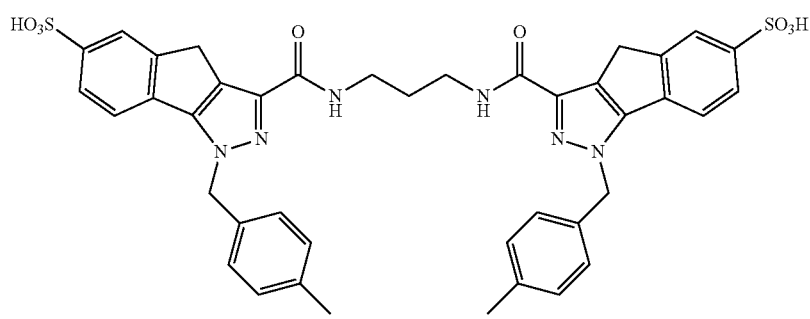
(IIGA)
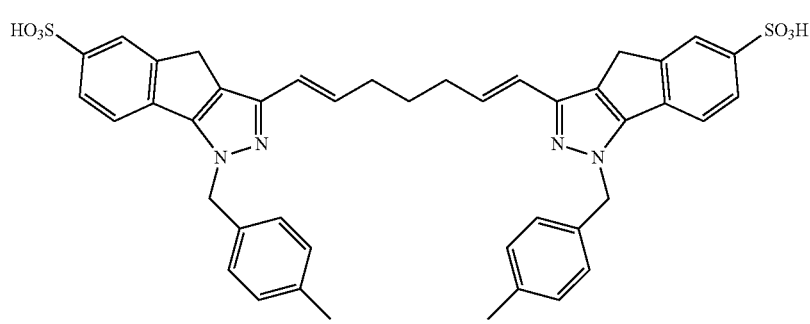
(IIGB)
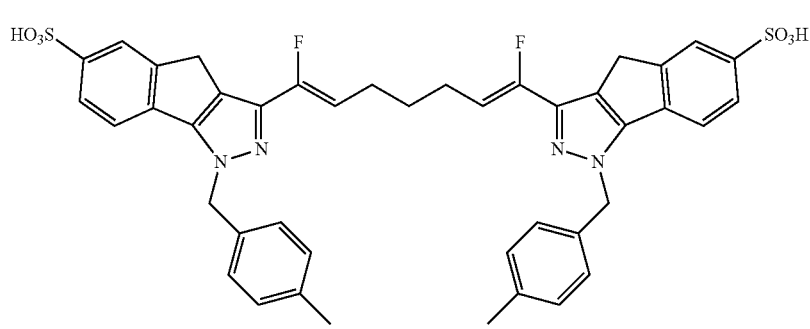
(IIGC)
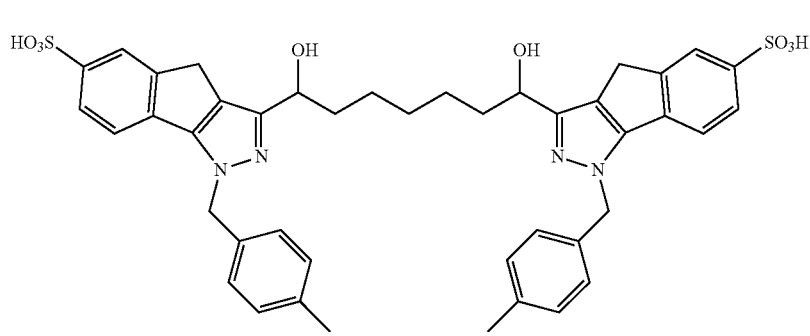
(IIGD)
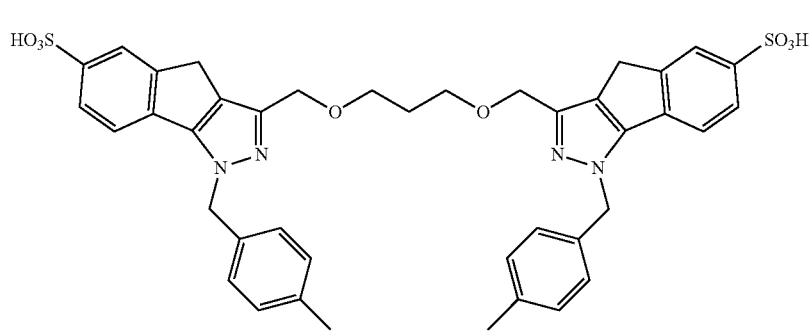
(IIGE)

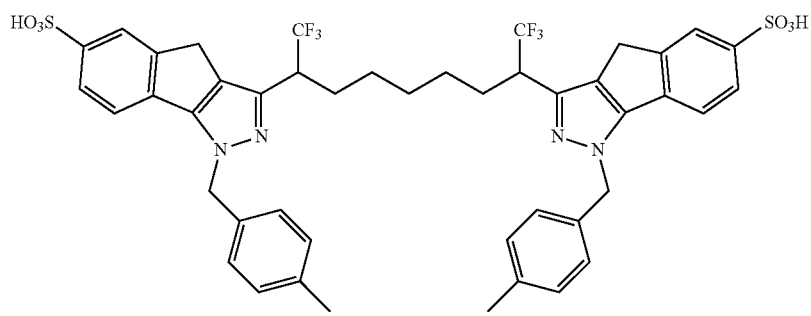
(IIGF)
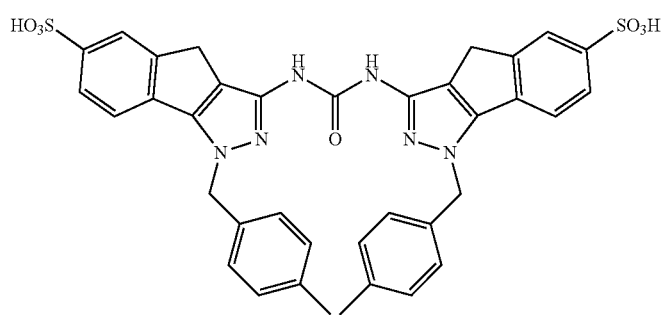
(IIGG)
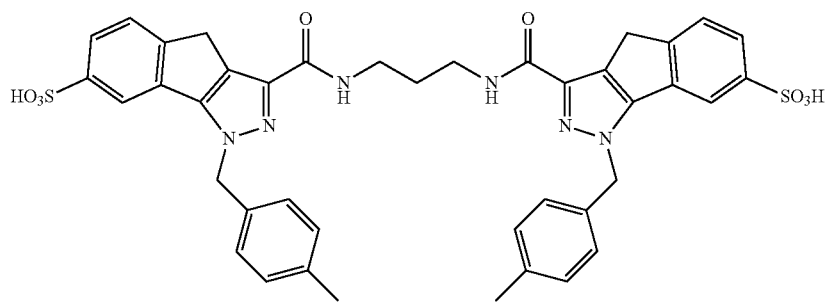
(IIHA)
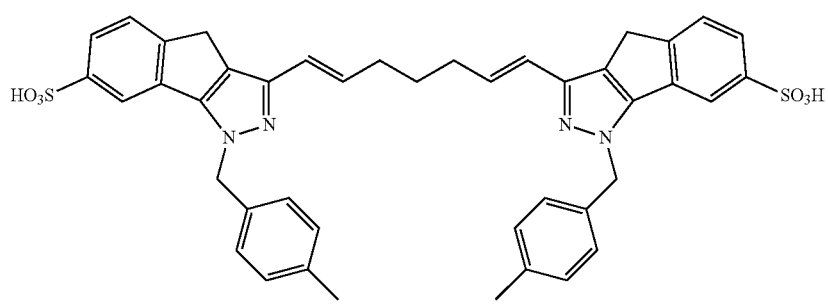
(IIHB)
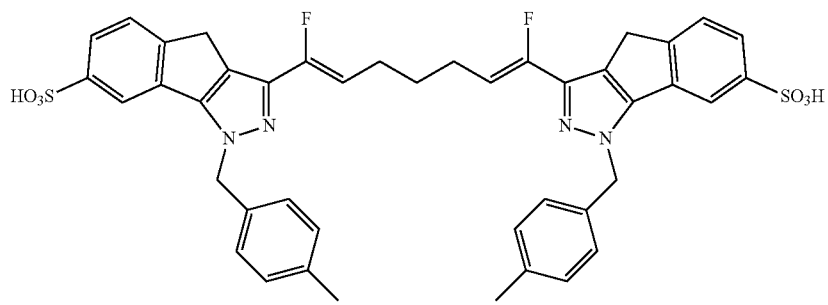
(IIHC)

-continued
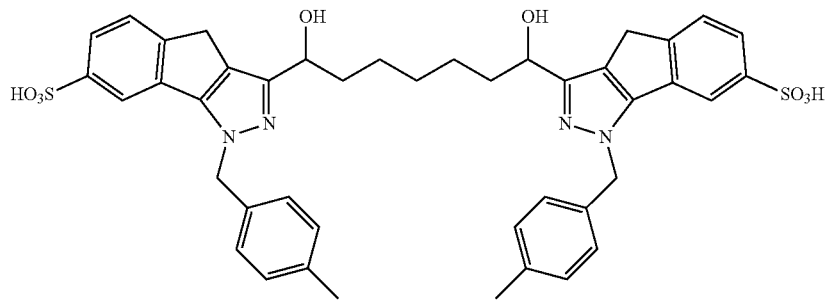
(IIHD)
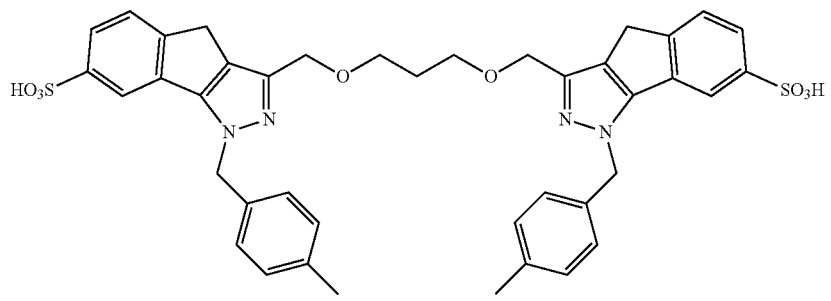
(IIHE)
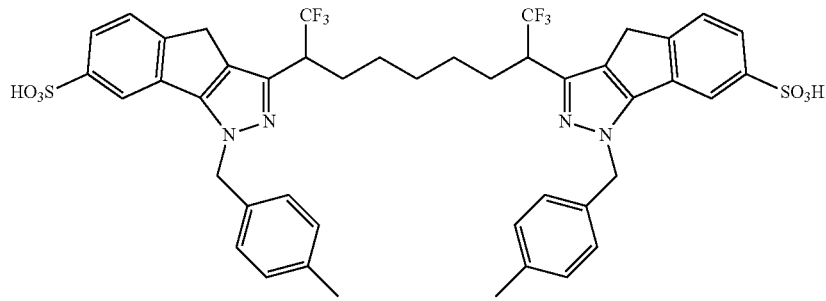
(IIHF)
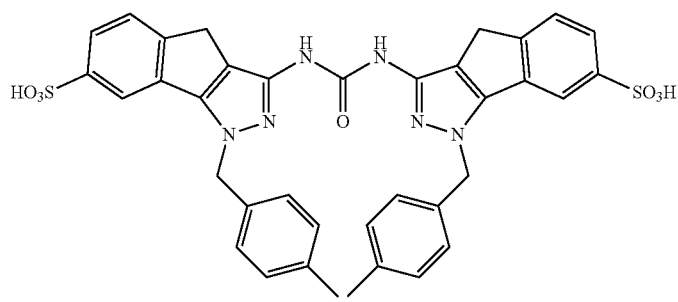
(IIHG)
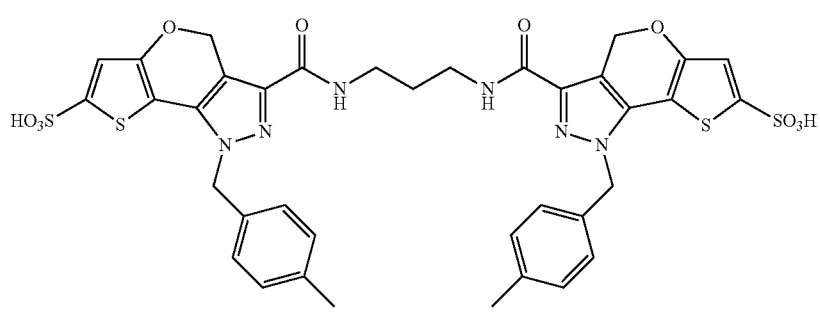
(IILA)

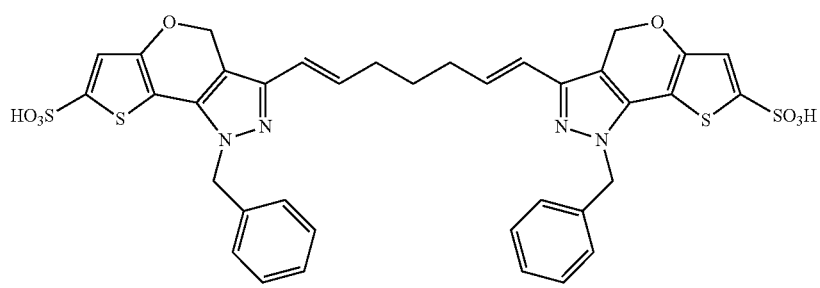
(IILB)
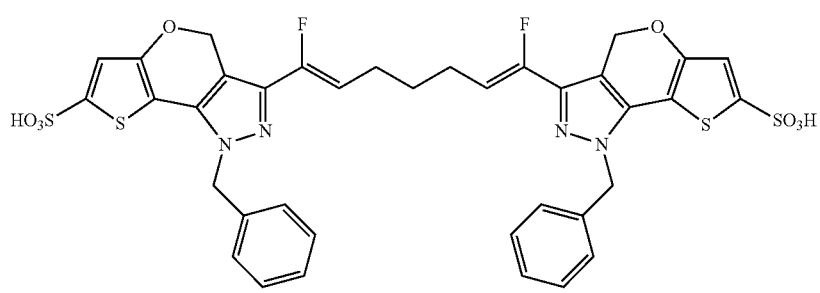
(IILC)
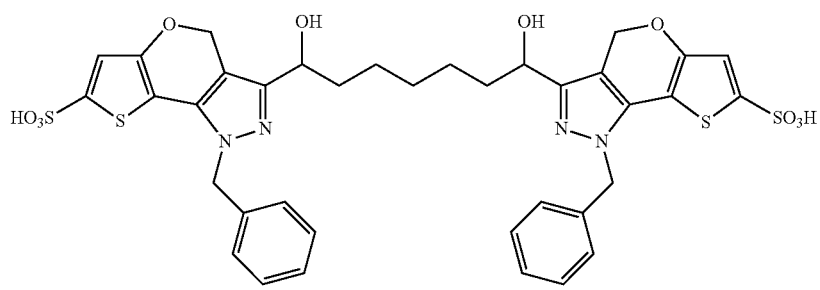
(IILD)
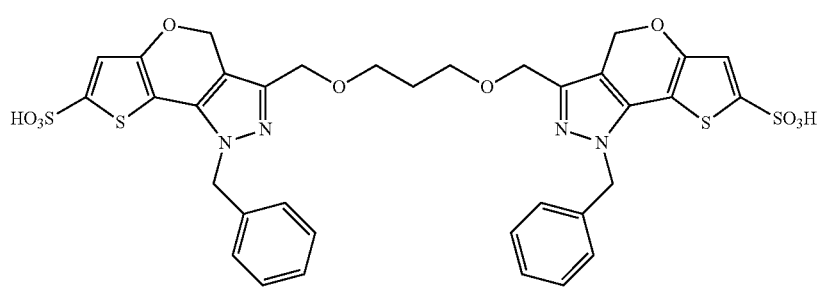
(IILE)
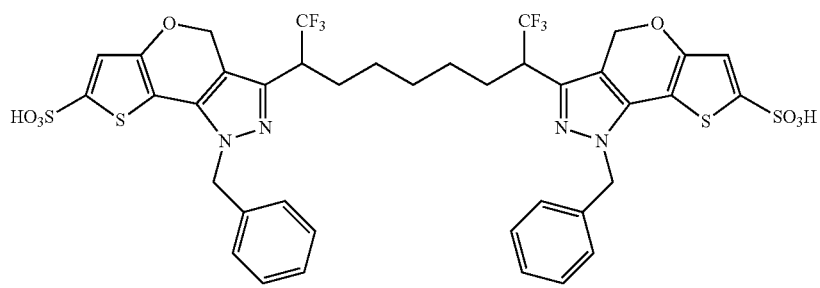
(IILF)

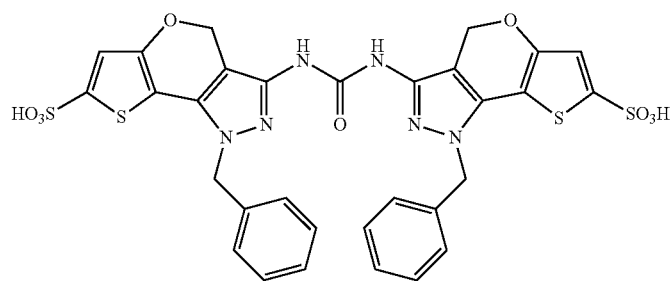
(IILG)
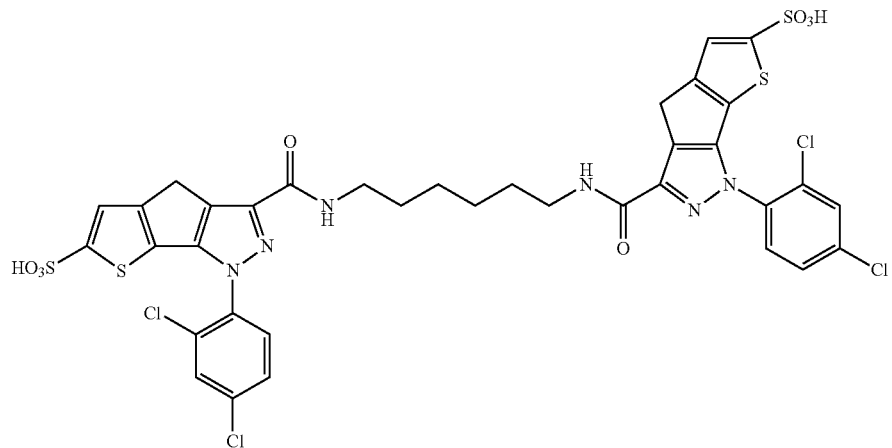
(IIIAA)
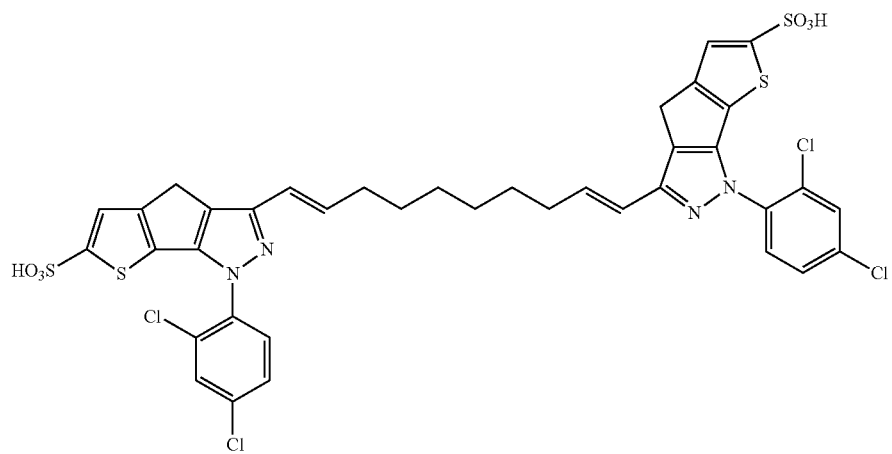
(IIIAB)
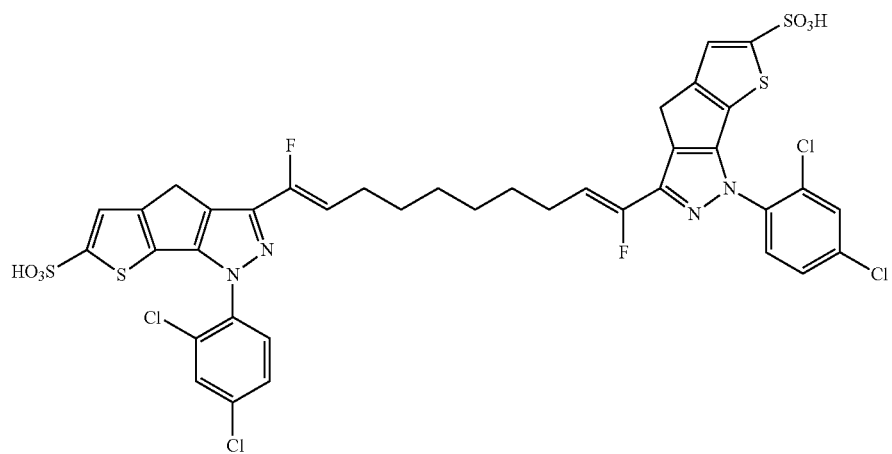
(IIIAC)

-continued
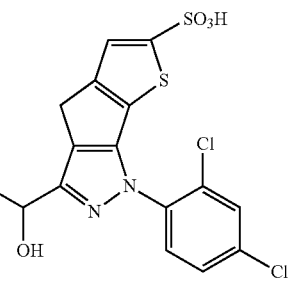
(IIIAD)
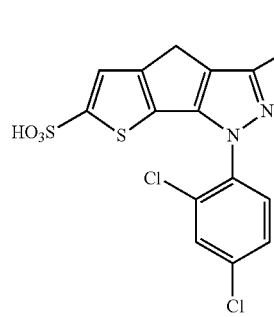

(IIIAE)
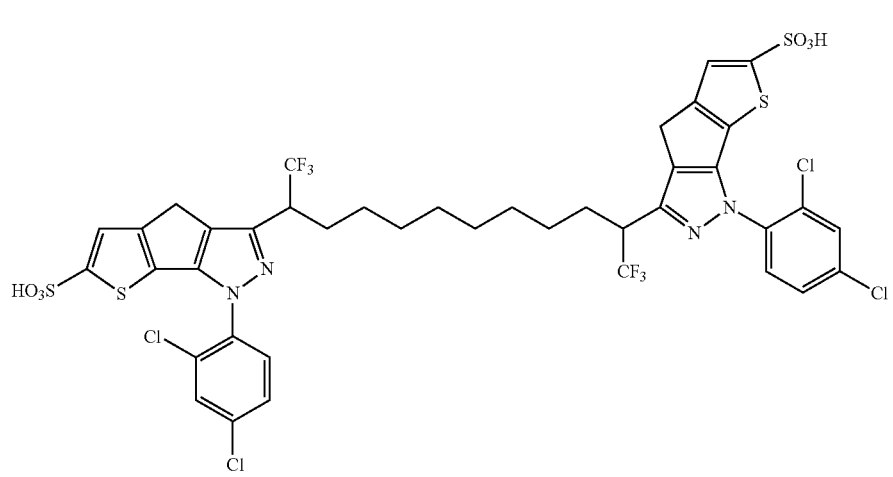
(IIIAF)

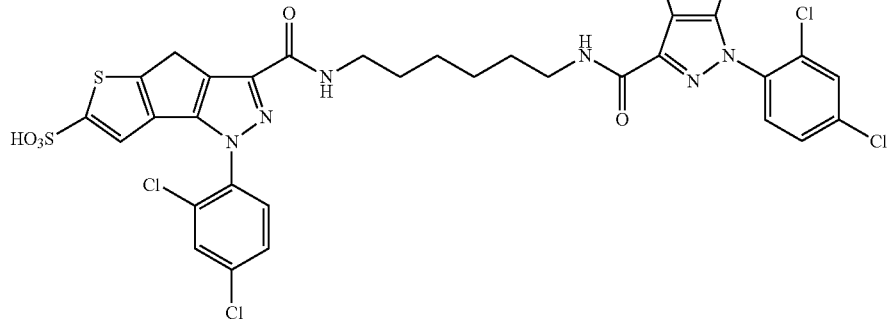
(IIIBA)
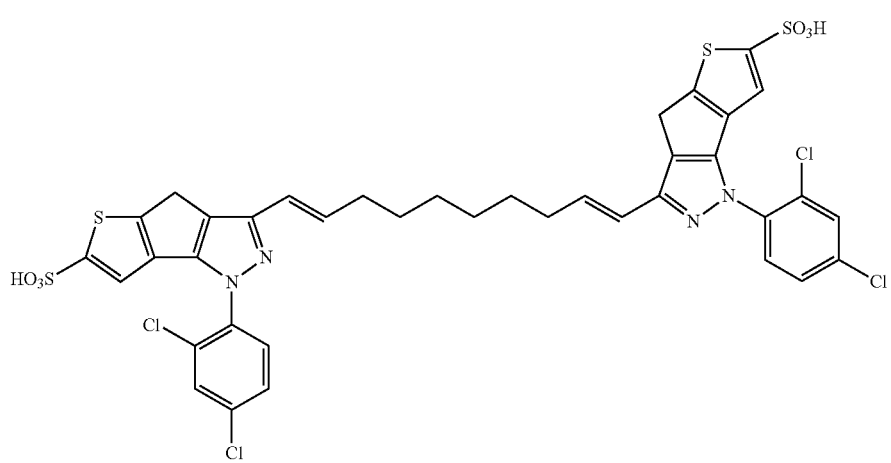
(IIIBB)
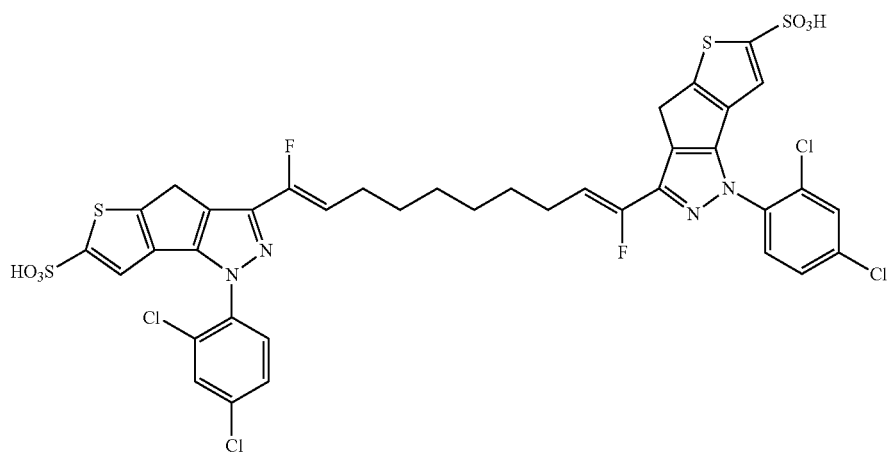
(IIIBC)

-continued
(IIIBD)
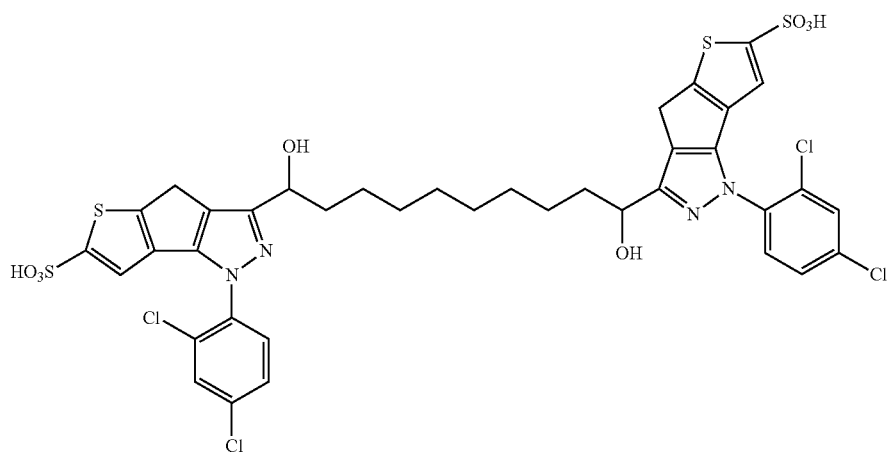
(IIIBE)
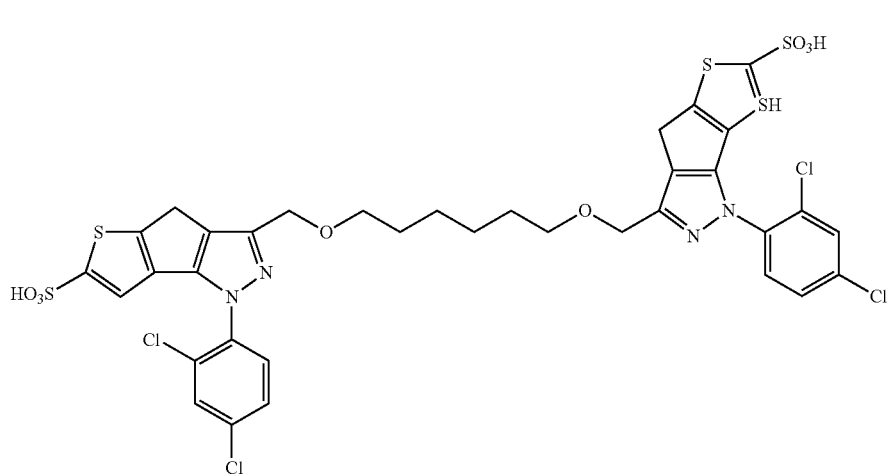
(IIIBF)
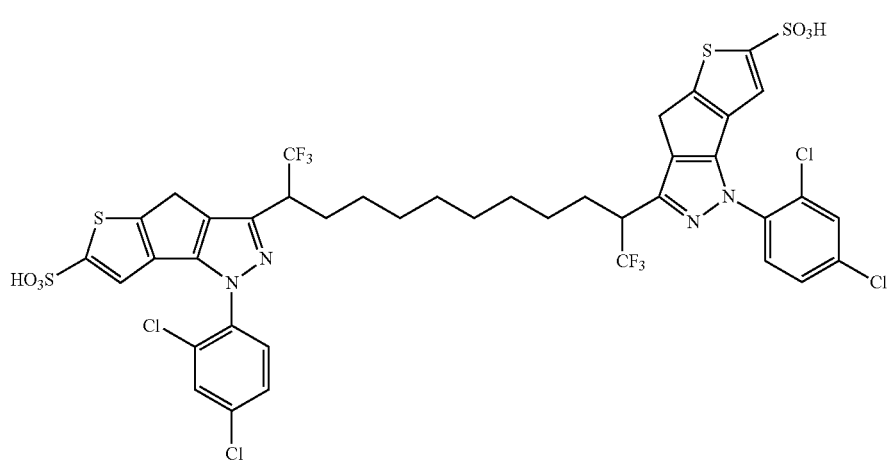

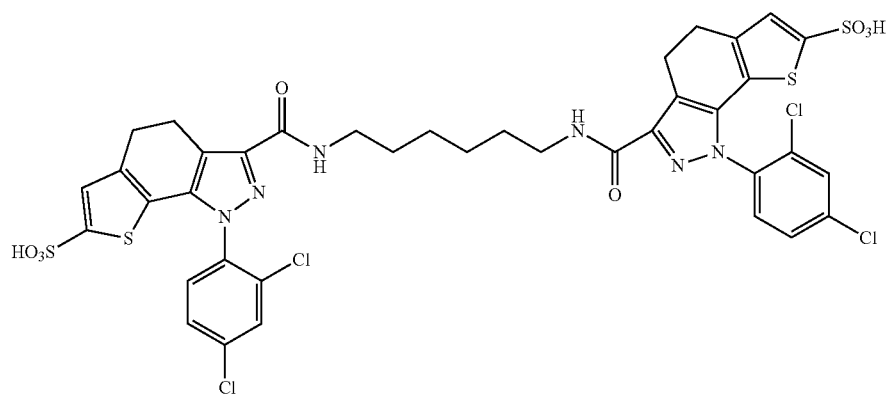
(IIICA)
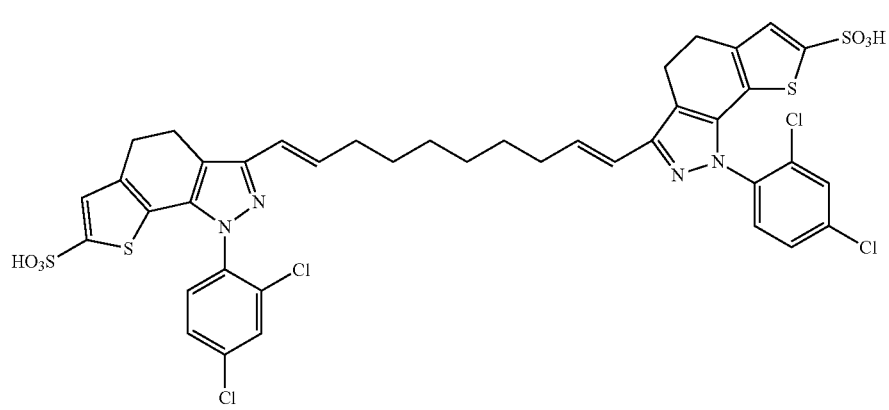
(IIICB)
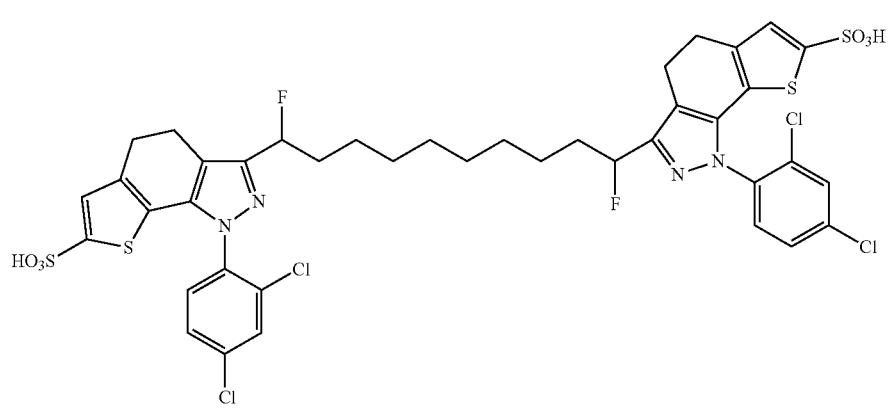
(IIICC)
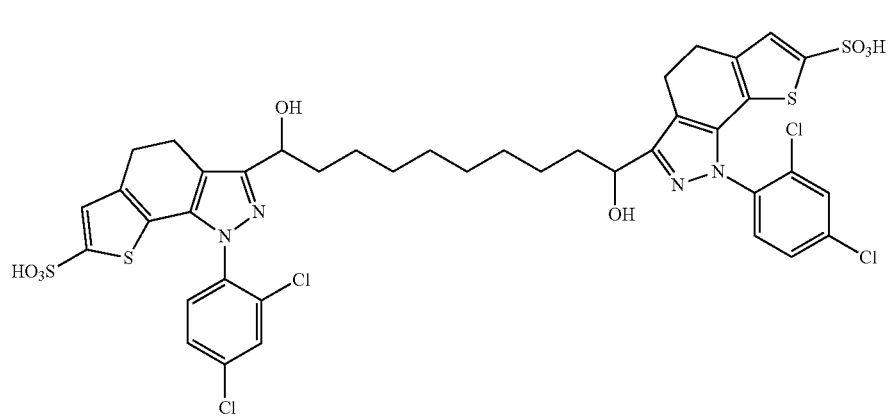
(IIICD)

-continued
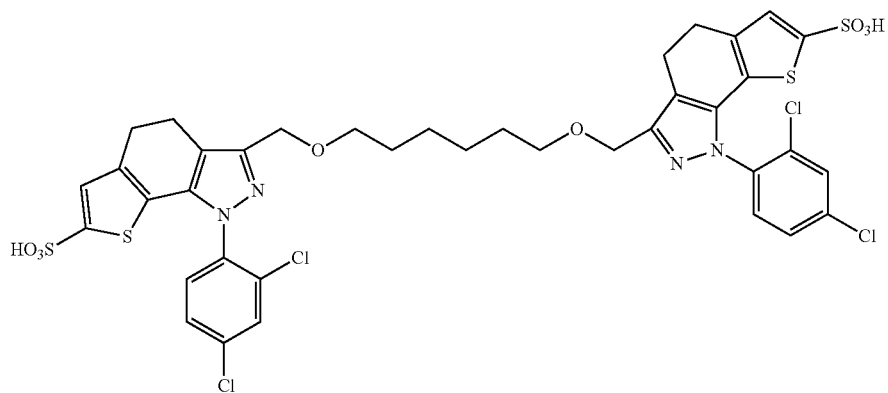
(IIICE)
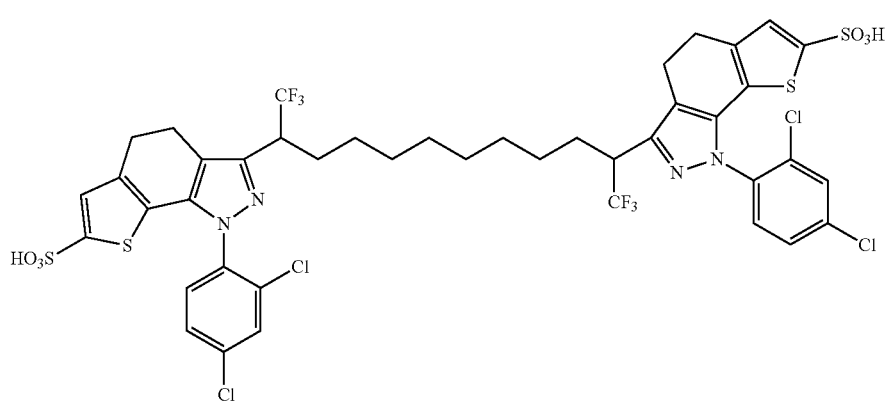
(IIICF)
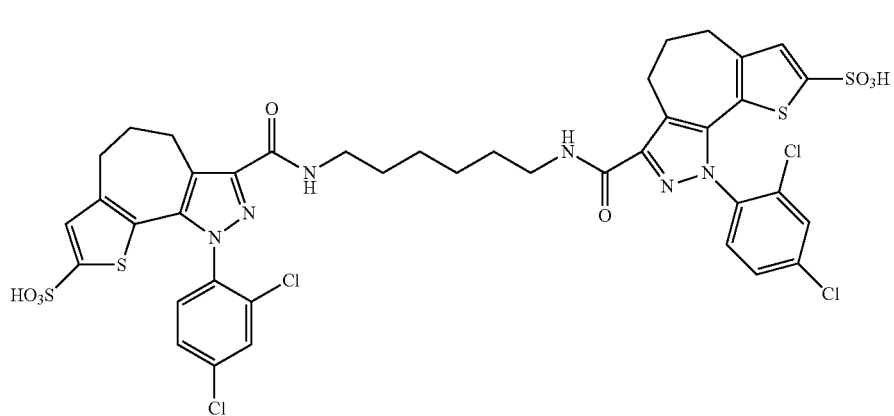
(IIIDA)
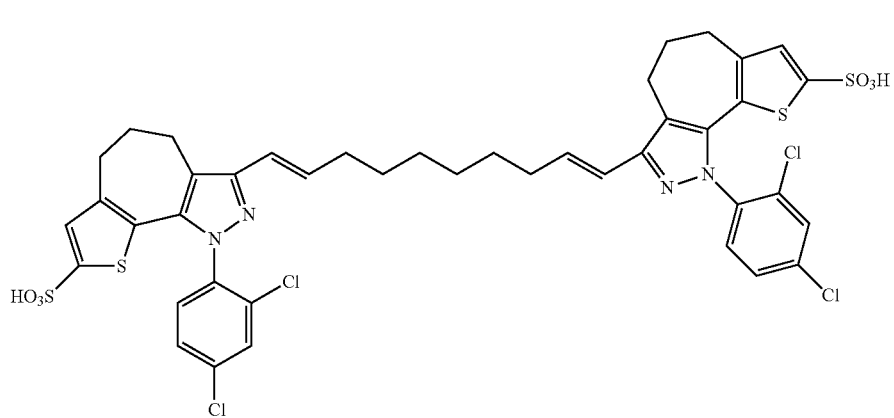
(IIIDB)

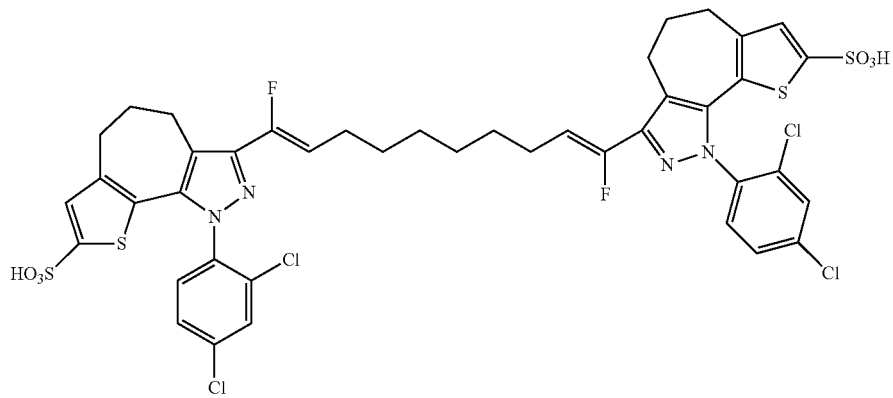
(IIIDC)
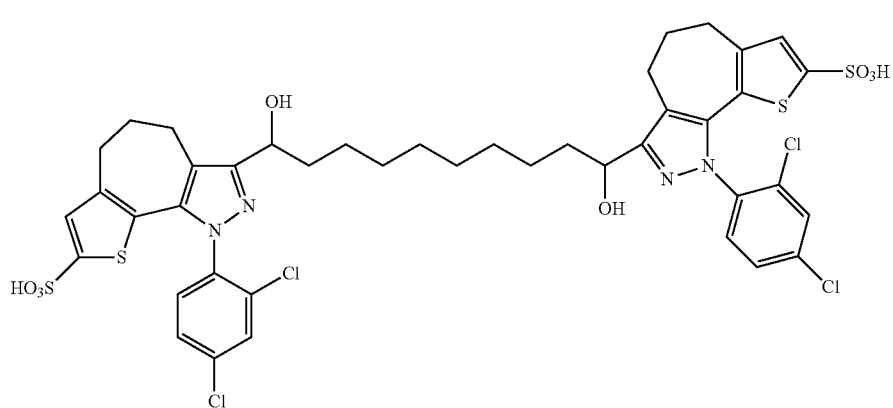
(IIIDD)
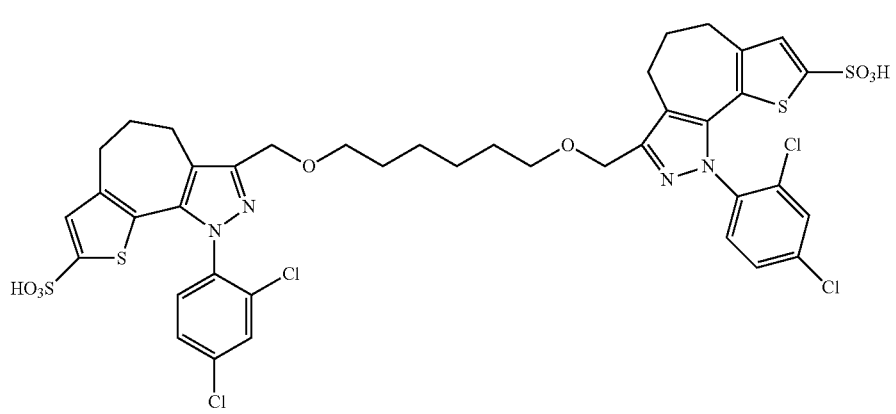
(IIIDE)
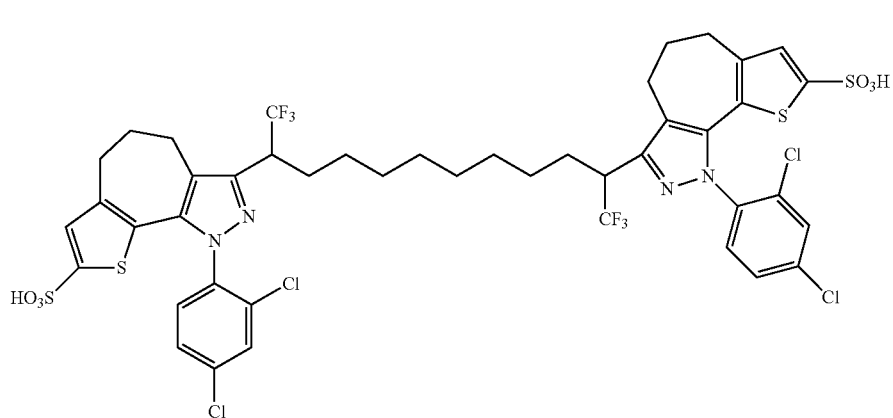
(IIIDF)

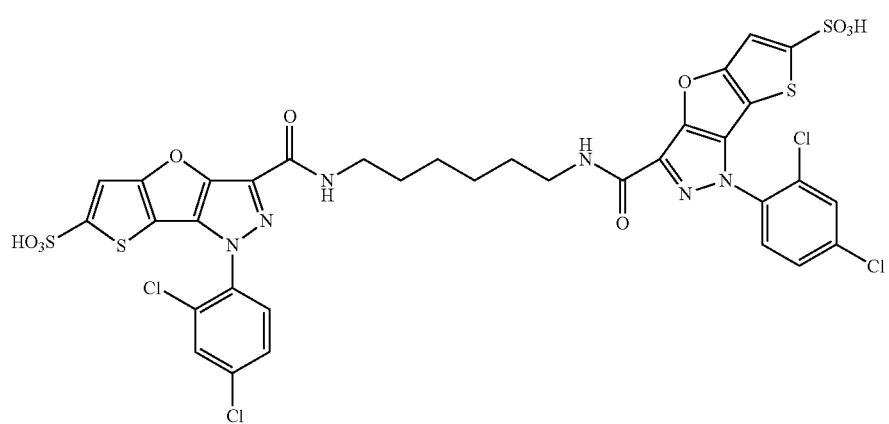
(IIIEA)
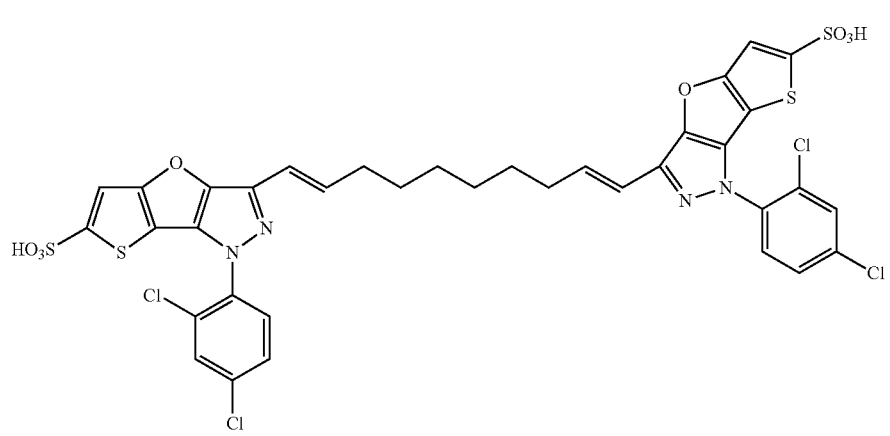
(IIIEB)
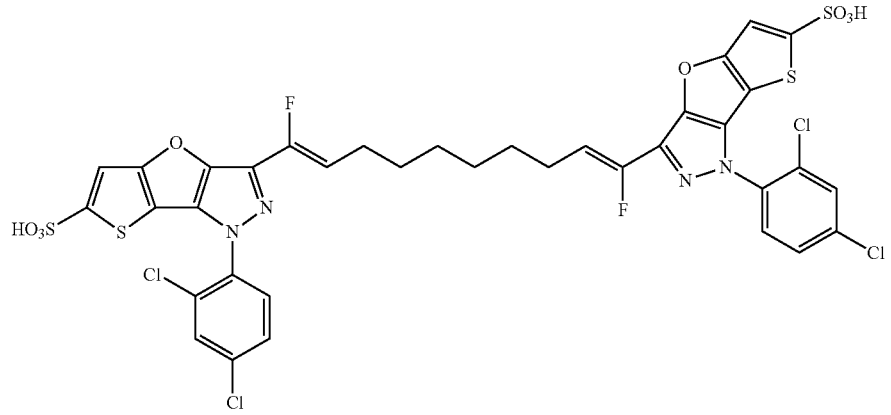
(IIIEC)
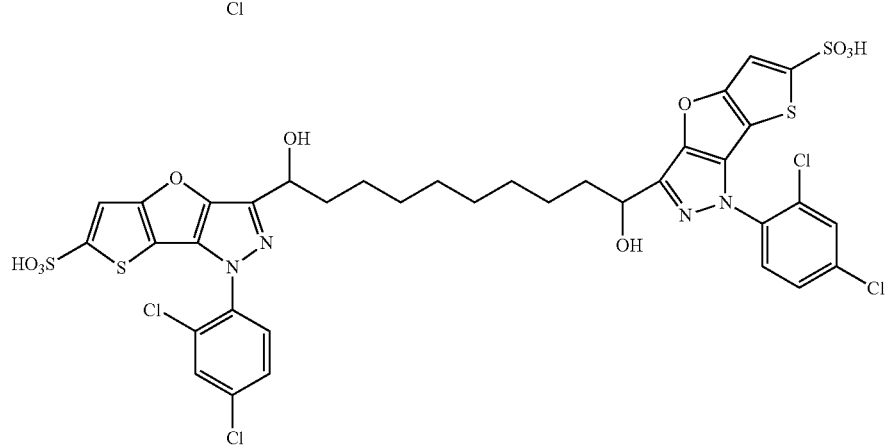
(IIIED)

-continued
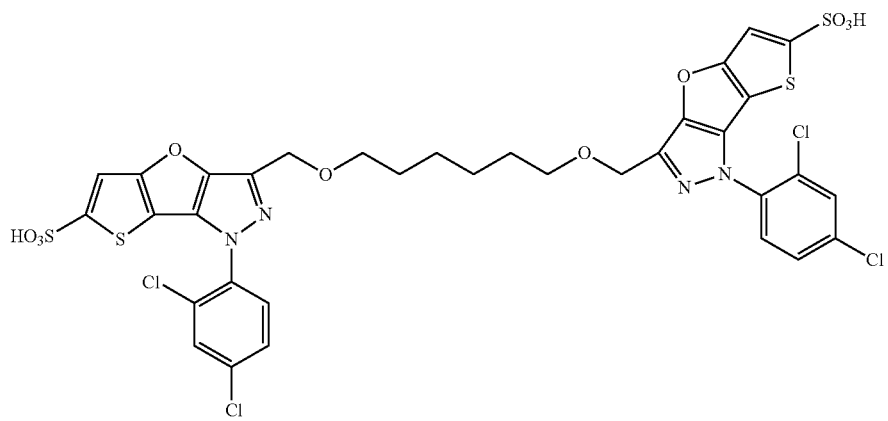
(IIIEE)
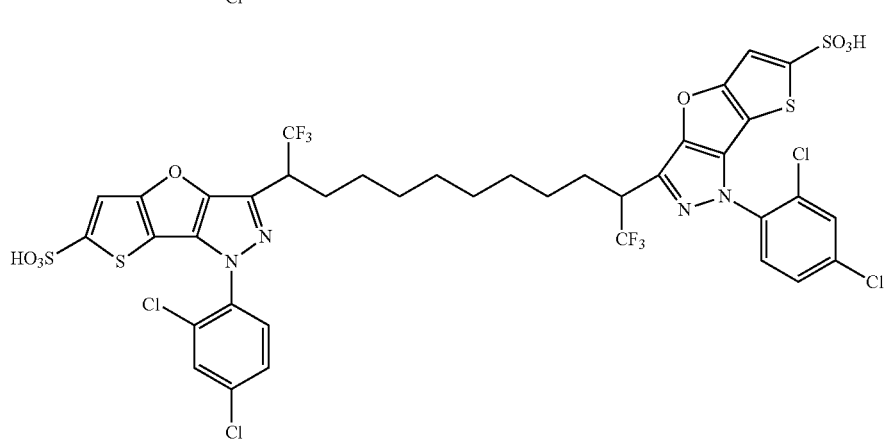
(IIIEF)
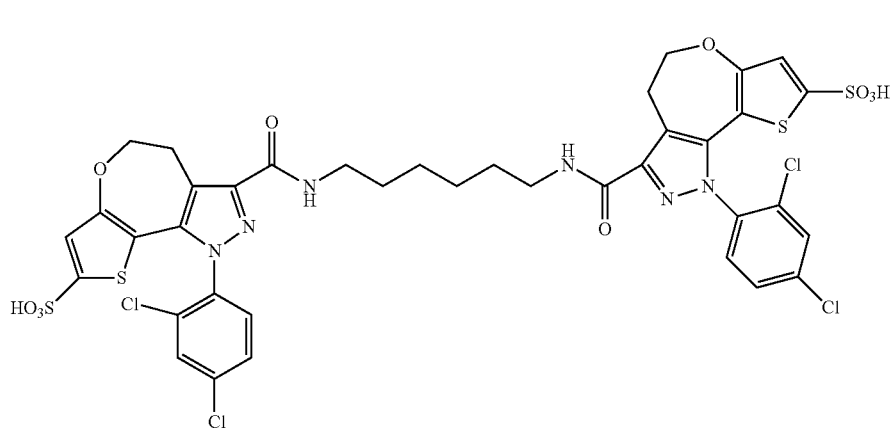
(IIIFA)
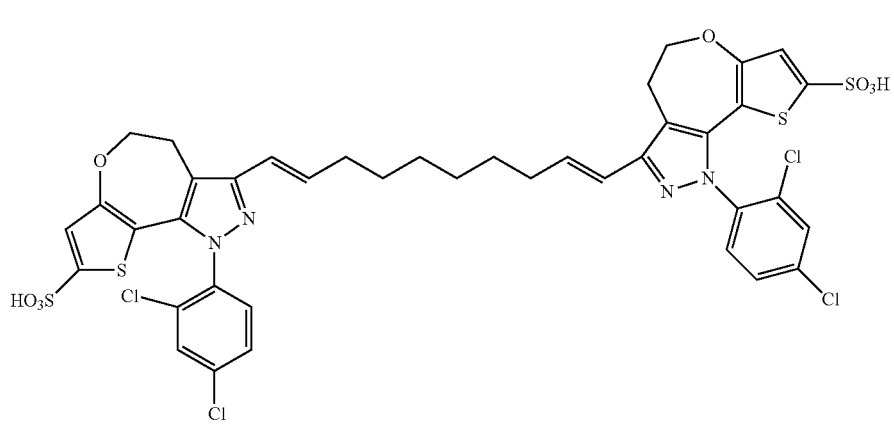
(IIIFB)

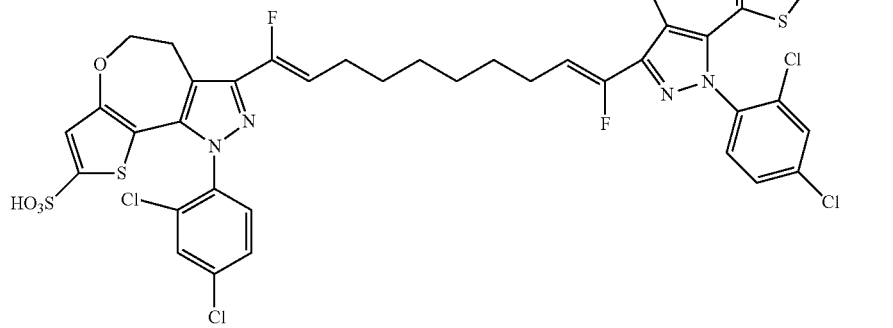
(IIIFC)
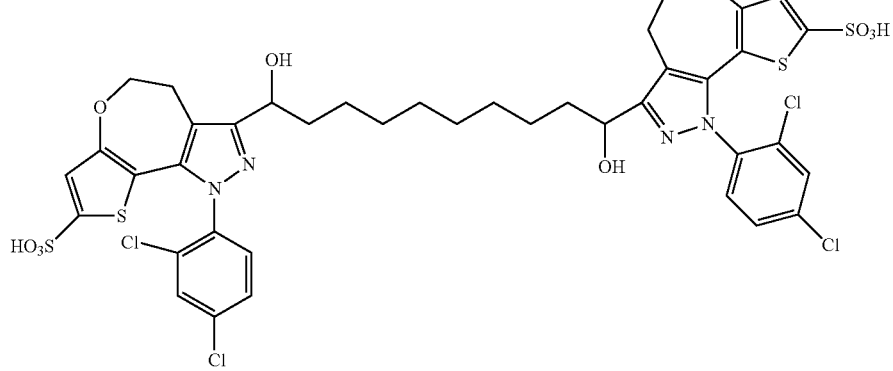
(IIIFD)
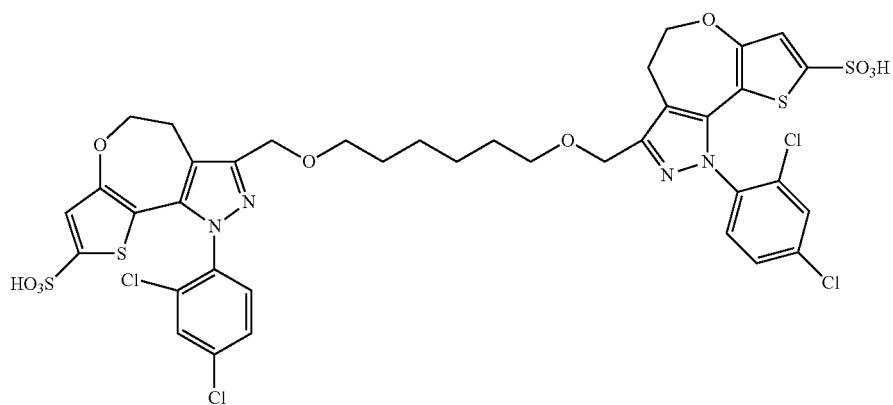
(IIIFE)
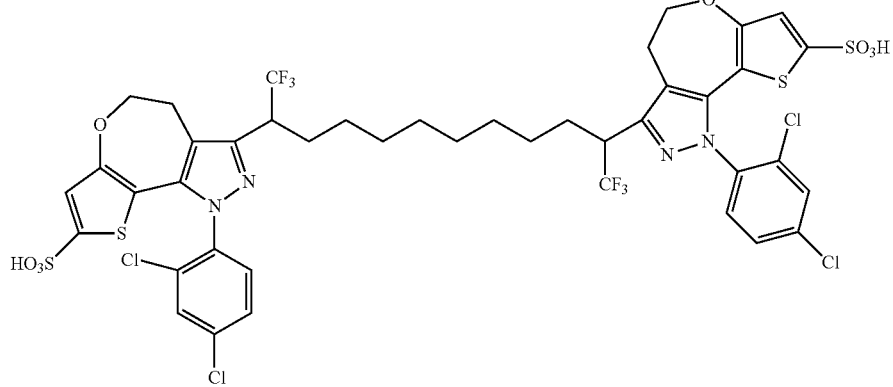
(IIIFF)

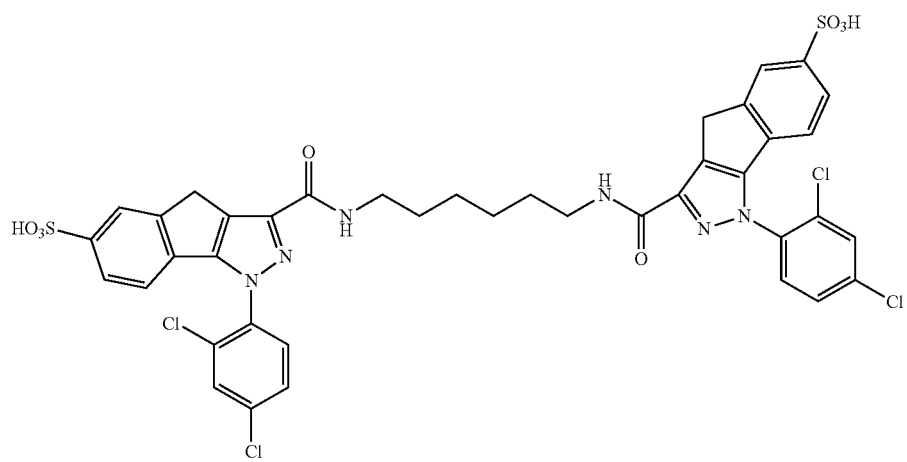
(IIIGA)
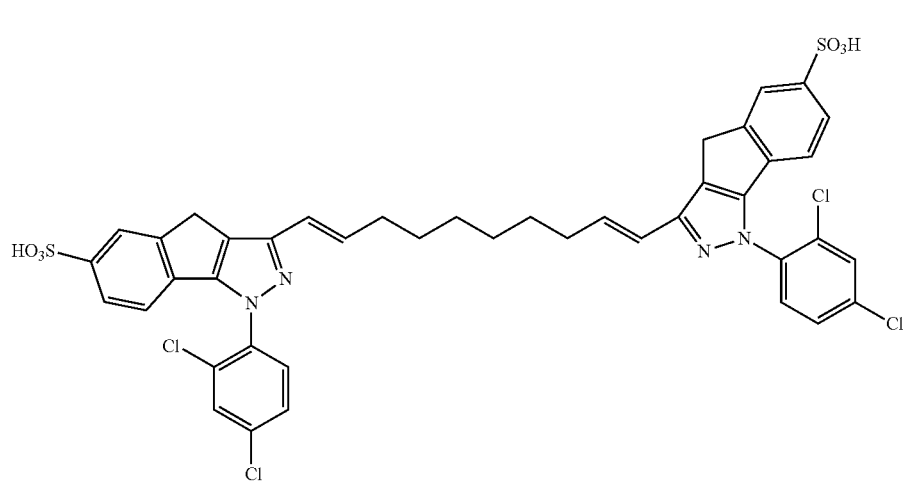
(IIIGB)
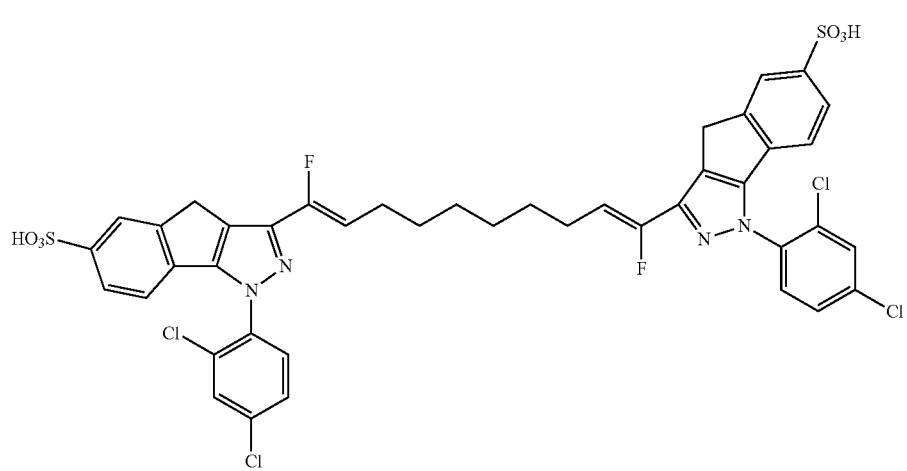
(IIIGC)

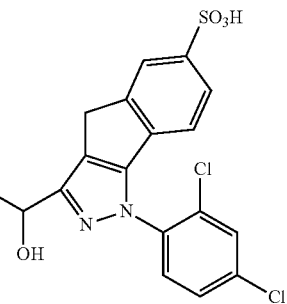
(IIIGD)
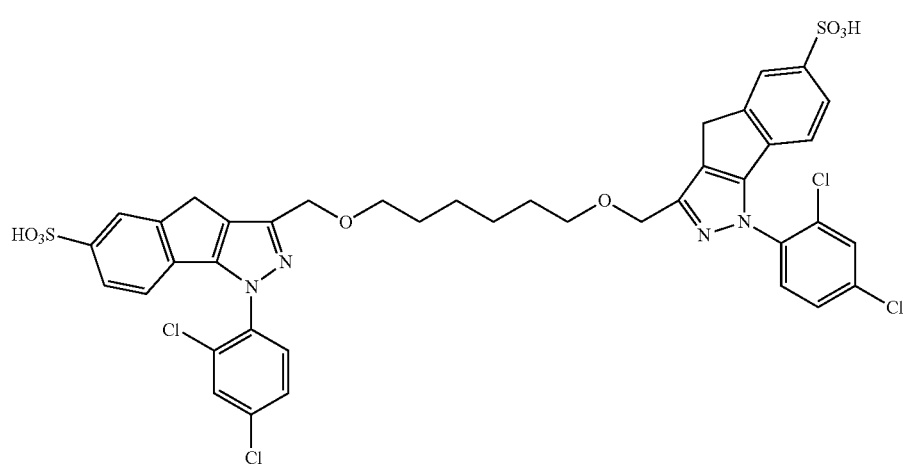
(IIIGE)
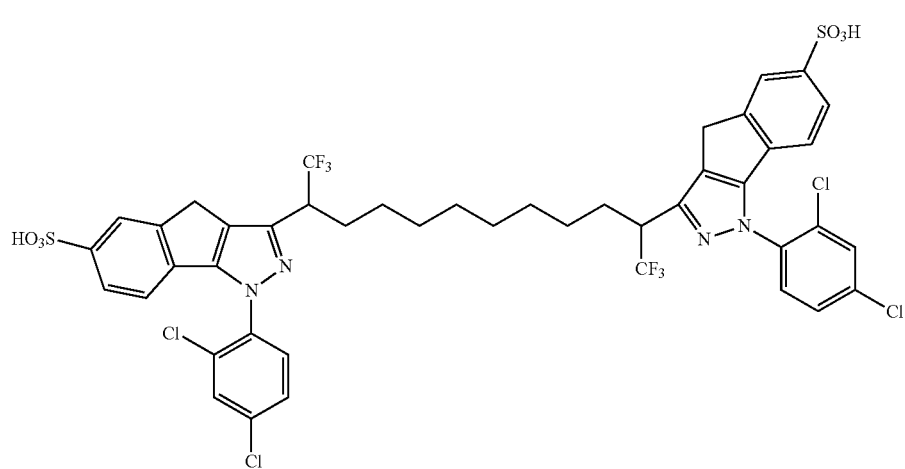
(IIIGF)

-continued
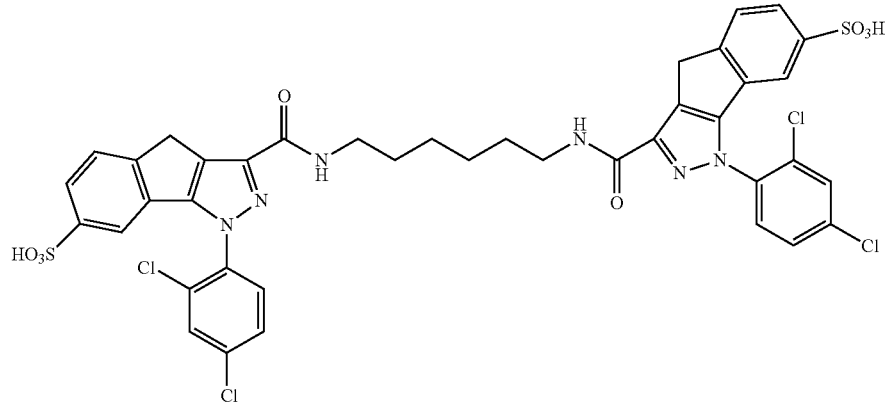
(IIIHA)
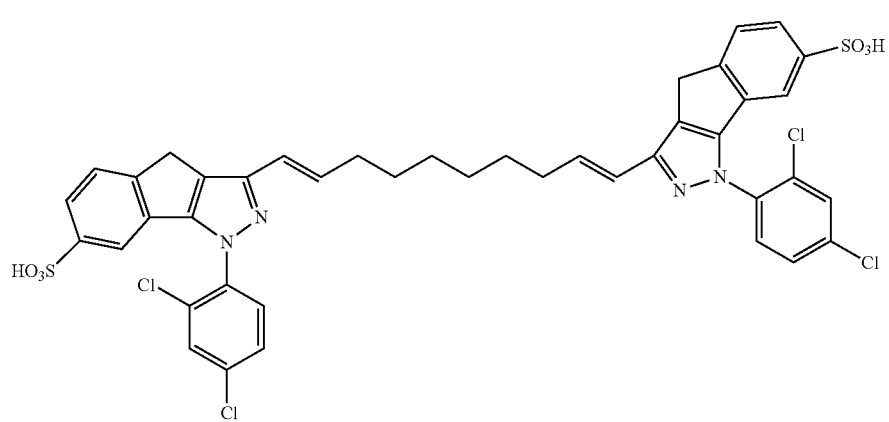
(IIIHB)
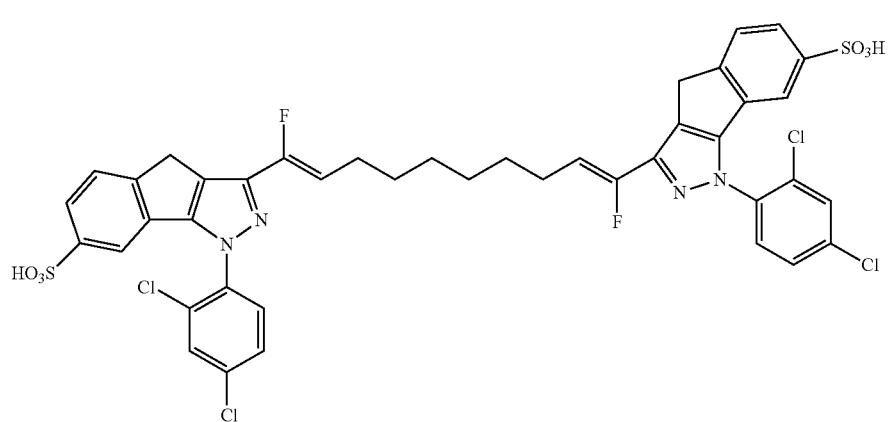
(IIIHC)
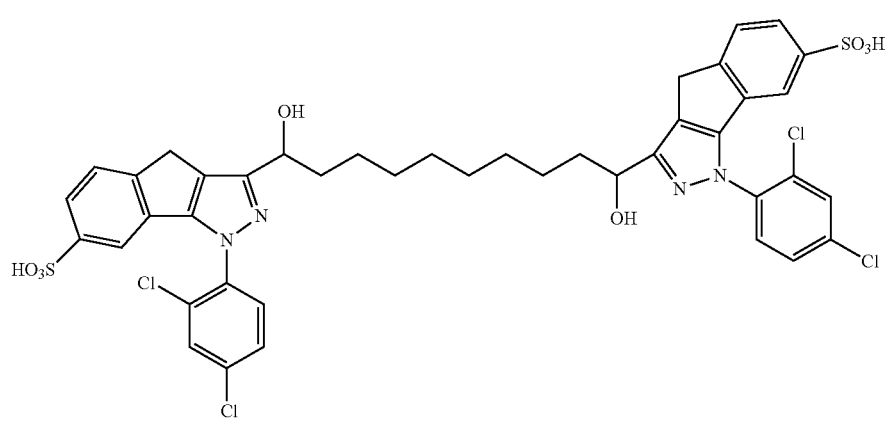
(IIIHD)

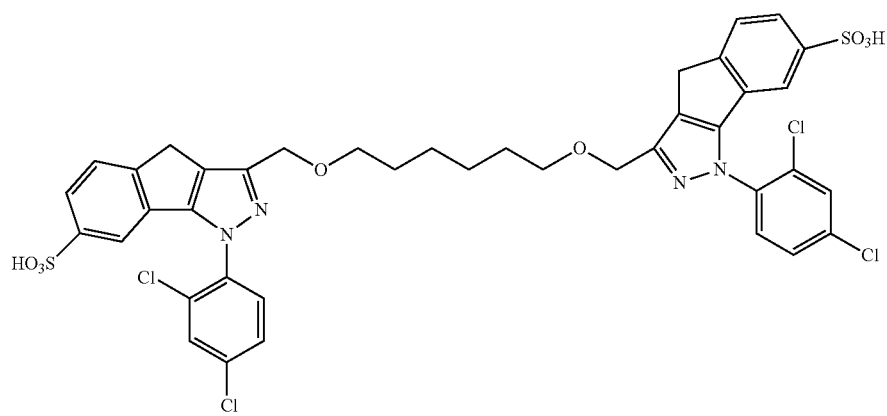
(IIIHE)
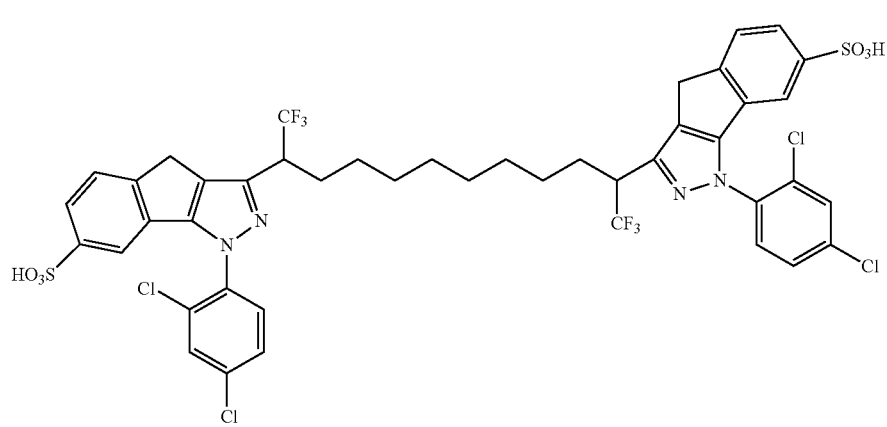
(IIIHF)
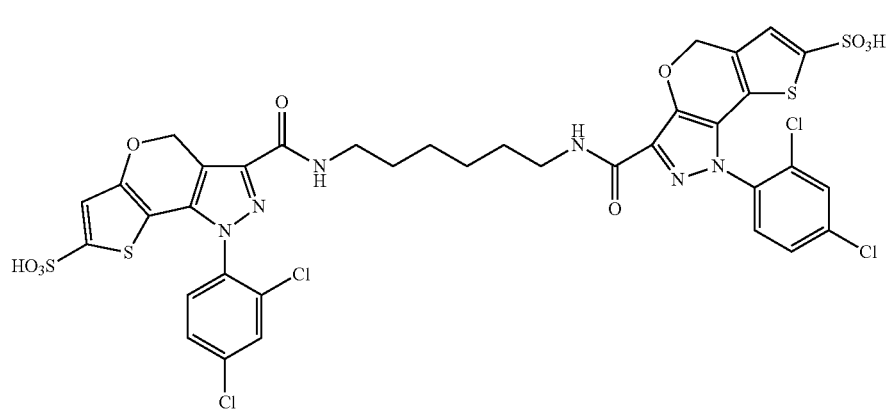
(IIILA)
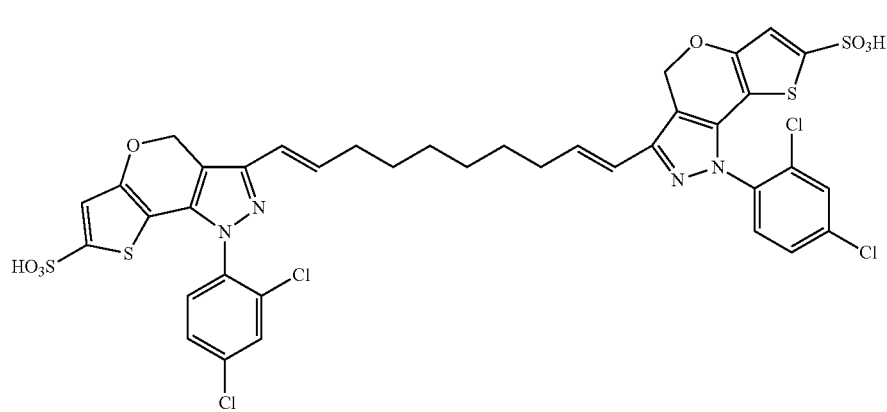
(IIILB)

(IIILC)
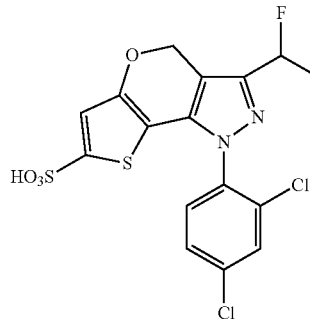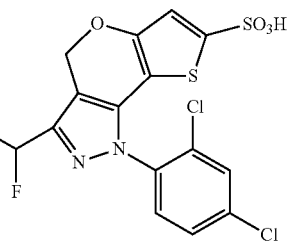
(IIILD)
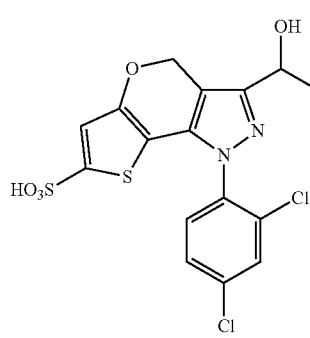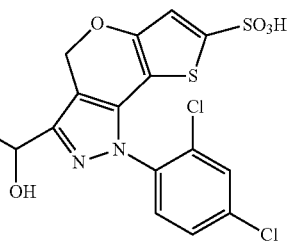
(IIILE)
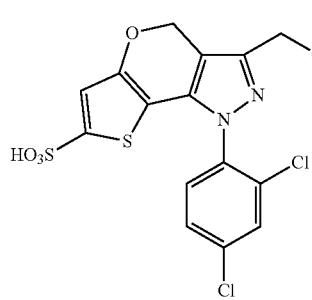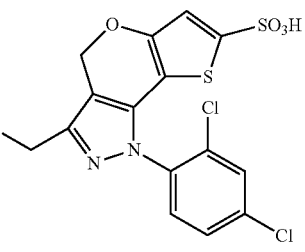
(IIILF)
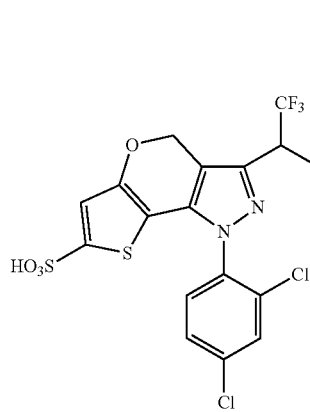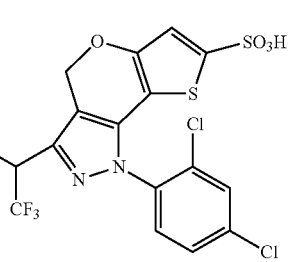

-continued
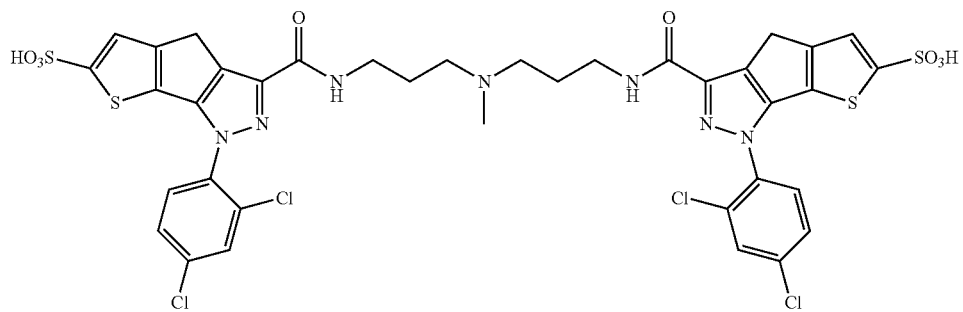
(IVAA)
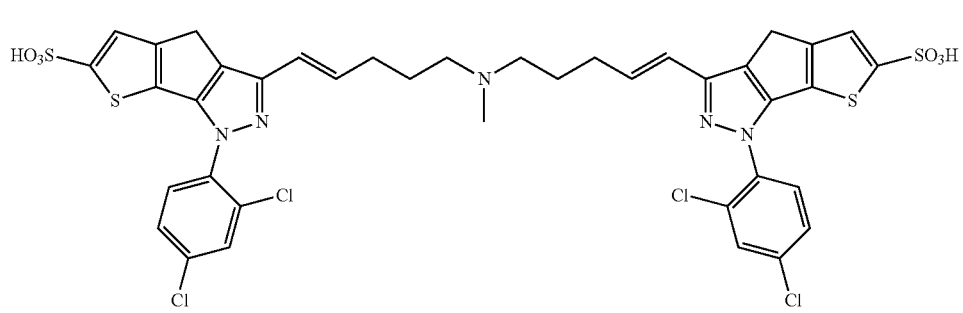
(IVAB)
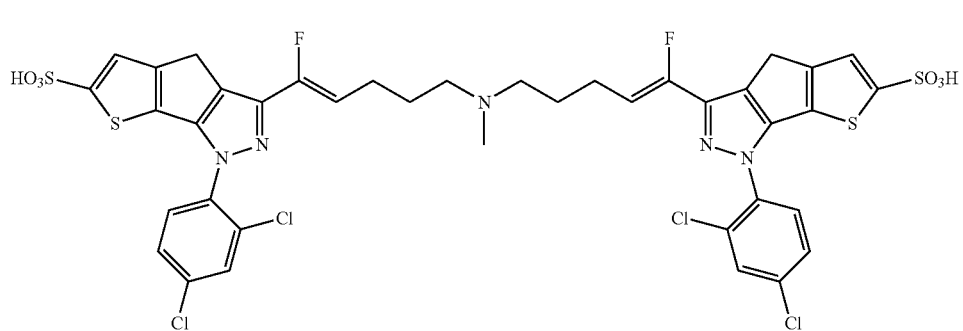
(IVAC)
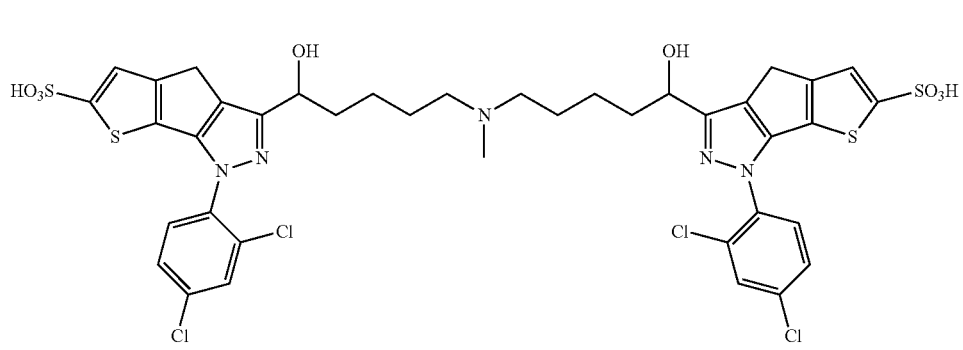
(IVAD)
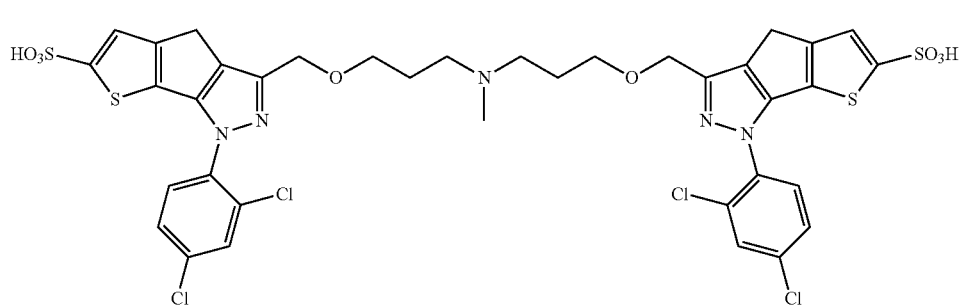
(IVAE)

-continued
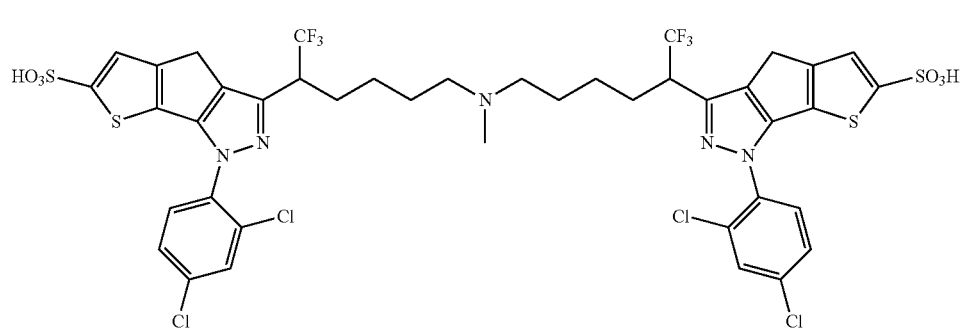
(IVAF)
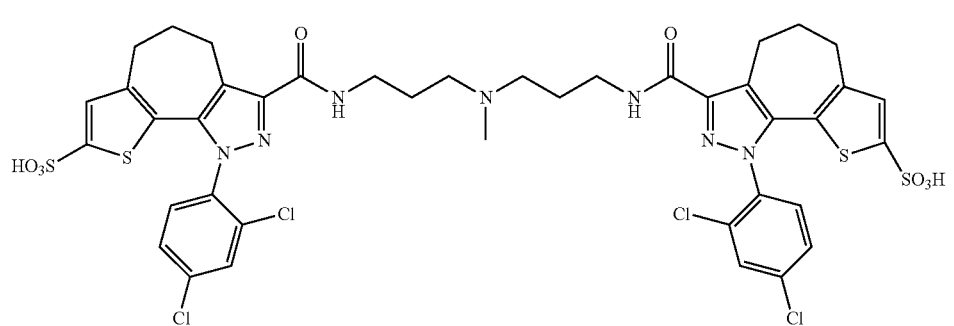
(IVDA)
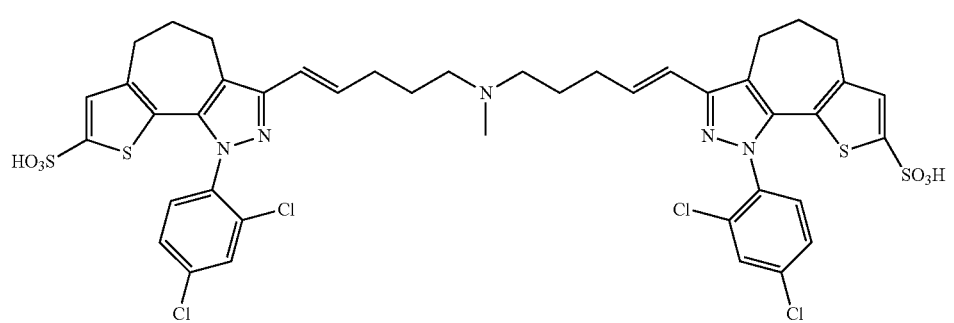
(IVDB)
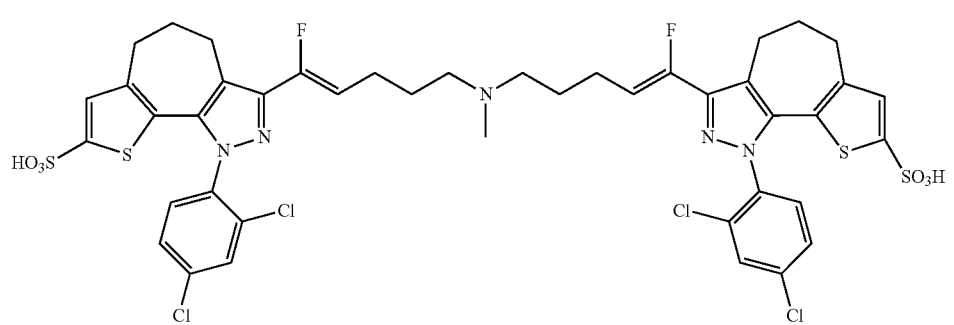
(IVDC)
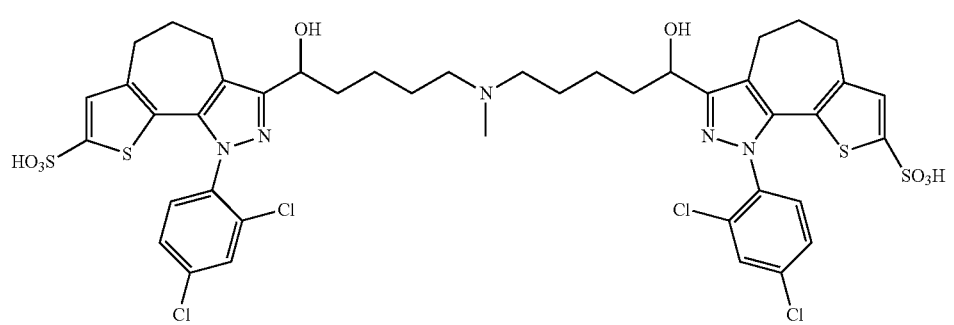
(IVDD)

-continued
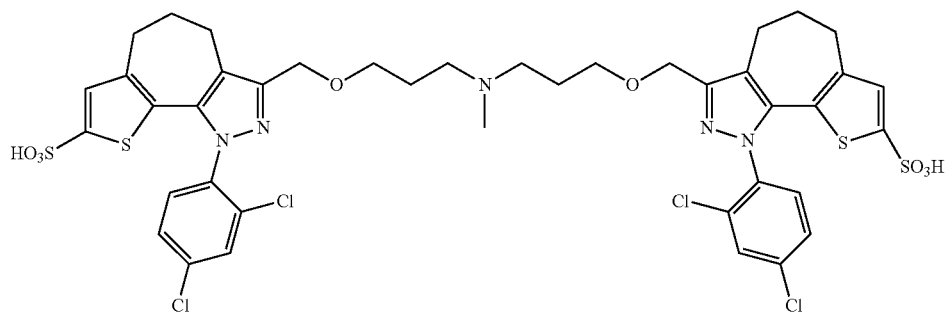
(IVDE)
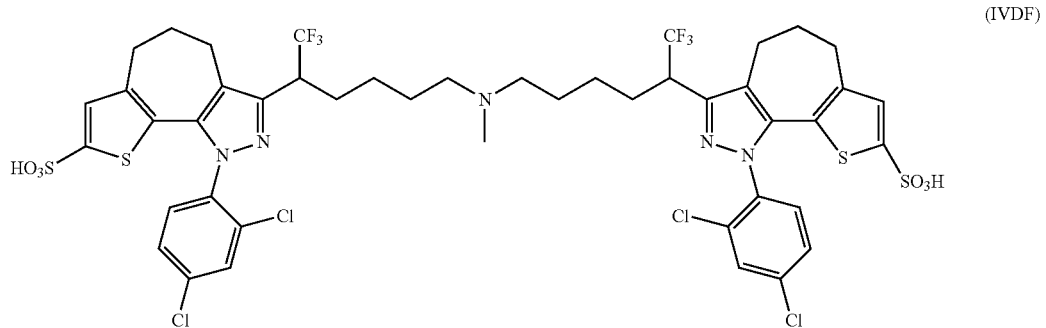
(IVDF)
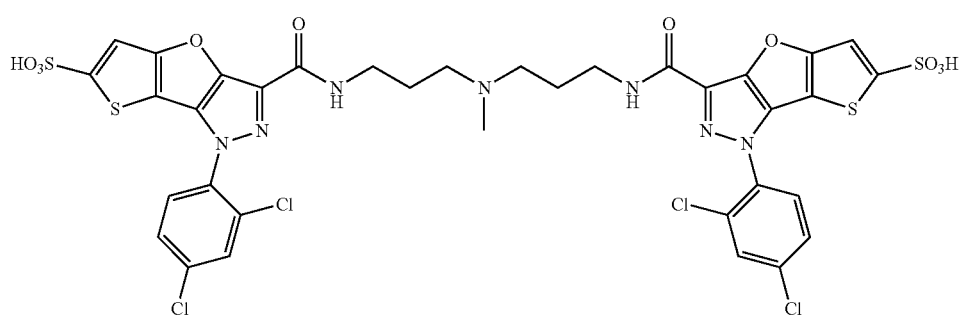
(IVEA)
(IVEB)
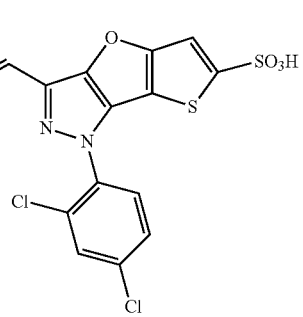
(IVEC)
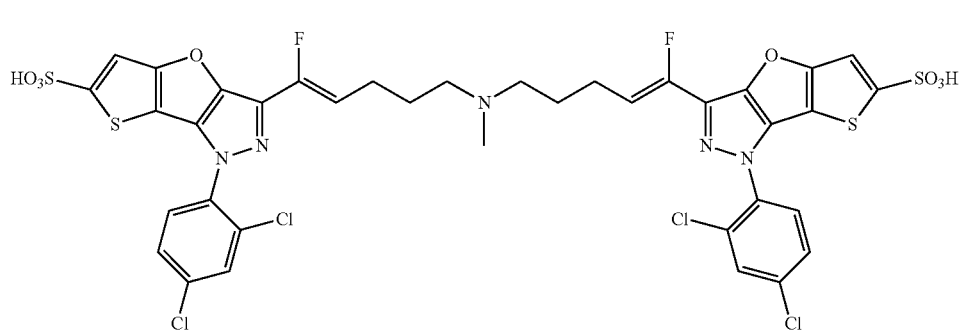

-continued
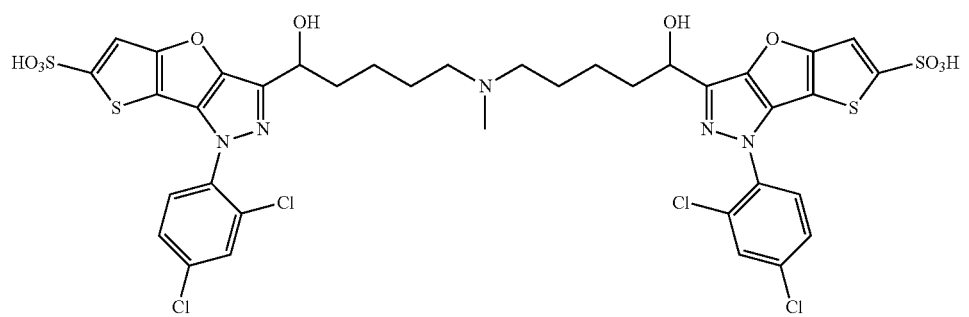
(IVED)
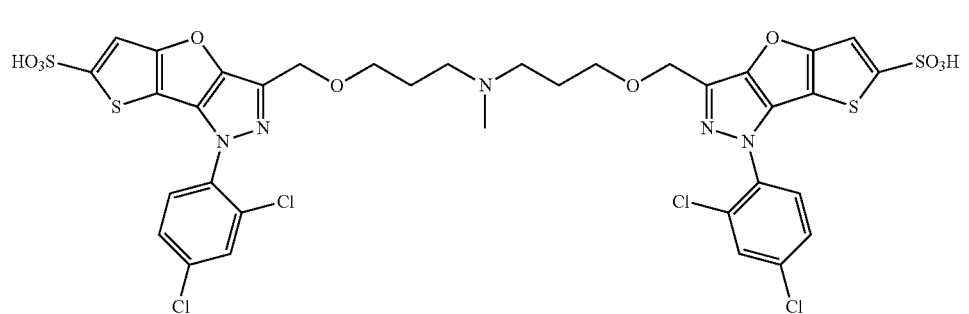
(IVEE)
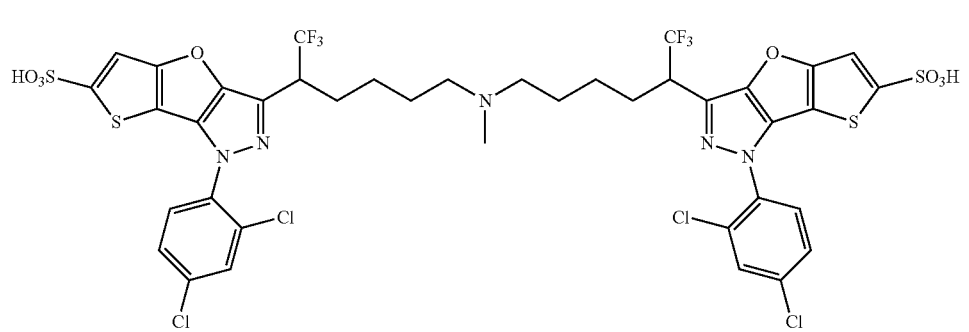
(IVEF)
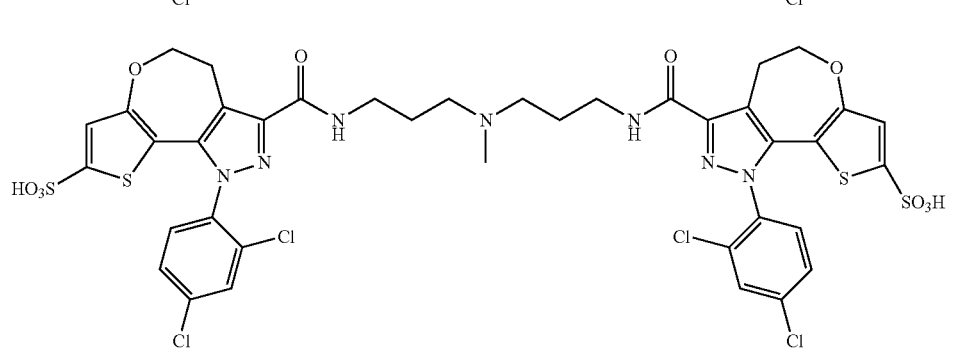
(IVFA)
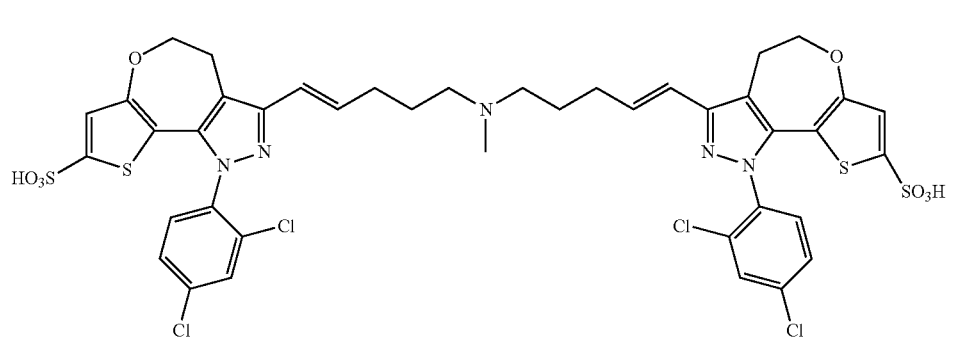
(IVFB)

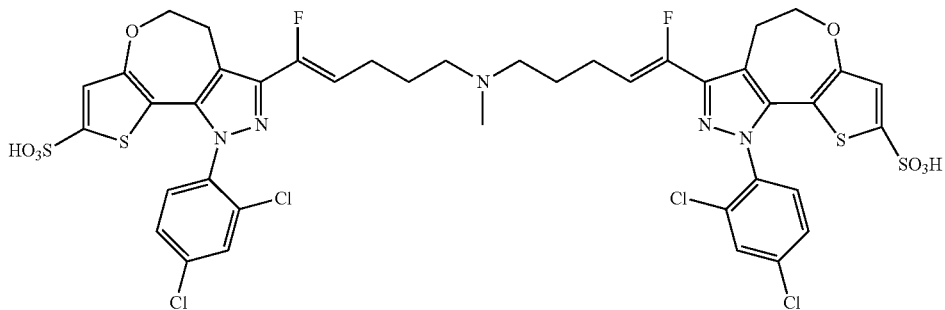

(IVFC)

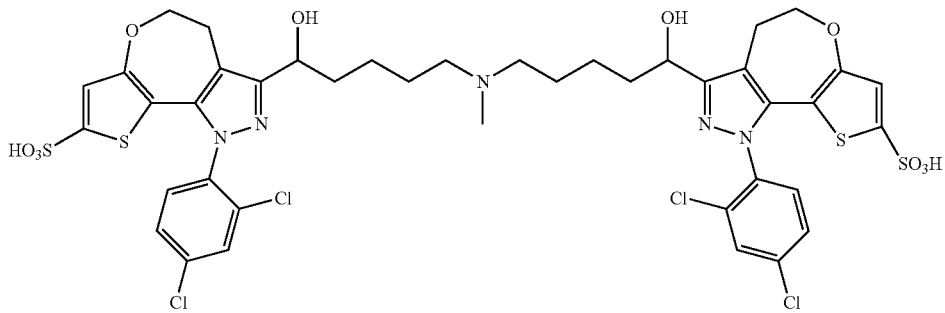

(IVFD)

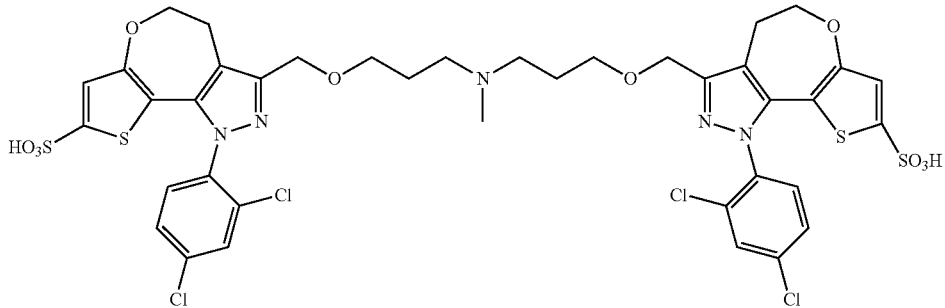

(IVFE)

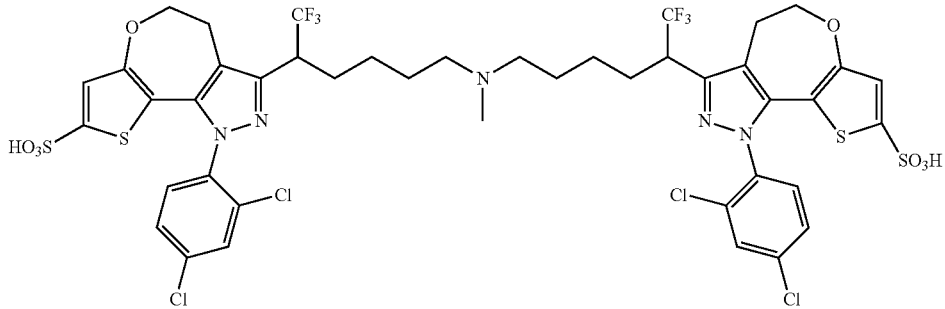

(IVFF)

Preferably, in the compounds of the invention of formula (I):
A and A' are as defined above,
T=G=N,
B and D, equal to each other, are selected between phenyl and monocyclic heteroaryl, wherein:

one hydrogen atom of said phenyl and monocyclic heteroaryl is substituted with one group selected between $SO_3H$ and $SO_3^-$,
Q, Z and L have the following meanings:
Q=Z=QA with L=L1;
Q=Z=QB with L=L2, wherein L2 Y=$Y_{50}$, $Y_{50}$ being as defined above;

R and X, equal to each other, are selected from:

$R_{30}$—W wherein W=$W_b$, $R_{30}$ being a bivalent aliphatic $C_2$-$C_6$ chain, linear or branched when possible, and $W_b$ as defined above, phenyl, benzyl wherein one or more hydrogen atoms of said phenyl or benzyl are optionally substituted with groups selected between halogen, linear or when possible branched $C_1$-$C_6$ alkyl.

When B and D are monocyclic heteroaryl, preferably monocyclic heteroaryl is thiophene.

Preferably CH=CH is excluded from the meanings of A and A'.

The compounds of formula (I) wherein the compounds are cis or trans isomers, E or Z isomers, or optical isomers of the compounds of formula (I) are a further object of the present invention.

By pharmaceutically acceptable salts are meant those obtained by reacting the compounds of the invention with organic or inorganic acids, or with organic or inorganic bases, acceptable for pharmaceutical use. For example for the compounds of formula (I) containing at least one acid group as COOH, COO⁻, SO₃H, SO₃⁻ and phenolic substituents, the corresponding alkaline or alkaline-earth metal salts can be mentioned, such as for example sodium, potassium, calcium, magnesium, quaternary ammonium salts, organic amine salts acceptable from the pharmaceutical point of view, such as for example triethylamine and N,N'-dimethylpiperazine. For example for the compounds of formula (I) containing at least one basic group the inorganic acid salts such as hydrochloric acid, sulphuric acid and phosphoric acid can be mentioned; the organic acid salts acceptable for pharmaceutical use, such as for example carboxylic or sulphonic acid salts as for example fumaric, oxalic, trifluoroacetic, acetic, succinic, glycolic, citric, tartaric, paratoluensulphonic acid salts, salts with aminoacids such as for example lysine and arginine can be mentioned. See the volume: "Remington, The Science and Practice of Pharmacy", vol. II, 1995, page 1457.

According to a further object of the present invention the compounds of formula (I) are in the form of the corresponding hydrates and solvates.

The meaning of the hydrate and solvate terms is well known to the skilled in the art. In particular, by hydrate it is meant a compound containing one or more hydration water molecules, generally from 1 to 10 water molecules. By solvate it is meant a compound containing one or more molecules of a solvent different from water.

It is another object of the present invention a process for preparing the compounds of formula (I) starting from the acids of formula (II) and (II-A)

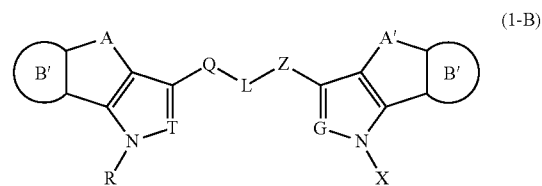

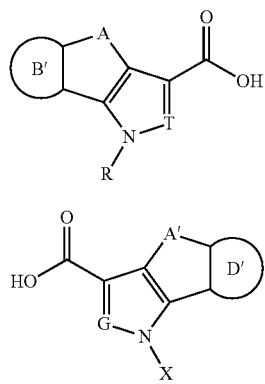

wherein B' and D', equal to or different from each other, have the meaning of heteroaryl or aryl, said aryl and heteroaryl having as substituents at least one hydrogen atom and optionally one or more G1 groups, equal to or different from each other,
comprising the following steps:
i) optional activation of the carboxylic group of the acid of formula (II) and of the acid of formula (II-A) to obtain the corresponding reactive derivatives of the acids of formula (II) and (II-A), selected from acyl halides, anhydrides, mixed anhydrides, imidazolides, ester-amide adducts, linear or branched C₁-C₄ alkyl esters;
ii) synthesis of the compound of formula (I-B):

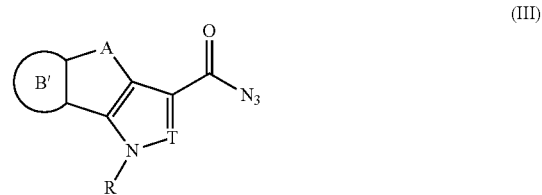

by using one of the synthesis processes ii-a)-ii-l), described hereinafter:
ii-a) when in (I-B) Q=Z=QA, a two-step synthesis is carried out:
first step: reaction of a reactive derivative of the acid of formula (II) and of the acid of formula (II-A) in an inert organic solvent with an azide of formula MeN₃, wherein Me is an alkaline metal, to obtain the acyl azides of formula (III) and of formula (III-A):

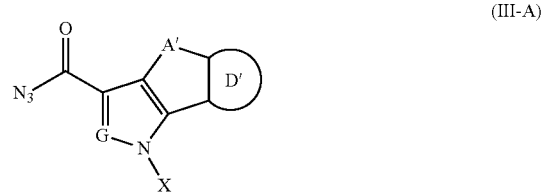

second step: transposition reaction of the acyl azides of formula (III) and (III-A) by reaction with urea;
ii-b) when Q=QF and Z=QF' a two-step synthesis is carried out:
first step: reduction of the acid of formula (II) and of the acid of formula (II-A), or esters thereof, to the corresponding primary alcohols of formula (IV) and (IV-A), respectively:

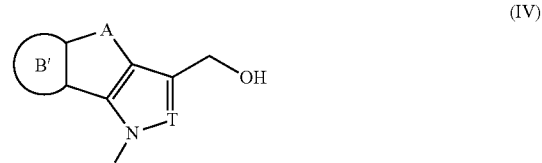

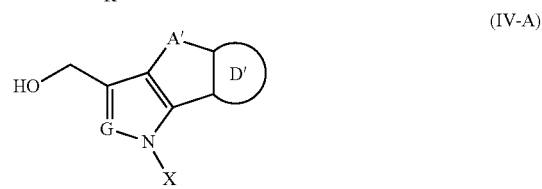

second step: reaction of the primary alcohols of formula (IV) and (IV-A) with an alkyl halide of formula U—Y—U, wherein U is halogen and Y is as defined above;

ii-c) when Q=Z=QB and L=L4, the synthesis is carried out according to one of the following processes:

first process: reaction of an ester of an acid of formula (II) and of an acid of formula (II-A) with trialkylaluminum and with an amine hydrochloride salt until disappearance of the ester function, followed by the addition to the reaction mixture of the compound of formula BrMg—Y—MgBr, wherein Y is as defined above, second process: reaction of the acid of formula II) and of the acid of formula (II-A), or of their reactive derivatives with a metallorganic salt of formula $^+$Me-Y-Me$^+$, wherein Me$^+$ is an alkaline metal cation, in an inert organic solvent, third process: reaction of a reactive derivative of the acid of formula (II) and of the acid of formula (II-A) with N,O-dimethylhydroxylamine hydrochloride in the presence of trialkylaluminum, obtaining the Weinreb amides of formula (V) and of formula (V-A), respectively:

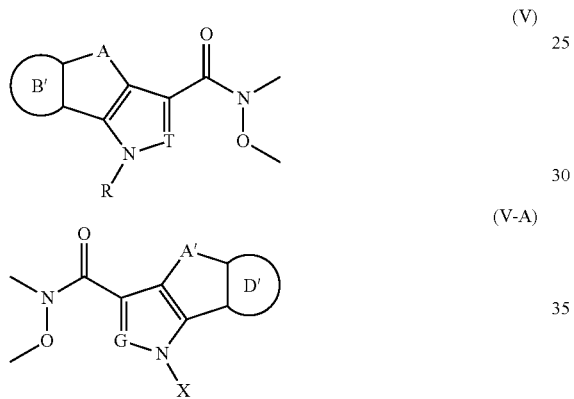

(V)

(V-A)

and following reaction of the amide of formula (V) and of the amide of formula (V-A) with a compound of formula BrMg—Y—MgBr, wherein Y is as defined above;

ii-d) when Q=Z=QB and L=L2, a reactive derivative of the acid of formula (II) and of the acid of formula (II-A) is reacted with a compound of formula (VI):

(VI)

wherein $R_1$ and Y are as defined above;

ii-e) when Q=Z=QC, a two-step synthesis is carried out:
first step: synthesis of the compound of formula (I) wherein Q and Z have the meaning of QB and L has the meaning of L4, by using one of the processes described above in ii-c),
second step: reduction of the two carbonyl functions in the compound obtained in the preceding step;

ii-f) when Q=Z=QD a five-step synthesis is carried out, of which the last is optional:
first step: synthesis of primary alcohols by reduction of the acid of formula (II) and of the acid of formula (II-A) according to the process described in the first step of ii-b), second step: conversion of the primary alcohol of the acid of formula (II) and of the acid of formula (II-A) into the corresponding bromine derivatives of formula (VII) and (VII-A) by reaction with a bromination agent:

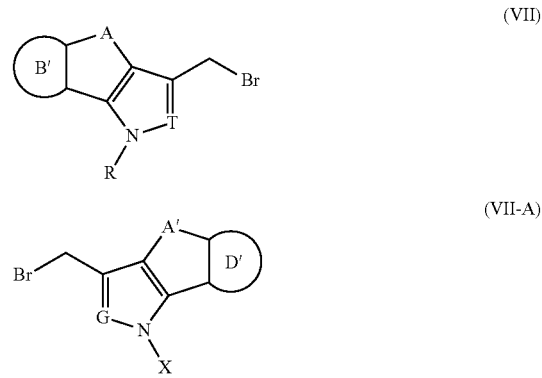

(VII)

(VII-A)

third step: synthesis of the phosphonium salt of the bromine derivatives by reaction with triphenylphosphine to yield the phosphonium salts of formula (VIII) and (VIII-A):

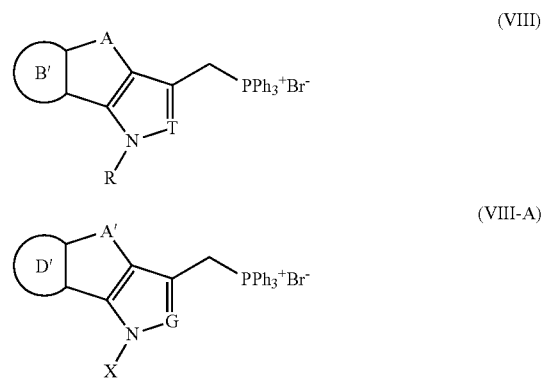

(VIII)

(VIII-A)

wherein Ph has the meaning of phenyl, fourth step: deprotonation of the phosphonium salts of formula (VIII) and (VIII-A) followed by the treatment of the compounds obtained with an aldehyde of formula (IX):

(IX)

wherein Y is as defined above, fifth optional step: separation of isomer E from isomer Z of the compound (I-B) obtained in the fourth step;

ii-g) when Q=QE and Z=QE' a six-step synthesis is carried out, the last being optional:

first step: preparation of the Weinreb amides of formula (V) and (V-A) according to the third process of ii-c), second step: reduction of the Weinreb amides to the corresponding aldehydes of formula (X) and (X-A):

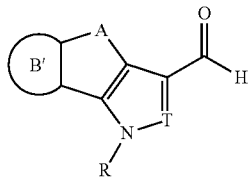
(X)

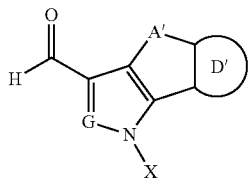
(X-A)

third step: condensation of the aldehydes of respectively formula (X) and (X-A) with diethylphosphite to yield, respectively, the compounds of formula (XI) and (XI-A):

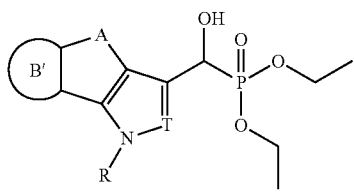
(XI)

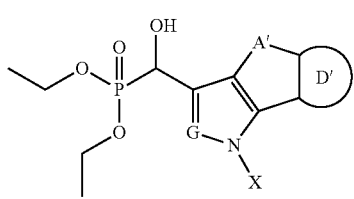
(XI-A)

fourth step: fluorination of the hydroxyl group in the compounds of formula (XI) and (XI-A) to give the corresponding fluoro-derivatives of formula (XII) and (XII-A):

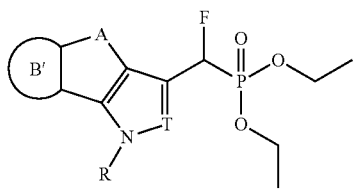
(XII)

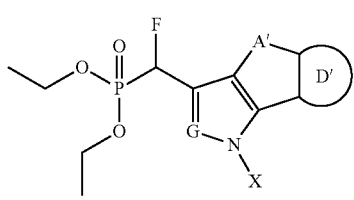
(XII-A)

fifth step: reaction of the fluoro-derivatives respectively of formula (XII) and (XII-A) with an aldehyde of formula (IX), sixth optional step: separation of isomer E from isomer Z of the compound obtained in the fifth step;

ii-h) when Q=Z=QH, a six-step synthesis is carried out:

first step: preparation of the Weinreb amides of formula (V) and (V-A) according to the third process of ii-c), second step: reduction of the Weinreb amides (V) and (V-A) to the corresponding aldehydes of formula (X) and (X-A) as described in the second step of ii-g), third step: trifluoromethylation of the aldehydes of formula (X) and (X-A) to yield the alcohols respectively of formula (XIII) and (XIII-A):

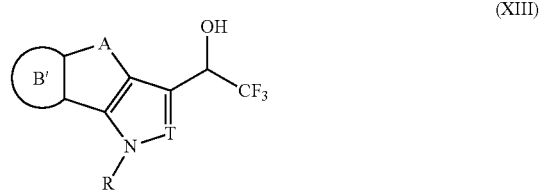
(XIII)

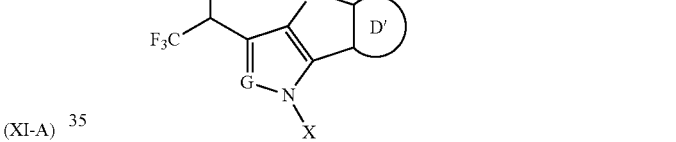
(XIII-A)

fourth step: oxidation of the alcohols of formula (XIII) and (XIII-A) to the corresponding ketones (XIV) and (XIV-A):

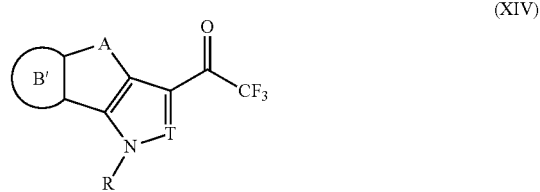
(XIV)

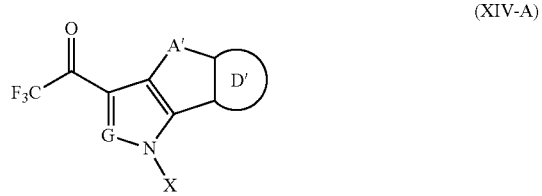
(XIV-A)

fifth step: condensation of the compounds of formula (XIV) and (XIV-A) with a compound of formula $NH_2$-$L_{50}$-$NH_2$, wherein $L_{50}$ is selected between L4 or L5 as defined above, obtaining the compound of formula (XV):

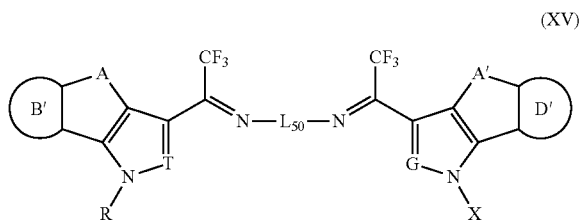

wherein A, R, T, G, X, A', B' and D' are as defined above, sixth step: reduction of the double bond in the groups -L-N=CH(CF$_3$)— of the compound of formula (XV);

ii-i) when Q=Z=QB and L=L3, the synthesis is carried out with one of the following alternative processes:

first process: reaction of an acid of formula (II) and of an acid of formula (II-A), or esters thereof, with an alcohol of formula (XVI):

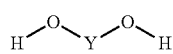

in the presence of strong inorganic acids, second process: reaction of a reactive derivative of an acid of formula (II) and of an acid of formula (II-A) with an alcohol of formula (XVI) in the presence of a weak organic base;

ii-l) when Q=QG and Z=QG' a three-step synthesis is carried out:

first step: reaction of a reactive derivative of the acids respectively of formula (II) and (II-A) with an hydrazine wherein one of the two amine groups is protected by a protecting group GP, obtaining respectively the compounds of formula (XVII) and (XVII-A):

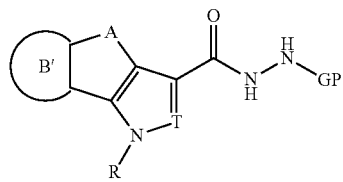

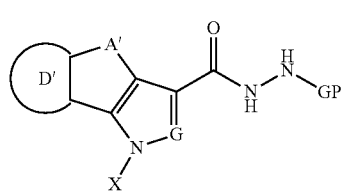

wherein GP is a protecting group of amine groups, second step: deprotection of the amine group linked to GP in the compounds of formula (XVII) and (XVII-A) to yield the compounds of formula (XVIII) and (XVIII-A), respectively:

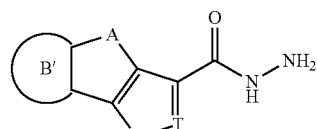

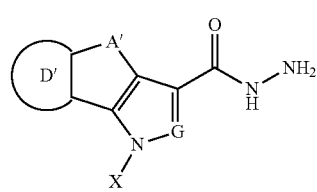

third step: reaction of the compounds of formula (XVIII) and (XVIII-A) with a compound of formula H-L-H, wherein L is a group selected between L6 and L7 as defined above;

iii) at least one hydrogen atom of the B' and D' rings of the compounds of formula (I-B) obtained according to the processes described sub ii), is substituted with at least one group selected from SO$_3^-$, SO$_3$H, COO$^-$, COOH to yield the compounds of formula (I).

The above described process for obtaining the compounds of formula (I) can also be carried out by reacting the acids of formula (II) and (II-A) according to step iii) by substituting at least one of the hydrogen atoms of the ring B' of the acid of formula (II) and, respectively, D' of the acid of formula (II-A) with at least one group selected from SO$_3^-$, SO$_3$H, COO$^-$, COOH. By this synthesis from the acid of formula (II) the acid of formula (II-B) is obtained and, respectively, from the acid of formula (II-A) the acid of formula (II-C):

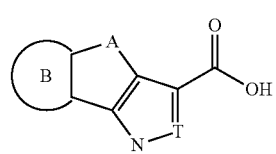

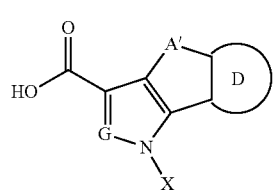

Then the optional step (i) and steps sub ii) are sequentially carried out.

The acids of formula (II-B) and (II-C) are prepared according to syntheses described in the prior art. The syntheses of these compounds are for example reported in U.S. Pat. No. 7,485,730, U.S. Pat. No. 5,547,975, U.S. Pat. No. 6,916,838, U.S. Pat. No. 7,384,960, and patent applications WO 03/070236, US 2010/0215759, US 2010/0215741.

The acids of formula (II-B) and (II-C) of the present invention comprise also their pharmaceutically acceptable salts, cis and trans isomers, E and Z isomers, optical isomers, hydrates and solvates.

In the following description by room temperature it is meant a temperature comprised between 20° C. and 30° C.

More in detail, in the above mentioned steps:

in i) the transformation of the acids of formula (II) and (II-A) into the corresponding reactive derivatives is carried out by using methods known to the skilled in the art. See for example the activation methods of the carboxylic acids reported in the article of Tetrahedron 61 (2005) 10827-10852.

Among the acrylic halides, acyl chloride is preferred. The preferred esters are ethyl esters.

In ii-a) the reactive derivatives of the acids of formula (II) and (II-A) that are used are preferably acyl halides, more preferably acyl chlorides. As an inert solvent for these reactive derivatives, dichloromethane can be used and, as azide, sodium azide $NaN_3$ solubilized in an aqueous solution, preferably in water. The synthesis of the first step of the acyl azides of formula (III) and (III-A) can be carried out at temperatures in the range 4°-40° C., preferably at room temperature. The reaction time is preferably comprised between 30 minutes and 4 hours, more preferably from 40 minutes to 120 minutes. Preferably, at the end of the first step the acyl azide is extracted from the reaction mixture with a volatile organic solvent, for example chloroform. The obtained organic phase is then dehydrated and concentrated under vacuum. Preferably the organic phase is dehydrated with $Na_2SO_4$. The reaction of the second step of ii-a) between urea and acyl azides is preferably carried out under reflux conditions in an inert organic solvent, for example toluene. The compound of formula (I) is preferably isolated after cooling the reaction mixture and subsequent filtration, washing and drying steps.

In ii-b) the reactive derivatives of the acids of formula (II) and (II-A) that are used are preferably the corresponding ethyl esters. The reduction reaction of the first step with the formation of the corresponding alcohols of formula (IV) and (IV-A) is carried out in an inert organic solvent, for example tetrahydrofuran, by operating preferably at temperatures in the range 4°-40° C., more preferably at room temperature. As a reducing agent an organic metal hydride can for example be used, such as di-isobutylaluminum hydride (DIBAL-H) or lithium hydride and aluminium $LiAlH_4$. In the second step the alcohols of formula (IV) and (IV-A) are reacted with the compound of formula U—Y—U in the presence of an alkaline hydride, for example sodium hydride, at temperatures comprised between 4 and 40° C., more preferably at room temperature.

In ii-c) first process, the temperature of the two reactions is comprised between −10 and 40° C., more preferably both reactions are initially carried out at 0° C. and then at room temperature. In the first reaction of the first process the ethyl esters of the acids respectively of formula (II) and (II-A) are preferably reacted with $Al(CH_3)_3$ as trialkylaluminum and with $HN(OCH_3).HCl$ as the amine hydrochloride salt. The solvent is for example dichloromethane. In the second process of ii-c) in the metallorganic salt, preferably $Me^+=Li^+$. In the third process the derivatives of the acids of formula (II) and (II-A) are preferably the corresponding esters, more preferably ethyl esters. The synthesis of the Weinreb amides of formula (V) and (V-A) is preferably carried out in the presence of $Al(CH_3)_3$ as trialkylaluminum, preferably in an inert organic solvent, for example dichloromethane, for a time comprised between 4 and 20 hours, more preferably from 12 to 18 hours, at temperatures in the range 4°-40° C., more preferably at room temperature.

The amides are recovered after evaporation under vacuum of the organic solvent and preferably purified by flash chromatography before the following reaction with BrMg—Y—MgBr. This reaction with the Grignard compound is carried out under anhydrous conditions, preferably in anhydrous tetrahydrofuran in an inert gas atmosphere, for example nitrogen. Preferably in this reaction the temperature initially is lower than 10° C., more preferably at 0° C., then the reaction mixture is brought to temperatures comprised between 11° and 40° C., preferably at room temperature. The reaction time is preferably in the range 12-36 hours, more preferably 18-30 hours. Preferably at the end of the reaction an aqueous solution of ammonium chloride and an inert organic solvent, for example diethyl ether ($Et_2O$) are added, the obtained organic phase is separated and the aqueous phase extracted with an inert organic solvent, for example $Et_2O$. The organic phases are then pooled and dehydrated, for example by treatment with $Na_2SO_4$, the mixture is filtered and concentrated under vacuum to remove the organic solvent, obtaining the compound of formula (I).

In ii-d) the reaction is preferably carried out in an inert organic solvent at temperatures comprised from 4° to 40° C., more preferably at room temperature. Among the reactive derivatives of the acids (II) and (II-A) for use in the reaction ethyl esters and ester-amide adducts, for example those obtained with HOBt (1-hydroxybenzotriazole) and EDC (1-(3-diamino propyl)-3-ethylcarbodiimide hydrochloride), are preferred.

In ii-e) the reaction conditions of the first step are according to anyone of the processes described in ii-c). The reduction reaction of the second step is preferably carried out in an inert organic solvent, for example tetrahydrofuran, with lithium hydride and aluminium or with sodium boron iodide. The reaction temperature is preferably in the range 4°-40° C., more preferably room temperature. Preferably the reaction mixture is filtered at the end of the reaction and the organic phase concentrated under vacuum to obtain the compounds of formula (I).

In ii-f) the first step is carried out under the same conditions of the first step of ii-b). In the second step the reaction is preferably carried out under anhydrous conditions in an inert organic solvent, for example anhydrous $CH_2Cl_2$ in an inert atmosphere, for example nitrogen. Bromination is preferably carried out by using $CBr_4$ in the presence of triphenylphosphine. Preferably the reaction temperature is in the range 4° to 40° C., more preferably room temperature. The reaction is preferably carried out in a time comprised between 30 minutes and 6 hours, more preferably between 60 and 120 minutes. In order to isolate the compounds of formula (VII) and (VII-A) the solvent is preferably removed under vacuum and the residue purified by chromatography. In the third step of ii-f) the reaction is preferably carried out in anhydrous environment, for example in anhydrous toluene in an inert atmosphere, for example nitrogen. The reaction times are preferably comprised between 10 and 24 hours, more preferably between 12 and 18 hours. The reaction is preferably carried out under reflux conditions. At the end of the reaction the compounds of formula (VIII) and (VIII-A) are preferably purified by washing with an organic solvent, for example with $Et_2O$. In the fourth step of ii-f) the reaction is preferably carried out in an anhydrous environment, for example in tetrahydrofuran in a nitrogen atmosphere. The reaction temperature is preferably lower than 10° C., more preferably lower than 4° C., still more preferably lower than 0° C. Preferably the reaction is carried out in the presence of an organic base, for example LDA (lithium di-isopropyl amide). The reaction time is preferably in the range 5-60 minutes, more preferably 10-20 minutes. Preferably at the end of the reaction an aqueous solution of $NH_4Cl$ is added and the reaction mixture is extracted with an organic solvent, for example $CH_2Cl_2$. The organic phases are then pooled and dehydrated, for example by treating with $Na_2SO_4$. After filtering, the organic phase is removed under vacuum and the obtained residue, containing the compounds (I-B), is purified by flash chromatography. The fifth optional step of ii-f) can be carried out by chromatography or flash chromatography.

In ii-g) the reaction conditions of the first step are the same as the third process described in ii-c). The reduction reaction of the second step leading to the aldehydes of formula (X) and (X-A) is preferably carried out under anhydrous conditions in an inert organic solvent, for example tetrahydrofuran in a nitrogen atmosphere. As a reducing agent $LiAlH_4$ can for example be used. The reaction temperature is preferably lower than 10° C., more preferably lower than 4° C., still more preferably it is 0° C. At the end of the reaction the reaction mixture is preferably treated with acid aqueous solutions, for example with a HCl aqueous solution. Then an extraction is carried out by using a volatile organic solvent, for example $Et_2O$. The extracted organic phases are pooled, dehydrated with $Na_2SO_4$, filtered, the solvent evaporated under vacuum. In the third step of ii-g) the condensation reaction is carried out in an inert organic solvent, for example toluene, in the presence of an amine, for example triethylamine. Preferably the reaction is carried out at temperatures in the range 4°-40° C., more preferably at room temperature. At the end of the reaction an aqueous solution containing a carbonate, for example $K_2CO_3$, is preferably added and then an extraction is carried out with an organic solvent, for example $Et_2O$. The pooled organic phases are anhydrified with $Na_2SO_4$, filtered, the solvent evaporated under vacuum. Preferably the obtained residue is purified by flash chromatography. In the fourth step of ii-g) the fluorination reaction of the hydroxyl group of the compounds of formula (XI) and (XI-A) is preferably carried out in an inert organic solvent, for example $CH_2Cl_2$, at temperatures lower than −20° C., preferably lower than −50° C., more preferably the temperature is −78° C. As a fluorinating agent DAST $((CH_3-CH_2)_2NSF_3)$ can for example be used.

Preferably at the end of this step a bicarbonate solution, for example $NaHCO_3$, is added and the reaction mixture extracted with an inert organic solvent, for example $CH_2Cl_2$. The organic phases are pooled, anhydrified with $Na_2SO_4$, filtered and the solvent evaporated under vacuum and the fluorinated compounds (XII and XII-A) recovered. In the fifth step of ii-g) the reaction of the fluoroderivatives (XII) and (XII-A) with the aldehyde (IX) to form an olefin is preferably carried out under anhydrous conditions, for example under nitrogen, by using an inert organic solvent, for example tetrahydrofuran. Preferably at the beginning the reaction is carried out at temperatures lower than −20° C., preferably lower than −50° C., more preferably the temperature is −78° C., then the reaction temperature is comprised in the range 4°-40° C., more preferably it is room temperature. The reaction time is preferably comprised between 3 and 24 hours, more preferably between 4 and 16 hours. Preferably at the end of the reaction water is added and the liquid phase is extracted for example with $Et_2O$ or with other volatile organic solvent. The organic phases are pooled, anhydrified with $Na_2SO_4$, filtered, the solvent evaporated under vacuum. The obtained residue is purified by flash chromatography. The sixth optional step of ii-g) can be carried out by chromatography or flash chromatography.

In ii-h), first step, the reaction conditions are the same as those of the third process of ii-c). In the second step of reduction of the Weinreb amides of formula (V) and (V-A) to the corresponding aldehydes of formula (X) and (X-A) the reaction conditions are the same as the second step of ii-g). In the trifluoromethylation reaction of the third step, a fluorinated alkylating agent is used. Preferably anhydrous conditions, for example in anhydrous tetrahydrofuran solvent in a nitrogen atmosphere, are used. As fluorinating agents tetrabutylammonium fluoride and trimethyl(trifluoromethyl)silane can for example be used. At the start of the reaction the temperature is preferably lower than 10° C., more preferably lower than 4° C., still more preferably the temperature is 0° C. The reaction is then preferably continued at temperatures in the range 4°-40° C., more preferably at room temperature. Preferably at the end of the reaction an aqueous $NH_4Cl$ solution is added and the reaction mixture is extracted with an organic solvent, for example ethyl acetate. The organic phases are pooled and dehydrated with $Na_2SO_4$, then the solvent is removed under vacuum and the residue purified by flash chromatography. In the fourth step of ii-h) the oxidation of the alcohols of formula (XIII) and (XIII-A) to the corresponding ketones of formula (XIV) and (XIV-A) can be carried out by using an oxidation agent for example oxalyl chloride. The reaction is preferably carried out under anhydrous conditions at temperatures lower than −50° C., for example in anhydrous dichloromethane under a nitrogen atmosphere at −75° C. Preferably the reaction is carried out in the presence of a weak organic base, for example triethylamine. At the end of the reaction an aqueous solution is preferably added and the reaction mixture is extracted with an organic solvent, for example ethyl acetate, then the organic phases are pooled and dehydrated with $Na_2SO_4$, the solvent removed under vacuum and the residue purified by flash chromatography. The condensation reaction of the fifth step of ii-h) is carried out in the presence of a weak acidic catalyst, for example pyridinium paratoluensulphonate. The reaction is carried out under reflux conditions removing the water being formed. The reaction time is comprised between 12 and 48 hours, preferably between 18 and 30 hours. Preferably at the end of the reaction the solvent is removed under vacuum and the residue purified by flash chromatography. In the sixth step of ii-h) the reduction reaction of the double bond is for example carried out in toluene in the presence of a reducing agent such as, for example, the borane-trimethylamine complex. In this case the gaseous HCl is also requested. The reaction is carried out at temperatures in the range 4°-40° C., more preferably at room temperature. Preferably at the end of the reaction, when using the above reducing agent, gaseous nitrogen is bubbled in the liquid phase. The solvent is then removed under vacuum and the obtained residue purified by flash chromatography.

The reaction of the first step of ii-i) is preferably carried out in an inert organic solvent, for example $CH_2Cl_2$, at temperatures in the range 4°-40° C., more preferably at room temperature. The strong inorganic acid catalysts that can be used are for example sulphuric acid or hydrochloric acid. The reaction of the second step of ii-i) is preferably carried out in an inert organic solvent, for example $CH_2Cl_2$, at temperatures in the range 4°-40° C., more preferably at room temperature. Weak organic bases, such as amines, for example triethylamine, are used. Preferably at the end of the reactions of the first and of the second process of ii-i) the organic solvent is removed under vacuum and the obtained residue is purified by chromatography.

In ii-l) the reaction of the first step is preferably carried out in an inert organic solvent, for example $CH_2Cl_2$, at temperatures in the range 4°-50° C., more preferably at room temperature. As GP protecting groups, the protecting groups of amine groups can be used. A thorough review of these protecting groups is reported in the book by P. G. M. Wuts and T. W. Greene "Greene's protective groups in organic synthesis", fourth Ed., Wiley-Interscience. These protecting groups comprise derivatives of urea, amides and carbamates such as for example BOC (terbutyl carbamate). The deprotection reaction of the amine group of the compounds of formula (XVII) and (XVII-A) (second step of ii-l)) is carried out according to known methods of the skilled in the art such as for example those described in the above reported text by P. G. M. Wuts and T. W. Greene. For example when GP is BOC the deprotection reaction can be carried out by treating the compounds of formula (XVII) and (XVII-A) with strong acids. Examples of these acids are trifluoroacetic acid and hydrofluoric acid. In the reaction of the third step of ii-l) the compound H-L-H being used preferably in the form of a reactive derivative of a carboxylic acid, such as for example those above reported for the acids of formula (II).

In step iii) the sulphonation reaction preferably is initially carried out at temperatures lower than 0° C., preferably at −10° C., in an inert organic solvent, for example dichloromethane, in the presence of acetic anhydride and $H_2SO_4$, for example concentrated $H_2SO_4$. After the adduct formation the reaction is continued at temperatures in the range 4°-40° C., more preferably at room temperature. The reaction time is preferably comprised between 4 and 24 hours, more preferably between 10 and 16 hours.

In step iii) the introduction of one or more —COOH groups in the rings B' and D' can be carried out by using known processes to the skilled in the art. Some of these processes are exemplified hereinafter:

iii-a)
first step: synthesis of acid chlorides by substituting one or more hydrogen atoms of B' and D' with —C(O)Cl groups by reaction of the compounds of formula (I-B) with phosgene, second step: hydrolysis of the acid chlorides;
iii-b)
first step: alkylation reaction of the B' and D' rings with an alkyl halide,
second step: oxidation of the alkyl group and conversion to —COOH group. The oxidation can be carried out for example by using inorganic oxidizing salts such as permanganates or chromates;
iii-c)
first step: insertion of the substituent —CN into the B' and D rings. The reaction requires the presence on these rings of a substituent group —$NH_2$, which is converted into the corresponding diazonium salt and then into —CN group, for example by a Sandmayer reaction with the use of $Cu(CN)_2$, second step: hydrolysis of the nitrile group to carboxyl;
iii-d)
first step: acylation of the B' and D' rings of the compounds (I-B) with acyl halides, for example by using $CH_3COCl$, second step: transformation of the acyl substituents of B' and D' into carboxyl groups, for example by treating with halogens in a basic environment;
iii-e) Kolbe-Schmitt reaction on the phenolic salts of the compounds of (I-B), wherein rings B' and D' have at least one hydrogen atom substituted with one hydroxy group. The phenolic salts are reacted, under pressure, with carbon dioxide to substitute the OH with COOH groups;
iii-f) reaction in the presence of the catalysts Pd of compounds of formula (I-B) having at least one hydrogen atom of rings B' and D' substituted with one halogen with silylcarboxylic acids releasing carbon monoxide in situ;
iii-g) hydroxycarbonylation reaction catalyzed by Pd of carbon monoxide, used in sub-stoichiometric amounts, with compounds of formula (I-B) having at least one hydrogen atom of rings B' and D' substituted with one halogen atom. According to this synthesis the halogen derivatives are reacted with stoichiometric amounts of potassium formate and ligands derived from phosphines in the presence of precatalysts formed of complexes of acyl-Pd(II), which release in situ the carbon monoxide and catalyze the substitution of the halogen groups with COOH. The ligands derived from phosphines that can be used are for example the following: $P(tBu)_3$ (Tri-tert-butylphosphine), $P(oTol)_3$ (Tri(o-tolyl)-phosphine), tBu-Brettphos(2-(Di-tert-butylphosphino)-2',4', 6'-triisopropyl-3,6-dimethoxy-1,1'-biphenyl), dppb (1,4-Bis (diphenyl-phosphino)butane), dppf (1,1'-Bis(diphenyl-phosphino)ferrocene), diPrpf (1,1'-bis (diisopropylphosphino)ferrocene), tBu-Josiphos ((R)-1-[(S)-2-Diphenyl phosphinoferrocenyl]ethyl-di-tert-butylphosphine).

The reactions described sub iii) leading to the introduction of sulphuric or carboxylic groups in B' and D' rings can also be used to convert the acids of formula (II) and (II-A) into the acids of formula (II-B) and (II-C), respectively.

As said, the acids of formula (II) and (II-A) and their reactive derivatives as defined above and related preparation processes are known. See for example U.S. Pat. No. 7,485, 730, U.S. Pat. No. 5,547,975, U.S. Pat. No. 6,916,838, U.S. Pat. No. 7,384,960, and patent applications WO 03/070236, US 2010/0215759, US 2010/0215741.

By using the above described processes, the compounds of the present invention are obtainable with high yields.

Preferably in the compounds of formula (I) of the present invention the $SO_3^-$, $SO_3H$, $COO^-$, COOH groups are one and no more than 2 for each of the rings B and D. Still more preferably there is one of the above groups for each of the B and D rings. Preferably the groups are equal to each other.

It is a further object of the present invention compounds of formula (I-B):

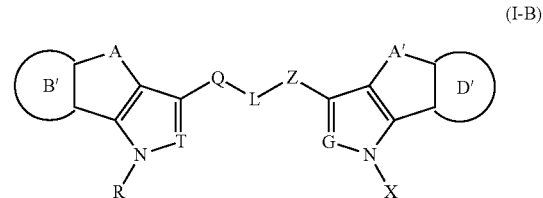

(I-B)

wherein:
A, T, Q, R, L, Z, G, X and A' are as defined in the compounds of formula (I); B' and D', equal or different, are selected from aryl and heteroaryl, said aryl and heteroaryl having as substituents at least one hydrogen atom and, optionally, one or more G1 groups, equal to or different from each other, the following compounds of formula (I-A) being excluded from the compounds of formula (I-B);

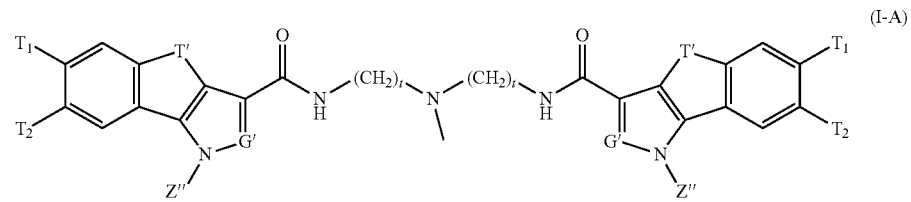

(I-A)

wherein:

t=2, 3,

Z" is a substituent selected from methyl, phenyl or 2,4 dichlorophenyl,

T' is selected between CH=CH and $CH_2$, $T_1$=H, Cl, $OCH_3$ $T_2$=H, Cl when T'=CH=CH and G'=CH, $T_1$=H, Cl, or $OCH_3$ and $T_2$=H, Cl, when T'=CH=CH and G'=N, $T_1$=$T_2$=H, when T'=$CH_2$ and G'=N or CH, $T_1$=$T_2$=H.

Preferably in compounds (I-B) B' and D' are equal to each other and are selected from phenyl and monocyclic heteroaryl, said phenyl and monocyclic heteroaryl having as substituents at least one hydrogen atom and, optionally, one or more G1 groups, equal to or different from each other.

More preferably in compounds (I-B) of the invention:

B' and D', equal to each other, have the meaning of phenyl and monocyclic heteroaryl, wherein the substituents of said phenyl and monocyclic heteroaryl comprise at least one hydrogen atom and, optionally, one or more substituting groups, equal to or different from each other selected from: halogen, linear or when possible branched $C_1$-$C_{20}$ alkyl, linear or when possible branched $C_2$-$C_{20}$ alkenyl, linear or when possible branched $C_2$-$C_{20}$ alkynyl, cyano, nitro, $SO_2NH_2$, $NH_2$, Q=Z=QA, L=L1;

Q=Z=QB, L=L2, Y=Y50, L2 and $Y_{50}$ being as defined above;

T and G are both nitrogen,

R and X, equal to each other, have the following meanings:

$R_{30}$—W with W=$W_b$ wherein $R_{30}$ is a bivalent aliphatic $C_2$-$C_6$ chain, linear or when possible branched and $W_b$ is as defined above, phenyl or benzyl, wherein one or more hydrogen atoms of said phenyl or benzyl are optionally substituted with groups selected from halogen, linear or when possible branched $C_1$-$C_6$ alkyl.

When in compounds (I-B) B' and/or D' have the meaning of monocyclic heteroaryl, said monocyclic heteroaryl is preferably thiophene.

A further object of the present invention is represented by the compounds of formula (I) for use as medicaments.

A still further object of the present invention are pharmaceutical compositions comprising the compounds of formula (I).

The pharmaceutical compositions of the present invention contain the compounds of formula (I) in the amount required for the specific pharmaceutical application.

In the pharmaceutical compositions the compound of formula (I) can be present as such or in the form of a corresponding salt or solvate, or also as an isomer, such as for example a cis or trans isomer, E or Z isomer, or an optical isomer when it contains one or more chiral centres.

The additives contained in the pharmaceutical compositions are excipients, carriers, dyestuffs, preservatives, aromas, etc., the use of which in pharmaceutical field is known. The amounts used of these various additives and excipients are those known for the specific applications.

The administration of the pharmaceutical compositions can take place by oral, subcutaneous, sublingual, intramuscular, intravenous, topic, transdermal, rectal, ophthalmic, intranasal, vaginal, intraperitoneal route.

The pharmaceutical compositions of the present invention comprise for example dispersions, solutions, micellar solutions, liquid crystals, emulsions, microemulsions, powders, microparticles, nanoparticles, capsules, aerosols, suppositories, tablets, syrups, elixirs, creams, gels, ointments, pastes, plasters, foams, etc. See for example the pharmaceutical compositions described in patent application WO 2004/011,468, herein incorporated by reference.

The pharmaceutical compositions can be obtained according to known processes of pharmaceutical technology. For example, they can be obtained according to the processes reported in U.S. Pat. No. 6,028,084, herein incorporated by reference.

For example pharmaceutical compositions, usable for the oral administration of the compounds of formula (I), their isomers or of the corresponding hydrates or solvates or pharmaceutically acceptable salts, are formed of 0.05-20% by weight of a compound of formula (I), including all the various isomers and the corresponding mixtures or of a corresponding hydrate or solvate or pharmaceutically acceptable salt, and of 2-10% by weight of a disintegrating agent such as for example cellulose, sodium carboxymethylcellulose or other cellulose derivatives. In all these formulations the sum of the active principle and of the various excipients, other than those indicated above, is such as to give 100% of the composition.

Pharmaceutical formulations usable both for oral and intraocular administration can comprise the compounds of formula (I), their isomers, including their salts, hydrates, solvates, together with hydroxypropylmethylcellulose. In particular they can comprise from 0.05 to 20% of the compounds of formula (I) and from 0.5 to 10% of hydroxypropylmethylcellulose (HPMC).

Specific pharmaceutical formulations for the oral administration in the form of capsules or tablets, other than the compounds of formula (I) and hydroxypropylmethylcellulose, can include other excipients, such as for example lactose monohydrate, magnesium stearate, microcrystalline cellulose, titanium oxide. In these preparations HPMC can be present in the capsule or tablet core and/or in the film-coating, when present, of the tablets (shell).

The pharmaceutical formulations of the invention can optionally contain also excipients such as hyaluronic acid and/or cyclodextrins, such as for example alpha, beta or gamma cyclodextrins or modified cyclodextrins, for example containing alkyl chains and/or PEG.

The pharmaceutical compositions of the invention can optionally contain magnetic compounds, such as for example iron oxides.

Pharmaceutical compositions of the compounds of formula (I) are for example those obtainable starting from emulsions or microemulsions wherein the compounds of the invention are mixed in the presence of surfactants and other additives, with an aqueous phase and optionally with an oil phase.

It is a further object of the present invention pharmaceutical formulations formed of microemulsions or emulsions, or comprising microemulsions or emulsions, comprising the following components (% by weight):

S) from 0.01 to 95% of one or more pharmaceutically acceptable compounds, selected from the following classes:
   surfactants selected from non-ionic, anionic, cationic and amphotheric, optionally containing fluorine atoms,
   polymers (Pol) forming organized structures such as aggregates, micelles, liquid crystals, vesicles, in the liquid in which they are solubilized, O) from 0 to 95% of one or more oils selected from the following classes of pharmaceutically acceptable compounds:
   esters of $C_4$-$C_{32}$ acids, optionally containing one or more unsaturations of ethylene type, $C_4$-$C_{32}$ acids optionally containing one or more unsaturations of ethylene type, usable when the final composition has a pH at which the acid is not transformed into the corresponding salt, PA) from 0.001 to 90% of compounds of formula (I), AD) from 0 to 60% by weight of one or more compounds selected from the following classes:
  modifiers of the water and/or oil polarity,
  modifiers of the film curvature of component S),
  co-surfactants, WA) from 0.001 to 99.9% of water or of a saline aqueous solution, optionally buffered, the sum of the components being 100%.

The compositions of the invention in the form of microemulsions are limpid and transparent, preferably liquid. When the viscosity is very high, the microemulsions of the invention are in the gel form, optionally formed of liquid crystals, such as for example lamellar, hexagonal, cubic liquid crystals.

In component S) the surfactants containing fluorine atoms can show (per)fluorinated chains, for example (per)fluoropolyether chains.

The liquids wherein the polymers of component S) are solubilized to form the organized structures are water and/or oil. The usable oils are reported herein further on and can be of both natural and synthetic origin.

By microemulsion a system is meant formed of two or more phases immiscible among each other, that is transparent, isotropic, comprising at least one aqueous phase and at least one oil phase, wherein the various phases are stabilized by component S), optionally in the presence of one or more compounds AD), for example co-surfactants. See for example R. K. Mitra, Physicochemical investigations of microemulsification of eucalyptus oil and water using mixed surfactants (AOT+Brij-35) and butanol, J. Colloid and Interface Science, 283 (2005) 565-577. Sometimes the oil phase in the microemulsions for pharmaceutical use is formed by the active principle as such, when it is lipophilic and thus insoluble in water or in an aqueous phase.

By emulsion it is meant a system formed of the same components of the microemulsion but of an opalescent or milky appearance, or it is in the form of a cream.

Preferred microemulsions or emulsions according to the present invention have the following composition (% by weight):
  from 0.01 to 90% of component S) as defined above,
  from 0 to 90% of one or more oils of component O),
  from 0.001 to 50% of compounds component PA),
  from 0 to 30% of component AD),
  from 0.1 to 99.9% of component WA),
the sum of the components being 100%.

More preferred microemulsions or emulsions have the following composition (% by weight):
  from 0.01 to 80% of component S),
  from 0 to 70% of one or more oils of component O),
  from 0.05 to 40% of compounds component PA),
  from 0 to 20% of component AD),
  from 10 to 99.9% of component WA),
the sum of the components being 100%.

Still more preferred microemulsions or emulsions have the following composition (% by weight):
  from 0.01 to 70% of component S),
  from 0.01 to 50% of one or more oils of component O),
  from 0.05 to 30% of compounds component PA),
  from 0 to 15% of component AD),
  from 20 to 99.9% of component WA),
the sum of the components being 100%.

The preferred surfactants component S) are those non-ionic and anionic. Among the non-ionic surfactants, the most preferred are those containing polyoxyalkylene chains, preferably polyoxyethylene chains. The following ones can for example be mentioned:

polyoxyl 35 castor oil, known for example under the trademark Cremophor® EL (BASF), prepared by ethoxylation of castor oil, polyoxyl 40 hydrogenated castor oil, known for example under the trademark Cremophor® RH40 (BASF), prepared by ethoxylation of hydrogenated castor oil, polyethylenglycol 15 hydroxystearate, known for example under the trademark Solutol® HS15 (BASF), prepared by reaction of 15 moles of ethylene oxide with 1 mole of 12-hydroxystearic acid, polyoxyethylene polysorbate, such as Tween® 80, Tween® 20, Tween® 60, Tween® 85, sorbitan esters of fatty acids, such as for example sorbitan monolaurate and sorbitan monostearate, commercialized for example under the name Span® 20 and Span® 60, respectively, vitamin E/TPGS: tocopheryl propylenglycol 1000 succinate, polyoxyethylen ethers of fatty acids, as for instance those of the series Brij®, such as Brij® 35, Brij® 76, Brij® 98, PEG-12-acyloxy-stearates, see for example C. E. McNamee et al. in "Physicochemical Characterization of PEG 1500-12-acyloxystearate micelles and liquid cristalline phases", Langmuir, 2005, 21, 8146-8154. Among these, the following can for example be mentioned:

PEG 1500 mono-12-capryloyloxy stearate (PEG 1500-$C_{18}C_8$)

PEG 1500 mono-12-caproyloxy stearate (PEG 1500-$C_{18}C_{10}$)

PEG 1500 mono-12-lauroyloxy stearate (PEG 1500-$C_{18}C_{12}$)

PEG 1500 mono-12-myristoyloxy stearate (PEG 1500-$C_{18}C_{14}$)

PEG 1500 mono-12-palmitoyloxy stearate (PEG 1500-$C_{18}C_{16}$).

Among anionic surfactants the following can for example be mentioned: soya lecithin, for example known under the trademark Epikuron® 200, bis-2-ethylhexylsulphosuccinate (AOT), sodium taurocholate.

Among cationic surfactants, hexadecyltrimethylammonium bromide (CTAB) and didodecylammonium bromide (DDAB) can for example be mentioned.

The polymers (Pol) which can be used as component S) must be soluble in the aqueous phase and/or in the oily phase. By soluble it is meant that the polymers must reach in the phase in which they are soluble concentrations at least equal to those allowing the formation of organized structures as aggregates, micelles, liquid crystals, vesicles. The presence of the mentioned organized structures can be detected by specific techniques of the physical chemistry of the dispersed systems, as for example Laser Light Scattering (LLS), Neutron Scattering, microscopy.

As said, the polymers component S) can be used also in combination with the above reported surfactants. Also in this case the concentration of the solubilized polymer in the used liquid phase must be such to lead to the formation of the above mentioned organized structures.

The polymers component S) are for example polyvinylpyrrolidone and vinylpyrrolidone/vinyl acetate copolymers, commercialized for example under the trademark Kollidon®, as Kollidon® 12PF and Kollidon® 17PF (BASF), and the block copolymers containing polyoxyalkylene chains, more preferably containing polyoxyethylene chains (PEO), as for example the block copolymers PEO with polyoxypropylene chains (PPO) characterized by PEO-PPO-PEO structures, commercially available for example under the trademark Pluronic® or Poloxamer® or Lutrol®, as Lutrol® F68 and Lutrol® F127 commercialized by Basf.

In component O) the acid esters are preferably obtained by esterification of the corresponding carboxylic acid with an alcohol having an aliphatic chain, preferably $C_1$-$C_5$, or having a polyoxyethylene chain, or with glycerine. In this case mono-, di- or triglycerides are obtained.

The following esters can for example be mentioned:
oleoyl macrogol 6 glyceride (unsaturated polyglycosylated glyceride), commercialized for example under the trademark Labrafil® 1944 CS, (Gattefossé),
propylenglycol caprylate caprate, known for example under the trademark Labrafac® PG (Gattefossé), propylenglycol monoester of the caprylic acid, commercialized for example under the trademark Capmul® PG-8 (Abitec),
glycerol oleate (for example Peceol® (Gattefossé)),
medium chain mono- and diglycerides, for example capric and caprylic acid glycerides (for example Capmul® MCM (Abitec), Imwitor® 308 (Sasol)),
polyglycerol oleate (for example Pluro® oleic (Gattefossé)),
capric/caprylic acid triglycerides (for example Miglyol® 812 and Miglyol® 810 (Sasol), Labrafac® CC CS (Gattefossé)),
ethyl butyrate, ethyl caprylate, ethyl oleate,
tripalmitine, commercialized for example under the trademark DYNASAN® 116 by Sasol.

Vegetable oils of pharmaceutical grade containing one or more of the above mentioned esters can also be used, for example soya oil.

The acids component O) are preferably carboxylic acids, more preferably fatty acids.

Among the acids component O) stearic acid, omega-3 and omega-6 acids can be mentioned.

In component AD) the modifiers of the water and/or oil polarity can for example be polyethylenglycols. Lutrol®E300 and Lutrol®E400 (BASF) can be mentioned. Aliphatic alcohols, for example ethanol, can also be used.

In component AD) the modifiers of the film curvature of component S) are for example aliphatic alcohols, preferably $C_2$-$C_5$.

In component AD) the co-surfactants can for example be the surfactant compounds as defined above, or aliphatic alcohols, preferably having a chain with at least 6 carbon atoms. The following compounds can for example be mentioned:
propylene glycol monolaurate, known for example under the trademark Capmul® PG12 (Gattefossé) or Lauroglycol® 90 (Gattefossé),
caprylocaproyl macrogol 8 glyceride (saturated ethyldiglycosylated glyceride) commercialized for example under the trademarks Labrasol®, Gelucire 44-14 (Gattefossé),
diethylenglycol monoethyl ether, known for example under the trademark Transcutol® (Gattefossé).

The compositions formed of microemulsions are stable in a wide range of temperature, generally from 0° C. to 80° C., preferably from 4° C. to 45° C.

Other pharmaceutical formulations comprising the compounds of formula (I) are those formed of micro- and/or nanoparticles of silica, or of lipids or of pharmaceutically acceptable polymers, wherein the compounds of the invention, present in concentrations comprised between 0.1 and 60% by weight with respect to silica, or to the lipids or to the polymers, are incorporated inside and/or on the surface of the micro- and nanoparticles.

As lipid particles, those based on fatty acids or esters thereof having a melting point higher than 40° C., more preferably higher than 50° C. can for example be mentioned. For example triglycerides of fatty acids, such as tripalmitine and lanolin are mentioned. The particles can also be formed of mixtures between fatty acids or fatty acid esters having a melting point higher than 40° C. and an oil, liquid at room temperature (20-25° C.), such as for example medium chain triglycerides, such as vegetable oils, Miglyol® 812 and Miglyol® 810 commercialized by Sasol. Alternatively these particles can be nanocapsules formed of a surface layer of soya lecithin englobing a liquid lipidic core, constituted for example by medium chain triglycerides, such as vegetable oils, Miglyol® 812 and Miglyol® 810 (see for example patent application US 2003/0152635).

The silica particles are preferably formed of hydrophilic silica. They can optionally contain one or more compounds component O) previously described for the emulsions and microemulsions, and/or lipids used for preparing the above described lipid particles. For example the particles of Lipo-Ceramic™ described by Simovic et al. in Mol. Pharmaceutics, 6, 2009, 861-872, can be used.

In the case of polymer particles those formed of the following polymers POL-A can for example be mentioned:
proteins, as albumin, optionally peghilated by functionalization with compounds having polyethylenglycol (PEG) chains, polysaccharides, as for example chitosan, dextran, starch and derivatives thereof as for example hydroxyethyl starch (HES), dendrimers, such as those described by Woo-Dong Jang et al. In Progress in Polymer Science 34, 2009, 1-23, carbon nanotubes,
polymerized cyclodextrins, such as beta-cyclodextrin polymers, optionally linked to PEG chains, as for example described in the article by T. Schluep et al. Clin. Cancer Res. 15, 2009, 181-189,
synthetic polymers such as polyorganophosphazenes, polyanhydrides, polyamides, polyorthoesters, polyalkylcyanoacrylates, polyesters as polylactate (PLA) and the polylactate/polyglycolate polymers (PLA/PLGA), polyhydroxyacids, polylactones, polyesteramides, polyaminoacids, polyanhydrides, polycarbonates, polyphosphazines, polyphosphoesters, polythioesters.

The particles containing the compounds of formula (I) can optionally be modified on the surface for example for one or more of the following reasons: to make the passage of the above compounds easier through the physiological barriers (for example the hematoencephalic barrier), to increase the residence time in circulation of the compounds of formula (I), to increase the absorption thereof, to obtain that the compounds of formula (I) can selectively reach the cells, tissues or organs to be treated. The modification of nano- and microparticles can be carried out by both chemico-physical adsorption (for example Van Der Waals forces) of one or more surface modifiers, and by chemical functionalization with one or more specific modifiers. In the latter case the modifiers are linked with covalent bonds to the particles. See for example E. Garcia et Al., "Colloidal carriers and blood-brain barrier (BBB) translocation: A way to deliver drugs to the brain", Int. J. of Pharmaceutics 298 (2005), 274-292.

Among the surface modifiers, the following ones can for example be mentioned:
compounds comprising polyoxyethylene or peghilated (PEG-based) chains, such as Tween 80, see for example J. Kreuter, "Nanoparticulate systems for brain delivery of drugs", *Advanced Drug Delivery Reviews*, 47, 2001, 65-81, M. T. Peracchia et al., "Synthesis of a Novel Poly(MePEG cyanoacrylate-coalkyl cyanoacrylate) amphiphilic copolymer for nanoparticle technology", Macromolecules, 30, 1997, 846-851,
proteins, such as plasma proteins, apolipoproteins can for example be mentioned, see US 2004/0131692, proteins can optionally be peghilated, antibodies or fragments thereof,
peptides,
compounds recognized by specific receptors expressed on physiological barriers, such as peptide compounds, proteins, synthesis or natural compounds having a structure different from peptides. See for example L. Costantino et al., "Peptide-derivatized biodegradable nanoparticles able to cross the blood-brain barrier", Journal of Controlled Release, 108, 2005, 84-96, B. Stella et al., "Design of folic acid-conjugated nanoparticles for drug targeting", J. of Pharmaceutical Sciences 89 11, November 2000 1452-1464.

The surface modifiers can be directly linked to the particles, as for example in the case of PEG chains of the poly (MePEGcyanoacrylate-co-alkyl cyanoacrylate) particles described in M. T. Peracchia et al., "Synthesis of a Novel Poly(MePEG cyanoacrylate-co-alkyl cyanoacrylate) amphiphilic copolymer for nanoparticle technology", Macromolecules, 30, 1997, 846-851.

The bond between surface modifiers and particles can be formed by reacting a functional group of the material constituting the particles (polymers, lipids or silica), for example OH, SH, COOH groups, ester, amide, amino, end groups containing a double bond, with a functional group of the modifiers, for example OH, SH, alkenyl, $OC(O)R_{10}$, $NR_{10}R_{11}$, wherein $R_{10}$ and $R_{11}$ equal or different are selected between H or alkyl, with formation of ester, thioester, amide groups, etc. Said reactions are carried out with the procedures and conditions known to the skilled in the field.

The surface modifiers can also be covalently linked to the particles through linker LK. The linkers usable according to the present invention are preferably stable in plasma. Pharmaceutically acceptable, metabolically cleavable linkers are still more preferred. Examples of linkers are the following bivalent groups: alkylene, alkenylene, alkynylene, heteroalkylene, arylene, heteroarylene, cycloalkylene, alkylcycloalkylene, heteroalkylcycloalkylene, heterocycloalkylene, arylalkylene, heteroarylalkylene. Optionally the preferred linkers contain S—S bonds or N—N bonds, peptide chains, the latter optionally containing S—S bonds and/or N—N bonds, and/or bivalent linkers of formula (DXI) and/or (DXII)

(DXI)

(DXII)

Examples of preferred linkers are those reported hereinafter (formulas from (XYZ1) to (XYZ22)):

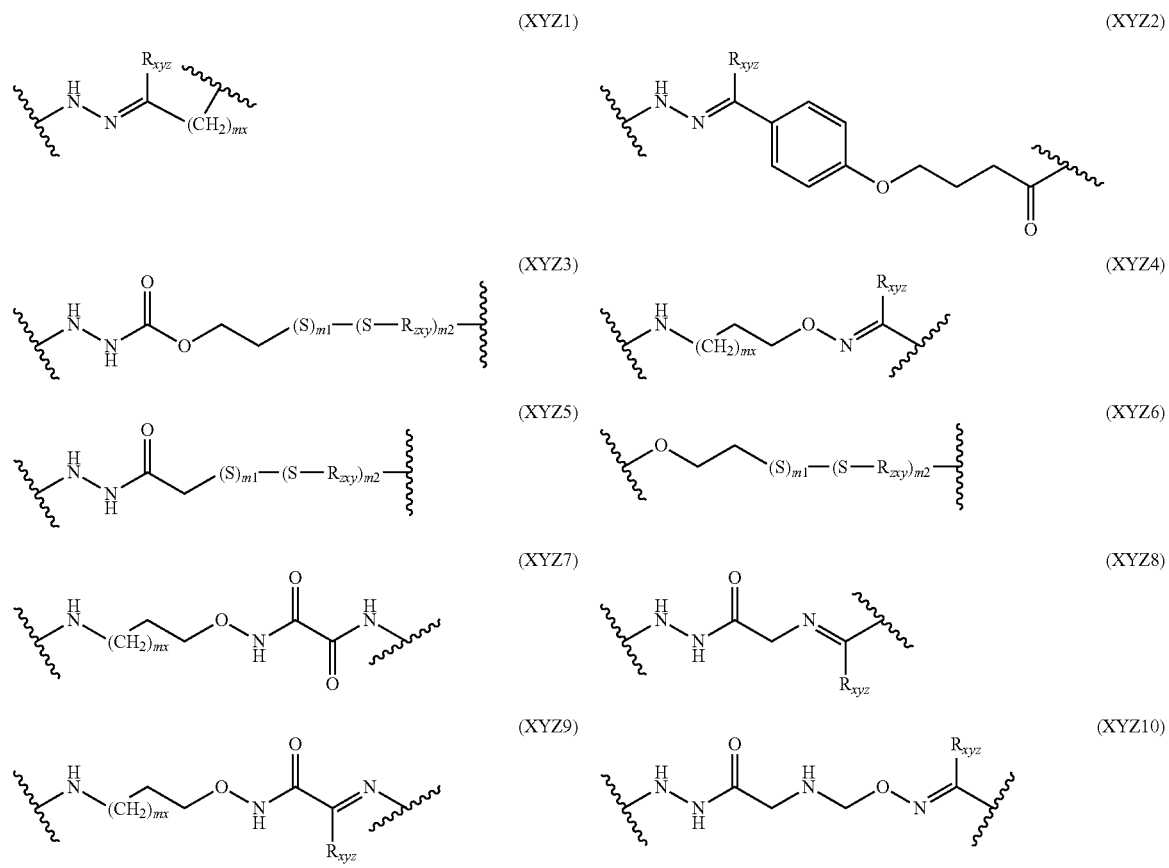

-continued
(XYZ11)
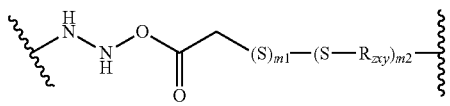
(XYZ12)
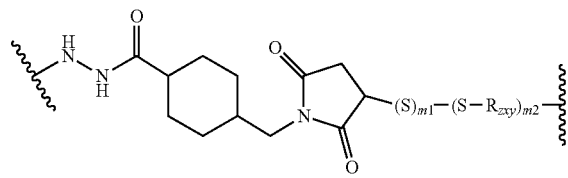
(XYZ13)
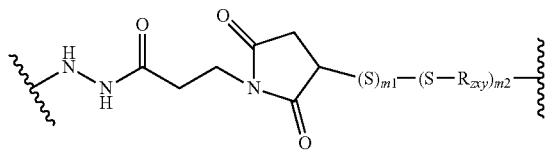
(XYZ14)
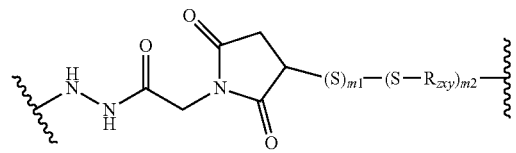
(XYZ15)
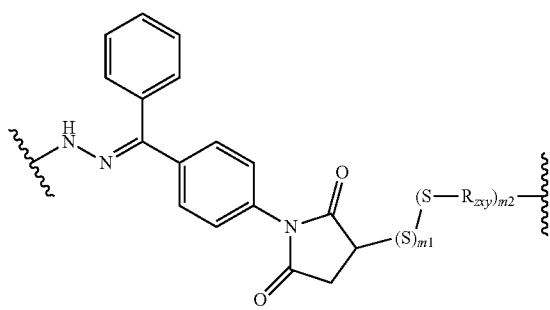
(XYZ16)
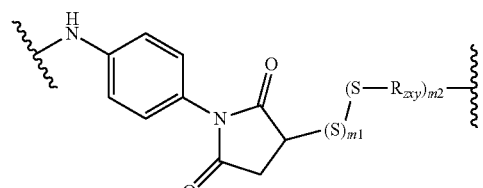
(XYZ17)
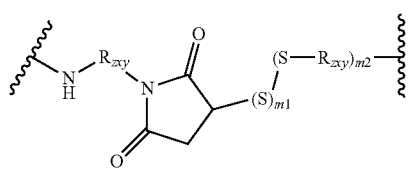
(XYZ18)
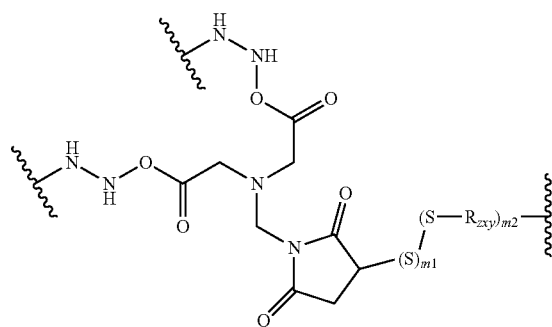
(XYZ19)
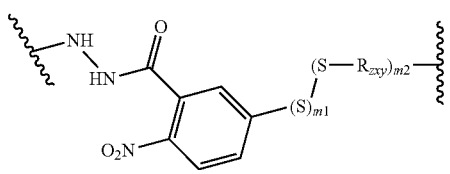
(XYZ20)
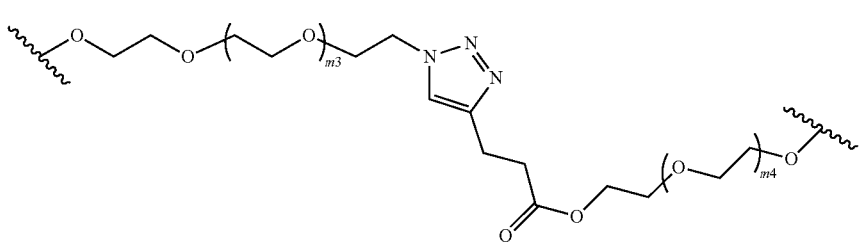

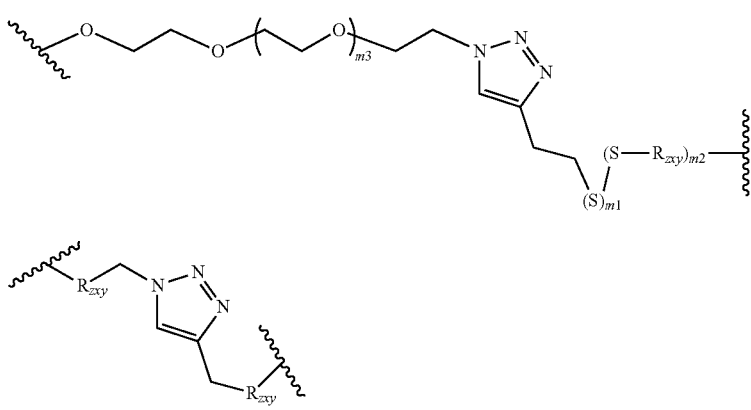

wherein:
mx is an integer from 0 to 20, preferably from 0 to 6,
m1 and m2, equal to or different from each other, are zero or 1,
m3 and m4, equal to or different from each other, are an integer from 0 to 200, preferably from 0 to 50, more preferably from 0 to 10,
$R_{xyz}$ has the meaning of H or alkyl, wherein alkyl is preferably a linear or when possible branched $C_1$-$C_5$ chain,
$R_{zxy}$ is a bivalent group selected from alkylene, alkenylene, alkynylene, heteroalkylene, arylene, heteroarylene, cycloalkylene, alkylcycloalkylene, heteroalkylcycloalkylene, heterocycloalkylene, arylalkylene, heteroarylalkylene.

The process for obtaining conjugated compounds constituted by the material forming the particles, here called MP (polymers, lipids or silica), linkers and surface modifiers MD can be carried out through the following steps:
Con-1) reaction between a functional MP group with a functional group $T_4$ of a LK precursor of formula $T_4$-LK-$T_3$, $T_3$ being another optionally protected functional group, with formation of a conjugate MP-LK-$T_3$,
Con-2) reaction of the conjugate MP-LK-$T_3$ with MD forming the conjugate MP-LK-MD.
In Con-1) the reacting functional group $T_4$ and the functional MP groups are for example selected from OH, SH, COOH, ester, amide, amino, end groups containing a double bond.
From the reaction of said functional groups for example ester, thioester, amide, etc. groups are formed.
In Con-2) the reaction takes place among the MD functional groups and $T_3$. When $T_3$ is a protected group, the reaction takes place after deprotection of $T_3$. The functional group $T_3$ and the functional MD groups are selected for example from those indicated in Con-1).
The reactions in Con-1) and Con-2) are carried out by using the methods and conditions known to the skilled in the field.

Surprisingly and unexpectedly the Applicant has found that the compounds of the present invention can be used as drugs to inhibit angiogenesis. In particular, the compounds of the present invention have shown a high inhibitory activity towards protein FGF-2, that is an effective angiogenesis mediator, combined with a reduced incidence of side effects.

The remarkable antiangiogenic activity of the compounds of the present invention affords their use in the treatment of angiogenesis-related diseases such as tumours, in particular solid tumours.

More specifically the present invention relates to the use of the compounds of formula (I) for the preparation of pharmaceutical compositions for the therapy and prophylaxis in mammals and in human beings of the angiogenesis and of diseases and disorders wherein angiogenesis is involved, more preferably wherein angiogenesis is mediated by FGF-2.

It is a further object of the present invention the use of the compounds of formula (I), and of the pharmaceutical compositions containing them, for the prophylaxis and the therapy in mammals and in human beings of the angiogenesis and of diseases and disorders where angiogenesis is involved. The diseases and disorders wherein angiogenesis is involved are for example neoplasias, atherosclerosis, psoriasis, arthritis, rheumatoid arthritis, gastric ulcer, endometriosis, Crohn syndrome, sclerodermia, cancer, with particular reference to solid tumours, also in association with other antitumoural drugs, such as for example chemotherapeutics or with radiotherapy or with antitumoural therapies based on the use of viruses, eye pathologies such as for example diabetic retinopathy and aged-related macular degeneration (in abbreviated form AMD).

In particular the administration of the compounds of formula (I) must be carried out with a sufficiently effective amount for the specific treatment. Similarly the dosages, the administration route and the posology will be determined depending on the disease severity, on the physical conditions and characteristics of the patient (for example age, weight, response to the active principle), of the pharmacokinetics and toxicology of the compounds of the invention selected for the specific treatment.

The preferred daily dosage is 0.01-1,000 mg of compounds of formula (I) of the invention per Kg of body weight of the mammal to be treated. In human beings, the preferred daily dosage range is 0.01-1,000 mg of the compound of the invention for Kg of body weight, still more preferred from 1 to 800 mg.

Optionally the use of the compounds of formula (I) can be carried out in association with other drugs. In particular the use of the compounds of formula (I) for the treatment of neoplasias, cancer and solid tumours can be carried out in association with other antitumoural drugs and with antitumoural therapies such as for example radiotherapy or antitumoural therapies based on the use of viruses, as for example oncolytic viruses, as for example oncolytic herpes virus. Examples of antitumoural drugs that can be used in association with those of the present invention are those belonging to the classes hereinafter described:
alkylating agents, for example Nitrogen mustard analogues (for example Cyclophosphamide, Chlorambucil, Melphalan, Chlormethine, Iphosphamide, Trophosphamide, Prednimustine), Alkyl sulphonates (for example Busulfan, treosulfan, Mannosulfan), Ethylene imines (for example Thiotepa, Triaziquinone, Carboquone), Nitrosoureas (for example Carmustine, Lomustine, Semustine, Streptozocin, Fotemustine, Nimustine, Ranimustine), Epoxides (for example Etoglucid), Mitobronitol, Pipobroman, Antimetabolites, for example the analogues of the folic acid (for example Methotrexate, Paltitrexid, Raltitrexed), the analogues of purines (for example Mercaptopurine, Tioguanine, Cladribine, Fludarabine), the analogues of pyrimidines (Cytarabine, Fluorouracil, Tegafur, Carmofur, Gemcitabine), natural alkaloids and other natural compounds, for example alkaloids of vinca (for example Vinblastine, Vincristine, Vindesine, Vinorelbine and mixtures thereof), the derivatives of Podophyllotoxin (for example Etoposide and Teniposide), the derivatives of Colchicine (for example Demecolcine), Taxanes (for example Paclitaxel and Docetaxel), tubulisine and derivatives thereof.

Cytotoxic antibiotics and correlated substances, for example Actinomycines (for example Dactinomycin), Anthracyclines and related substances (for example Doxorubicin, Daunorubicin, Epirubicin, Aclarubicin, Zorubicin, Idraubicin, Mitoxantrone, Piraubicin), Bleomycin, Plicaycin, Mitomycin, Topoisomerase inhibitors, such as camptothecins (for example Irinotecan and Topotecan), topoisomerase inhibitors of type II (for example Amsacrine, Etoposide Phosphate and other derivatives of natural alkaloids of *Podophyllum peltatum*).

Other antineoplastic agents, such as Cisplatin, Carboplatin, Procrbazine, Asparginase, Altretamine, Hydroxycarbamide, Lonidamine, Pentostatin, Miltefosine, Masoprocol, Estramustine, Dacarbazine, Tretinoin, Porfimer sodium, Mitoguazone, Tiazofurine, tamoxifen.

FIGS. 1A-1B show aorta sections taken from C57BL/6 mice as described in Example 20.

The following examples are reported for a better understanding of the present invention but are not meant to limit the scope of the invention.

EXAMPLES

Example 1

Synthesys of the compound N,N'-(propan-1,3-diyl) bis[1-(2,4-dichlorophenyl)]-1,4-dehydro-thieno[3',2': 4,5]cyclopenta[1,2-c]pyrazol-3-carboxamide]

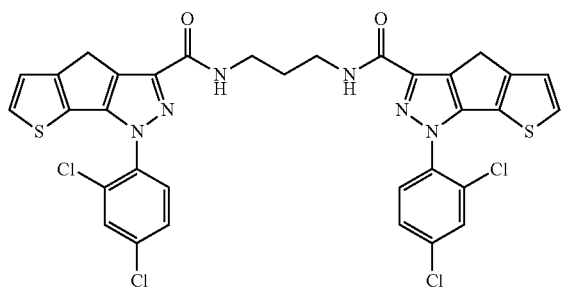 [SMILES: O=C(NCCCNC(=O)c1nn(-c2ccc(Cl)cc2Cl)c2c1Cc1ccsc1-2)c1nn(-c2ccc(Cl)cc2Cl)c2c1Cc1ccsc1-2]

1a. Synthesys of 3-chloro-1-(thiophen-2-yl)propan-1-one

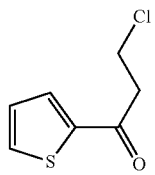

18.1 g of 3-chloropropionyl chloride (142 mmol) are solubilized in dichloromethane (50 mL). The obtained solution is dropwise added to a suspension of $AlCl_3$ (21.6 g; 160 mmoles) in dichloromethane (100 mL). It is left under stirring for 15 minutes at room temperature. A solution of thiophene (12.0 g; 142 mmoles) in dichloromethane (50 mL) is then slowly added while maintaining the temperature at 0° C. At the end the temperature is let to rise to room temperature while stirring for 4 hours. The reaction mixture is poured in a water/ice mixture and then extraction is carried out with diethyl ether. The organic phase is anhydrified with sodium sulphate, filtered and the solvent removed under vacuum. 23.9 g of 3-chloro-1-(thiophen-2-yl)propan-1-one are obtained (yellow oil, yield 99%). $R_f$=0.75 (ligroin/ethyl acetate 7/3 volume/volume); $^1H$ NMR ($CDCl_3$) δ (ppm): 7.66 (dd, 1H, ArH), 7.60 (dd, 1H, ArH); 7.07 (dd, 1H, ArH), 3.82 (t, 2H, $CH_2$); 3.31 (t, 2H, $CH_2$); $^{13}C$ NMR ($CDCl_3$) δ (ppm): 189.5, 143.6, 134.4, 132.5, 128.3, 41.8, 38.6; FT-IR (film) $v_{max}$: 3093.3, 1657.7, 1413.0, 1240.3, 850.4, 720.7 $cm^{-1}$.

1b. Synthesys of 1-(thiophen-2-yl)-prop-2-en-1-one

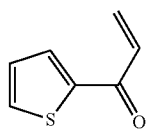

12 g of 3-chloro-1-(thiophen-2-yl)propan-1-one) prepared in Example 1a are solubilized in ethyl ether (180 mL). Triethylamine (10.2 g; 100 mmoles) is added at room temperature. The mixture is left under stirring for 60 hours, then washed with a HCl 10% solution and extracted with ethyl ether (2×20 mL). The organic phase is anhydrified with sodium sulphate, filtered and the solvent removed under vacuum. 9.4 g of 1-(thiophen-2-yl)-prop-2-en-1-one are obtained (yellow oil, yield 99%). $R_f$=0.74 (ligroin/ethyl acetate 8/2 volume/volume); $^1H$ NMR ($CDCl_3$) δ (ppm): 7.76 (m, 1H, ArH), 7.68 (m, 1H, ArH), 7.10 (m, 2H, ArH), 6.49 (m, 1H, $CH_2$), 5.87 (m, 1H, $CH_2$); $^{13}C$ NMR ($CDCl_3$) δ (ppm):

182.4, 144.6, 134.4, 132.5, 131.9, 129.4, 128.3; FT-IR (film) ν$_{max}$: 3094.5, 1645.1, 1409.7, 1240.2, 850.4, 716 cm$^{-1}$.

1c. Synthesis of 4H-cyclopenta[b]thiophen-6(5H)-one

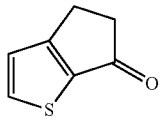

To a solution of 1-(thiophen-2-yl)-prop-2-en-1-one (8.5 g; 62 mmoles) of Example 1b in 1,2-dichloroethane (47 mL) a solution of sulphuric acid (47 mL) is added dropwise at room temperature. The mixture is then heated to 80° C. for 75 minutes. Then cooling to room temperature is carried out and the cooled liquid mass is poured in an ice bath. An extraction with dichloromethane (2×20 mL) is then carried out and the organic phase washed with a 5% NaHCO$_3$ solution, anhydrified with sodium sulphate, filtered and concentrated under vacuum. The obtained residue is purified by chromatography on silica gel with a ligroin/ethyl acetate mixture (elution gradient from 10% to 80% ethyl acetate). After solvent removal 2.4 g of 4H-cyclopenta[b]thiophen-6(5H)-one are isolated (yellow solid; yield 28%). R$_f$=0.54 (ligroin/ethyl acetate 9/7 volume/volume); $^1$H NMR (CDCl$_3$) δ (ppm): 7.89 (d, 1H, ArH), 7.05 (d, 1H, ArH), 3.01 (m, 4H, CH$_2$); $^{13}$C NMR (CDCl$_3$) δ (ppm): 197.3, 169.0, 141.2, 140.5, 124.0, 41.2, 24.0 FT-IR (film) ν$_{max}$: 3063.8, 1668.5, 1419.1, 1248.1, 960.7, 749.8 cm$^{-1}$.

1d. Synthesis of 1-(6-oxo-5,6-dehydro-4H-cyclopenta[b]-thiophen-5-il)pentan-1,2-dione

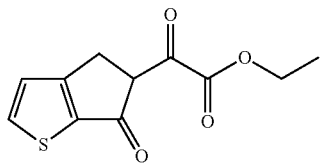 [SMILES: CCOC(=O)C(=O)C1Cc2ccsc2C1=O]

Under a nitrogen flow 0.8 g of metal sodium are solubilized in absolute ethanol (20 mL) at room temperature. Diethyl oxalate (3.7 g; 25 mmoles) is then added dropwise to the solution. Then a solution of 4H-cyclopenta[b]thiophen-6(5H)-one (2.4 g; 17 mmoles) in absolute ethanol (140 mL) is slowly added under stirring. Stirring is continued for 4 hours at room temperature, then the reaction mass is poured in a mixture of ice and 1N HCl solution and it is extracted with chloroform. The organic phase is anhydrified with sodium sulphate, filtered and the solvent removed under vacuum, obtaining 3.9 g of 1-(6-oxo-5,6-dehydro-4H-cyclopenta[b]thiophen-5-yl)pentan-1,2-dione (white solid; yield 95%). R$_f$=0.54 (ligroin/ethyl acetate 9/7 volume/volume); $^1$H NMR (CDCl$_3$) δ (ppm): 7.97 (d, 1H, ArH), 7.14 (d, 1H, ArH), 4.41 (q, 2H, OCH$_2$), 3.87 (s, 2H, CH$_2$), 1.42 (t, 3H, CH$_3$); $^{13}$C NMR (CDCl$_3$) δ (Ppm): 191.3, 164.2, 162.6, 151.4, 141.4, 140.7, 123.8, 120.4, 62.2, 29.8, 14.2; FT-IR (film) ν$_{max}$: 2987.3, 1765.1, 1741.2, 1645.0, 1612.7, 1182.1, 1110.8, 766.0 cm$^{-1}$.

1e. Synthesis of Ethyl 1-(2',4'-dichlorophenyl)-1,4-dehydro-thieno[3',2':4,5]cyclopenta[1,2-c]pyrazol-3-carboxylate

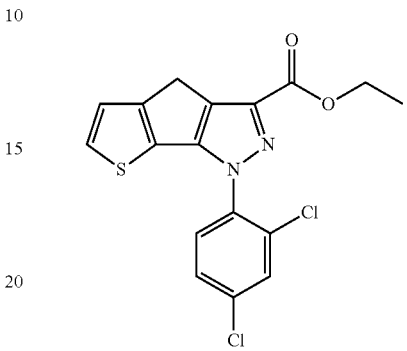

3.8 g of 2,4-dichlorophenylhydrazine hydrochloride are added to an acetic acid (32 mL) solution of 1-(6-oxo-5,6-dehydro-4H-cyclopenta[b]thiophen-5-yl)pentan-1,2-dione (3.9 g; 16 mmoles) prepared in example 1d. It is left under stirring for 4 hours at room temperature and then the reaction mixture is heated under reflux for 16 hours. At the end, after cooling to room temperature, the reaction mixture is diluted with water (50 mL). The precipitate formed is filtered, washed with water and anhydrified. 3.7 g of ethyl 1-(2',4'-dichlorophenyl)-1,4-dehydro-thieno[3',2':4,5]cyclopenta[1,2-c]pyrazol-3-carboxylate are obtained (yellow solid; yield 60%). R$_f$=0.63 (ligroin/ethyl acetate 8/2 volume/volume); $^1$H NMR (CDCl$_3$) δ (ppm): 7.61 (d, 1H, ArH), 7.58 (d, 1H, ArH), 7.43 (dd, 1H, ArH), 7.30 (d, 1H, ArH), 7.13 (d, 1H, ArH), 4.47 (q, 2H, OCH$_2$), 3.73 (s, 2H, CH$_2$), 1.44 (t, 3H, CH$_3$); $^{13}$C NMR (CDCl$_3$) δ (ppm): 167.3, 155.0, 149.2, 139.4, 136.2, 135.4, 132.0, 130.8, 130.6, 130.2, 129.3, 128.3, 123.5, 28.5; FT-IR (film) ν$_{max}$: 2976.4, 2926.6, 1727.5, 1262.7, 1175.8, 1102.7 cm$^{-1}$.

1f. Synthesis of 1-(2',4'-dichlorophenyl)-1,4-dehydro-thieno[3',2':4,5]cyclopenta[1,2-c]pyrazol-3-carboxylic acid

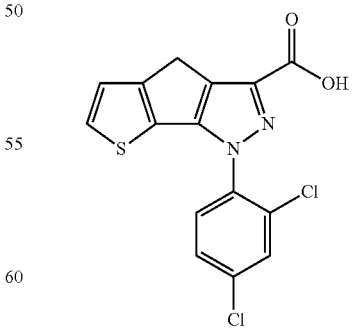

To a solution in tetrahydrofuran (THF)/H$_2$O 4/1 volume/volume (5 mL) of ethyl 1-(2',4'-dichlorophenyl)-1,4-dehydro-thieno[3',2':4,5]cyclopenta[1,2-c]pyrazol-3-carboxylate (200 mg; 0.5 mmoles) prepared in example 1e, lithium hydroxide (30 mg; 0.7 mmoles) is added. The mixture is heated to 60° C. for 5 hours, then it is cooled at room temperature and diluted with water (3 mL). A 1N HCl solution is added to bring the pH of the reaction mixture between 1-2. A precipitate is formed is that collected by filtration and washed with ethyl ether (2×10 mL). 200 mg of 1-(2',4'-dichlorophenyl)-1,4-dehydro-thieno[3',2':4,5]cyclo-penta[1,2-c]pyrazol-3-carboxylic acid are isolated (yellow solid; yield 88%). $R_f$=0.47 (chloroform/methanol 3/1 volume/volume); $^1$H NMR (DMSO) δ (ppm): 13.15 (s, 1H, OH), 8.03 (d, 1H, ArH), 7.79 (d, 1H, ArH), 7.71 (dd, 1H, ArH), 7.59 (d, 1H, ArH), 7.25 (d, 1H, ArH), 3.71 (s, 2H, $CH_2$); $^{13}$C NMR (DMSO) δ (ppm): 163.3, 155.5, 148.2, 140.3, 135.8, 135.6, 131.8, 130.7, 130.5, 130.4, 129.8, 129.4, 129.2, 124.4, 28.6; FT-IR (film) $\nu_{max}$: 3093.8, 2904.8, 2578.4, 1696.6, 1471.4, 1299.3, 1178.7, 715.2 $cm^{-1}$.

1g. Synthesis of N,N'-(propan-1,3-diyl)bis[1-(2,4-dichloro phenyl)]-1,4-dehydro-thieno[3',2':4,5]cyclopenta[1,2-c]pyrazol-3-carboxamide]

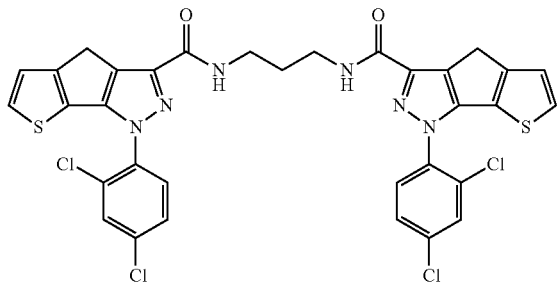 [SMILES: O=C(NCCCNC(=O)c1nn(-c2ccc(Cl)cc2Cl)c2c1Cc1ccsc1-2)c1nn(-c2ccc(Cl)cc2Cl)c2c1Cc1ccsc1-2]

A solution in toluene (21 mL) of the compound 1-(2',4'-dichlorophenyl)-1,4-dehydro-thieno[3',2':4,5]cyclopenta[1,2-c]pyrazol-3-carboxylic acid (400 mg; 1 mmole) prepared in example 1g, and thionyl chloride (400 mg; 2.9 mmoles), is heated under reflux for one hour. At the end the solvent is removed under vacuum and the obtained residue is dissolved in dichloromethane (7 mL). A solution in dichloromethane (7 mL) of triethylamine (300 mg; 2.5 mmoles) and 1,3-diaminopropane (70 mg; 1 mmole) is dropwise added while cooling at 0° C. The temperature of the resulting mixture is let to rise to room temperature under stirring continued for 16 hours. The solvent is removed under vacuum and the obtained residue is purified by flash chromatography on silica gel by using as eluent a mixture chloroform/methanol 25/1 volume/volume. After evaporation of the solvent 400 mg of N,N'-(propan-1,3-diyl)bis[1-(2,4-dichlorophenyl)]-1,4-dehydro-thieno-[3',2':4,5]cyclo-penta[1,2-c]pyrazol-3-carboxamide] are obtained (white solid, yield 60%). $R_f$=0.76 (chloroform/methanol 30/1 volume/volume); $^1$H NMR (CDCl$_3$) δ (ppm): 7.61 (d, 2H, ArH), 7.50 (d, 2H, ArH), 7.39 (dd, 2H, ArH), 7.32 (t, 2H, NH), 7.29 (d, 2H, ArH), 7.14 (d, 2H, ArH), 3.75 (s, 4H, $CH_2$), 3.58 (q, 4H, $CH_2$), 1.94 (q, 2H, $CH_2$), $^{13}$C NMR (CDCl$_3$) δ (ppm): 162.2, 155.3, 148.8, 142.1, 135.7, 135.6, 130.7, 130.6, 130.4, 130.3, 129.0, 128.2, 127.6, 123.6, 36.6, 30.0, 28.3; FT-IR (film) $\nu_{max}$: 3367.4, 1658.6, 1485.8, 1181.1, 708.8 $cm^{-1}$.

Example 2

Synthesis of 3,3'-(propane-1,3-diylbis(azanediyl))bis (oxomethylene)bis(1-(2,4-dichlorophenyl)-1,4-dihydro-thieno[3',2':4,5]cyclopenta[1,2-c]pyrazole-6-sulfonic acid)

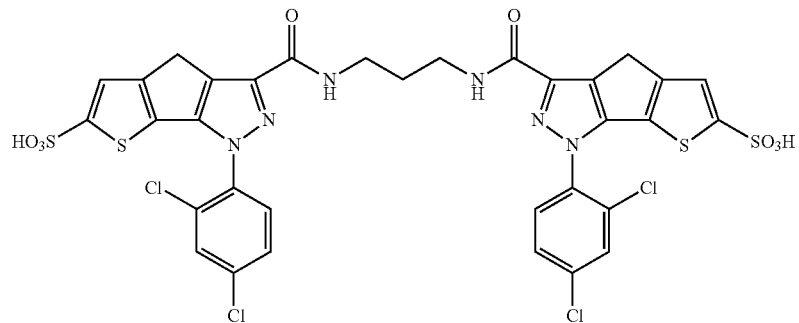 [SMILES: O=C(NCCCNC(=O)c1nn(-c2ccc(Cl)cc2Cl)c2c1Cc1cc(S(=O)(=O)O)sc1-2)c1nn(-c2ccc(Cl)cc2Cl)c2c1Cc1cc(S(=O)(=O)O)sc1-2]

100 mg of the diamide prepared in example 1 are dissolved in dichloromethane (5 mL). The solution is cooled at −10° C. A mixture of acetic anhydride (84 mg; 0.8 mmoles) and sulphuric acid 98% (30 mg; 0.3 mmoles) is added. The resulting mixture is left under stirring for 16 hours while letting the temperature of the solution to rise to room temperature. The solvent is removed under vacuum and the thus obtained residue purified on a chromatographic column of silica gel eluted with a mixture chloroform/methanol 2/1 volume/volume. After solvent removal, 90 mg of the titled compound were isolated (white solid, yield 75%). $R_f$=0.22 (chloroform/methanol 2/1 volume/volume); $^1$H NMR (DMSO) δ (ppm): 8.46 (t, 2H, NH), 8.06 (d, 2H, ArH), 7.83 (d, 2H, ArH), 7.73 (dd, 2H, ArH), 7.28 (s, 2H, ArH), 3.71 (s, 4H, $CH_2$), 3.34 (q, 4H, $NHCH_2$), 1.78 (q, 2H, $NHCH_2CH_2$); $^{13}$C NMR (DMSO) δ (ppm): 161.4, 154.1, 154.0, 148.4, 142.8, 135.7, 135.4, 130.7, 130.6, 130.5, 129.9, 129.4, 129.3, 122.6, 36.5, 29.9, 28.8; FT-IR (film) $v_{max}$: 3381.4, 1643.0, 1486.9, 1171.2, 1064.2, 647.1 cm$^{-1}$.

Example 3

Synthesis of N,N'-(hexan-1,6-diyl)bis[1-(2,4-dichlorophenyl)]-1,4-dehydro-thieno[3',2':4,5]cyclopenta[1,2-c]pyrazol-3-carboxamide]

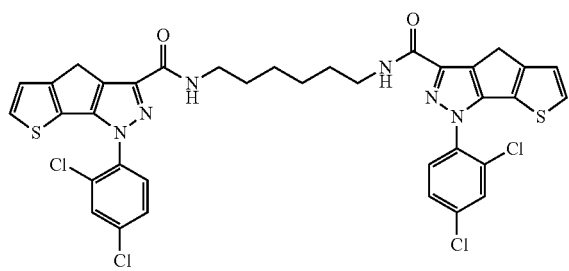 [SMILES: O=C(NCCCCCCNC(=O)c1nn(-c2ccc(Cl)cc2Cl)c2c1Cc1ccsc1-2)c1nn(-c2ccc(Cl)cc2Cl)c2c1Cc1ccsc1-2]

100 mg of 1-(2',4'-dichlorophenyl)-1,4-dehydro-thieno[3',2':4,5]cyclopenta[1,2-c]pyrazol-3-carboxylic acid prepared in example 1f and 100 mg of thionyl chloride are dissolved in toluene (6 mL). The solution is heated under reflux for one hour. The solvent is then removed under vacuum and the obtained residue dissolved in dichloromethane (2 mL). A solution of triethylamine (70 mg; 0.7 mmoles) and 1,6-hexamethylenediamine (32 mg; 0.3 mmoles) in dichloromethane (2 mL) is dropwise added. The temperature of the solution is let to rise to room temperature while stirring for 16 hours. The solvent is removed under vacuum and the obtained residue is purified by flash chromatography on silica gel by using as eluent a mixture chloroform/methanol 48:1 volume/volume. 84 mg of N,N'-(hexan-1,6-diyl)bis[1-(2,4-dichlorophenyl)]-1,4-dehydro-thieno[3',2':4,5]cyclopenta[1,2-c]pyrazol-3-carboxamide] are recovered (white solid; yield 77%). R$_f$=0.38 (chloroform/methanol 96/1 volume/volume); $^1$H NMR (CDCl$_3$) δ (ppm): 7.64 (d, 2H, ArH), 7.54 (d, 2H, ArH), 7.43 (dd, 2H, ArH), 7.29 (d, 2H, ArH), 7.14 (d, 2H, ArH), 6.95 (t, 2H, NH), 3.76 (s, 4H, CH$_2$), 3.45 (q, 4H, CH$_2$), 1.64 (q, 4H, CH$_2$), 1.45 (q, 4H, CH$_2$); $^{13}$C NMR (CDCl$_3$) δ (ppm): 161.8, 155.4, 148.8, 142.3, 135.7, 135.6, 130.8, 130.7, 130.4, 130.3, 129.0, 128.2, 127.6, 123.6, 39.0, 29.6, 28.3, 26.7; FT-IR (film) $v_{max}$: 2932.3, 1647.7, 1488.5, 1186.6, 978.6, 713.3 cm$^{-1}$.

Example 4

Synthesis of 3,3'-(hexane-1,6-diylbis(azanediyl))bis(oxo methylene)bis(1-(2,4-dichlorophenyl)-1,4-dihydro-thieno[3',2':4,5]cyclopenta[1,2-c]pyrazole-6-sulfonic acid)

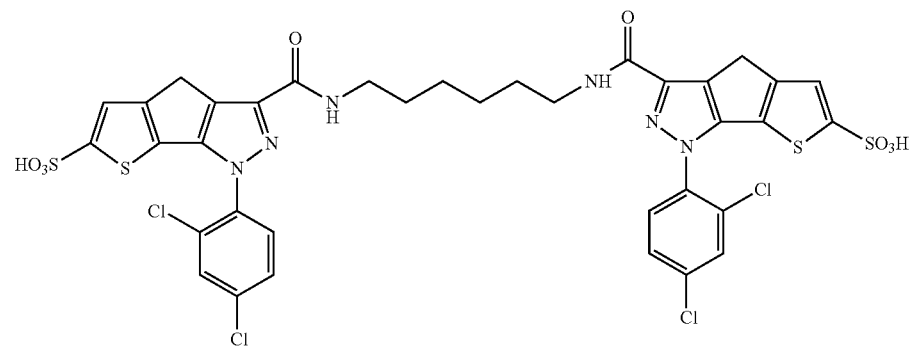 [SMILES: O=C(NCCCCCCNC(=O)c1nn(-c2ccc(Cl)cc2Cl)c2c1Cc1cc(S(=O)(=O)O)sc1-2)c1nn(-c2ccc(Cl)cc2Cl)c2c1Cc1cc(S(=O)(=O)O)sc1-2]

80 mg of the compound prepared in example 3 are solubilized in dichloromethane (5 mL). The solution is cooled at −10° C. and a mixture of acetic anhydride (60 mg; 0.6 mmoles) and sulphuric acid 98% (20 mg; 0.2 mmoles) is added. The solution is left under stirring for 16 hours while letting the temperature of the solution to rise to room temperature. The solvent is removed under vacuum and the obtained residue is purified by chromatography on silica gel by using as eluent a chloroform/methanol 2:1 volume/volume mixture. 30 mg of the titled compound are obtained (white solid; yield 29%). R$_f$=0.20 (chloroform/methanol 2/1 volume/volume); $^1$H NMR (DMSO) δ (ppm): 8.32 (t, 2H, NH), 8.06 (d, 2H, ArH), 7.83 (d, 2H, ArH), 7.73 (dd, 2H, ArH), 7.27 (s, 2H, ArH), 3.69 (s, 4H, CH)), 3.27 (q, 4H, NHCH$_2$), 1.56 (q, 2H, NHCH$_2$CH$_2$), 1.35 (q, 2H, NHCH$_2$CH$_2$CH$_2$); $^{13}$C NMR (DMSO) δ (ppm): 161.3, 154.1, 154.0, 148.3, 142.9, 135.7, 135.4, 130.6, 130.5, 129.9, 129.4, 129.3, 122.5, 39.0, 29.7, 28.8, 26.7; FT-IR (film) $v_{max}$: 3396.2, 1632.7, 1486.2, 1177.9, 1062.6, 649.2 cm$^{-1}$.

Example 5

Synthesis of the compound N,N'-(propan-1,3-diyl)bis[1-(4-methyl benzyl)]-1,4-dehydro-thieno[3',2':4,5]cyclopenta[1,2-c]pyrazol-3-carboxamide]

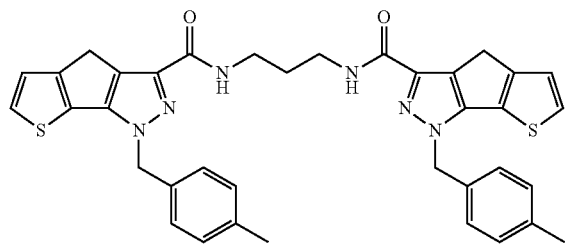 [SMILES: Cc1ccc(Cn2nc(C(=O)NCCCNC(=O)c3nn(Cc4ccc(C)cc4)c4c3Cc3ccsc3-4)c3c2-c2sccc2C3)cc1]

5a. Synthesis of ethyl 1-[(4'-methyl)phenyl]methyl-1,4-dehydro-thieno[3',2':4,5]cyclopenta[1,2-c]pyrazol-3-carboxylate

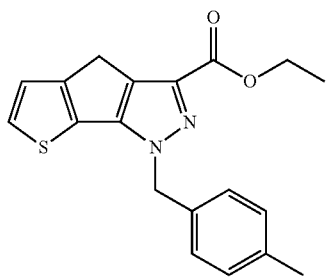 [SMILES: CCOC(=O)c1nn(Cc2ccc(C)cc2)c2c1Cc1ccsc1-2]

1.7 g of p-methyl-benzylhydrazine hydrochloride are added to an acetic acid (16 mL) solution of 1-(6-oxo-5,6-dehydro-4H-cyclopenta[b]thiophen-5-yl)pentan-1,2-dione (2.1 g; 8.8 mmoles) prepared in example 1d. The mixture is left under stirring for 4 hours at room temperature and then heated under reflux conditions for 16 hours. At the end the reaction mixture is cooled at room temperature and diluted with water (40 mL). A precipitate is formed that is filtered, washed with water and dehydrated, obtaining 2.8 g of ethyl 1-[(4'-methyl)phenyl]methyl-1,4-dehydro-thieno[3',2':4,5]cyclopenta[1,2-c]pyrazol-3-carboxylate (yellow solid; yield 95%). $R_f$=0.42 (ligroin/ethyl acetate 8/2 volume/volume); $^1$H NMR (CDCl$_3$) δ (ppm): 7.28 (d, 2H, ArH), 7.17 (m, 3H, ArH), 7.03 (d, 1H, ArH), 5.46 (s, 2H, CH$_2$), 4.44 (q, 2H, OCH$_2$), 3.58 (s, 2H, CH$_2$), 2.33 (s, 3H, CH$_3$), 1.43 (t, 3H, CH$_3$); $^{13}$C NMR (CDCl$_3$) δ (ppm): 162.5, 153.8, 146.4, 138.5, 137.1, 132.3, 131.8, 130.6, 129.7, 128.3, 127.3, 123.5, 60.9, 56.1, 28.2, 21.2, 14.5; FT-IR (film) $v_{max}$: 3431.5, 3101.7, 3026.0, 2983.4, 1724.9, 1257.0, 1247.1, 1234.2, 1109.0, 1087.0, 1017.1, 791.8, 782.0, 729.6, 715.3, 621.1, 594.5 cm$^{-1}$.

5b. Synthesis of 1-[(4-methyl)benzyl]-1,4-dehydro-thieno[3',2':4,5]cyclopenta[1,2-c]pyrazol-3-carboxylic acid

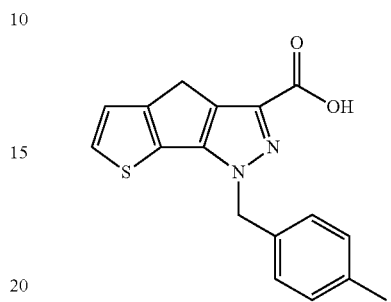

1 g of ethyl 1-[(4'-methyl)phenyl]methyl-1,4-dehydro-thieno[3',2':4,5]cyclopenta[1,2-c]pyrazol-3-carboxylate prepared in example 5a is solubilized in 25 mL of THF/H$_2$O 4:1 volume/volume. To the obtained solution lithium hydroxide (150 mg; 3.6 mmoles) is added. The mixture is heated to 60° C. for 5 hours, then it is cooled at room temperature and diluted with water (10 mL). A solution of HCl 1N is then added to lower the pH in the range 1-2. A precipitate is formed which is filtered, washed with ethyl ether (2×20 mL) and dried. 270 mg of 1-[(4-methyl)benzyl]-1,4-dehydro-thieno[3',2':4,5]cyclopenta[1,2-c]pyrazol-3-carbo-xylic acid are obtained (yellow solid; yield 30%). $R_f$=0.58 (chloroform/methanol 3/1 volume/volume); $^1$H NMR (DMSO) δ (ppm): 12.83 (s, 1H, OH), 7.48 (d, 1H, ArH), 7.20 (m, 5H, Aril), 5.47 (s, 2H, CH$_2$), 3.54 (s, 2H, CH$_2$), 2.27 (s, 3H, CH$_3$); $^{13}$C NMR (DMSO) δ (ppm): 162.5, 153.8, 146.4, 138.5, 137.1, 132.3, 131.8, 130.6, 129.7, 128.3, 127.3, 123.5, 60.7, 56.1, 28.2, 21.2, 14.5; FT-IR (film) $v_{max}$: 3080.7, 2903.4, 1677.5, 1310.3, 1271.9, 1246.2, 1178.7, 873.1, 715.9, 591.5 cm$^{-1}$.

5c. Synthesis of the compound N,N'-(propan-1,3-diyl)bis[1-(4-methyl benzyl)]-1,4-dehydro-thieno[3',2':4,5]cyclopenta[1,2-c]pyrazol-3-carboxamide]

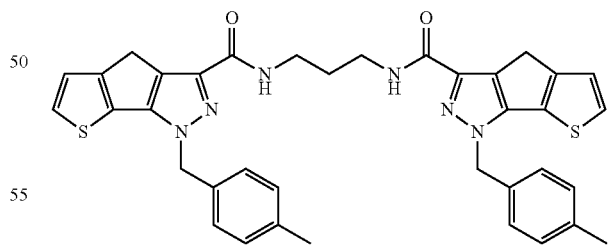

400 mg of 1-[(4-methyl)benzyl]-1,4-dehydro-thieno[3',2':4,5]cyclopenta[1,2-c]pyrazol-3-carboxylic acid prepared in example 5b and 300 mg of thionyl chloride are solubilized in toluene (18 mL). The solution is heated under reflux for one hour. The solvent is then removed under vacuum and the residue is dissolved in dichloromethane (6 mL). A solution in dichloromethane (6 mL) of triethylamine (200 mg; 2.1 mmoles) and 1,3-diaminopropane (63 mg; 0.9 mmoles) is dropwise added while cooling and maintaining the temperature at 0° C. The reaction mass is let to warm to room temperature under stirring continued for 16 hours. The solvent is then removed under vacuum and the obtained residue is purified by flash chromatography on silica gel eluted with a chloroform/methanol 75/1 volume/volume mixture. 270 mg of N,N'-(propan-1,3-diyl)bis[1-(4-methylbenzyl)]-1,4-dehydro-thieno[3',2':4,5]cyclopenta[1,2-c]pyrazol-3-carboxamide] are obtained (white solid, yield 50%). $R_f$=0.55 (chloroform/methanol 75/1 volume/volume); $^1$H NMR (CDCl$_3$) δ (ppm): 7.30 (t, 2H, NH), 7.20 (m, 10H, ArH), 7.05 (d, 2H, ArH), 5.33 (s, 4H, CH$_2$), 3.65 (s, 4H, CH$_2$), 3.58 (q, 4H, CH$_2$), 2.33 (s, 6H, CH$_3$), 1.94 (q, 2H, CH$_2$); $^{13}$C NMR (CDCl$_3$) δ (ppm): 162.7, 154.4, 146.7, 139.9, 138.4, 132.1, 130.5, 130.3, 129.7, 128.1, 126.9, 123.7, 55.7, 36.4, 30.1, 28.1, 21.2; FT-IR (film) $v_{max}$: 3446.0, 2942.8, 2914.0, 1633.1, 1551.2, 1434.0, 1295.8, 1018.8, 770.1, 749.9, 730.5, 718.8, 701.2, 624.2, 588.7, 569.4, 533.9, 517.5 cm$^{-1}$.

Example 6

Synthesis of 3,3'-(propane-1,3-diylbis(azanediyl))bis(oxo methylene)bis(1-(4-methylbenzyl)-1,4-dihydro-thieno[3',2':4,5]cyclopenta[1,2-c]pyrazole-6-sulfonic acid)

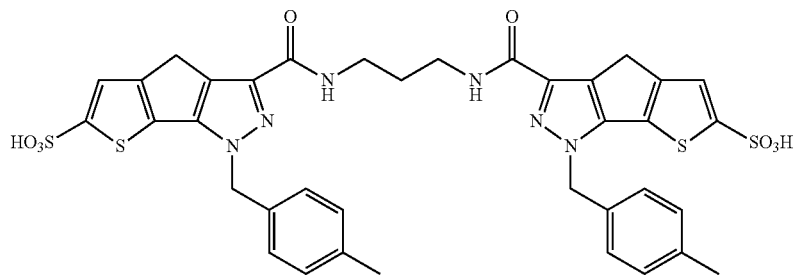 [SMILES: Cc1ccc(Cn2nc(C(=O)NCCCNC(=O)c3nn(Cc4ccc(C)cc4)c4c3Cc3cc(S(=O)(=O)O)sc3-4)c3c2-c2sc(S(=O)(=O)O)cc2C3)cc1]

100 mg of the compound prepared in example 5c are solubilized in dichloromethane (5 mL). The solution is cooled at −10° C. A mixture of acetic anhydride (96 mg; 0.9 mmoles) and sulphuric acid 98% (34 mg; 0.3 mmoles) is added and then the mixture is let to warm to room temperature under stirring for 16 hours. At the end the solvent is removed under vacuum and the obtained residue is purified by chromatography on a silica gel column eluted with a chloroform/methanol 2/1 volume/volume mixture. 110 mg of the titled compound are obtained (white solid; yield 90%). $R_f$=0.21 (chloroform/methanol 2/1 volume/volume); $^1$H NMR (DMSO) δ (ppm): 8.28 (t, 2H, NH), 7.19 (m, 8H, ArH), 7.14 (s, 2H, ArH), 5.43 (s, 4H, CH$_2$), 3.51 (s, 4H, CH$_2$), 3.30 (q, 4H, NHCH$_2$), 2.27 (s, 6H, CH$_3$), 1.73 (q, 2H, NHCH$_2$CH$_2$); $^{13}$C NMR (DMSO) δ (ppm): 161.8, 156.1, 153.4, 152.8, 146.2, 140.4, 138.0, 133.4, 129.9, 129.8, 128.1, 122.5, 55.1, 36.4, 28.5, 21.2; FT-IR (film) $v_{max}$: 3397.6, 2922.2, 2851.8, 1716.5, 1633.9, 1556.6, 1180.0, 1060.3, 1000.1, 770.8, 620.1 cm$^{-1}$.

Example 7

Synthesis of N,N'-(hexan-1,6-diyl)bis[1-(4-methylbenzyl)]-1,4-dehydro-thieno[3',2':4,5]cyclopenta[1,2-c]pyrazol-3-carboxamide]

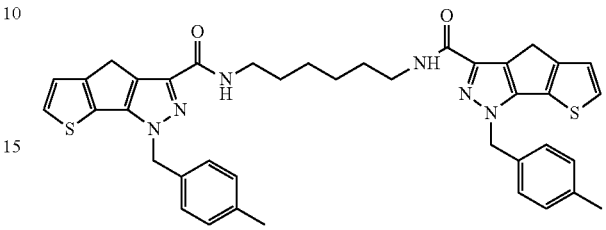

100 mg of 1-[(4-methyl)benzyl]-1,4-dehydro-thieno[3',2':4,5]cyclopenta[1,2-c]pyrazol-3-carboxylic acid prepared in example 5b and 100 mg of thionyl chloride are solubilized in toluene (10 mL). The solution is heated under reflux conditions for one hour. The solvent is then removed under vacuum and the residue solubilized in dichloromethane (4 mL). A solution in dichloromethane (4 mL) of triethylamine (85 mg; 0.9 mmoles) and 1,6-hexandiamine (40 mg; 0.3 mmoles) is dropwise added, while cooling and maintaining the temperature at 0° C. Then the reaction mixture is let to warm to room temperature while maintaining the reaction mixture under stirring for 16 hours. At the end the solvent is removed under vacuum and the obtained residue is purified by flash chromatography on silica gel by using as eluent a chloroform/methanol 48/1 volume/volume mixture. 70 mg of N,N'-(hexan-1,6-diyl)bis[1-(4-methylbenzyl)]-1,4-dehydro-thieno[3',2':4,5]cyclopenta[1,2-c]pyrazol-3-carboxamide] are obtained (white solid, yield 30%). $R_f$=0.52 (chloroform/methanol 48/1 volume/volume); $^1$H NMR (CDCl$_3$) δ (ppm): 7.22 (m, 4H, ArH), 7.13 (m, 6H, ArH), 7.05 (d, 2H, ArH), 6.96 (t, 2H, NH), 5.35 (s, 4H, CH$_2$), 3.64 (s, 4H, CH$_2$), 3.58 (q, 4H, CH$_2$), 3.42 (q, 4H, CH$_2$), 2.33 (s, 6H, CH$_3$), 1.66 (q, 4H, CH$_2$), 1.46 (q, 4H, CH$_2$); $^{13}$C NMR (CDCl$_3$) δ (ppm): 162.3, 154.5, 146.8, 140.1, 138.4, 132.2, 130.4, 130.3, 129.7, 128.1, 126.9, 123.7, 55.6, 39.0, 29.7, 28.1, 26.7, 21.2; FT-IR (film) $v_{max}$: 3337.6, 3068.6, 2925.7, 2855.6, 1641.4, 1541.0, 1481.4, 1295.8, 1269.5, 1137.2, 1022.1, 779.5, 741.6, 554.7 cm$^{-1}$.

Example 8

Synthesis of 3,3'-(hexane-1,6-diylbis(azanediyl))bis(oxo methylene)bis(1-(4-methylbenzyl)-1,4-dihydro-thieno[3',2':4,5]cyclopenta[1,2-c]pyrazole-6-sulfonic acid)

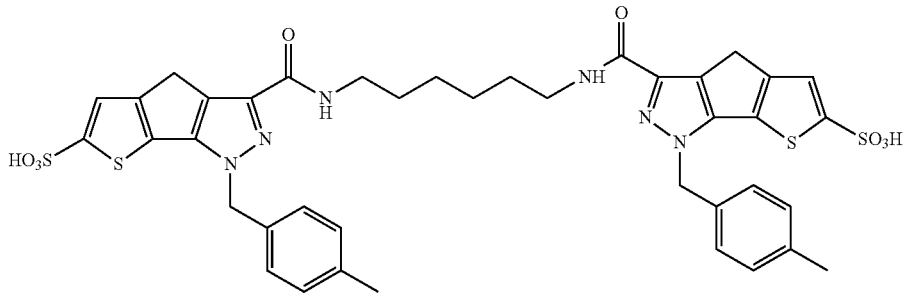 [SMILES: Cc1ccc(Cn2nc(C(=O)NCCCCCCNC(=O)c3nn(Cc4ccc(C)cc4)c4c3Cc3cc(S(=O)(=O)O)sc3-4)c3c2-c2sc(S(=O)(=O)O)cc2C3)cc1]

70 mg of the compound prepared in example 7 are solubilized in dichloromethane (5 mL). The mixture is cooled at −10° C. A mixture of acetic anhydride (60 mg; 0.6 mmoles) and sulphuric acid 98% (21 mg; 0.2 mmoles) is added. The solution is let to warm to room temperature while kept under stirring for 16 hours. The solvent is then removed under vacuum and the obtained residue purified by chromatography on silica gel by using as eluent a chloroform/methanol 2/1 volume/volume mixture. 70 mg of the titled compound are obtained (white solid; yield 80%). $R_f$=0.20 (chloroform/methanol 2/1 volume/volume); $^1$H NMR (DMSO) δ (ppm): 8.11 (t, 2H, NH), 7.18 (m, 8H, ArH), 7.15 (s, 2H, ArH), 5.41 (s, 4H, CH$_2$), 3.49 (s, 4H, CH$_2$), 3.22 (q, 4H, NHCH$_2$), 2.25 (s, 6H, CH$_3$), 1.52 (q, 2H, NHCH$_2$CH$_2$), 1.31 (q, 2H, NHCH$_2$CH$_2$CH$_2$); $^{13}$C NMR (DMSO) δ (ppm): 161.8, 153.1, 152.8, 146.1, 140.5, 138.0, 133.4, 130.0, 129.9, 128.1, 122.7, 55.1, 38.9, 29.7, 28.5, 26.7, 21.2; FT-IR (film) $\nu_{max}$: 3565.3, 3445.2, 2923.4, 2854.7, 1634.0, 1199.8, 1175.4, 1031.1, 997.1, 878.2, 721.0, 705.0, 590.6 cm$^{-1}$.

Example 9

Synthesis of the compound N,N'-(propan-1,3-diyl)bis[1-(2,4-dichloro phenyl)]-1,4-dehydro-thieno[3',2':4,5]cyclohepta[1,2-c]pyrazol-3-carboxamide]

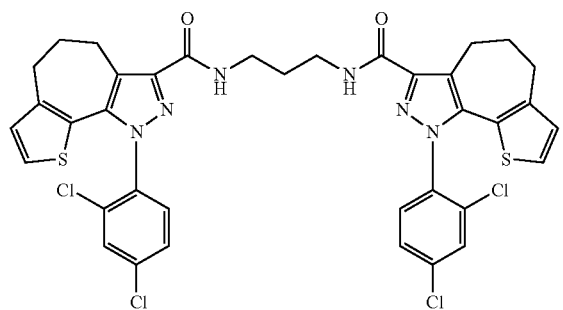 [SMILES: O=C(NCCCNC(=O)c1nn(-c2ccc(Cl)cc2Cl)c2c1CCCc1ccsc1-2)c1nn(-c2ccc(Cl)cc2Cl)c2c1CCCc1ccsc1-2]

9a. Synthesis of the 5-(thiophen-3-yl)-pent-4-enoic acid

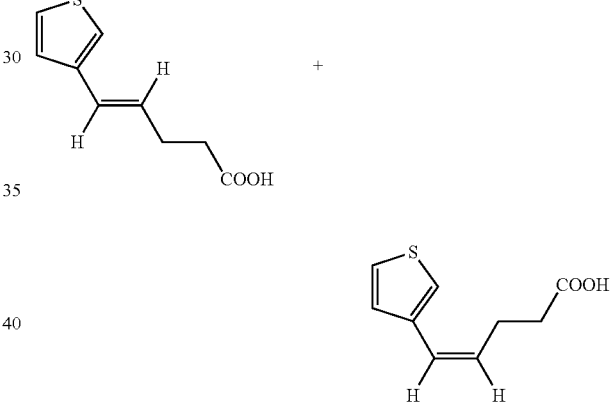

To a suspension in DMSO/THF 1:1 volume/volume (26 mL) of 3-thiophencarboxaldehyde (2.0 g; 18 mmoles) and 2-(carboxyethyl) (triphenyl)phosphonium bromide (8.9 g; 21 mmoles) 5.3 g of potassium t-butoxide are added. The reaction mixture is left under stirring for 2 hours at room temperature. Then the organic phase is washed with water (20 mL) and extracted with chloroform (2×20 mL). The solvent is removed and the aqueous phase is acidified with concentrated HCl and extracted with chloroform (2×20 mL). The organic phase is recovered and washed with water and dried with sodium sulphate. After filtration, the organic phase is concentrated under vacuum. The obtained residue is purified by chromatography on silica gel by using as eluent a ligroin/ethyl acetate 1:1 volume/volume mixture. 2.3 g of a mixture of the two cis and trans diastereoisomers of the 5-(thiophen-3-il)-pent-4-enoic acid are obtained (yield 70%). $R_f$=0.35 (ligroin/ethyl acetate 6/4 volume/volume); $^1$H NMR (CDCl$_3$) δ (ppm): 7.29 (m, 1H, ArH), 7.23 (m, 1H, ArH), 7.18 (m, 2H, ArH), 7.09 (m, 2H, ArH), 6.44 (m, 2H, CH), 6.06 (m, 1H, CH), 5.57 (m, 2H, CH), 2.68 (m, 2H, CH$_2$), 2.52 (m, 6H, CH$_2$); $^{13}$C NMR (CDCl$_3$) δ (ppm): 179.2, 179.1, 139.9, 138.2, 128.9, 128.5, 127.9, 125.9, 125.5, 125.2, 124.9, 124.5, 123.1, 121.2, 33.9, 33.8, 27.8, 24.2; FT-IR (film) $v_{max}$: 3098.1, 2923.5, 1693.2, 1410.6, 1267.7, 1242.6, 1206.6, 1155.3, 966.1, 755.4 cm$^{-1}$.

9b. Synthesis of the 5-(thiophen-3-yl)-pentanoic acid

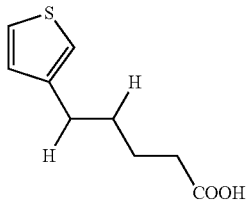 [SMILES: O=C(O)CCCCc1ccsc1]

3.3 g of the cis and trans mixture of 5-(thiophen-3-yl)-pent-4-enoic acid prepared in example 9a are solubilized in absolute ethanol (50 mL). The compound is then submitted to an hydrogenation reaction with hydrogen (3 atm of H$_2$) on Pd/C 10% (180 mg) carried out at room temperature for a time of 18 hours. The reaction mixture is then filtered on celite and washed with methanol (3×10 mL). The solvent is removed under vacuum, obtaining 2.6 g of the 5-(thiophen-3-yl)-pentanoic acid (yield 80%). $R_f$=0.35 (ligroin/ethyl acetate 6/4 volume/volume); $^1$H NMR (CDCl$_3$) δ (ppm): 8.35 (s, 1H, OH broad), 7.24 (m, 1H, ArH), 6.93 (m, 2H, ArH), 2.66 (m, 2H, CH$_2$), 2.38 (m, 2H, CH$_2$), 1.69 (m, 4H, CH$_2$); $^{13}$C NMR (CDCl$_3$) δ (ppm): 179.8, 142.3, 128.2, 125.3, 120.1, 33.9, 29.9, 24.4; FT-IR (film) $v_{max}$: 2944.3, 2865.4, 1692.9, 1462.7, 1425.3, 1307.6, 1258.2, 1212.9, 1190.2, 930.2, 750.8, 592.0 cm$^{-1}$.

9c. Synthesis of 6,7-dehydro-4H-cyclohepta[b]thiophen-8(5H)-one

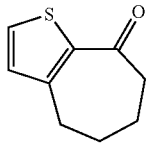 [SMILES: O=C1CCCCc2ccsc21]

1 g of the compound 5-(thiophen-3-yl)-pentanoic acid prepared in example 9b is solubilized in anhydrous ethyl ether (15 mL). Thionyl chloride (710 mg; 6.0 mmoles) and two drops of pyridine are added. The solution is heated under reflux conditions for 3 hours. The solvent is then removed under vacuum and the obtained organic residue is solubilized in dichloromethane (4 mL). After cooling at 0° C., a solution of SnCl$_4$ (2.5 g; 9.7 mmoles) in dichloromethane (52 mL) is added. The reaction mixture is then let to warm to room temperature while kept under stirring for 14 hours. At the end a 2N HCl solution is added. The organic phase is then separated, anhydrified with sodium sulphate, filtered and concentrated under vacuum. The obtained residue is purified by chromatography on silica gel using as eluent a ligroin/ethyl acetate 7/1 volume/volume mixture. 250 mg of 6,7-dehydro-4H-cyclohepta[b]thiophen-8(5H)-one are obtained (yield 28%). $R_f$=0.66 (ligroin/ethyl acetate 7/1 volume/volume); $^1$H NMR (CDCl$_3$) δ (ppm): 7.49 (d, 1H, ArH), 6.90 (d, 1H, ArH), 2.98 (m, 2H, CH$_2$), 2.77 (m, 2H, CH$_2$), 1.91 (m, 4H, CH$_2$); $^{13}$C NMR (CDCl$_3$) δ (ppm): 195.8, 148.8, 141.0, 132.4, 131.2, 41.5, 29.4, 25.4, 21.6; FT-IR (film) $v_{max}$: 3097.9, 2935.1, 2864.8, 1633.8, 1528.3, 1414.0, 1285.9, 839.2, 738.2, 692.4, 659.3, 540.3 cm$^{-1}$.

9d. Synthesis of ethyl 2-oxo-2-(8-oxo-5,6,7,8-tetrahydro-4H-cyclohepta[b]thiophen-7-il)acetate

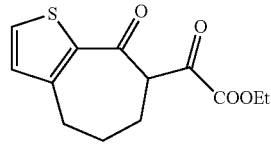 [SMILES: CCOC(=O)C(=O)C1CCCc2ccsc2C1=O]

200 mg of sodium are solubilized in absolute ethanol (5 mL) at room temperature under a nitrogen flow. To this solution diethyl oxalate (880 mg; 6.0 mmoles) is dropwise added. Then a solution in absolute ethanol (33 mL) of 6,7-dehydro-4H-cyclohepta[b]thiophen-8(5H)-one (670 mg; 4.0 mmoles) prepared in example 9c is slowly added. It is left under stirring for 4 hours at room temperature and then the organic solution is poured into an ice mixture with an aqueous HCl 1N solution. The aqueous phase is extracted with chloroform. The organic phase is anhydrified with sodium sulphate, filtered and concentrated under vacuum. 560 mg of ethyl 2-oxo-2-(8-oxo-5,6,7,8-tetrahydro-4H-cyclo hepta[b]thiophen-7-yl)acetate are obtained (yellow solid; yield 53%).

$R_f$=0.54 (ligroin/ethyl acetate 9/7 volume/volume); $^1$H NMR (CDCl$_3$) δ (ppm): 7.71 (d, 1H, ArH), 7.50 (d, 1H, ArH), 7.07 (d, 1H, ArH), 6.90 (d, 1H, ArH), 4.35 (q, 2H, OCH$_2$), 3.11 (m, 2H, CH$_2$), 2.96 (m, 2H, CH$_2$), 2.78 (m, 2H, CH$_2$), 2.63 (m, 2H, CH$_2$), 1.99 (m, 2H, CH$_2$), 1.90 (m, 2H, CH$_2$), 1.36 (t, 3H, CH$_3$); $^{13}$C NMR (CDCl$_3$) δ (ppm): 196.8, 177.5, 168.6, 158.4, 156.0, 153.4, 149.6, 140.6, 134.8, 134.4, 133.3, 133.0, 132.7, 131.6, 131.3, 128.1, 126.5, 124.9, 114.6, 63.5, 41.3, 32.1, 29.4, 25.3, 22.9, 21.5, 21.3, 14.1, 13.9; FT-IR (film) $v_{max}$: 1762.0, 1738.8, 1713.7, 1642.8, 1599.5, 1415.5, 1286.7, 1272.6, 1184.3, 839.9, 742.2 cm$^{-1}$.

9e. Synthesis of ethyl 1-(2',4'-dichlorophenyl)-1,4,5,6-tetrahydro-thieno[3',2':6,7]cyclohepta[1,2-c]pyrazol-3-carboxylate

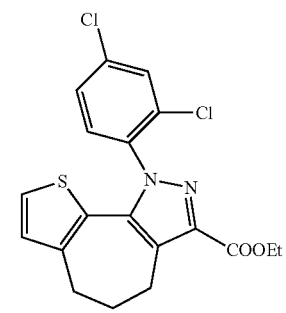 [SMILES: CCOC(=O)c1nn(-c2ccc(Cl)cc2Cl)c2c1CCCc1ccsc1-2]

560 mg of ethyl 2-oxo-2-(8-oxo-5,6,7,8-tetrahydro-4H-cyclo hepta[b]thiophen-7-yl)acetate prepared in example 9d are solubilized in absolute ethanol (11 mL). 580 mg of 2,4-dichlorophenyl-hydrazine hydrochloride are added. The reaction mixture is heated under reflux conditions for 14 hours. The solvent is removed under vacuum and the obtained residue is purified by chromatography on silica gel by using as eluent a mixture of ligroin/ethyl acetate 9:1 volume/volume. 300 mg of ethyl 1-(2',4'-dichlorophenyl)-1,4,5,6-tetrahydro-thieno[3',2':6,7]-cyclo-hepta[1,2-c]pyrazol-3-carboxylate are obtained (orange solid; yield 35%). $R_f$=0.20 (ligroin/ethyl acetate 9/1 volume/volume); $^1$H NMR (CDCl$_3$) δ (ppm): 7.55 (d, 1H, ArH), 7.48 (d, 1H, ArH), 7.42 (dd, 1H, ArH), 7.03 (d, 1H, ArH), 6.79 (d, 1H, ArH), 4.44 (q, 2H, OCH$_2$), 3.29 (m, 2H, CH$_2$), 2.99 (m, 2H, CH$_2$), 2.06 (m, 2H, CH$_2$), 1.42 (t, 3H, CH$_3$); $^{13}$C NMR (CDCl$_3$) δ (ppm): 162.8, 143.2, 142.4, 137.2, 136.4, 135.3, 131.9, 130.3, 130.0, 128.1, 124.8, 124.2, 122.4, 61.0, 30.9, 26.1, 24.4, 14.5; FT-IR (film) $v_{max}$: 3092.7, 2928.9, 1712.5, 1486.6, 1446.9, 1245.6, 1190.9, 1100.3, 947.0, 713.9, 641.6, 610.6 cm$^{-1}$.

9f. Synthesis of 1-(2',4'-dichlorophenyl)-1,4,5,6-tetra hydrothieno[3',2':6,7]cyclohepta[1,2-c]pyrazol-3-carboxylic acid

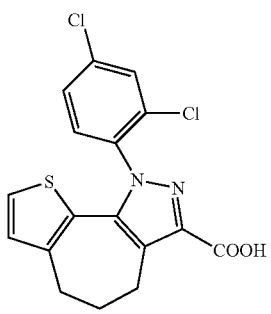 [SMILES: O=C(O)c1nn(-c2ccc(Cl)cc2Cl)c2c1CCCc1ccsc1-2]

300 mg of ethyl 1-(2',4'-dichlorophenyl)-1,4,5,6-tetrahydro-thieno[3',2':6,7]cyclohepta[1,2-c]pyrazol-3-carboxylate prepared in example 9e are solubilized in THF/H$_2$O 4:1 (7 mL). Lithium hydroxide (72 mg; 2.7 mmoles) is added and the mixture is heated to 60° C. for 5 hours. After cooling at room temperature, it is diluted first by adding water (5 mL) and then a HCl 1N solution to lower the pH to 1-2. A precipitate is formed which is recovered by filtration and then washed with ethyl ether (2×10 mL). 200 mg of 1-(2',4'-dichlorophenyl)-1,4,5,6-tetrahydro-thieno[3',2':6,7]cyclohepta[1,2-c]pyrazol-3-carboxylic acid are obtained (white solid; yield 72%). $R_f$=0.76 (chloroform/methanol 9/1 volume/volume); $^1$H NMR (CDCl$_3$) δ (ppm): 7.58 (d, 1H, ArH), 7.45 (m, 2H, ArH), 7.04 (d, 1H, ArH), 6.80 (d, 1H, ArH), 3.30 (m, 2H, CH$_2$), 3.00 (m, 2H, CH$_2$), 2.07 (m, 2H, CH$_2$); $^{13}$C NMR (CDCl$_3$) δ (ppm): 163.4, 143.6, 141.3, 139.3, 137.5, 136.0, 135.0, 131.6, 130.5, 130.2, 128.2, 125.1, 123.8, 122.4, 31.0, 25.9, 24.1; FT-IR (film) $v_{max}$: 3078.0, 2929.3, 2854.1, 2715.1, 1683.4, 1450.3, 1386.6, 1251.4, 1204.2, 705.8, 665.3 cm$^{-1}$.

9g. Synthesis of the compound N,N'-(propan-1,3-diyl)bis[1-(2,4-dichlorophenyl)]-1,4-dehydro-thieno[3',2':4,5]cyclo-hepta[1,2-c]pyrazol-3-carboxamide]

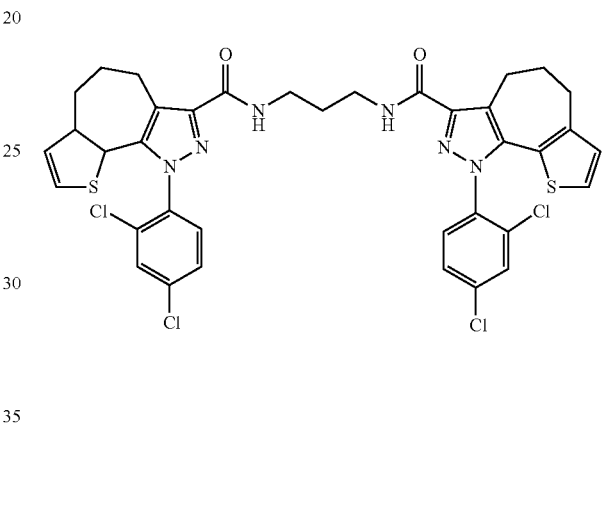

200 mg of 1-(2',4'-dichlorophenyl)-1,4,5,6-tetrahydro-thieno[3',2':6,7]cyclohepta[1,2-c]pyrazol-3-carboxylic acid prepared in example 9f and 200 mg of thionyl chloride are solubilized in toluene (10 mL). The mixture is heated under reflux conditions for one hour. The solvent is then removed under vacuum and the obtained residue is dissolved in dichloromethane (4 mL). The solution is cooled at 0° C. and a solution in dichloromethane (7 mL) of triethylamine (100 mg; 1.3 mmoles) and 1,3-diaminopropane (40 mg; 0.5 mmoles) is dropwise added. The reaction mixture is let warm to room temperature under stirring continued for 16 hours. The solvent is then removed under vacuum and the obtained residue is purified by flash chromatography on silica gel by using as eluent a chloroform/methanol 36:1 volume/volume mixture. 200 mg of N,N'-(propan-1,3-diyl)bis[1-(2,4-dichlorophenyl)]-1,4-dehydro-thieno[3',2':4,5]cyclohepta[1,2-c]pyrazol-3-carbox-amide] are obtained (white solid, yield 96%). $R_f$=0.39 (chloroform/methanol 36/1 volume/volume); $^1$H NMR (CDCl$_3$) δ (ppm): 7.56 (d, 2H, ArH), 7.43 (m, 4H, ArH), 7.15 (t, 2H, NH), 7.01 (d, 2H, ArH), 6.78 (d, 2H, ArH), 3.50 (m, 4H, CH$_2$), 3.34 (m, 4H, CH$_2$), 2.98 (t, 4H, NH), 2.03 (m, 4H, CH$_2$), 1.89 (q, 2H, CH$_2$); $^{13}$C NMR (CDCl$_3$) δ (ppm): 163.1, 144.3, 143.1, 138.6, 137.1, 136.4, 135.2, 131.8, 130.5, 130.2, 128.2, 124.6, 124.4, 121.0, 36.5, 31.2, 30.0, 25.8, 24.4;

FT-IR (film) $v_{max}$: 3086.3, 2962.0, 1657.9, 1526.3, 1485.8, 1258.3, 1097.6, 808.3, 721.1 cm$^{-1}$.

Example 10

Synthesis of 3,3'-(propane-1,3-diylbis(azanediyl))bis(oxomethylene)bis(1-(2,4-dichlorophenyl)-1,4-dihydro-thieno[3',2':4,5]cyclohepta[1,2-c]pyrazole-8-sulfonic acid)

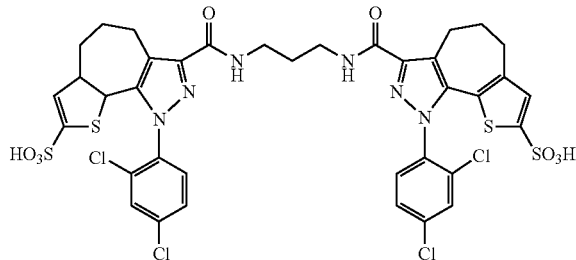 [SMILES: O=C(NCCCNC(=O)c1nn(-c2ccc(Cl)cc2Cl)c2c1CCCC1C=C(S(=O)(=O)O)SC21)c1nn(-c2ccc(Cl)cc2Cl)c2c1CCCc1cc(S(=O)(=O)O)sc1-2]

70 mg of the compound prepared in example 9 are solubilized in dichloromethane (3 mL). The solution is cooled at −10° C. and a mixture of acetic anhydride (55 mg; 0.5 mmoles) and sulphuric acid 98% (20 mg; 0.2 mmoles) is added. The reaction mixture is let warm to room temperature by stirring for a time of 16 hours. The solvent is then removed under vacuum and the obtained residue is purified by chromatography on silica gel using as eluent a chloroform/methanol 2:1 volume/volume mixture. 90 mg of the titled compound are obtained (white solid; yield 98%). $R_f$=0.35 (chloroform/methanol 2/1 volume/volume); $^1$H NMR (DMSO) δ (ppm): 8.29 (t, 2H, NH), 7.94 (d, 2H, ArH), 7.76 (d, 2H, ArH), 7.68 (dd, 2H, ArH), 6.88 (s, 2H, ArH), 3.19 (m, 8H, CH$_2$), 2.87 (q, 4H, NHCH$_2$), 1.88 (q, 4H, CH$_2$), 1.66 (q, 2H, NHCH$_2$CH$_2$); $^{13}$C NMR (DMSO) δ (ppm): 162.4, 150.1, 144.8, 142.3, 138.1, 136.7, 136.6, 134.6, 133.2, 130.5, 129.3, 129.2, 124.1, 120.9, 36.3, 31.1, 29.9, 25.8, 24.5; FT-IR (film) $v_{max}$: 3398.1, 2927.1, 1716.3, 1644.6, 1585.5, 1538.9, 1184.9, 1063.4, 1008.9, 625.6 cm$^{-1}$.

Example 11

Synthesis of the compound N,N'-(propan-1,3-diyl)bis[1-(pentyl)]-1,4-dehydro-thieno[3',2':4,5]cyclopenta[1,2-c]pyrazol-3-carboxamide]

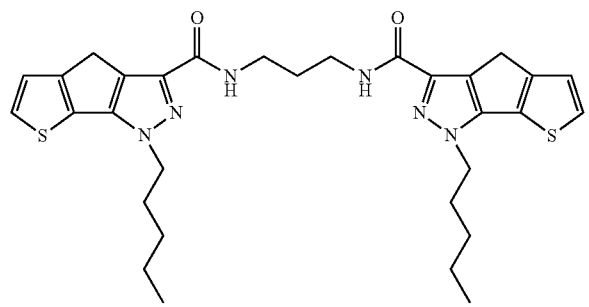 [SMILES: CCCCCn1nc(C(=O)NCCCNC(=O)c2nn(CCCCC)c3c2Cc2ccsc2-3)c2c1-c1sccc1C2]

11a. Synthesis of t-butyl-2-pentylidenhydrazincarboxylate

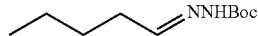

A solution of valeraldehydede (2.0 g; 23 mmoles) and t-butylcarbazate (3.1 g; 23 mmoles) in hexane (25 mL) is heated under reflux conditions for 30 minutes. At the end the solution is cooled at room temperature. The solvent is removed under vacuum and the obtained residue purified by chromatography on silica gel eluting with chloroform. 4.1 g of t-butyl-2-pentylidenhydrazinecarboxylate (white solid; yield 89%) are obtained. $R_f$=0.32 chloroform; $^1$H NMR (CDCl$_3$) δ (ppm): 8.02 (s broad, 1H, NH), 7.19 (t, 1H, CH), 2.29 (m, 2H, CH$_2$), 1.46 (m, 11H, CH$_2$ and CH$_3$), 1.36 (m, 2H, CH$_2$), 0.91 (t, 3H, CH$_3$); $^{13}$C NMR (CDCl$_3$) δ (ppm): 147.6, 146.7, 80.8, 31.9, 28.8, 28.3, 22.3, 13.8.

11b. Synthesis of t-butyl-2-pentylhydrazincarboxylate

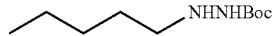

6.65 g of NaBH$_3$CN are solubilized in acetic acid (10.5 g; 175 mmoles). The solution is cooled at 0° C. and a solution in anhydrous THF (35 mL; 0.15 M) of t-butyl-2-pentylidenhydrazincarboxylate (7.00 g; 35 mmoles) prepared in example 11a is dropwise added. The reaction mixture is then let to warm to room temperature under stirring for 24 hours. The organic phase is washed with a 10% NaHCO$_3$ solution and then extracted with chloroform. The organic phase is recovered and the solvent removed under vacuum. The obtained residue is purified by chromatography on silica gel using as eluent a chloroform/methanol 90:1 volume/volume mixture. 6.3 g of t-butyl-2-pentylhydrazincarboxylate are obtained (white solid; yield 90%).

Rf=0.70 (chloroform/methanol 90/1 volume/volume); $^1$H NMR (CDCl$_3$) δ (ppm): 6.69 (s broad, 1H, NH), 6.30 (d broad, 1H, NH), 3.10 (m, 1H, CH$_2$), 2.97 (m, 1H, CH$_2$), 1.61 (m, 2H, CH$_2$), 1.44 (s, 9H, CH$_3$), 1.26 (m, 4H, CH$_2$), 0.84 (t, 3H, CH$_3$).

11c. Synthesis of pentylhydrazine hydrochloride 420 mg of t-butyl-2-pentylhydrazincarboxylate prepared in example 11b are solubilized in methanol (3.1 mL). HCl 37% (1.08 g; 10 mmoles) is added dropwise. The mixture is then left under stirring for 4 hours at 40° C. and then concentrated under vacuum. The obtained residue is purified by chromatography on silica gel using as eluent a chloroform/methanol 90:10 volume/volume mixture to remove the unreacted starting product, and then with methanol only. 168 mg of pentylhydrazine hydrochloride are obtained (white solid, yield 80%). ¹H NMR (DMSO) δ (ppm): 3.20 (m, 2H, CH₂), 2.77 (m, 2H, CH₂), 1.47 (m, 2H, CH₂), 1.20 (m, 4H, CH₂), 0.78 (t, 3H, CH₃).

11d. Synthesis of ethyl 1-pentyl-1,4-dehydro-thieno [3',2':4,5]cyclo penta[1,2-c]pyrazol-3-carboxylate

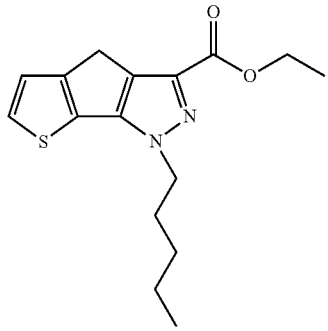 [SMILES: CCCCCn1nc(C(=O)OCC)c2c1-c1sccc1C2]

500 mg of pentylhydrazine hydrochloride prepared in example 11c and 670 mg of 1-(6-oxo-5,6-dehydro-4H-cyclopenta[b]thiophen-5-yl)-pentan-1,2-dione) prepared in example 1d are dispersed in absolute ethanol (13 mL). The mixture is left 4 hours under stirring at room temperature and then heated under reflux conditions for 16 hours. The reaction mixture is then cooled at room temperature, washed with water (40 mL) and extracted with ethyl acetate. The organic phase is dried with sodium sulphate, filtered and concentrated under vacuum. The obtained residue is purified by chromatography on silica gel by using as eluent a ligroin/ethyl acetate 1:1 volume/volume mixture. 584 mg of ethyl 1-pentyl-1,4-dehydro-thieno[3',2':4,5]cyclopenta[1,2-c]pyrazol-3-carboxylate are obtained (brown solid; yield 69%).

$R_f$=0.78 (ligroin/ethyl acetate 1/1 volume/volume); ¹H NMR (CDCl₃) δ (ppm): 7.30 (d, 1H, ArH), 7.15 (d, 1H, ArH), 4.43 (q, 2H, OCH₂), 4.31 (t, 2H, CH₂), 3.62 (s, 2H, CH₂), 1.99 (q, 2H, CH₂), 1.42 (t, 3H, CH₃), 1.36 (m, 4H, CH₂), 0.89 (t, 3H, CH₃); ¹³C NMR (CDCl₃) δ (ppm): 162.5, 153.9, 146.3, 133.1, 131.6, 130.3, 126.6, 123.8, 60.9, 52.3, 29.9, 28.8, 28.2, 22.2, 14.5, 13.9; FT-IR (film) ν$_{max}$: 3090.6, 3062.9, 2954.7, 2927.7, 2857.1, 1673.9, 1440.7, 1272.1, 1192.2, 1092.0, 966.0, 815.2, 749.2, 701.7, 549.7 cm⁻¹.

11e. Synthesis of 1-(pentyl)-1,4-dehydro-thieno[3', 2':4,5]cyclopenta[1,2-c]pyrazol-3-carboxylic acid

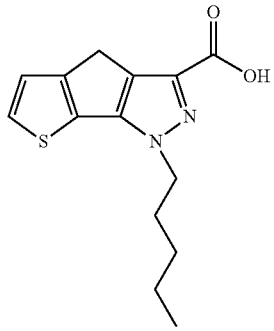 [SMILES: CCCCCn1nc(C(=O)O)c2c1-c1sccc1C2]

350 mg of ethyl 1-pentyl-1,4-dehydro-thieno[3',2':4,5]cyclo penta[1,2-c]pyrazol-3-carboxylate prepared in example 11d are solubilzed in THF/H₂O 4:1 volume/volume (10 mL). Lithium hydroxide (290 mg; 7.0 mmoles) is added. The reaction mixture is heated to 80° C. for 2 hours and at the end cooled at room temperature. Water (5 mL) is then added followed by a 1N HCl solution to have a pH comprised between 1-2. A precipitate is formed which is filtered and washed with ethyl ether (2×10 mL). 200 mg of 1-(pentyl)-1, 4-dehydro-thieno[3',2':4,5]-cyclopenta[1,2-c]pyrazol-3-carboxylic acid are isolated (yellow solid; yield 65%). $R_f$=0.53 (chloroform/methanol 9/1 volume/volume); ¹H NMR (DMSO) δ (ppm): 12.61 (s broad, 1H, OH), 7.57 (d, 1H, ArH), 7.23 (d, 1H, ArH), 4.25 (t, 2H, CH₂), 3.55 (s, 2H, CH₂), 1.86 (q, 2H, CH₂), 1.25 (m, 4H, CH₂), 0.82 (t, 3H, CH₃); ¹³C NMR (DMSO) δ (ppm): 163.5, 154.3, 146.0, 137.5, 131.4, 129.9, 128.2, 124.5, 51.8, 29.6, 28.6, 28.3, 22.1, 14.2; FT-IR (film) ν$_{max}$: 3082.2, 2946.2, 2869.5, 1737.6, 1681.6, 1373.2, 1236.1, 1044.2, 916.5, 711.1, 589.5 cm⁻¹.

11f. Synthesis of N,N'-(propan-1,3-diyl)bis[1-(pentyl)]-1,4-dehydro-thieno[3',2':4,5]cyclopenta[1,2-c] pyrazol-3-carboxamide]

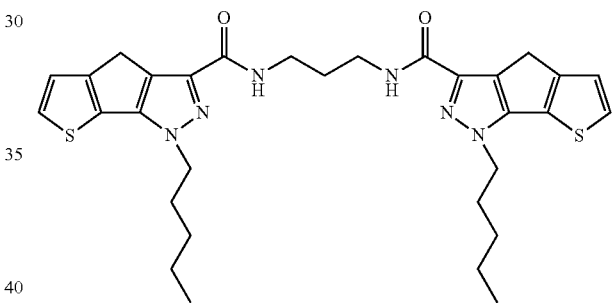

200 mg of the 1-(pentyl)-1,4-dehydro-thieno[3',2':4,5]cyclo penta[1,2-c]pyrazol-3-carboxylic acid prepared in example 11e and 250 mg of thionyl chloride are solubilized in toluene (24 mL). The mixture is heated under reflux conditions for one hour. The solvent is then removed under vacuum. The obtained residue is solubilised in dichloromethane (8 mL). The solutions is cooled at 0° C., and a solution in dichloromethane (8 mL) of triethylamine (180 mg; 1.8 mmoles) and 1,3-diaminopropane (50 mg; 0.72 mmoles) is dropwise added. The mixture is let warm to room temperature under stirring continued for 16 hours. At the end the solvent is removed under vacuum and the obtained residue is purified by flash chromatography on silica gel using as eluent a chloroform/methanol 36:1 volume/volume mixture. 120 mg of N,N'-(propan-1,3-diyl)bis[1-(pentyl)]-1,4-dehydro-thieno-[3',2':4,5]cyclopenta-[1,2-c]-pyrazol-3-carboxamide] are obtained (white solid, yield 55%). $R_f$=0.37 (chloroform/methanol 36/1 volume/volume); ¹H NMR (CDCl₃) δ (ppm): 7.30 (d, 2H, ArH), 7.25 (t, 2H, NH), 7.15 (d, 2H, ArH), 4.21 (t, 4H, CH₂), 3.68 (s, 4H, CH₂), 3.56 (q, 4H, CH₂), 1.96 (m, 6H, CH₂), 1.36 (m, 8H, CH₂), 0.90 (t, 4H, CH₃); ¹³C NMR (CDCl₃) δ (ppm): 162.8, 154.4, 146.7, 139.7, 130.2, 129.6, 126.4, 123.9, 51.9, 36.3, 30.1, 29.8, 28.8, 28.1, 22.2, 13.9; FT-IR (film) ν$_{max}$: 3336.8, 2927.2, 1635.3, 1544.9, 1437.3, 1182.9, 1012.7, 677.3, 590.3 cm⁻¹.

Example 12

Synthesis of 3,3'-(propane-1,3-diylbis(azanediyl))bis(oxomethylene)bis(1-penthyl-1,4-dihydro-thieno[3',2':4,5]cyclopenta[1,2-c]pyrazole-6-sulfonic acid)

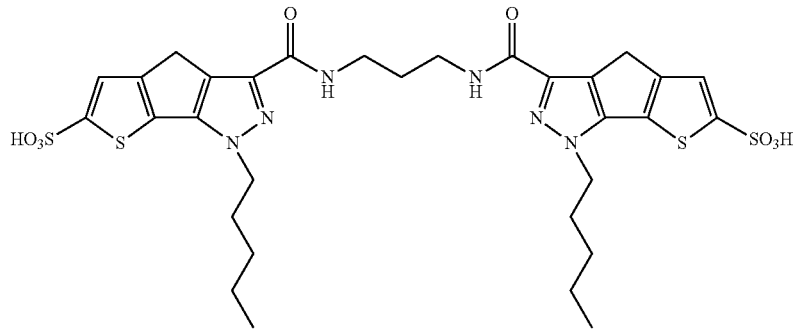 [SMILES: CCCCCn1nc(C(=O)NCCCNC(=O)c2nn(CCCCC)c3c2Cc2cc(S(=O)(=O)O)sc2-3)c2c1-c1sc(S(=O)(=O)O)cc1C2]

120 mg of the compound prepared in example 11 are solubilized in dichloromethane (4 mL). The solution is cooled to −10° C. and a mixture of acetic anhydride (123 mg; 1.2 mmoles) and sulphuric acid 98% (40 mg; 0.4 mmoles) is added. The reaction mixture is allowed to warm to room temperature by leaving under stirring for 16 hours. The solvent is then removed under vacuum and the obtained residue purified by chromatography on silica gel using as eluent a chloroform/methanol 2:1 volume/volume mixture. 100 mg of the titled compound are obtained (white solid; yield 66%). $R_f$=0.18 (chloroform/methanol 2/1 volume/volume); $^1$H NMR (DMSO) δ (ppm): 8.17 (t, 2H, NH), 7.20 (s, 2H, ArH), 4.21 (t, 4H, CH$_2$), 3.52 (s, 4H, CH$_2$), 3.25 (m, 4H, CH$_2$), 1.85 (q, 4H, CH$_2$), 1.69 (q, 2H, CH$_2$), 1.25 (m, 8H, CH$_2$), 0.82 (t, 6H, CH$_3$); $^{13}$C NMR (DMSO) δ (ppm): 161.7, 152.8, 146.1, 140.4, 129.7, 129.2, 122.8, 51.6, 36.4, 29.8, 29.7, 28.7, 26.7, 22.1, 14.3; FT-IR (film) $v_{max}$: 3370.5, 1634.5, 1202.6, 1060.1, 1006.6, 921.1, 780.7 cm$^{-1}$.

Example 13

Synthesis of N,N'-(hexan-1,6-diyl)bis[1-(pentyl)]-1,4-dehydro-thieno[3',2':4,5]cyclopenta[1,2-c]pyrazol-3-carboxamide]

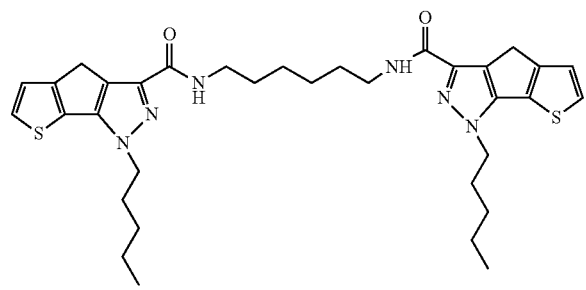 [SMILES: CCCCCn1nc(C(=O)NCCCCCCNC(=O)c2nn(CCCCC)c3c2Cc2ccsc2-3)c2c1-c1sccc1C2]

155 mg of the 1-(pentyl)-1,4-dehydro-thieno[3',2':4,5]cyclopenta[1,2-c]pyrazol-3-carboxylic acid prepared in example 11e and 190 mg of thionyl chloride are solubilized in toluene (18 mL). The mixture is heated under reflux conditions for one hour. The solvent is then removed under vacuum. The obtained residue is dissolved in dichloromethane (6 mL). The solution is cooled at 0° C. and a solution in dichloromethane (6 mL) of triethylamine (138 mg; 1.4 mmoles) and 1,6-hexandiamine (64 mg; 0.55 mmoles) is dropwise added. The reaction mixture is let to warm to room temperature by stirring continued for 16 hours. The solvent is removed under vacuum and the obtained residue purified by flash chromatography on silica gel using as eluent a chloroform/methanol 36:1 volume/volume mixture. 60 mg of N,N'-(hexan-1,6-diyl)bis[1-(pentyl)]-1,4-dehydro-thieno[3',2':4,5]cyclo-penta[1,2-c]pyrazol-3-carboxamide] are obtained (white solid, yield 36%). $R_f$=0.46 (chloroform/methanol 36/1 volume/volume); $^1$H NMR (CDCl$_3$) δ (ppm): 7.29 (t, 2H, NH), 7.15 (d, 2H, ArH), 6.90 (t, 2H, NH), 4.21 (t, 4H, CH$_2$), 3.67 (s, 4H, CH$_2$), 3.44 (q, 4H, CH$_2$), 1.97 (q, 4H, CH$_2$), 1.66 (q, 4H, CH$_2$), 1.46 (q, 4H, CH$_2$), 1.36 (m, 8H, CH$_2$), 0.90 (t, 4H, CH$_3$); $^{13}$C NMR (CDCl$_3$) δ (ppm): 162.3, 154.4, 146.7, 139.9, 130.2, 129.6, 126.4, 123.9, 51.9, 39.0, 36.3, 29.8, 29.7, 28.8, 28.1, 26.7, 22.2, 13.9

FT-IR (film) $v_{max}$: 3390.1, 2931.0, 1650.2, 1540.4, 1471.8, 1182.8, 708.3, 587.5 cm$^{-1}$.

Example 14

Synthesis of 3,3'-(hexane-1,6-diylbis(azanediyl))bis(oxomethylene)bis(1-pentyl-1,4-dihydro-thieno[3',2':4,5]cyclopenta[1,2-c]pyrazole-6-sulfonic acid)

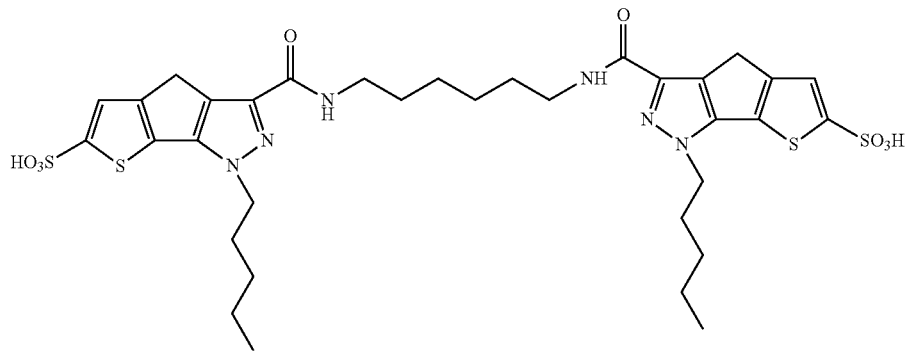 [SMILES: CCCCCn1nc(C(=O)NCCCCCCNC(=O)c2nn(CCCCC)c3c2Cc2cc(S(=O)(=O)O)sc2-3)c2c1-c1sc(S(=O)(=O)O)cc1C2]

40 mg of the compound prepared in example 13 are solubilized in dichloromethane (2 mL). The mixture is cooled to −10° C. and a mixture of acetic anhydride (37 mg; 0.36 mmoles) and sulphuric acid 98% (12 mg; 0.12 mmoles) is added. After the addition the solution is let to warm to room temperature by stirring continued for 16 hours. The solvent is then removed under vacuum and the obtained residue is purified by chromatography on silica gel using as eluent a chloroform/methanol 2:1 volume/volume mixture. 20 mg of the titled compound are obtained (white solid; yield 43%). $R_f$=0.18 (chloroform/methanol 2/1 volume/volume); $^1$H NMR (DMSO) δ (ppm): 8.02 (t, 2H, NH), 7.21 (s, 2H, ArH), 4.21 (t, 4H, CH$_2$), 3.50 (s, 4H, CH$_2$), 3.18 (q, 4H, CH$_2$), 1.84 (q, 4H, CH$_2$), 1.49 (q, 4H, CH$_2$), 1.26 (m, 12H, CH$_2$), 0.82 (t, 6H, CH$_3$); $^{13}$C NMR (DMSO) δ (ppm): 161.9, 153.0, 152.8, 146.2, 140.4, 129.7, 129.2, 122.8, 51.7, 36.4, 29.7, 28.7, 28.5, 22.1, 14.3; FT-IR (film) $v_{max}$: 3414.0, 2931.6, 2859.7, 1715.9, 1633.5, 1227.4, 1194.4, 1058.5, 1003.9, 771.4, 666.2 cm$^{-1}$.

Example 15

Synthesis of the Compound Having Formula

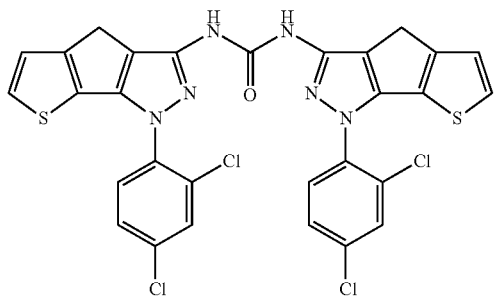 [SMILES: O=C(Nc1nn(-c2ccc(Cl)cc2Cl)c2c1Cc1ccsc1-2)Nc1nn(-c2ccc(Cl)cc2Cl)c2c1Cc1ccsc1-2]

15a. Synthesis of 1-(2',4'-dichlorophenyl)-1,4-dehydro-thieno[3',2':4,5]cyclopenta[1,2-c]pyrazol-3-acylazide

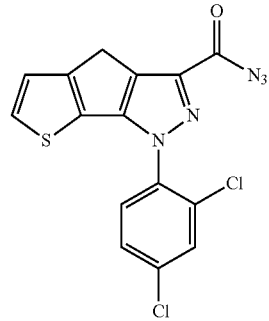 [SMILES: [N-]=[N+]=NC(=O)c1nn(-c2ccc(Cl)cc2Cl)c2c1Cc1ccsc1-2]

2 g of the 1-(2',4'-dichlorophenyl)-1,4-dehydro-thieno[3',2':4,5]cyclopenta[1,2-c]pyrazol-3-carboxylic acid prepared in example 1f and 2 g of thionyl chloride are solubilized in toluene (21 mL). The mixture is heated under reflux conditions for one hour. The solvent is then removed under vacuum and the obtained residue is solubilized in dichloromethane (30 mL). To the organic phase a solution of sodium azide (600 mg; 1.3 mmoles) in water (1.2 mL) is dropwise added at room temperature. Stirring is continued for one hour at room temperature. At the end the mixture is extracted with chloroform. The organic phase is dried with sodium sulphate and concentrated under vacuum. 2 g of 1-(2',4'-dichlorophenyl)-1,4-dehydro-thieno[3',2':4,5]-cyclopenta[1,2-c]pyrazol-3-acylazide are obtained (white solid, yield 99%). $R_f$=0.28 (ligroin/ethyl acetate 14/1 volume/volume); $^1$H NMR (CDCl$_3$) δ (ppm): 7.63 (d, 2H, ArH), 7.56 (d, 2H, ArH), 7.44 (dd, 2H, ArH), 7.33 (d, 2H, ArH), 7.15 (d, 2H, ArH), 3.75 (s, 2H, CH$_2$); $^{13}$C NMR (CDCl$_3$) δ (ppm): 167.3, 155.0, 149.2, 139.8, 136.2, 135.4, 132.0, 130.8, 130.6, 130.2, 129.3, 128.3, 123.5, 28.5; FT-IR (film) $v_{max}$: 3102.6, 294.3, 2132.4, 1688.7, 1462.5, 1268.1, 1172.3, 1000.6, 976.7, 823.2, 811.9, 703.7 cm$^{-1}$.

15b. Synthesis of the compound of formula

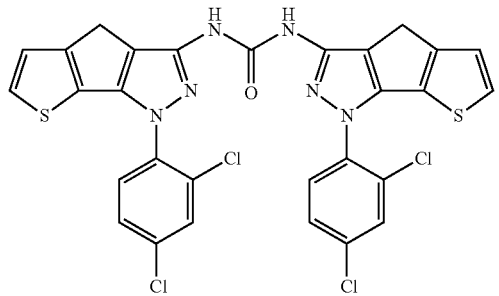 [SMILES: O=C(Nc1nn(-c2ccc(Cl)cc2Cl)c2c1Cc1ccsc1-2)Nc1nn(-c2ccc(Cl)cc2Cl)c2c1Cc1ccsc1-2]

500 mg of 1-(2',4'-dichlorophenyl)-1,4-dehydro-thieno[3', 2':4,5]cyclopenta[1,2-c]pyrazol-3-acylazide of example 15a are solubilized in toluene (20 mL). The mixture is heated under reflux conditions for one hour. Then it is cooled at room temperature, filtered and the obtained residue is dried. 180 mg of the compound having the formula above reported are obtained (white solid, yield 42%). Rf=0.63 (chloroform/methanol 37/1 volume/volume); $^1$H NMR (DMSO) δ (ppm): 9.48 (s broad, 2H, NH), 7.97 (d, 2H, ArH), 7.68 (d, 2H, ArH), 7.64 (dd, 2H, ArH), 7.55 (d, 2H, ArH), 7.24 (d, 2H, ArH), 3.76 (s, 4H, CH$_2$); $^{13}$C NMR (DMSO) δ (ppm): 155.4, 151.7, 147.4, 144.1, 136.1, 134.3, 130.7, 130.2, 130.0, 129.9, 129.2, 128.7, 124.4, 118.6; FT-IR (film) $v_{max}$: 3221.4, 3106.5, 1698.4, 1601.6, 1552.6, 1525.6, 1511.8, 943.7, 813.1, 717.3, 704.1, 633.3, 590.4 cm$^{-1}$.

Example 16

Synthesis of the Compound of Formula

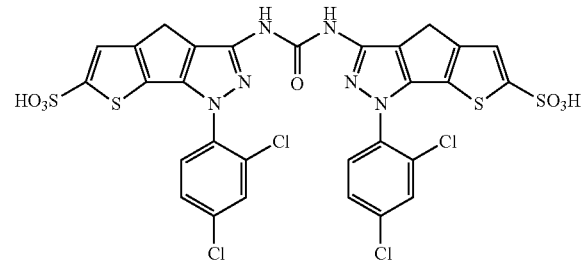 [SMILES: O=C(Nc1nn(-c2ccc(Cl)cc2Cl)c2c1Cc1cc(S(=O)(=O)O)sc1-2)Nc1nn(-c2ccc(Cl)cc2Cl)c2c1Cc1cc(S(=O)(=O)O)sc1-2]

60 mg of the compound prepared in example 15b are solubilized in dichloromethane (3 mL). The solution is cooled at −10° C. and a mixture of acetic anhydride (110 mg; 1.1 mmoles) and sulphuric acid 98% (30 mg; 0.40 mmoles) is added. The reaction mixture is then let to warm to room temperature under stirring for a time of 16 hours. The solvent is then removed under vacuum and the obtained residue purified by chromatography on silica gel by using as eluent a chloroform/methanol 2:1 volume/volume mixture. 30 mg of the compound having the above reported formula are obtained (white solid; yield 40%). $R_f$=0.35 (chloroform/methanol 2/1 volume/volume); $^1$H NMR (DMSO) δ (ppm): 9.49 (s broad, 2H, NH), 7.95 (d, 2H, ArH), 7.65 (m, 4H, ArH), 7.224 (s, 2H, ArH), 3.72 (s, 4H, CH$_2$); $^{13}$C NMR (DMSO) δ (ppm): 153.7, 153.6, 151.6, 147.4, 140.0, 136.0, 134.3, 130.7, 130.0, 129.9, 129.5, 129.2, 122.5, 118.4, 30.9; FT-IR (film) $v_{max}$: 3213.5, 3086.5, 1697.8, 1515.4, 1479.0, 1218.9, 1190.3, 1073.8, 651.0 cm$^{-1}$.

Example 17

Evaluation of the Binding of the Compounds of the Invention to FGF-2

For the evaluation of the binding of the compounds of the invention to FGF-2, the test described in G. Colombo et al. J. Biol. Chem., 285: 8733, 2010 has been used. In this reference the binding test has been used to assay the binding of compound sm27 to FGF-2. Specifically, the test allows to evaluate the capability of the compounds under examination to compete with the biotinylated TS3R domain (the recombinant part of Thrombospondine 1 (TSP-1) containing the bond sequence for FGF-2), for the binding to FGF-2 immobilized on a plastic support.

In detail, FGF-2 (0.1 µg) has been immobilized on 96 well plates (DELFIA microtitration plates, Perkin Elmer) leaving into contact for one night at 4° C. by using known techniques. After saturation of the non specific sites with 1% BSA, the compounds to be tested and then the biotinylated TS3R domain (10 nM) in PBS 1% BSA were added. After a period of incubation of 3 hours, the plate was washed and treated with Eu-Labeled Streptavidin 1:1000 and incubated again for one further hour. The amount of TS3R bound to FGF was determined with DELFIA Enhancement Solution, measuring the resolved fluorescence (Victor, PerkinElmer).

The test was carried out on the compounds of examples 2, 4, 8, 10 and 12. The used concentrations were respectively of 10 and 100 µM. The obtained results are reported in Table 1 and have been expressed as inhibition percentage of the TS3R/FGF-2 binding induced by the compounds of the invention vs. the control (TS3R/FGF-2 binding in the absence of the compounds of the invention). As a reference compound sm27 was used and assayed at a concentration of 100 µM. The results show that the compounds of the invention have an inhibitory activity on the TS3R/FGF-2 binding and are therefore capable to bind to FG2-2. The compounds of the invention in this test are as effective as sm27 at the assayed dose of 100 µM.

Example 18

Evaluation of the Activity of the Compounds of the Invention in Inhibiting the Binding of FGF-2 to Endothelial Cells Sub-confluent BAEC cells (Bovine Aortic Endothelial Cells), in 96 well plates, were incubated with DMEM without serum for 30 minutes at 4° C. The compound of the invention to be assayed and FGF-2, labelled with europium (FGF-Eu, 10 ng/ml), were added in DMEM containing 0.15% gelatine and HEPES 25 mM. The plate was incubated for 2 hours at 4° C. After washings with cold medium, the amount of FGF-Eu bound to the cells was determined with DELFIA Enhancement Solution by measuring the time resolved fluorescence (Victor, PerkinElmer).

The compounds obtained in examples 2, 4, 8 and 10 were used at a concentration of 100 µM. As a reference the compound sm27 was used. The obtained results are reported in Table 2 and are expressed as inhibition percentage of the FGF-2 binding to endothelial cells induced by the compounds of the invention and by sm27 vs. the control (FGF-2 bond to endothelial cells in absence of inhibition). The value obtained with the control was assumed as 100% binding. The results show that the compounds of the invention are capable of inhibiting the FGF-2 bond to endothelial cells and furthermore have a higher inhibitory activity than the reference compound sm27.

Example 19

Evaluation of the Activity of the Compounds of the Invention in Inhibiting the Proliferation of Endothelial Cells Induced by FGF-2

BAEC cells (25000/ml) in DMEM 1.5% FCS were sown in 96 well plates. After 24 h the culture medium was substituted with DMEM 0.5% FCS containing the compounds of the invention at different concentrations in the range indicated herein below, and FGF-2 (5 ng/ml) or 10% FCS, added as stimulator of the cellular proliferation. After 72 h of incubation, the cells were fixed and stained with Crystal Violet, (Sigma). The stain was then eluted by using a solution 1:1 of ethanol and sodium citrate 0.1M and the absorption of the solution determined at the wave length of 540 nm.

In this test the compounds of examples 2, 4, 8 and 10 were used. For each compound several concentrations comprised between 10 and 100 µM were prepared. The obtained results are reported in Table 3 and have been given as percent reduction of the cellular proliferation of endothelial cells in the presence of FGF-2, induced by the compounds of the invention, with respect to the control (proliferation in the presence of FGF-2 only). These results show that the compounds of the invention are more active than the reference compound sm27 of inhibiting cellular proliferation of the endothelial cells induced by FGF-2.

Example 20

Angiogenesis Test Ex Vivo (Aorta Section)

Aorta sections (aorta rings of about 1 mm) taken from C57BL/6 mice, are dipped in a Matrigel gel (BD Biosciences), in 96 well plates, in DMEM 5% FCS containing FGF-2 (30 ng/ml) together with the compounds of the invention at concentrations in the range indicated herein below. By using an inverted microscope (IX70; Olympus) after some days it is observed in the plate the formation of a network of capillary structures irradiating from the aorta section. Images were taken and analyzed by ImageJ 1.41. After eleven days from the beginning of the experiment the angiogenic response is quantified as sprouting area, therefore subtracting the area of the aorta section.

The compounds of the examples 2, 4 and 10 and, as a reference, the reference compound sm27 at concentrations comprised between 50 and 100 µM were used. In Table 4 the results are reported, expressed as a percent variation (decrease) of the sprouting area with respect to that of the control (presence of FGF-2 only). These results show that the compounds of the invention are capable of significantly reducing the sprouting area vs. that of the control. The compounds of the invention are therefore capable of inhibiting the angiogenesis induced by FGF-2 and besides they result more active than the reference compound sm27.

In FIG. 1 the aorta sections are reported, analyzed after eleven days in absence (left photo—(a)) or in the presence (right photo (b)) of the compound obtained in example 10 (concentration 100 µM). By comparing the two aorta sections the antiangiogenic effect induced by the compounds of the invention is quite evident.

TABLE 1

| Compound | Concentration (µM) | % TS3R/FGF-2 binding vs. control |
|---|---|---|
| Example 2 | 10 | 25 ± 3 |
|  | 100 | 13 ± 3 |
| Example 4 | 10 | 40 ± 2 |
|  | 100 | 20 ± 1 |
| Example 8 | 10 | 61 ± 5 |
|  | 100 | 25 ± 4 |
| Example 10 | 10 | 70 ± 3 |
|  | 100 | 21 ± 7 |
| sm27 | 100 | 17 ± 5 |
| Control | — | 100 |

Inhibition of the TS3R/FGF-2 binding induced by the compounds of the invention and of the reference compound sm27. The results are expressed as percentage of the TS3R/FGF-2 binding vs. the control (TS3R/FGF-2 binding in absence of inhibition) assumed to give 100% binding. The values in the Table are the average of 3 experiments.

TABLE 2

| Compound | Inhibition of the FGF-2 binding to endothelial cells (% binding) FGF-2/endothelial cells vs. control) at the dose of 100 µM |
|---|---|
| Example 2 | 22 ± 3 |
| Example 4 | 30 ± 3 |
| Example 8 | 28 ± 4 |
| Example 10 | 27 ± 3 |
| sm 27 | 40 ± 2 |
| Control | 100 |

Inhibiting activity of the compounds of the invention and of the reference compound sm27 on the binding of FGF-2 to the endothelial cells. The results are expressed as percentage of binding with respect to the control (FGF-2 binding to endothelial cells in the absence of inhibitors), assumed to give 100% binding. The values in the Table are the average of 3 experiments.

TABLE 3

| Compound | Concentration (µM) | Cell proliferation (% vs. control) |
|---|---|---|
| Example 2 | 10 | 90 ± 3 |
|  | 50 | 20 ± 4 |
|  | 100 | 8 ± 3 |
| Example 4 | 10 | 92 ± 4 |
|  | 50 | 70 ± 6 |
|  | 100 | 30 ± 7 |
| Example 8 | 10 | 95 ± 2 |
|  | 50 | 80 ± 4 |
|  | 100 | 36 ± 5 |
| Example 10 | 10 | 81 ± 4 |
|  | 50 | 10 ± 3 |
|  | 100 | 8 ± 3 |
| sm27 | 100 | 60 ± 6 |
| Control | — | 100 |

Inhibiting activity of the compounds of the invention and of the reference compound sm27 on the proliferation of endothelial cells induced by FGF-2. The values reported in the Table are expressed as percentage with respect to the control (presence of FGF-2 without inhibitors) that it is assumed to give 100% of the cell proliferation. The values reported in the Table are the average of 4-6 experiments.

TABLE 4

| Compounds | Concentration (µM) | Sprouting area (% vs. control) |
|---|---|---|
| Example 2 | 50 | 43.9 ± 9 |
|  | 75 | 10.5 ± 5 |
|  | 100 | 1.8 ± 0.7 |
| Example 4 | 75 | 21.0 ± 5 |
|  | 100 | 15.8 ± 4 |

TABLE 4-continued

| Compounds | Concentration (µM) | Sprouting area (% vs. control) |
|---|---|---|
| Example 10 | 50 | 12.3 ± 5 |
| sm27 | 100 | 44.0 ± 8 |

Inhibitory activity of the compounds of the invention on the angiogenesis induced by FGF-2 in the experimental model of the aorta ring. The results are expressed as a per cent variation (inhibition) of the sprouting area in the presence of the compounds of the invention and of sm27, referred to the control (only FGF-2) assumed to give 100% of sprouting area. The values reported in the Table are the average of six experiments.

Example 21 Comparative

By using the test in vitro described in example 17 the binding to FGF-2 of the compounds (2p) and (2r) having the formulas herein below reported, has been assayed. These compounds are disclosed by G. A. Pinna et al. on Il Farmaco 58 (2003) 749-763.

Example 23 Comparative

Example 20 has been repeated by using the compounds (2p) and (2r). The results are reported in Table 7 and show that the sprouting area is superimposable on that obtained with the control. Therefore the compounds do not result active in inhibiting the angiogenesis induced by FGF-2.

TABLE 5

| Compound | Concentration (µM) | % TS3R/FGF-2 binding vs. Control |
|---|---|---|
| Compound (2p) | 100 | 96 ± 3 |
| Compound (2r) | 100 | 98 ± 6 |
| Control | — | 100 |

Inhibition of the TS3R/FGF-2 binding from the compounds (2p) and (2r) of the prior art. The results are expressed as in Table 1 and are the average of 3 experiments.

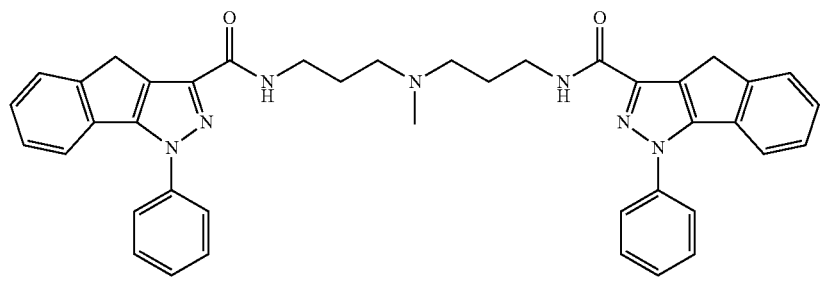

(2p)

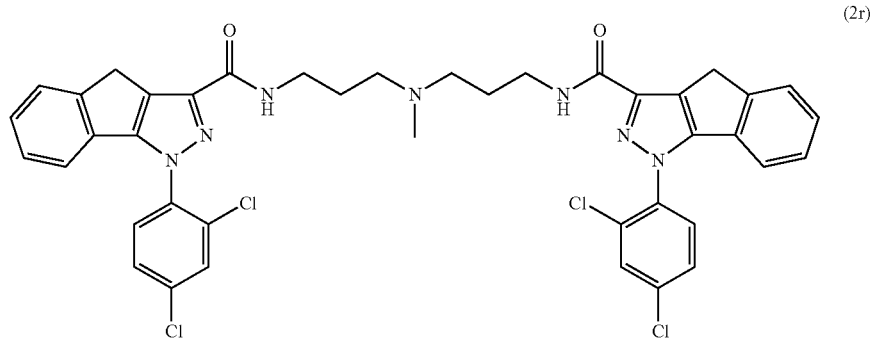

(2r)

The results are reported in the following Table 5. It is noted that these prior art compounds, differently from the compounds of the invention (Table 1), do not show any significant binding to FGF-2. In fact there is no difference between the inhibition percentage of the TS3R/FGF-2 binding induced by compounds (2p) and (2r) vs. the control.

Example 22 Comparative

Example 18 has been repeated by using the two compounds of the prior art (2p) and (2r).

The results are reported in the following Table 6 and show that these compounds do not show any significant inhibitory activity of the FGF-2 binding with the endothelial cells with respect to the control.

TABLE 6

| Compound | Concentration (µM) | Cell proliferation (% vs. control) |
|---|---|---|
| Compound (2r) | 100 | 94 ± 6 |
| Compound (2p) | 100 | 97 ± 4 |
| Control | — | 100 |

Inhibitory activity of compounds (2p) and (2r) on the proliferation of endothelial cells induced by FGF-2. The results are expressed as in Table 2 and are the average of 3 experiments

TABLE 7

| Compound | Concentration (μM) | Sprouting area (% vs. control) |
| --- | --- | --- |
| Compound (2r) | 100 | 91.1 ± 6 |
| Compound (2p) | 100 | 95.5 ± 5 |
| Control | — | 100 |

Inhibitory activity of compounds (2p) and (2r) on the angiogenesis induced by FGF-2 in the experimental model of the aorta ring. The results are expressed as in Table 4. Each result is the average of six expriments.

Example 22

Synthesis of compound 3,3'-(propane-1,3-diylbis(azanediyl))bis(oxomethylene)bis(1-(2,4-dichlorophenyl)-6-methyl-1H-benzofuro[3,2-c]pyrazole-5-sulfonic acid)

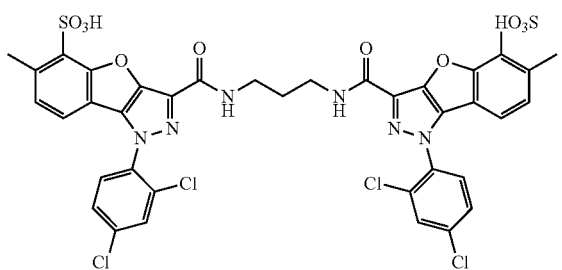

22a: Synthesis of 6-methylbenzofuran-3(2H)-one

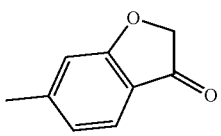

1-bromo-2-(2-hydroxy-4-methylphenyl)acetophenone was obtained according to the synthesis described by L. C. King et al. in J. Org. Chem. 29 (1964) 3459-3461, by reacting 1-(2-hydroxy-4-methyl-phenyl)-ethanone with $CuBr_2$ in ethyl-acetate at 77° C.

A solution of 1-bromo-2-(2-hydroxy-4-methylphenyl)acetophenone (1.0 g, 4.36 mmol) and sodium acetate (0.36 g, 4.38 mmol) in absolute ethanol (10 ml) was refluxed under stirring for 15 hours. The mixture was poured into water and extracted with dichloromethane (3×10 ml). The organic phase was dried over $Na_2SO_4$, then concentrated under reduced pressure to yield an oil which was purified by flash chromatography (eluent oil ether/ethyl ether 9/1 v/v on silica gel). 0.25 g (38% yield) of a yellow solid, corresponding to 6-methylbenzofuran-3(2H)-one were recovered.

22b: Synthesis of ethyl 2-(3-hydroxy-6-methylbenzofuran-2yl)-2-oxoacetate

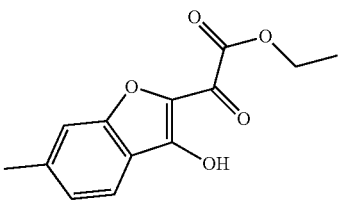 [SMILES: CCOC(=O)C(=O)c1oc2cc(C)ccc2c1O]

Ethyl 2-(3-hydroxy-6-methylbenzofuran-2yl)-2-oxoacetate was obtained according to the synthesis described in Example 1.9b of US Patent Application 2010/0215741. Metallic sodium (0.13 g; 2.24 mmol) was added in small pieces to absolute ethanol (3 ml). The suspension was left under reflux until complete solubilization of the metallic sodium. To the so obtained solution diethyloxalate (0.80 ml; 5.87 mmol) was added, followed by dripping a solution of 1-bromo-2-(2-hydroxy-4-methylphenyl)acetophenone (0.39 g; 2.63 mmol) in absolute ethanol (30 ml). The reaction mixture was kept under stirring at room temperature for 20 hours, then poured in a mixture formed of ice and HCl 1N. The aqueous solution was extracted with chloroform (3×20 ml). The organic phase was dried over $Na_2SO_4$, then concentrated under reduced pressure to obtain an oil which is triturated with oil ether/ethyl ether. 0.47 g (73% yield) of ethyl 2-(3-hydroxy-6-methylbenzofuran-2yl)-2-oxoacetate were recovered under the form of a yellow solid. Rf=0.48 (eluent dichloromethane/acetone 7/3); m.p.: 113-115° C.; IR (nujol) ($\lambda=cm^{-1}$) 3406 (OH as tautomer mixture), 1691 (COOEt), 1651 (C=O); $^1$H-NMR (CDCl$_3$) δ 1.50 (t, J=7.2 Hz, 3H), 2.51 (s, 3H), 4.56 (q, J=7.2 Hz, 2H), 7.13 (d, J=8.4 Hz, 1H), 7.26 (s, 1H), 7.71 (d, J=8.4 Hz, 1H), 11.87 (br s, 1H).

22c: Synthesis of (Z)-ethyl 2-(2-(2,4-dichlorophenyl)hydrazone)-2-(3-hydroxy-6-methylbenzofuran-2-yl)acetate

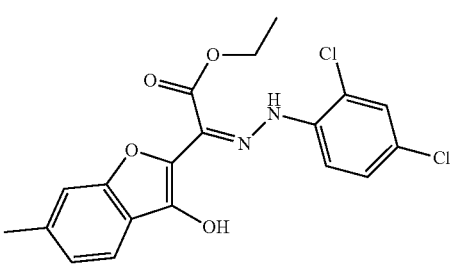 [SMILES: CCOC(=O)/C(=N\Nc1ccc(Cl)cc1Cl)c1oc2cc(C)ccc2c1O]

(Z)-ethyl 2-(2-(2,4-dichlorophenyl)hydrazone)-2-(3-hydroxy-6-methylbenzofuran-2-yl)acetate was obtained according to the synthesis described in Example 1.9c of US Patent Application 2010/0215741. A solution of the compound obtained in Ex. 22b (1.07 g; 4.31 mmol) and 2,4-dichlorophenylhydrazine hydrochloride (1.20 g; 5.60 mmol) in absolute ethanol (1.15 ml) was prepared. The solution was reacted under reflux conditions for 1.5 hours, then cooled to room temperature and poured on ice. A precipitate was formed that was filtered under reduced pressure, then air dried to obtain 1.37 g (78% yield) of a solid residue corresponding to (Z)-ethyl 2-(2-(2,4-dichlorophenyl)hydrazone)-2-(3-hydroxy-6-methylbenzofuran-2-yl)acetate. Rf=0.42 (eluent oil ether/ethyl acetate 9.5/0.5 v/v on silica gel); m.p.: 190-192° C.; IR (nujol) (λ=cm$^{-1}$) 3423 (OH as tautomer mixture), 1619 (COOEt); $^1$H-NMR (CDCl$_3$) δ 0.83 (t, J=7.4 Hz, 3H), 2.46 (s, 3H), 4.07 (q, J=7.0 Hz, 2H), 5.28 (br s, 1H), 6.96-6.92 (m, 2H), 7.34-7.21 (m, 2H), 7.62-7.57 (m, 2H), 12.80 (br s, 1H).

22d: Synthesis of the ethyl ester of 1-(2,4-dichlorophenyl)-6-methyl-1H-benzofuro[3,2-c]pyrazole-3-carboxylic acid

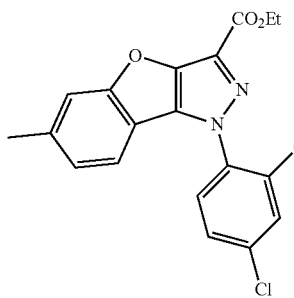

The compound was obtained according to the synthesis described in Example 1.9d of US Patent Application 2010/0215741. To a solution of the compound prepared in Ex. 22c (0.5 g; 1.23 mmol) in toluene (6 ml) a catalytic amount of p-toluenesulfonic acid (0.023 g, 0.123 mmol) was added. The obtained mixture was reacted at the reflux temperature for a time of 30 hours, then the solvent was removed under reduced pressure. The residue was purified by flash chromatography (eluent oil ether/ethyl ether 8/2 v/v on silica gel). 0.25 g (52% yield) of a yellow solid corresponding to the ethyl ester of 1-(2,4-dichlorophenyl)-6-methyl-1H-benzofuro[3,2-c]pyrazole-3-carboxylic acid were recovered. Rf=0.30 (eluent oil ether/ethyl ether 8/2 v/v on silica gel); m.p.: 138-140° C.; IR (nujol) (λ=cm$^{-1}$) 1635 (COOEt); $^1$H-NMR (CDCl$_3$) δ 1.49 (t, J=7.2 Hz, 3H), 2.51 (s, 3H), 4.55 (q, J=7.4 Hz, 2H), 7.10 (d, J=8.6 Hz, 1H), 7.31 (d, J=8.0 Hz, 1H), 7.43-7.48 (m, 2H), 7.64-7.67 (m, 2H).

22e: Synthesis of 1-(2,4-dichlorophenyl)-6-methyl-1H-benzofuro[3,2-0c]pyrazole-3-carboxylic acid

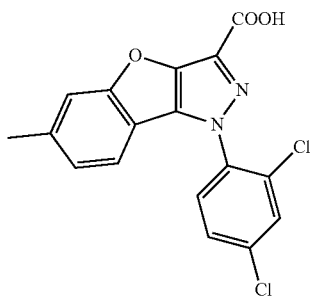 [SMILES: Cc1ccc2c(c1)oc1c(C(=O)O)nn(-c3ccc(Cl)cc3Cl)c12]

The compound was obtained according to the synthesis described in Example 2.9 of US Patent Application 2010/0215741. 0.17 g (0.44 mmol) of the compound obtained in Ex. 22d and potassium hydroxide (0.32 g, 5.7 mmol) were reacted in 5.6 ml of ethanol/water 1/1 (v/v) solution at the reflux temperature for a time of 4 hours. The obtained mixture was cooled to room temperature and then poured in a mixture formed of ice and HCl 1N. The resulting precipitate was filtered under reduced pressure, washed with water and air dried to obtain in a quantitative yield a solid corresponding to 1-(2,4-dichlorophenyl)-6-methyl-1H-benzofuro[3,2-c]pyrazole-3-carboxylic acid. Rf=0.30 (eluent chloroform/methanol 8/2 v/v on silica gel); m.p.: 228-230° C.; IR (nujol) (λ=cm$^{-1}$) 3417 (OH), 1637 (COOH); $^1$H-NMR (CDCl$_3$) δ 2.47 (s, 3H), 7.20 (d, J=12.0 Hz, 1H), 7.37 (d, J=7.8 Hz, 1H), 7.64 (s, 1H), 7.74 (dd, J=4.0, 12.0 Hz, 1H), 7.85 (d, J=7.8 Hz, 1H), 8.06 (d, J=4.0 Hz, 1H).

22f: Synthesis of N,N'-(propane-1,3-diyl)bis[1-(2,4-dichlorophenyl)-6-methyl-1H-benzofuro[3,2-c]pyrazole-3-carboxamide]

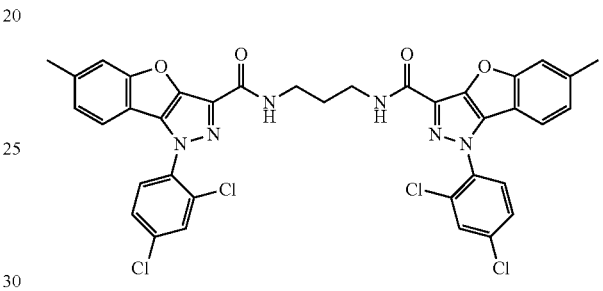

The synthesis of Ex. 11f was repeated but replacing 1-(pentyl)-1,4-dihydro-thieno[3',2':4,5]cyclopenta[1,2-c]pyrazole-3-carboxylic acid with 1-(2,4-dichlorophenyl)-6-methyl-1H-benzofuro[3,2-c]pyrazole-3-carboxylic acid. 130 mg of a white solid corresponding to N,N'-(propane-1,3-diyl)bis[1-(2,4-dichlorophenyl)-6-methyl-1H-benzofuro[3,2-c]pyrazole-3-carboxamide] were obtained. $^1$H-NMR (CDCl$_3$) δ 1.89 (q, 2H), 2.47 (s, 6H), 3.45 (q, 4H), 6.93-7.20 (m, 4H), 7.39 (dd, 2H), 7.59 (d, 2H), 7.74 (dd, 2H), 7.82 (d, 2H).

22g: Synthesis of 3,3'-(propane-1,3-diylbis(azanediyl))bis(oxomethylene)bis(1-(2,4-dichlorophenyl)-6-methyl-1H-benzofuro[3,2-c]pyrazole-5-sulfonic acid)

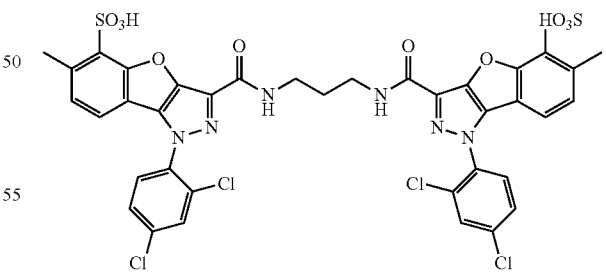

The synthesis of Ex. 12 was repeated but replacing the compound of Ex. 11 with that of Ex. 22f. 105 mg of a white solid corresponding to 3,3'-(propane-1,3-diylbis(azanediyl))bis(oxomethylene)bis(1-(2,4-dichlorophenyl)-6-methyl-1H-benzofuro[3,2-c]pyrazole-5-sulfonic acid) were obtained. $^1$H-NMR (CDCl$_3$) δ 1.80 (q, 2H), 2.64 (s, 6H), 3.34 (q, 4H), 6.98-7.18 (m, 2H), 7.69 (d, 2H), 7.73 (dd, 2H), 7.83 (d, 2H), 8.03 (d, 2H).

Example 23

Synthesis of 3,3'-(propane-1,3-diylbis(azanediyl))bis(oxomethylene)bis(8-chloro-1-(2'-4'-dichlorophenyl)-1,4,5,6-tetrahydrobenzo[6,7]cyclohepta[1,2-c]pyrazole-7-sulfonic acid)

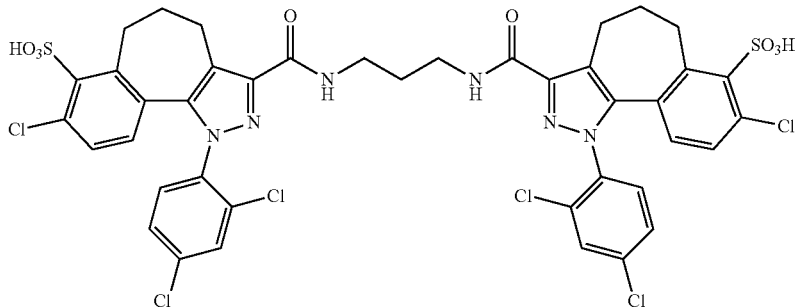 [SMILES: O=C(NCCCNC(=O)c1nn(-c2ccc(Cl)cc2Cl)c2c1CCCc1c-2ccc(Cl)c1S(=O)(=O)O)c1nn(-c2ccc(Cl)cc2Cl)c2c1CCCc1c-2ccc(Cl)c1S(=O)(=O)O]

23a: Synthesis of 8-chloro-1-(2'-4'-dichlorophenyl)-1,4,5,6-tetrahydrobenzo[6,7]cyclohepta[1,2-c]pyrazole-3-carboxylic acid

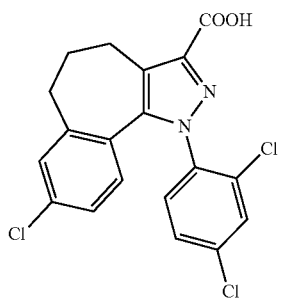 [SMILES: O=C(O)c1nn(-c2ccc(Cl)cc2Cl)c2c1CCCc1cc(Cl)ccc1-2]

8-chloro-1-(2'-4'-dichlorophenyl)-1,4,5,6-tetrahydrobenzo[6,7]cyclohepta[1,2-c]pyrazole-3-carboxylic acid was obtained according to the synthesis described in Example 2.3 of US Patent Application 2010/0215741.

7-chloro-2,3,4,5-tetrahydro-benzocycloheptan-1-one (12.84 mmoles) was reacted with metal sodium and diethyl oxalate to afford ethyl α-(7-chloro-1-oxo-2,3,4,5-tetrahydro-benzocyclohepten-2-yl)-α-oxo-acetate. 3.39 mmoles of this compound was refluxed with 2,4-dichlorophenylhydrazine hydrochloride (3.90 mmoles) in 8 ml of glacial acetic acid for 8 hours. At the end of the reaction the mixture was filtered. A residue was recovered that was washed with water and then air dried to yield ethyl 8-chloro-1-(2'-4'-dichlorophenyl)-1,4,5,6-tetrahydro-benzo[6,7]cyclohepta[1,2-c]pyrazole-3-carboxylate.

2.29 mmoles of the ethyl ester were solubilized in 15 ml of ethanol/water solution (1:1 v/v), then 1.67 grams of solid KOH were added. The reaction mixture was kept under stirring at the reflux temperature for a time of 4 hours and then poured into a mixture formed of ice and HCl 1N. A white precipitate was obtained. The precipitate was filtered, washed with water and dried in the air to yield 8-chloro-1-(2'-4'-dichlorophenyl)-1,4,5,6-tetrahydrobenzo[6,7]cyclohepta[1,2-c]pyrazole-3-carboxylic acid (yield of the ester hydrolysis: 95%). IR (nujol) ($\lambda=cm^{-1}$) 3410, 1715; $^1$H-NMR (CDCl$_3$) δ 2.25-2.29 (m, 2H), 2.68 (t, 2H, J=6.4 Hz), 3.09-3.24 (m, 2H), 4.52 (bs, 1H), 6.63 (d, 1H, J=8.4 Hz), 7.05 (dd, 1H, J=2.2 and 8.2 Hz), 7.31 (d, 1H, J=2.0 Hz), 7.40-7.45 (m, 2H), 7.52 (d, 1H, J=8.0 Hz).

23b: Synthesis of N,N'-(propane-1,3-diyl)bis[8-chloro-1-(2'-4'-dichlorophenyl)-1,4,5,6-tetrahydrobenzo[6,7]cyclohepta[1,2-c]pyrazole-3-carboxamide]

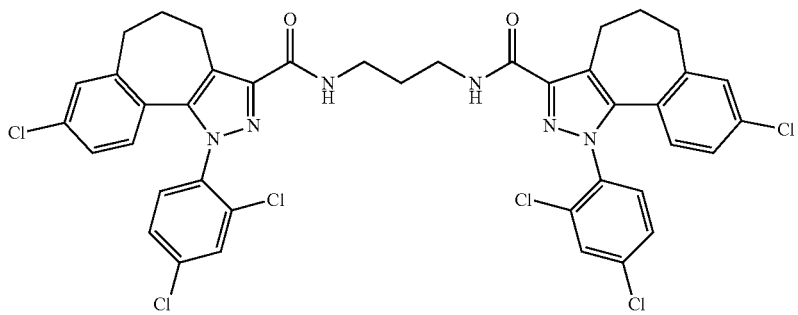 [SMILES: O=C(NCCCNC(=O)c1nn(-c2ccc(Cl)cc2Cl)c2c1CCCc1cc(Cl)ccc1-2)c1nn(-c2ccc(Cl)cc2Cl)c2c1CCCc1cc(Cl)ccc1-2]

The synthesis of Ex. 11f was repeated but replacing 1-(pentyl)-1,4-dihydro-thieno[3',2':4,5]cyclopenta[1,2-c]pyrazole-3-carboxylic acid with 8-chloro-1-(2'-4'-dichlorophenyl)-1,4,5,6-tetrahydrobenzo[6,7]cyclohepta[1,2-c]pyrazole-3-carboxylic acid. 110 mg of a white solid corresponding to N,N'-(propane-1,3-diyl)bis[8-chloro-1-(2'-4'-dichlorophenyl)-1,4,5,6-tetrahydrobenzo[6,7]cyclohepta[1,2-c]pyrazole-3-carboxamide] were obtained. $^1$H-NMR (CDCl$_3$) δ

1.93 (q, 2H), 2.23-2.32 (m, 4H), 2.65 (t, 4H), 3.15-3.24 (m, 4H), 3.52 (q, 4H), 7.32-7.45 (m, 4H), 7.48 (dd, 2H), 7.59 (d, 2H), 7.68 (dd, 4H).

23c: Synthesis of 3,3'-(propane-1,3-diylbis(azanediyl))bis(oxomethylene)bis(8-chloro-1-(2'-4'-dichlorophenyl)-1,4,5,6-tetrahydrobenzo[6,7]cyclohepta[1,2-c]pyrazole-7-sulfonic acid)

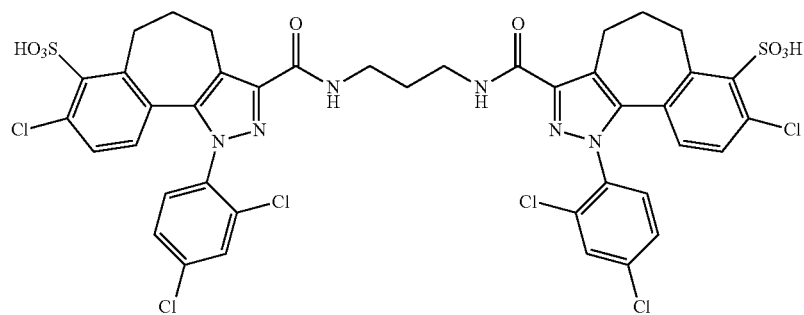 [SMILES: O=C(NCCCNC(=O)c1nn(-c2ccc(Cl)cc2Cl)c2c1CCCc1c-2ccc(Cl)c1S(=O)(=O)O)c1nn(-c2ccc(Cl)cc2Cl)c2c1CCCc1c-2ccc(Cl)c1S(=O)(=O)O]

The synthesis of Ex. 12 was repeated but replacing the compound of Ex. 11 with that of Ex. 23b. 90 mg of a white solid corresponding to 3,3'-(propane-1,3-diylbis(azanediyl))bis(oxomethylene)bis(8-chloro-1-(2'-4'-dichlorophenyl)-1,4,5,6-tetrahydrobenzo[6,7]cyclohepta[1,2-c]pyrazole-7-sulfonic acid) were obtained. $^1$H-NMR (CDCl$_3$) δ 1.79 (q, 2H), 2.21-2.38 (m, 4H), 2.65 (t, 4H), 3.35-3.42 (m, 8H), 7.59-7.69 (m, 4H), 7.72 (dd, 2H), 7.80 (d, 2H), 8.06 (d, 2H).

Example 24

Synthesis of 3,3'-(propane-1,3-diylbis(azanediyl))bis(oxomethylene)bis(1-(2'-4'-dichlorophenyl)-1,4,5,6-tetrahydro-benzo[6,7]cyclohepta[1,2-c]pyrazole-8-sulfonic acid)

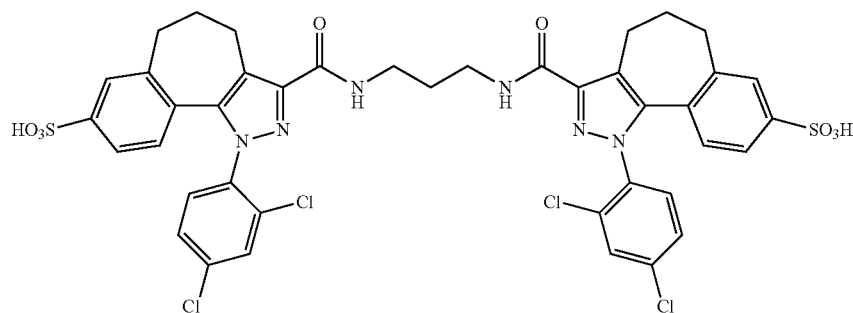 [SMILES: O=C(NCCCNC(=O)c1nn(-c2ccc(Cl)cc2Cl)c2c1CCCc1cc(S(=O)(=O)O)ccc1-2)c1nn(-c2ccc(Cl)cc2Cl)c2c1CCCc1cc(S(=O)(=O)O)ccc1-2]

24a: Synthesis of the 1-(2'-4'-dichlorophenyl)-1,4,5,6-tetrahydrobenzo[6,7]cyclohepta[1,2-c]pyrazole-3-carboxylic acid

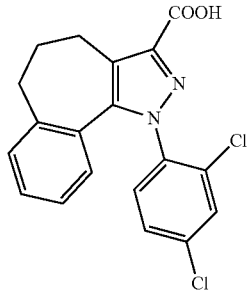 [SMILES: O=C(O)c1nn(-c2ccc(Cl)cc2Cl)c2c1CCCc1ccccc1-2]

The same procedure described in Ex. 23a was followed but starting from benzosuberone instead than from 7-chloro-2,3,4,5-tetrahydro-benzocycloheptan-1-one. At the end of the synthesis, 1-(2'-4'-dichlorophenyl)-1,4,5,6-tetrahydrobenzo[6,7]cyclohepta[1,2-c]pyrazole-3-carboxylic acid was obtained, which corresponds to the compound 8f described in Murineddu G. et al. J. Med. Chem. 2005 48 7351-7362. Rf=0.48 (eluent chloroform/methanol 9/1 v/v on silica gel); m.p.: 262-264° C.; IR (nujol) ($\lambda$=cm$^{-1}$) 1695; $^1$H-NMR (CDCl$_3$) $\delta$ 2.25-2.31 (m, 2H), 2.71 (t, 2H, J=6.2 Hz), 2.75-3.20 (m, 2H), 3.70 (br s, 1H, OH exchange with D$_2$O), 6.69 (d, 1H, J=7.6 Hz), 7.05 (t, 1H, J=7.0 Hz), 7.20-7.50 (m, 4H), 7.54 (d, 1H, J=8.0 Hz).

24b: Synthesis of N,N'-(propane-1,3-diyl)bis[1-(2'-4'-dichlorophenyl)-1,4,5,6-tetrahydrobenzo[6,7]cyclohepta[1,2-c]pyrazole-3-carboxamide]

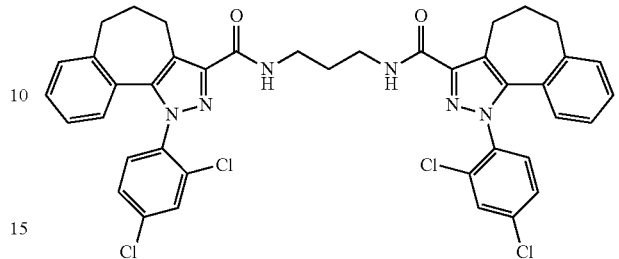

The synthesis of Ex. 11f was repeated but replacing 1-(pentyl)-1,4-dihydro-thieno[3',2':4,5]cyclopenta[1,2-c]pyrazole-3-carboxylic acid with 1-(2'-4'-dichlorophenyl)-1,4,5,6-tetrahydrobenzo[6,7]cyclohepta[1,2-c]pyrazole-3-carboxylic acid. 100 mg of a white solid corresponding to N,N'-(propane-1,3-diyl)bis[1-(2'-4'-dichlorophenyl)-1,4,5,6-tetrahydrobenzo[6,7]cyclohepta[1,2-c]pyrazole-3-carboxamide] were obtained. $^1$H-NMR (CDCl$_3$) $\delta$ 1.95 (q, 2H), 2.23-2.32 (m, 4H), 2.73 (t, 4H), 2.95-3.18 (m, 4H), 3.56 (q, 4H), 7.07-7.35 (m, 8H), 7.37 (dd, 2H), 7.53 (d, 2H), 7.65 (d, 4H).

24c: Synthesis of 3,3'-(propane-1,3-diylbis(azanediyl))bis(oxomethylene)bis(1-(2'-4'-dichlorophenyl)-1,4,5,6-tetrahydrobenzo[6,7]cyclohepta[1,2-c]pyrazole-8-sulfonic acid)

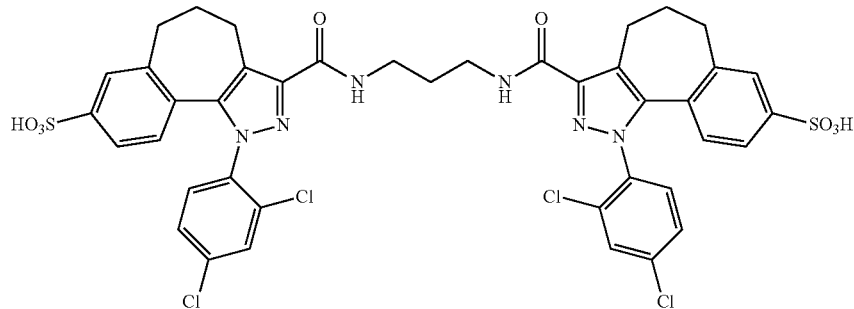 [SMILES: O=C(NCCCNC(=O)c1nn(-c2ccc(Cl)cc2Cl)c2c1CCCc1cc(S(=O)(=O)O)ccc1-2)c1nn(-c2ccc(Cl)cc2Cl)c2c1CCCc1cc(S(=O)(=O)O)ccc1-2]

The synthesis of Ex. 12 was repeated but replacing the compound of Ex. 11 with that of Ex. 24b. 100 mg of a white solid corresponding to 3,3'-(propane-1,3-diylbis(azanediyl))bis(oxomethylene)bis(1-(2'-4'-dichlorophenyl)-1,4,5,6-tetrahydrobenzo[6,7]cyclohepta[1,2-c]pyrazole-8-sulfonic acid) were obtained. $^1$H-NMR (CDCl$_3$) $\delta$ 1.77 (q, 2H), 2.16-2.34 (m, 4H), 2.61 (t, 4H), 3.31-3.45 (m, 8H), 7.59-7.69 (m, 4H), 7.74-7.95 (m, 4H), 8.01 (d, 2H), 8.04 (d, 2H).

Example 25

Synthesis of 3,3'-(propane-1,3-diylbis(azanediyl))bis(oxomethylene)bis(8-chloro-1-(2'-4'-dichlorophenyl)-4,5-dihydrobenzo-1H-6oxa-cyclohepta[1,2-c]pyrazole-7-sulfonic acid)

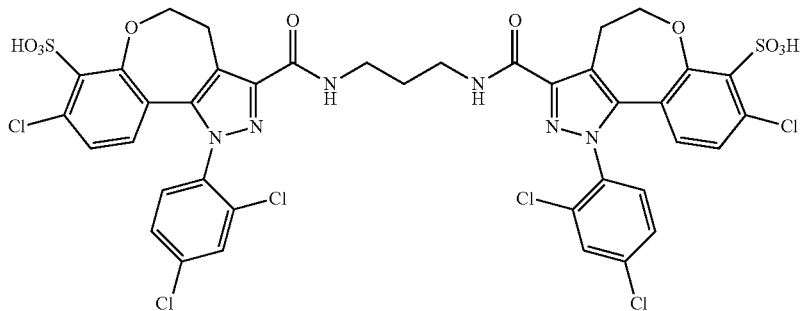 [SMILES: O=C(NCCCNC(=O)c1nn(-c2ccc(Cl)cc2Cl)c2c1CCOc1c-2ccc(Cl)c1S(=O)(=O)O)c1nn(-c2ccc(Cl)cc2Cl)c2c1CCOc1c-2ccc(Cl)c1S(=O)(=O)O]

25a: Synthesis of 8-chloro-1-(2'-4'-dichlorophenyl)-4,5-dihydrobenzo-1H-6oxa-cyclohepta[1,2-c]pyrazole-3-carboxylic acid

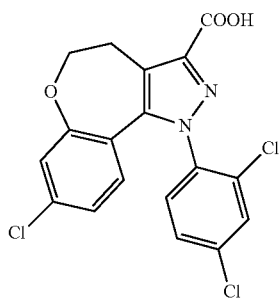

8-chloro-1-(2'-4'-dichlorophenyl)-4,5-dihydrobenzo-1H-6oxa-cyclohepta[1,2-c]pyrazole-3-carboxylic acid was obtained according to the synthesis described in Example 2.5 of US Patent Application 2010/0215741.

A dispersion was prepared by suspending 1 eq of NaOH (flakes) in 3-chlorophenol (1 eq). The obtained dispersion was heated to 170° C. up to complete solubilization of the base. 1.4 Eq. of γ-butyrolactone were then dropwise added maintaining the reaction mixture at 170° C. for 5 hours. The reaction mixture was then poured into ice and then acidified with HCl 6N. The reaction product was extracted with CHCl$_3$, dehydrated over Na$_2$SO$_4$ and concentrated under vacuum. The residue was purified by flash chromatography (eluent oil ligroin/ethyl acetate 4:1 v/v) to obtain a yellow solid corresponding to 4-(3-chlorophenoxy)butyric acid. 27.96 mmoles of 4-(3-chlorophenoxy)butyric acid were added to 48 grams of polyphosphoric acid and the resulting mixture was maintained under stirring at 90° C. for 2 hours. At the end the reaction mixture was then poured on ice and extracted with CH$_2$Cl$_2$. The pooled organic phases were washed with a 10% Na$_2$CO$_2$ aqueous solution, dehydrated over Na$_2$SO$_4$, and concentrated under vacuum. The residue was purified by flash chromatography (oil ligroin/ethyl acetate 9/1 v/v). An orange oil corresponding to 8-chloro-1-oxo-2,3,4,5-tetrahydrobenzo-cycloheptan-5-one was obtained.

2 eq of metallic sodium were added to 5 ml of anhydrous ethanol and the resulting dispersion was maintained under stirring at room temperature up to complete sodium solubilization. 1 eq of ethyl oxalate and 30 ml of a solution of 8-chloro-1-oxo-2,3,4,5-tetrahydrobenzo-cycloheptan-5-one (1 eq) in anhydrous ethanol were added to the formerly prepared solution. The reaction mixture was maintained under stirring at room temperature for 1.5 hours and then poured on a mixture formed of ice and HCl 2N. The obtained solution was extracted with ethyl acetate and the recovered organic phase was washed with water, dehydrated on Na$_2$SO$_4$, and concentrated under vacuum. The residue was purified by flash chromatography (eluent oil ligroin/ethyl acetate 4/1 v/v) to obtain the diketoester γ-(7-chloro-5-oxo-2,3,4,5-tetrahydrobenzocycloheptan-2-yl)-aoxoacetate.

1 eq of the diketoester and 1.1 eq of 2,4-dichlorophenyl-hydrazine hydrochloride in 50 ml of ethanol were heated at reflux for 90 minutes. The reaction solvent was then removed under vacuum and the residue was purified by flash chromatography (eluent oil ligroin/ethyl acetate 9/1 v/v). The compound ethyl 8-chloro-1-(2',4'-dichlorophenyl)-4,5-dihydrobenzo-1H-oxa-cyclohepta[1,2-c]pyrazole-3-carboxylate was isolated as an orange solid.

1 eq of the compound was dispersed in 10 ml of methanol. To said dispersion 7 ml of methanol containing 2 eq of KOH were added. The obtained methanolic solution was maintained under reflux conditions for 12 hours and then poured into a mixture formed of ice and HCl 1N. A yellow precipitate was formed which was filtered, washed with water, and then dried under a nitrogen flow. 8-chloro-1-(2'-4'-dichlorophenyl)-4,5-dihydrobenzo-1H-6oxa-cyclohepta[1,2-c]pyrazole-3-carboxylic acid was isolated in a 90.0% yield. Rf=0.38 (eluent chloroform/methanol 9/1 v/v on silica gel); m.p.: 230-231° C.; IR (nujol) (λ=cm$^{-1}$) 1689; $^1$H-NMR (CDCl$_3$/DMSO) δ 3.10-3.45 (br s, 3H, 1 OH exchang. with D$_2$O), 4.30-4.48 (m, 2H), 6.67 (d, 1H, J=8.4 Hz), 6.83 (dd, 1H, J=8.2 Hz), 7.13 (s, 1H), 7.44-7.50 (m, 3H).

25b: Synthesis of N,N'-(propane-1,3-diyl)bis[8-chloro-1-(2'-4'-dichlorophenyl)-4,5-dihydrobenzo-1H-6oxa-cyclohepta[1,2-c]pyrazole-3-carboxamide]

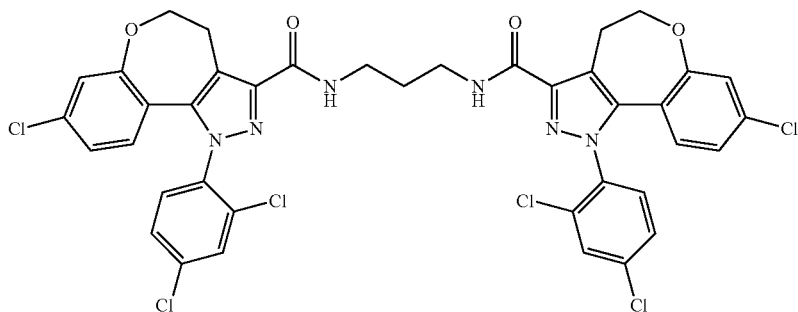 [SMILES: O=C(NCCCNC(=O)c1nn(-c2ccc(Cl)cc2Cl)c2c1CCOc1cc(Cl)ccc1-2)c1nn(-c2ccc(Cl)cc2Cl)c2c1CCOc1cc(Cl)ccc1-2]

The synthesis of Ex. 11f was repeated but replacing 1-(pentyl)-1,4-dihydro-thieno[3',2':4,5]cyclopenta[1,2-c]pyrazole-3-carboxylic acid with 8-chloro-1-(2'-4'-dichlorophenyl)-4,5-dihydrobenzo-1H-6oxa-cyclohepta[1,2-c]pyrazole-3-carboxylic acid. 115 mg of a white solid corresponding to N,N'-(propane-1,3-diyl)bis[8-chloro-1-(2'-4'-dichlorophenyl)-4,5-dihydrobenzo-1H-6oxa-cyclohepta[1,2-c]pyrazole-3-carboxamide] were obtained. $^1$H-NMR (CDCl$_3$) δ 1.96 (q, 2H), 3.10-3.50 (m, 4H), 3.57 (q, 4H), 4.28-4.57 (m, 4H), 7.25 (s, 2H), 7.39 (dd, 2H), 7.42-7.49 (m, 4H), 7.50 (d, 2H), 7.61 (d, 2H).

25c: Synthesis of 3,3'-(propane-1,3-diylbis(azanediyl))bis(oxomethylene)bis(8-chloro-1-(2'-4'-dichlorophenyl)-4,5-dihydrobenzo-1H-6oxa-cyclohepta[1,2-c]pyrazole-7-sulfonic acid)

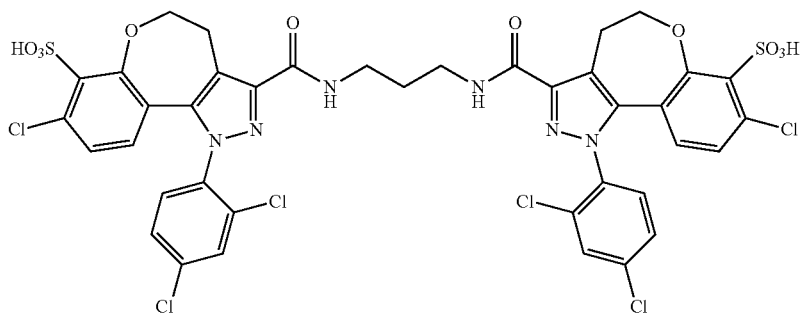 [SMILES: O=C(NCCCNC(=O)c1nn(-c2ccc(Cl)cc2Cl)c2c1CCOc1c-2ccc(Cl)c1S(=O)(=O)O)c1nn(-c2ccc(Cl)cc2Cl)c2c1CCOc1c-2ccc(Cl)c1S(=O)(=O)O]

The synthesis of Ex. 12 was repeated but replacing the compound of Ex. 11 with that of Ex. 25b. 100 mg of a white solid corresponding to 3,3'-(propane-1,3-diylbis(azanediyl))bis(oxomethylene)bis(8-chloro-1-(2'-4'-dichlorophenyl)-4,5-dihydrobenzo-1H-6oxa-cyclohepta[1,2-c]pyrazole-7-sulfonic acid) were obtained. $^1$H-NMR (CDCl$_3$) δ 1.75 (q, 2H), 3.25-3.45 (m, 4H), 3.35 (q, 4H), 4.32-4.58 (m, 4H), 7.39-7.62 (m, 4H), 7.75 (dd, 2H), 7.79 (d, 2H), 8.02 (d, 2H).

Example 26

Synthesis of 3,3'-(propane-1,3-diylbis(azanediyl))bis(oxomethylene)bis(6-bromo-1-(2,4-dichlorophenyl)-4,5-dihydro-1H-thieno[3,2-g]indazole-7-sulfonic acid)

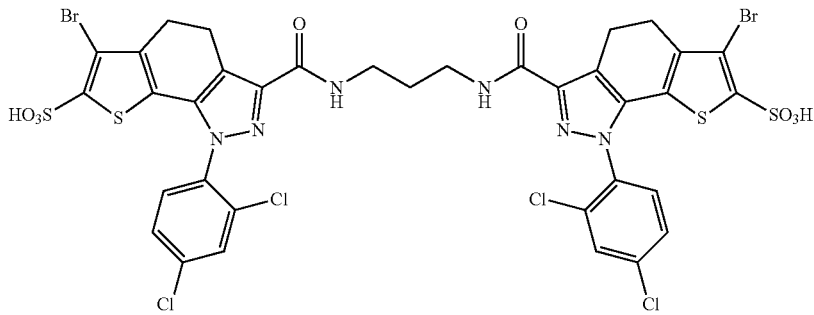 [SMILES: O=C(NCCCNC(=O)c1nn(-c2ccc(Cl)cc2Cl)c2c1CCc1c-2sc(S(=O)(=O)O)c1Br)c1nn(-c2ccc(Cl)cc2Cl)c2c1CCc1c-2sc(S(=O)(=O)O)c1Br]

26a: Synthesis of 6-bromo-1-(2',4'-dichlorophenyl)-4,5-dihydro-1H-thieno[3,2-g]indazol-3-carboxylic acid

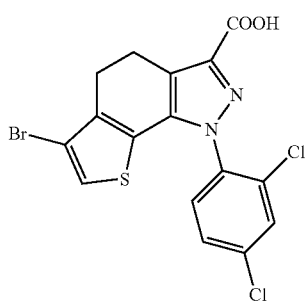 [SMILES: O=C(O)c1nn(-c2ccc(Cl)cc2Cl)c2c1CCc1c(Br)csc1-2]

6-bromo-1-(2',4'-dichlorophenyl)-4,5-dihydro-1H-thieno[3,2-g]indazol-3-carboxylic acid was obtained according to the synthesis described in Example 2.5 of U.S. Pat. No. 7,485,730. Metallic sodium (9.42 mmoles) was added in small pieces to absolute ethanol (5 ml). The dispersion thus formed was maintained under reflux conditions up to complete solubilization. Diethyl oxalate (4.7 mmoles) was added to the obtained solution at room temperature. Then dropwise a solution of 3-bromo-4,5,6,7-tetrahydro-benzo[b]thiophene-7-one (4.7 mmoles) in absolute ethanol (5 ml) was added. The reaction mixture was kept under stirring at room temperature for 1 hour and then poured in a mixture formed of ice and HCl 1N. A yellow precipitate was formed which was filtered, washed with water and dried. The dried product corresponds to ethyl 3-bromo-7-oxy-4,5,6,7-tetrahydro-1-benzo[b]thiophene-5-carboxylate. 2,4-dichlorophenylhydrazine hydrochloride (1.93 mmoles) and ethyl 3-bromo-7-oxy-4,5,6,7-tetrahydro-1-benzo[b]thiophene-5-carboxylate (1.75 mmoles) were dispersed in 11.67 ml of ethanol. The mixture was reacted at the reflux temperature for a time of 2 hours, then cooled down to room temperature. After solvent removal, a raw solid was obtained. The raw solid was treated with ether and purified by flash chromatography (eluent oil ligroin/ethyl acetate 9/1 v/v) to obtain a solid corresponding to the ethyl ester of 6-bromo-1-(2',4'-dichlorophenyl)-4,5-dihydro-1H-thieno[3,2-g]indazole-3-carboxylic acid.

1.14 mmoles of the ethyl ester was dispersed in 10 ml of methanol. To the dispersion 4.2 ml of methanol containing 2.28 mmoles of KOH were added. The obtained methanolic solution was maintained under reflux conditions for 8 hours and then poured into a mixture formed of ice and HCl 1N. A precipitate was formed which was filtered, washed with water, and then dried under a nitrogen flow. 6-bromo-1-(2',4'-dichlorophenyl)-4,5-dihydro-1H-thieno[3,2-g]indazol-3-carboxylic acid was isolated in a 90.0% yield. M.p.: 239-242° C.; IR (nujol) ($\lambda$=cm$^{-1}$) 3413, 1694; $^1$H-NMR (CDCl$_3$/DMSO) $\delta$ 2.97 (t, 3H, J=8.0 Hz), 3.24 (t, 2H, J=8.0 Hz), 5.86 (br s, 1H, OH exchange with D$_2$O), 7.10 (s, 1H), 7.42-7.45 (m, 2H), 7.62 (s, 1H).

26b: Synthesis of N,N'-(propane-1,3-diyl)bis[6-bromo-1-(2',4'-dichlorophenyl)-4,5-dihydro-1H-thieno[3,2-g]indazol-3-carboxamide]

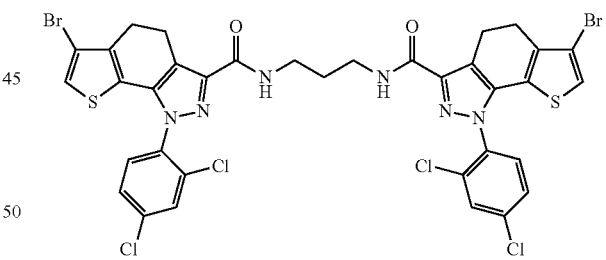

The synthesis of Ex. 11f was repeated but replacing 1-(pentyl)-1,4-dihydro-thieno[3',2':4,5]cyclopenta[1,2-c]pyrazole-3-carboxylic acid with 6-bromo-1-(2',4'-dichlorophenyl)-4,5-dihydro-1H-thieno[3,2-g]indazol-3-carboxylic acid. 98 mg of a white solid corresponding to N,N'-(propane-1,3-diyl)bis[6-bromo-1-(2',4'-dichlorophenyl)-4,5-dihydro-1H-thieno[3,2-g]indazol-3-carboxamide] were obtained. $^1$H-NMR (CDCl$_3$) $\delta$ 1.95 (q, 2H), 2.93 (t, 4H), 3.35 (t, 4H), 3.56 (q, 4H), 7.15 (s, 2H), 7.37 (dd, 2H), 7.48 (d, 2H), 7.64 (d, 2H).

26c: Synthesis of 3,3'-(propane-1,3-diylbis(azanediyl))bis(oxomethylene)bis(6-bromo-1-(2,4-dichlorophenyl)-4,5-dihydro-1H-thieno[3,2-g]indazole-7-sulfonic acid)

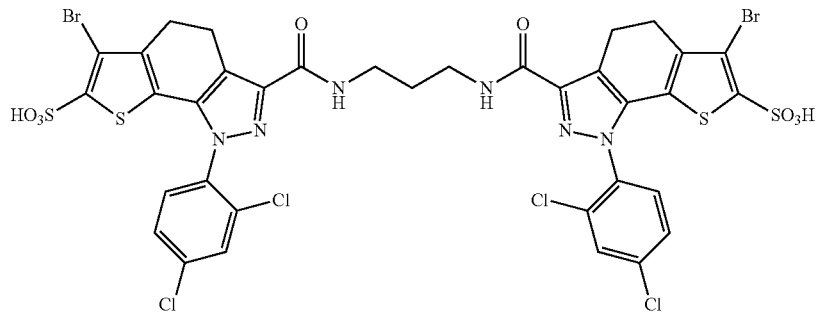 [SMILES: O=C(NCCCNC(=O)c1nn(-c2ccc(Cl)cc2Cl)c2c1CCc1c-2sc(S(=O)(=O)O)c1Br)c1nn(-c2ccc(Cl)cc2Cl)c2c1CCc1c-2sc(S(=O)(=O)O)c1Br]

The synthesis of Ex. 12 was repeated but replacing the compound of Ex. 11 with that of Ex. 26b. 88 mg of a white solid corresponding to 3,3'-(propane-1,3-diylbis(azanediyl))bis(oxomethylene)bis(6-bromo-1-(2,4-dichlorophenyl)-4,5-dihydro-1H-thieno[3,2-g]indazole-7-sulfonic acid) were obtained. $^1$H-NMR (CDCl$_3$) δ 1.75 (q, 2H), 2.93 (t, 4H), 3.34 (q, 4H), 3.38 (t, 4H), 7.74 (dd, 2H), 7.82 (d, 2H), 8.03 (d, 2H).

Example 27

Synthesis of the Compound

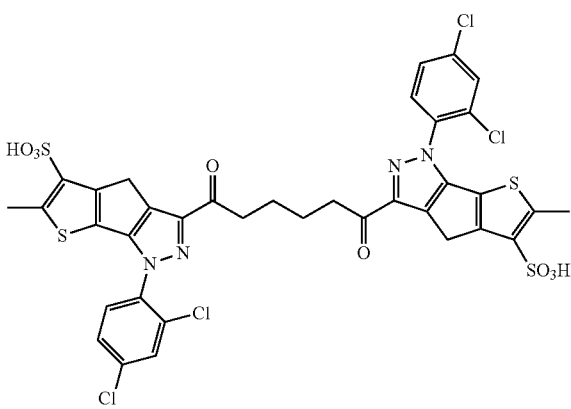

27a: Synthesis of ethyl 1-(2'-4'-dichlorophenyl)-6-methyl-1,4-dihydro-thieno[3',2':4,5]cyclopenta[1,2-c]pyrazole-3-carboxylate

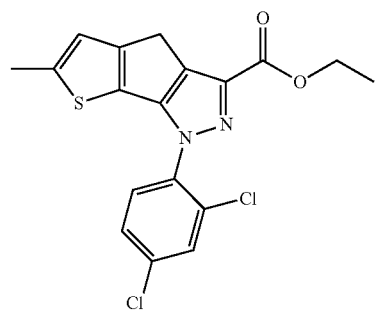 [SMILES: CCOC(=O)c1nn(-c2ccc(Cl)cc2Cl)c2c1Cc1cc(C)sc1-2]

Ethyl 1-(2'-4'-dichlorophenyl)-6-methyl-1,4-dihydro-thieno[3',2':4,5]cyclopenta[1,2-c]pyrazole-3-carboxylate was obtained according to the synthesis described in Example 1.7 of Patent Application US 2010/0215759.

Metallic sodium (0.60 g) was added in small portions to absolute ethanol (15 ml) while stirring up to complete solubilization. To this solution diethyl oxalate (1.92 g). By dripping, a solution of 2-methyl-4H-5,6-dihydro-cyclopenta[b]thiophen-6-one (13.14 mmoles) in absolute ethanol (40 ml), were then added. The reaction mixture was kept under stirring at room temperature for 5 hours and then poured into a mixture formed of ice and HCl 1N. A white precipitate was formed that was filtered, washed with water and dried in the air. The obtained compound corresponded to ethyl α-(2-methyl-6-oxo-4H-5,6-dihydro-cyclopenta[b]thiophen-5-yl)-α-oxo-acetate.

A mixture, prepared with 3.95 mmoles of ethyl α-(2-methyl-6-oxo-4H-5,6-dihydro-cyclopenta[b]thiophen-5-yl)-α-oxo-acetate, 4.55 mmoles of 2,4-dichlorophenylhydrazine hydrochloride, and 8 ml of glacial acetic acid, was heated at reflux for 8 hours, then cooled at room temperature. The formed precipitate was filtered, washed with water and dried in the air to give ethyl 1-(2'-4'-dichlorophenyl)-6-methyl-1,4-dihydro-thieno-[3',2':4,5]cyclopenta[1,2-c]pyrazole-3-carboxylate (yield 60%). IR (nujol) ($\lambda$=cm$^{-1}$) 1725; $^1$H-NMR (CDCl$_3$) $\delta$ 1.43 (t, 3H, J=7.0 Hz), 2.54 (s, 3H), 3.65 (s, 2H), 4.46 (q, 2H, J=7.0 Hz), 6.85 (s, 1H), 7.42 (dd, 1H, J=2.2 and 8.4 Hz), 7.54-7.61 (m, 2H).

27b: Synthesis of N-methoxy-N-methyl-1-(2'-4'-dichlorophenyl)-6-methyl-1,4-dihydro-thieno[3',2':4,5]cyclopenta[1,2-c]pyrazole-3-carboxamide

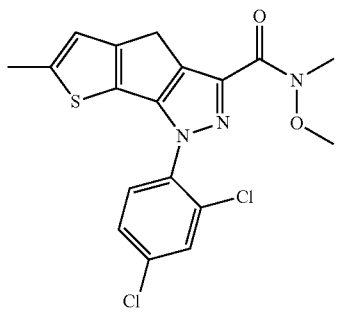

N-methoxy-N-methyl-1-(2'-4'-dichlorophenyl)-6-methyl-1,4-dihydro-thieno[3',2':4,5]cyclopenta[1,2-c]pyrazole-3-carboxamide was obtained according to the synthesis described in Example 3.15a of Patent Application US 2010/0215759. Trimethylaluminium (0.92 ml of a 2 M solution in hexane) was added dropwise to a suspension of dimethylhydroxylamine hydrochloride (1.84 mmoles) in CH$_2$Cl$_2$ (3 ml) at 0° C. The reaction mixture was kept under stirring at 0° C. for 45 minutes and then continuing at room temperature for 40 minutes. A solution was obtained, that was dropwise added, under stirring, of a solution in CH$_2$Cl$_2$ (2 ml) of the compound obtained in Ex. 27a (0.92 mmoles). Stirring was continued for further 4 hours at room temperature. The reaction mixture was then cooled to 0° C., and a 10% HCl solution was carefully added dropwise until acid pH. The mixture was extracted with CH$_2$Cl$_2$, washed with water and brine, dried over Na$_2$SO$_4$, and filtered. The residue obtained after evaporation of the solvent under reduced pressure was purified by flash chromatography (eluent petroleum ether/ethyl acetate 7/3 v/v). The compound N-methoxy-N-methyl-1-(2'-4'-dichlorophenyl)-6-methyl-1,4-dihydro-thieno[3',2':4,5]cyclopenta[1,2-c]pyrazole-3-carboxamide was obtained as a white solid. Yield 60%. IR (nujol) ($\lambda$=cm$^{-1}$) 1686; $^1$H-NMR (CDCl$_3$) $\delta$ 2.51 (s, 3H); 3.53 (bs, 3H), 3.63 (s, 2H), 3.82 (s, 3H), 6.85 (s, 1H), 7.41 (dd, 1H, J=2.2 and 8.6 Hz), 7.55 (d, 1H, J=8.6 Hz), 7.60 (d, 1H, J=1.9 Hz).

27c: Synthesis of the Compound

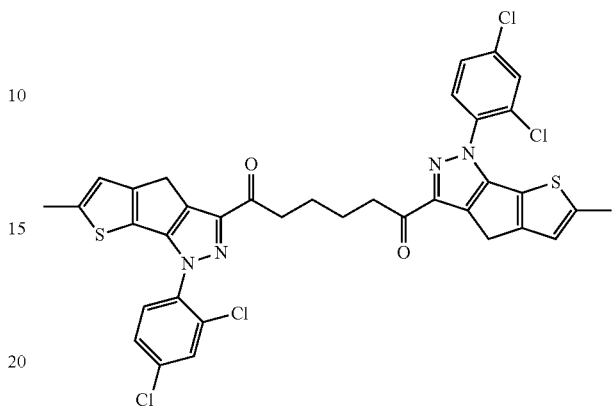

3.86 ml of a 0.5 M solution of butane-1,4-dimagnesium bromide in THF were added dropwise at 0° C., under a nitrogen atmosphere, to 10 ml of a THF solution containing 1.28 mmoles of the compound prepared in Ex. 27b. The reaction mixture was slowly warmed to room temperature and then kept under stirring at room temperature for 24 hours. The temperature of the mixture was then lowered to 0° C. 30 ml of a saturated NH$_4$Cl water solution, maintained at 0° C., were added dropwise. The reaction mixture was again warmed up to room temperature, then diluted with ethylacetate (25 ml). The aqueous and the organic phases were separated. The aqueous layer was extracted with ethylacetate (3×20 ml), and the combined organic layers were washed with water, dried over Na$_2$SO$_4$, and filtered. The residue obtained after solvent evaporation under reduced pressure was purified by flash chromatography (eluent petroleum ether/diethyl ether 9/1 v/v) obtaining the titled compound (Yield 50%). $^1$H-NMR (CDCl$_3$) $\delta$ 1.76-1.94 (m, 4H), 2.51 (s, 6H); 2.83-2.97 (m, 4H), 3.65 (s, 4H), 6.87 (s, 2H), 7.39 (dd, 2H), 7.50 (d, 2H), 7.61 (d, 2H).

27d: Synthesis of the Compound

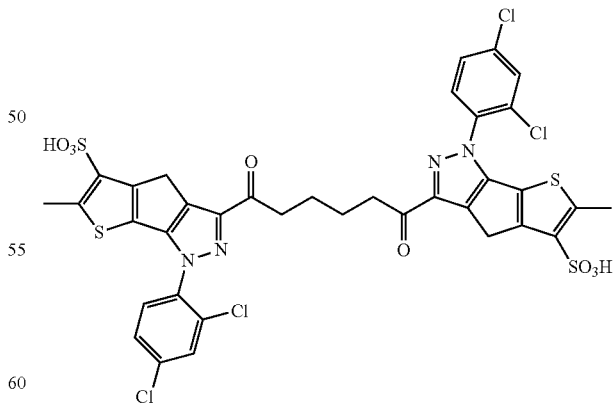

The synthesis of Ex. 12 was repeated but replacing the compound of Ex. 11 with that of Ex. 27c. 96 mg of a white solid corresponding to the titled compound were obtained. $^1$H-NMR (CDCl$_3$) $\delta$ 1.78-1.97 (m, 4H), 2.64 (s, 6H); 2.73-2.91 (m, 4H), 3.85 (s, 4H), 7.75 (dd, 2H), 7.83 (d, 2H), 8.02 (d, 2H).

28: Synthesis of the Compound

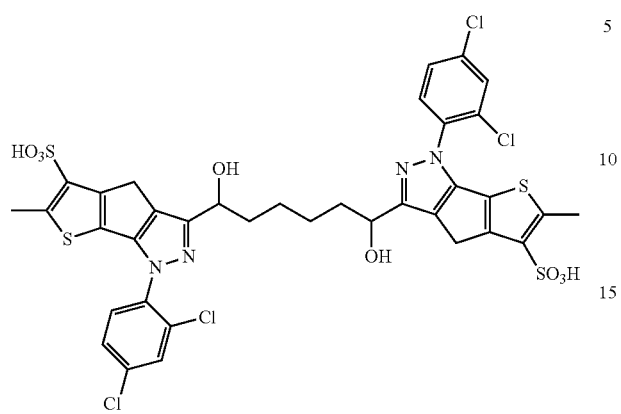

28a: Synthesis of the Compound

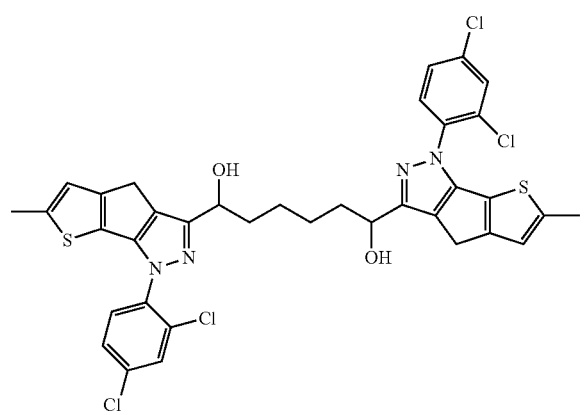

To a suspension of the compound obtained in Ex. 27c (0.12 mmoles) in methanol (3 ml) sodium borohydride (0.50 mmoles) was added. The obtained mixture was stirred at room temperature for 2 hours. The reaction mixture was then diluted with $CHCl_3$ and washed with water. The organic layer was dried over $Na_2SO_4$, filtered, and concentrated under reduced pressure. The titled compound was obtained (Yield 90%). $^1$H-NMR (CDCl$_3$) δ 1.15-1.30 (m, 4H), 1.76-1.94 (m, 4H), 2.53 (s, 6H), 3.65-3.81 (m, 4H), 4.93-5.02 (m, 2H), 6.78 (s, 2H), 7.36 (dd, 2H), 7.49 (d, 2H), 7.59 (d, 2H).

28b: Synthesis of the Compound

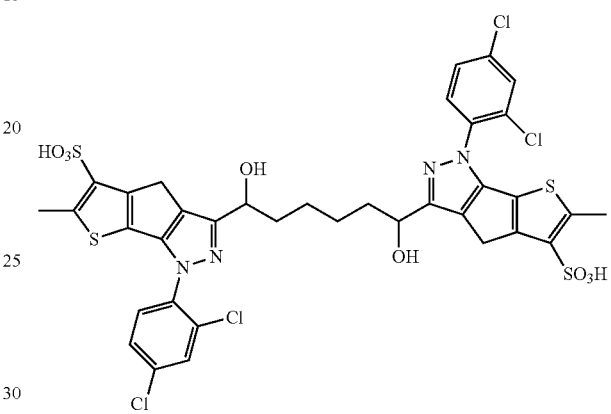

The synthesis of Ex. 12 was repeated but replacing the compound of Ex. 11 with that of Ex. 28a. 88 mg of a white solid corresponding to the titled compound were obtained. $^1$H-NMR (CDCl$_3$) δ 1.22-1.30 (m, 4H), 1.56-1.84 (m, 4H), 2.36 (s, 6H), 3.75-3.87 (m, 4H), 5.03-5.12 (m, 2H), 7.73 (dd, 2H), 7.82 (d, 2H), 8.05 (d, 2H).

Example 29

Synthesis of the Compound

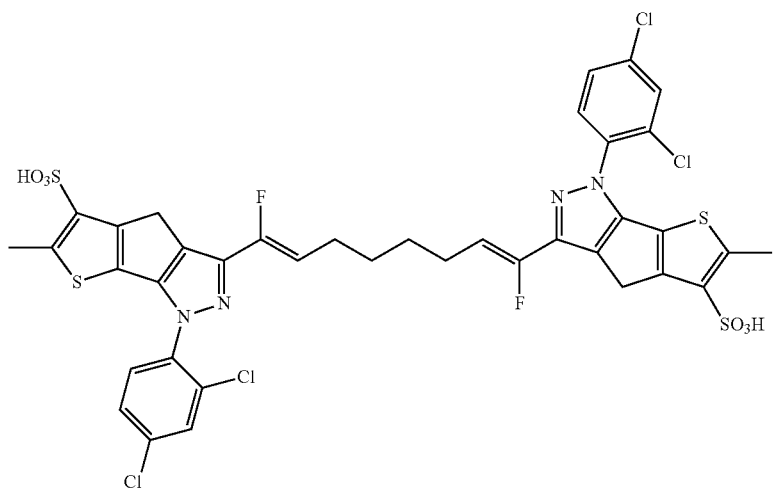

29a: Synthesis of 1-(2'-4'-dichlorophenyl)-6-methyl-1,4-dihydro-thieno[3',2':4,5]cyclopenta[1,2-c]pyrazole-3-carbaldehyde

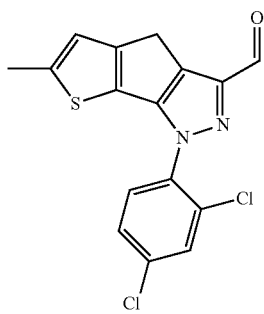 [SMILES: Cc1cc2c(s1)-c1c(c(C=O)nn1-c1ccc(Cl)cc1Cl)C2]

The compound prepared in Ex. 27b (1.65 mmoles) was dissolved in 7 ml of dry THF and added dropwise to a stirred suspension of LiAlH$_4$ (1.98 mmoles) in dry THF (10 ml) under nitrogen at 0° C. The mixture was stirred for 20 minutes at the same temperature, then the reaction was quenched by adding 10% HCl, poured into brine, and extracted with diethyl ether. The organic layer was dried over Na$_2$SO$_4$ and filtered, then the solvent was evaporated under reduced pressure obtaining 1-(2'-4'-dichlorophenyl)-6-methyl-1,4-dihydro-thieno[3',2':4,5]cyclo-penta[1,2-c]pyrazole-3-carbaldehyde. Yield 92%. $^1$H-NMR (CDCl$_3$) δ 2.32 (s, 3H), 3.78 (s, 2H), 7.00 (s, 1H), 7.58-7.92 (m, 3H), 10.12 (s, 1H).

29b: Synthesis of diethyl[1-(2'-4'-dichlorophenyl)-6-methyl-1,4-dihydro-thieno[3',2':4,5]cyclopenta[1,2-c]pyrazole-3-yl]hydroxymethylphosphonate

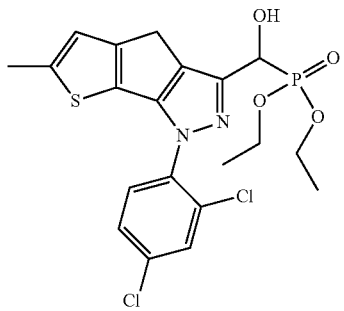 [SMILES: CCOP(=O)(OCC)C(O)c1nn(-c2ccc(Cl)cc2Cl)c2c1Cc1cc(C)sc1-2]

Triethylamine (1.68 mmoles) was added to a stirred mixture of diethyl phosphite (3.82 mmoles) in toluene (5 ml) at room temperature. After 5 minutes a solution of the compound prepared in Ex. 29a (1.56 mmoles) in toluene (5 ml) was added. The reaction mixture was maintained under reflux conditions for 24 hours, then 3.12 mmoles of K$_2$CO$_3$ were added and the mixture was stirred for 2 hours. The reaction mixture was then washed with water, extracted with diethyl ether, dried over Na$_2$SO$_4$ and filtered. The solvent was evaporated under reduced pressure. A crude product was obtained that was purified by flash chromatography (ethyl acetate/petroleum ether 7/3 v/v) yielding diethyl[1-(2'-4'-dichlorophenyl)-6-methyl-1,4-dihydro-thieno[3',2':4,5]cyclopenta[1,2-c]pyrazole-3-yl]hydroxymethylphosphonate. Yield 75%. $^1$H-NMR (CDCl$_3$) δ 1.25-1.38 (m, 6H), 2.35 (s, 3H), 3.81 (s, 2H), 4.08-4.25 (m, 4H), 5.10 (d, 1H), 6.98 (s, 1H), 7.37-7.69 (m, 3H).

29c: Synthesis of diethyl[1-(2'-4'-dichlorophenyl)-6-methyl-1,4-dihydro-thieno[3',2':4,5]cyclopenta[1,2-c]pyrazole-3-yl]fluoromethylphosphonate

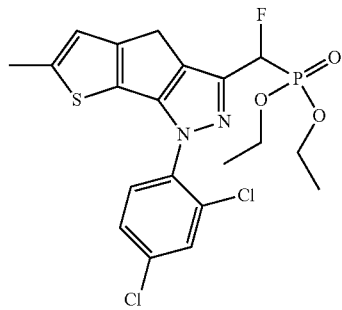 [SMILES: CCOP(=O)(OCC)C(F)c1nn(-c2ccc(Cl)cc2Cl)c2c1Cc1cc(C)sc1-2]

1 mmole of DAST (Diethylaminosulfur trifluoride) was added to a stirred solution of the compound prepared in Ex. 29b (0.83 mmoles) in CH$_2$Cl$_2$ (2 ml) at −78° C. After 1 hour at −78° C., the reaction mixture was poured carefully into a saturated NaHCO$_3$ (4 ml) aqueous solution at room temperature. The aqueous layer was extracted with CH$_2$Cl$_2$ (3×4 ml) and the combined organic phases were dried over Na$_2$SO$_4$ and filtered. The solvent was evaporated under reduced pressure obtaining a crude product which was purified by flash chromatography (eluent ethyl acetate/petroleum ether 4/6 v/v) yielding diethyl[1-(2'-4'-dichlorophenyl)-6-methyl-1,4-dihydro-thieno[3',2':4,5]cyclo-penta[1,2-c]pyrazole-3-yl]fluoromethylphosphonate. Yield 70%. $^1$H-NMR (CDCl$_3$) δ 1.31 (t, 3H), 1.37 (t, 3H), 2.40 (s, 3H), 3.85 (s, 2H), 4.08-4.25 (m, 2H), 4.26-4.35 (m, 2H), 5.87 (d, 1H), 6.99 (s, 1H), 7.45-7.78 (m, 3H).

29d: Synthesis of the Compound

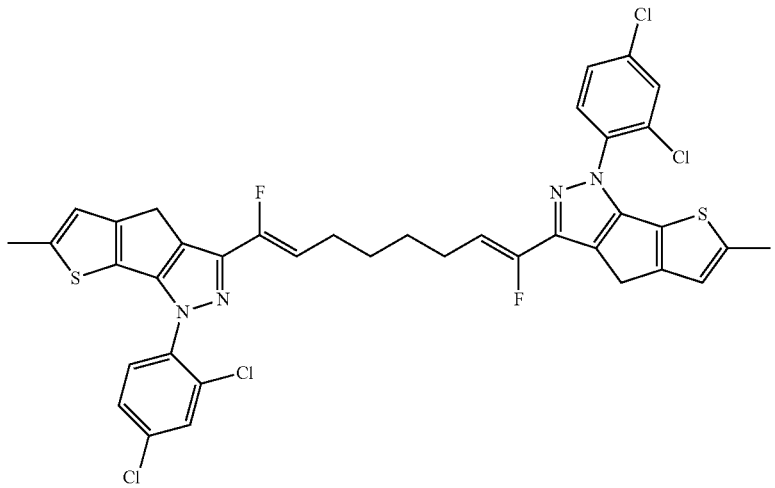

0.11 mmoles of adipaldheyde was added under nitrogen to a stirred solution of the compound prepared in Ex. 29c (0.36 mmoles) dissolved in 2.4 ml of THF. The resulting mixture was cooled to −78° C., then 0.95 mmoles of a solution 2M of lithium diisopropylamide (LDA) in THF/cyclohexane/ethyl-benzene were added dropwise. The resulting solution was stirred at −78° C. for 30 minutes, then it was warmed at room temperature and stirred for further 18 hours. The reaction mixture was then poured into water and the aqueous layer extracted with ether. The combined organic phases were washed, in the order, with a 10% HCl solution, water, and brine. The organic phase was dried over $Na_2SO_4$ and filtered. The solvent was evaporated under reduced pressure. The left residue was purified by flash chromatography (petroleum ether/diethyl ether 96/4 v/v) obtaining the titled compound. Yield 35%. $^1$H-NMR (CDCl$_3$) δ 1.76-1.94 (m, 4H), 2.51 (s, 6H), 2.83-2.97 (m, 4H), 3.65 (s, 4H), 5.37-5.45 (m, 2H), 6.87 (s, 2H), 7.39 (dd, 2H), 7.50 (d, 2H), 7.61 (d, 2H).

29e: Synthesis of the Compound

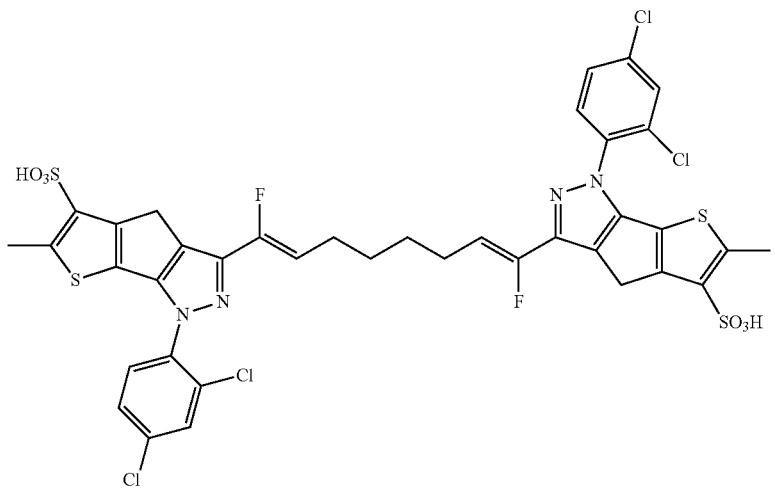

The synthesis of Ex. 12 was repeated but replacing the compound of Ex. 11 with that of Ex. 29d. 89 mg of a white solid corresponding to the titled compound were obtained. $^1$H-NMR (CDCl$_3$) δ 1.78-1.97 (m, 4H), 2.64 (s, 6H), 2.73-2.91 (m, 4H), 3.85 (s, 4H), 5.38-5.51 (m, 2H), 7.75 (dd, 2H), 7.83 (d, 2H), 8.02 (d, 2H).

Example 30

Synthesis of the Compound

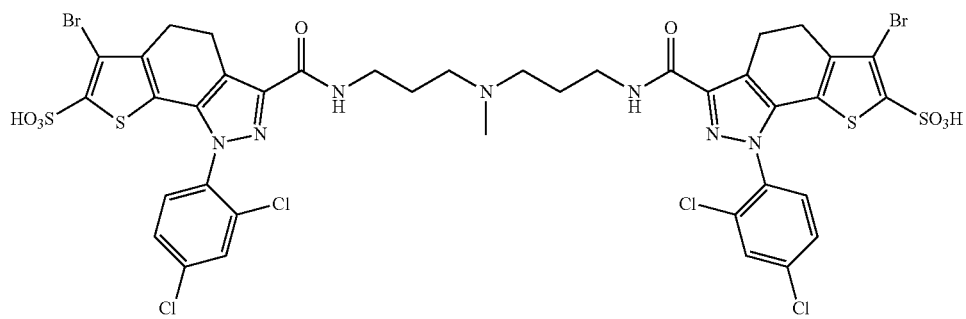 [SMILES: CN(CCCNC(=O)c1nn(-c2ccc(Cl)cc2Cl)c2c1CCc1c-2sc(S(=O)(=O)O)c1Br)CCCNC(=O)c1nn(-c2ccc(Cl)cc2Cl)c2c1CCc1c-2sc(S(=O)(=O)O)c1Br]

30a: Synthesis of the Compound

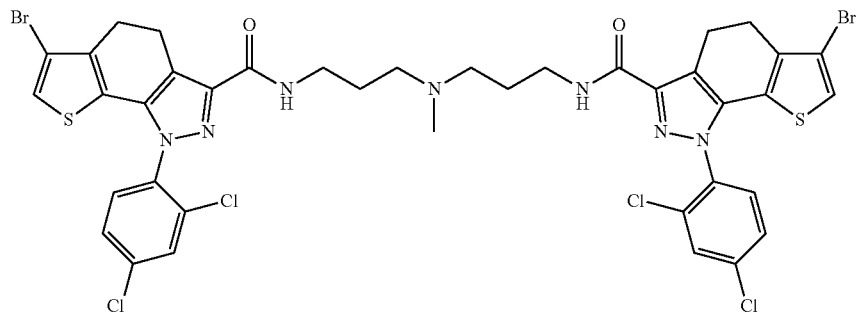 [SMILES: CN(CCCNC(=O)c1nn(-c2ccc(Cl)cc2Cl)c2c1CCc1c(Br)csc1-2)CCCNC(=O)c1nn(-c2ccc(Cl)cc2Cl)c2c1CCc1c(Br)csc1-2]

1 mmole of 6-bromo-1-(2',4'-dichlorophenyl)-4,5-dihydro-1H-thieno[3,2-g]indazol-3-carboxylic acid prepared in Ex. 26a and 1.1 mmoles of 1,1'-carbonyldiimidazole (CDI) in 2.5 ml of DMF were mixed under stirring at room temperature and stirring continued for 3 hours, then 0.5 mmoles of CH$_3$N(CH$_2$CH$_2$CH$_2$NH$_2$)$_2$ in DMF (2 ml) were added. The reaction mixture was stirred at room temperature for 48 hours. The solvent was then removed under reduced pressure and the obtained residue was purified by flash chromatography (eluent CHCl$_3$/CH$_3$OH 9/1 v/v) obtaining the titled compound. Yield 38%. $^1$H-NMR (CDCl$_3$) δ 1.82 (q, 4H), 2.38 (s, 3H), 2.55 (t, 4H), 2.88-3.35 (m, 8H), 3.56 (q, 4H), 7.14 (s, 2H), 7.36 (dd, 2H), 7.47 (d, 2H), 7.63 (d, 2H).

30b: Synthesis of Compound

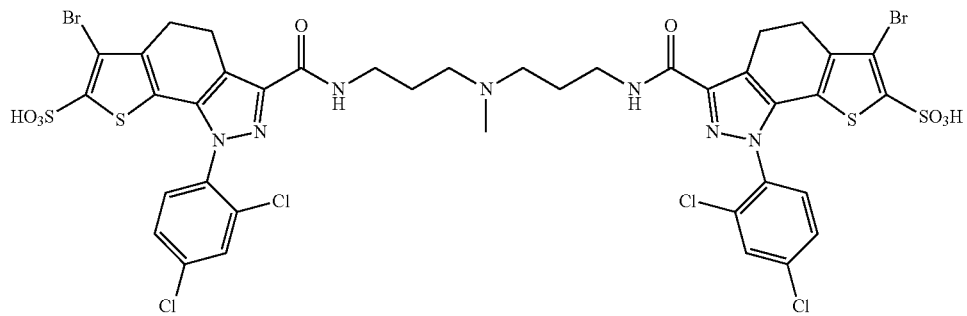 [SMILES: CN(CCCNC(=O)c1nn(-c2ccc(Cl)cc2Cl)c2c1CCc1c-2sc(S(=O)(=O)O)c1Br)CCCNC(=O)c1nn(-c2ccc(Cl)cc2Cl)c2c1CCc1c-2sc(S(=O)(=O)O)c1Br]

The synthesis of Ex. 12 was repeated but replacing the compound of Ex. 11 with that of Ex. 30a. 77 mg of a white solid corresponding to the titled compound were obtained. 1H-NMR (CDCl$_3$) δ 1.87 (q, 4H), 2.43 (s, 3H), 2.57 (t, 4H), 2.90-3.42 (m, 8H), 3.58 (q, 4H), 7.74 (dd, 2H), 7.82 (d, 2H), 8.03 (d, 2H).

The invention claimed is:
1. Compounds of formula (I) and pharmaceutically acceptable salts thereof, cis and trans isomers, isomers E and Z, optical isomers, hydrates, and solvates thereof

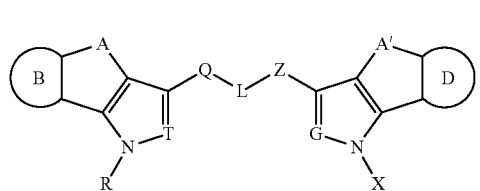

(I)

wherein:
A is selected from: O, CH$_2$, CH$_2$—CH$_2$, CH═CH, CH$_2$—CH$_2$—CH$_2$, CH$_2$—CH$_2$—CH$_2$—CH$_2$, O—CH$_2$, O—CH$_2$—CH$_2$, or O—CH$_2$—CH$_2$—CH$_2$
wherein when A is selected from O—CH$_2$, O—CH$_2$—CH$_2$, or O—CH$_2$—CH$_2$—CH$_2$, the oxygen atom is linked to the adjacent carbon atom shared with ring B,
A' has the following meanings:
  A'=A when A=O, CH$_2$, CH$_2$—CH$_2$, CH═CH, CH$_2$—CH$_2$—CH$_2$, or CH$_2$—CH$_2$—CH$_2$—CH$_2$
  A'=CH$_2$—O when A=O—CH$_2$,
  A'=CH$_2$—CH$_2$—O when A=O—CH$_2$—CH$_2$,
  A'=CH$_2$—CH$_2$—CH$_2$—O when A=O—CH$_2$—CH$_2$—CH$_2$,
wherein when A' is selected from CH$_2$—O, CH$_2$—CH$_2$—O or CH$_2$—CH$_2$—CH$_2$—O, the oxygen atom is linked to the adjacent carbon atom shared with ring D, T and G, equal to or different from each other, are selected between N or CH, R and X, equal to or different from each other, are selected from:
  heteroaryl, etheroarylalkyl, aryl, arylalkyl, arylalkenyl, cycloalkyl, cycloalkylalkyl, heterocycloalkyl, or heterocycloalkylalkyl, wherein one or more hydrogen atoms of said heteroaryl, heteroaryl alkyl, aryl, arylalkyl, arylalkenyl, cycloalkyl, cycloalkylalkyl, heterocyclo alkyl, heterocycloalkylalkyl are optionally substituted with one or more of the following groups, equal to or different from each other: OH, halogen, linear or when possible branched C$_1$-C$_7$ alkyl, linear or when possible branched C$_2$-C$_7$ alkenyl, linear or when possible branched C$_2$-C$_7$ alkynyl, linear or when possible branched C$_1$-C$_7$ alkylthio, linear or when possible branched C$_1$-C$_7$ alkoxy, linear or when possible branched C$_1$-C$_7$ haloalkyl, linear or when possible branched C$_1$-C$_7$ haloalkoxy, SO$_2$NH$_2$, SO$_3$H, COOH, cyano, nitro, or NR$_{10}$R$_{11}$, wherein R$_{10}$ and R$_{11}$, equal to or different from each other, are selected from H, linear or when possible branched C$_1$-C$_7$ alkyl, or cycloalkyl,
  R$_{30}$—W wherein R$_{30}$ is a linear or when possible branched bivalent aliphatic C$_1$-C$_{10}$ chain, W is selected from hydrogen, halogen, isothiocyanate, CN, OH, OCH$_3$, NH$_2$, SO$_2$NH$_2$ or CH═CH$_2$
B and D, equal to or different from each other, are selected between heteroaryl and aryl, wherein:
at least one of the hydrogen atoms of said heteroaryl and aryl are substituted with groups selected from SO$_3^-$, SO$_3$H, COO$^-$, COOH, one or more of the remaining hydrogen atoms of said heteroaryl and aryl are optionally substituted with G1 groups, equal to or different from each other, selected from OH, halogen, linear or when possible branched C$_1$-C$_{20}$ alkyl, linear or when possible branched C$_2$-C$_{20}$ alkenyl, linear or when possible branched C$_2$-C$_{20}$ alkynyl, linear or when possible branched C$_1$-C$_{20}$ alkylthio, linear or when possible branched C$_1$-C$_{20}$ alkoxy, linear or when possible branched C$_1$-C$_{20}$ haloalkyl, linear or when possible branched C$_1$-C$_{20}$ haloalkoxy, cyano, nitro, SO$_2$NH$_2$, COOR$_{19}$, or NR$_{20}$R$_{21}$ wherein R$_{19}$ is a group selected from linear or when possible branched C$_1$-C$_{20}$ alkyl, linear or when possible branched C$_2$-C$_{20}$ alkenyl, linear or when possible branched C$_2$-C$_{20}$ alkynyl, heteroaryl, heteroarylalkyl, aryl, arylalkyl, arylalkenyl, cycloalkyl, cycloalkylalkyl, heterocycloalkyl or heterocyclo alkylalkyl, R$_{20}$ and R$_{21}$, equal to or different from each other have the meaning of R$_{19}$ or H,
Q is a bivalent group selected from the following:

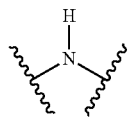

QA

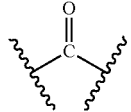

QB

-continued

QC
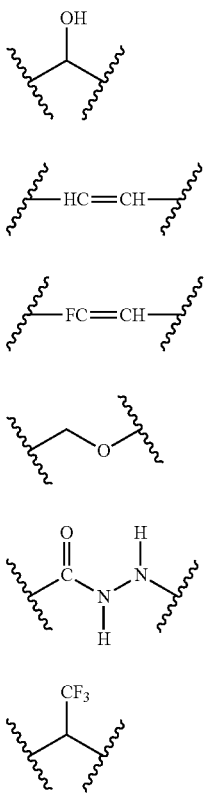
QD

QE

QF

QG

QH

Z is a bivalent group having the following meanings:
Z=Q when Q is selected from QA, QB, QC, QD, or QH
Z=QE' when Q=QE QE'
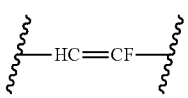

Z=QF' when Q=QF,

QF'

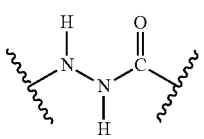

Z=QG' when Q=QG,

QG'

L is a bivalent group having the following meanings:
L=L1 when Q=Z=QA,

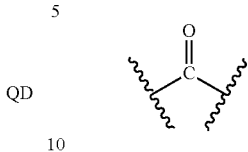 L1

L is selected between L2 or L3 when Q=Z=QB,

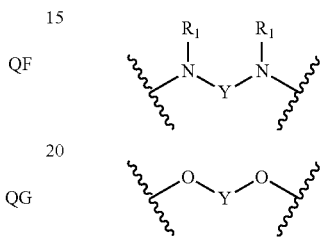

L2

L3 wherein $R_1$ is selected from H, $CH_3$ or $CH_2$—$CH_3$,
L=L4 when Q=Z and Q is selected from QA, QB, QC, QD, or QH, or
when Q=QF and Z=QF',
when Q=QE and Z=QE',

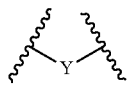 L4

-L=L5 when Q=Z and Q=QH,

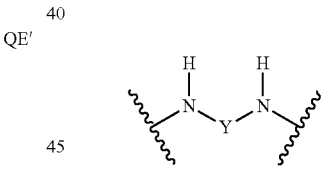 L5

L is selected between L6 or L7 when Q=QG and Z=QG',

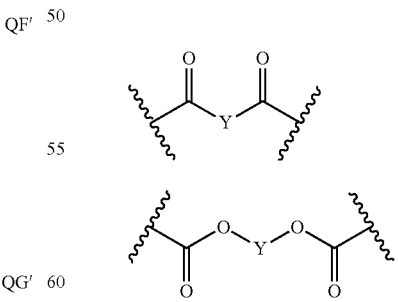

L6

L7

Y being a bivalent group selected from: linear or when possible branched $C_2$-$C_{20}$ alkylene,
$CH_2$-$A_1$-$CH_2$ wherein $A_1$ is a linear or when possible branched $C_2$-$C_{20}$ alkenylene, $CH_2$-$A_2$-$CH_2$ wherein $A_2$ is a linear or when possible branched C2-C20 alkynylene, $CH_2$—$CH_2$—(O—$CH_2$—$CH_2$)$_k$—O—$CH_2$—$CH_2$ wherein k is an integer comprised between 4 and 30, or Y is selected from the following groups:

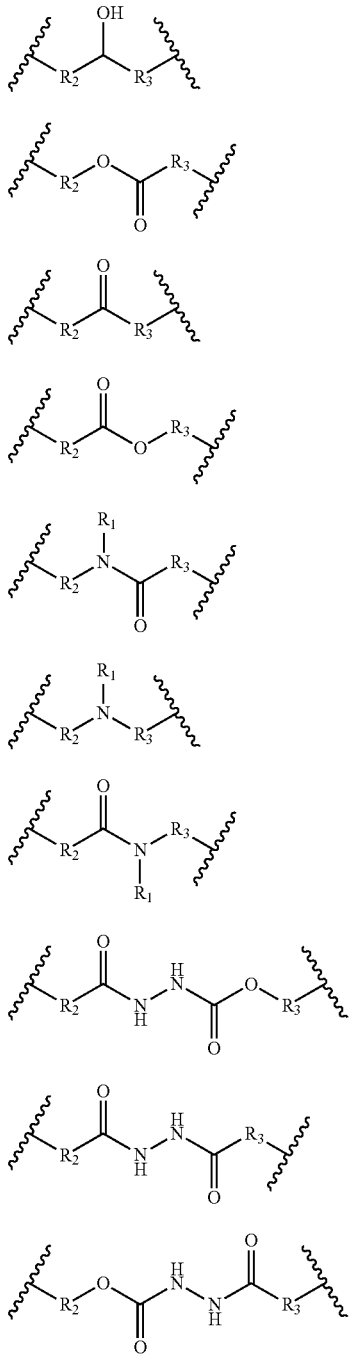

wherein:
$R_1$ is as defined above,
$R_2$ and $R_3$, equal to or different from each other, have the meaning of linear or when possible branched $C_1$-$C_{20}$ alkylene, $CH_2$-$A_1$-$CH_2$ and $CH_2$-$A_2$-$CH_2$,
wherein $A_1$ and $A_2$ are as defined above.

2. Compounds according to claim 1, wherein T=G, R=X, B=D.

3. Compounds according to claim 1 wherein T and G, equal to each other, are nitrogen.

4. Compounds according to claim 1 wherein T=G, R=X, B and D equal to each other, have the meaning of monocyclic heteroaryl and phenyl, wherein one hydrogen atom of said monocyclic heteroaryl and phenyl is substituted with a group selected from $SO_3^-$, $SO_3H$, $COO^-$, COOH and wherein one or more hydrogen atoms of said monocyclic heteroaryl and phenyl are optionally substituted with one or more G1 groups, equal to or different from each other.

5. Compounds according to claim 1, wherein T and G, equal to each other, are nitrogen and in the bivalent substituent L Y=$Y_{100}$, $Y_{100}$ being selected from linear or when possible branched $C_2$-$C_{20}$ alkylene, Y1, Y3, Y5, Y6, Y7, wherein:

$R_1$ is as defined above, R2 and $R_3$, equal to or different from each other, are linear or when possible branched $C_1$-$C_{20}$ alkylene, B and D, equal to each other, are selected between phenyl and monocyclic heteroaryl, wherein one hydrogen atom of said phenyl and monocyclic heteroaryl is substituted with one group selected from $SO_3H$, $SO_3^-$, $COO^-$, COOH and the other hydrogen atoms are optionally substituted with G1 groups, R and X, equal to each other, are selected from the following groups:

GA, having the following meanings: monocyclic heteroaryl, monocyclic heteroarylalkyl, phenyl, monocyclic arylalkyl, monocyclic arylalkenyl, monocyclic cycloalkyl, monocyclic cycloalkylalkyl, monocyclic heterocycloalkyl or monocyclic heterocycloalkyl alkyl, wherein one or more hydrogen atoms of said monocyclic heteroaryl, monocyclic heteroarylalkyl, phenyl, monocyclic arylalkyl, monocyclic arylalkenyl, monocyclic cycloalkyl, monocyclic cycloalkylalkyl, monocyclic heterocycloalkyl, monocyclic heterocyclo alkylalkyl are optionally substituted with groups, equal to or different from each other, selected from OH, halogen, linear or when possible branched $C_1$-$C_7$ alkyl, linear or when possible branched $C_2$-$C_7$ alkenyl, linear or when possible branched $C_2$-$C_7$ alkynyl, linear or when possible branched $C_1$-$C_7$ alkylthio, linear or when possible branched $C_1$-$C_7$ alkoxy, linear or when possible branched $C_1$-$C_7$ haloalkyl, linear or when possible branched $C_1$-$C_7$ haloalkoxy, $SO_2NH_2$, $SO_3H$, COOH, cyano, nitro, or $NR_{10}R_{11}$ wherein $R_{10}$ and $R_{11}$, equal to or different from each other, are selected from H, linear or when possible branched $C_1$-$C_7$ alkyl, or cycloalkyl, $R_{30}$—W wherein $R_{30}$ is as defined above and W=$W_a$ is selected from hydrogen, halogen, OH, $OCH_3$, $NH_2$, $SO_2NH_2$ or CH=$CH_2$.

6. Compounds according to claim 1 wherein:

Y has the meaning of $Y_{100}$ as defined above,

T and G are nitrogen,

B and D, equal to each other, are selected from phenyl and thiophene, wherein one hydrogen atom of said phenyl and thiophene is substituted with a group selected from $SO_3H$, $SO_3^-$, $COO^-$, COOH, R and X, equal to each other, are selected from the groups GA and $R_{30}$—W with W=$W_aR_{30}$ and $W_a$ being as defined above.

7. Compounds according to claim 1, selected from the following:

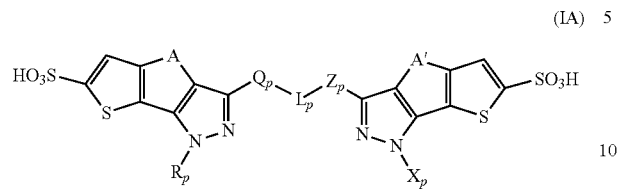
(IA)

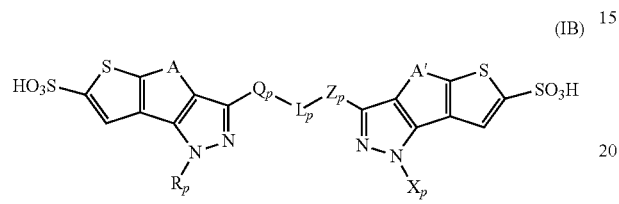
(IB)

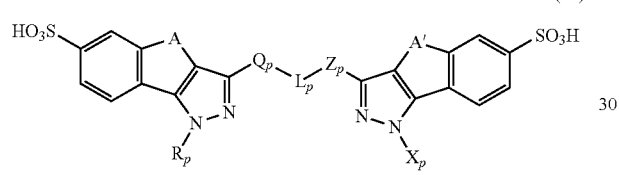
(IC)

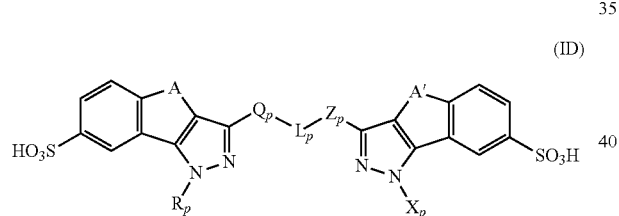
(ID)

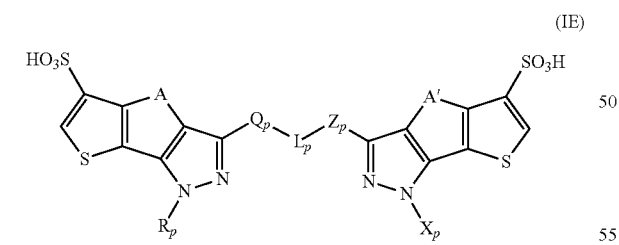
(IE)

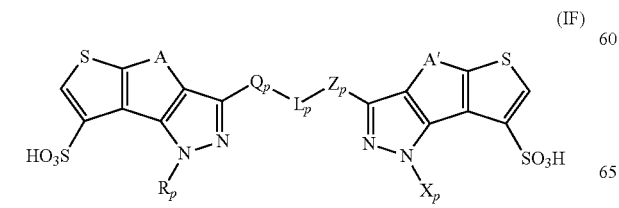
(IF)

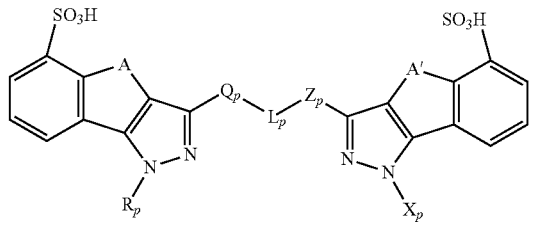
(IG)

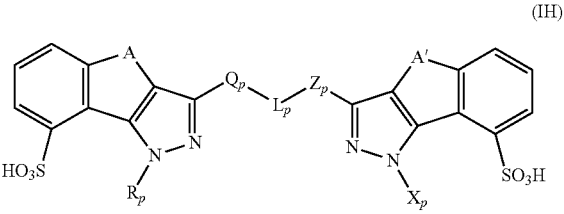
(IH)

wherein:

A and A' are as defined above, $R_p$ and $X_p$ equal to each other, have the following meanings:

phenyl, thiophene, benzyl and cyclohexyl, wherein one or more hydrogen atoms of said phenyl, thiophene, benzyl and cyclohexyl are optionally substituted with groups, equal to or different from each other, selected from halogen, linear or when possible branched $C_1$-$C_7$ alkyl, $SO_2NH_2$, $SO_3H$, COOH, cyano, nitro, or $NR_{104}R_{114}$ wherein $R_{104}$ and $R_{114}$, equal to or different from each other, are selected from H and linear or when possible branched $C_1$-$C_7$ alkyl, $R_{30}$—W with W=$W_b$, wherein $R_{30}$ is as defined above and $W_b$ is a group selected from hydrogen and halogen, Qp and $Z_p$, equal to each other, are selected between the bivalent groups QA and QB, as defined above, $L_p$ has the following meanings:

$L_p$=L1 when $Q_p$=$Z_p$=QA, $L_p$=L5' when $Q_p$=$Z_p$=QB,

L5' having the following formula

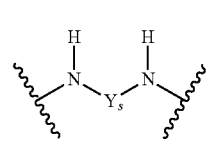
L5' wherein $Y_S$ has the meaning of $Y_{100}$.

8. Compounds according to claim 1, selected from the following:
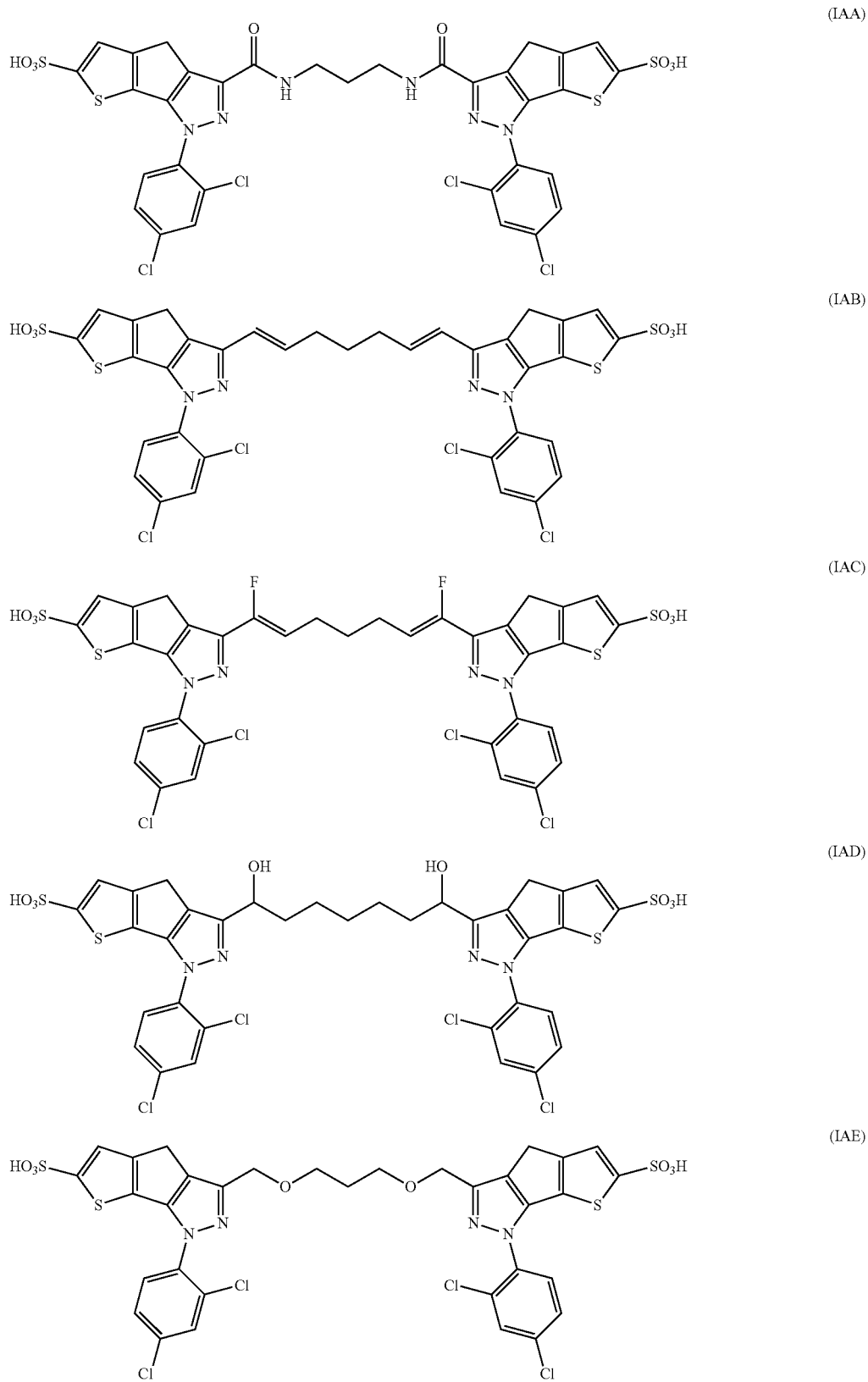

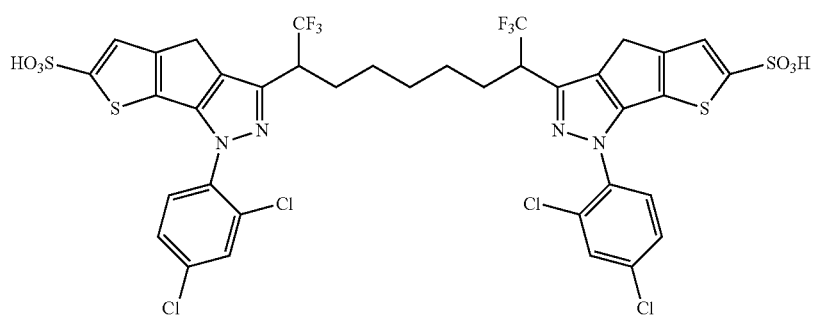
(IAF)
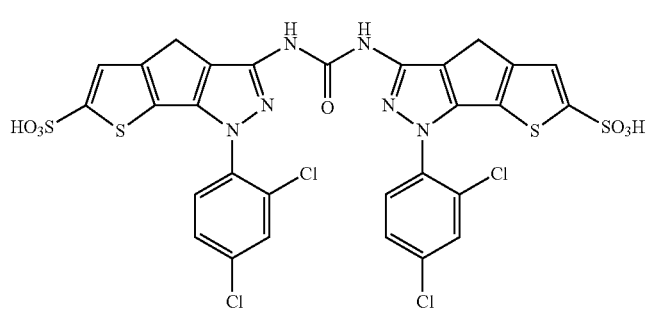
(IAG)
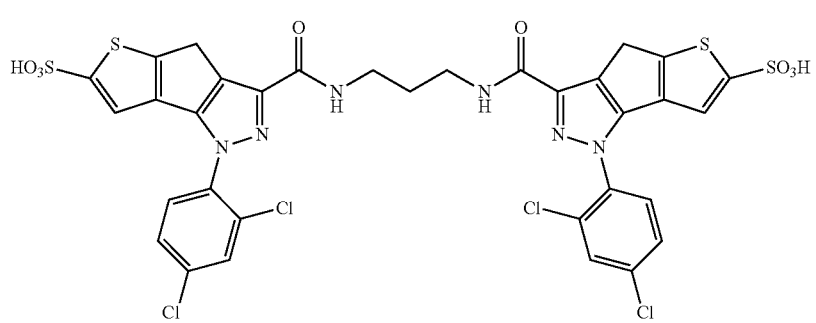
(IBA)
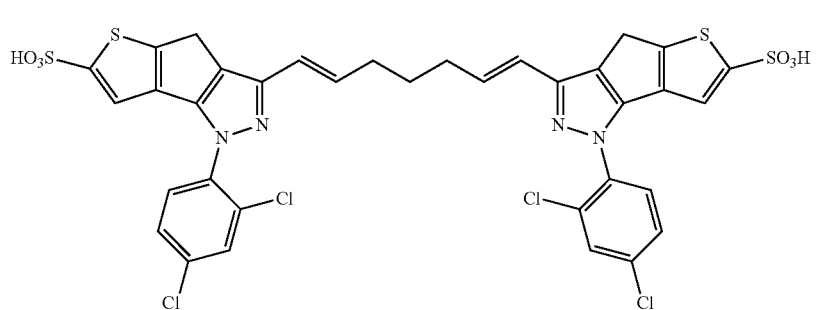
(IBB)
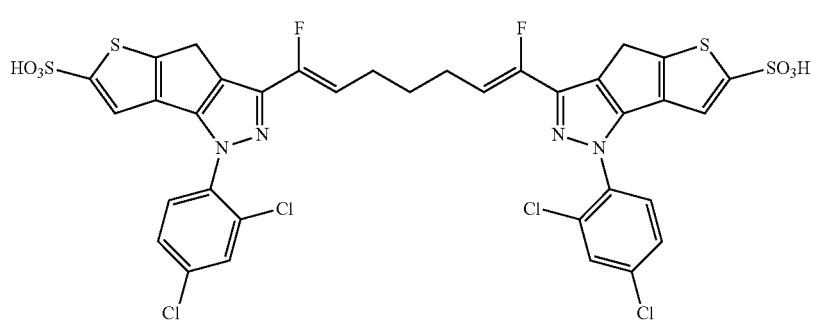
(IBC)

-continued
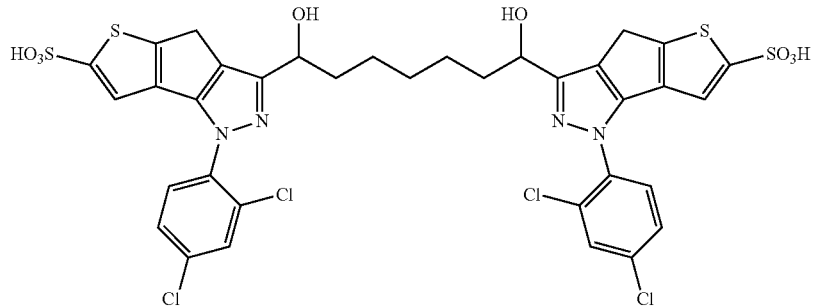
(IBD)
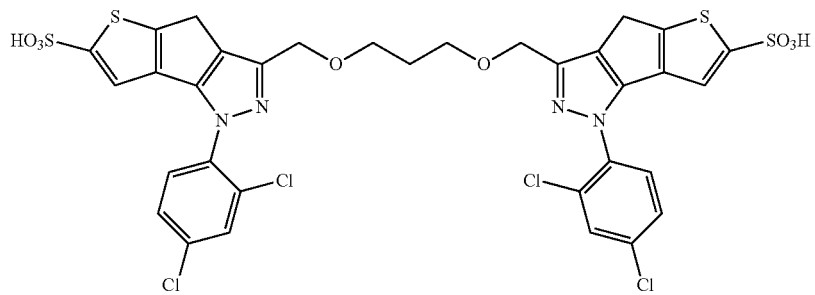
(IBE)
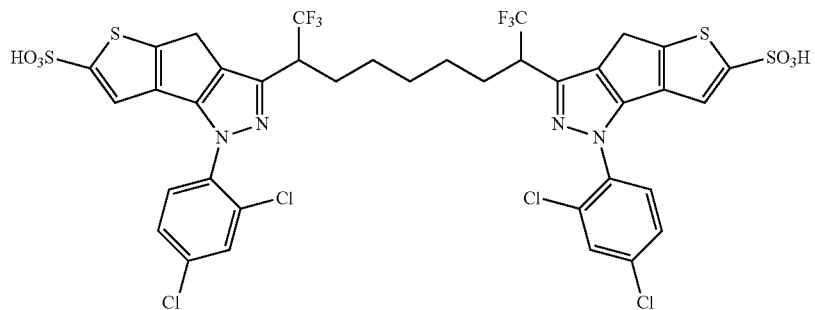
(IBF)
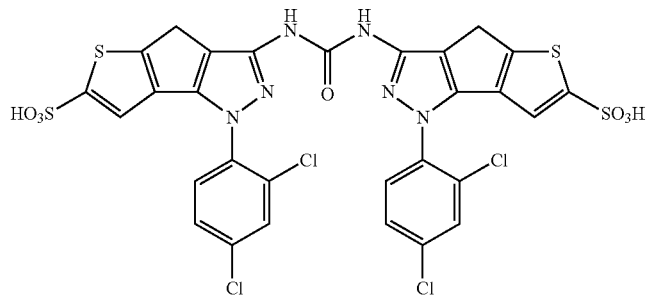
(IBG)
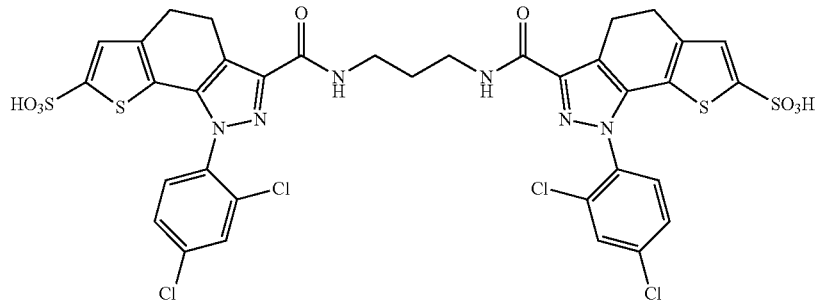
(ICA)

-continued
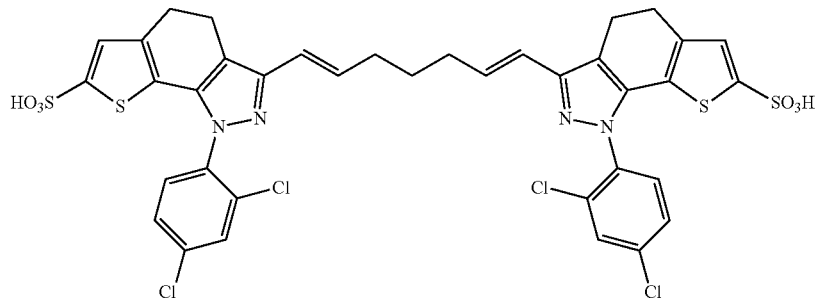
(ICB)
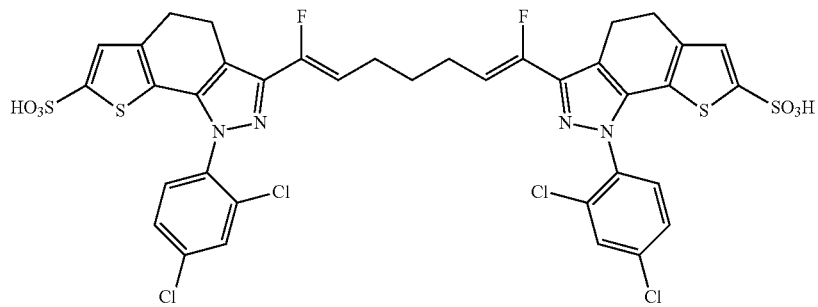
(ICC)
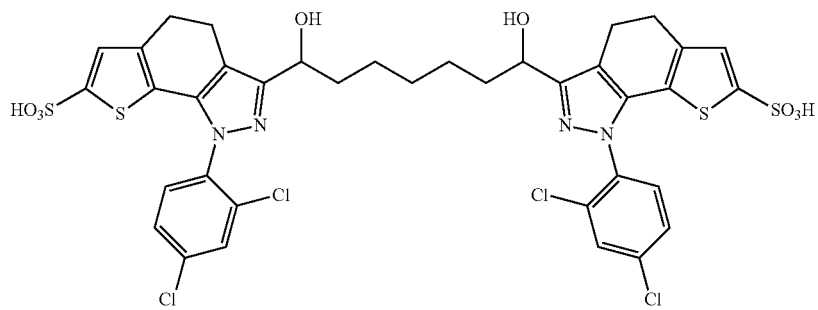
(ICD)
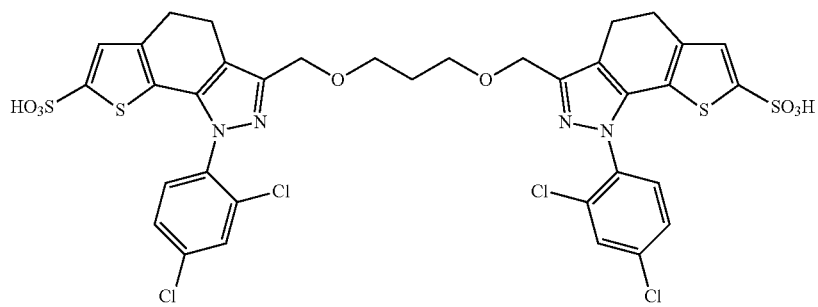
(ICE)
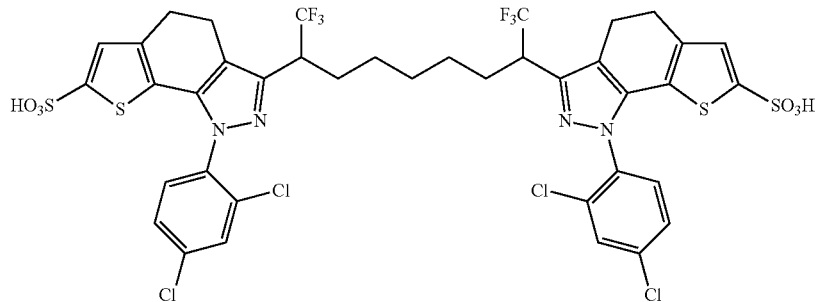
(ICF)

-continued
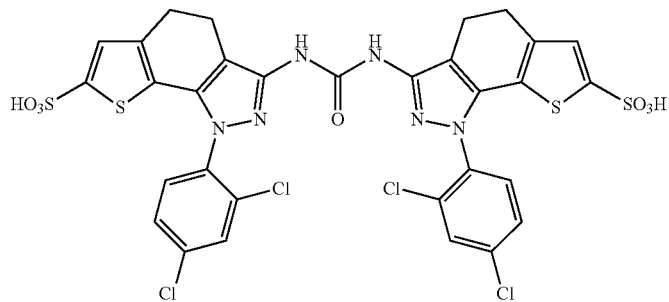
(ICG)
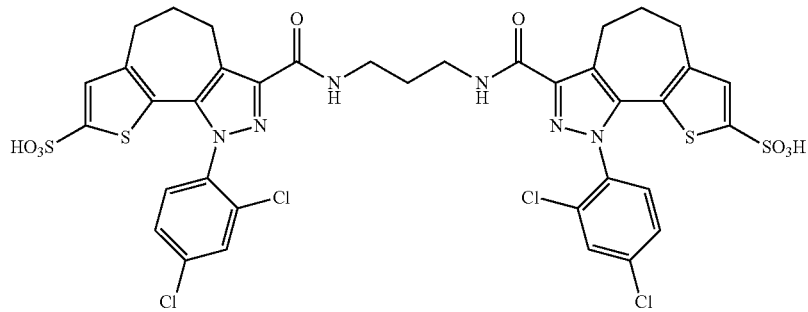
(IDA)
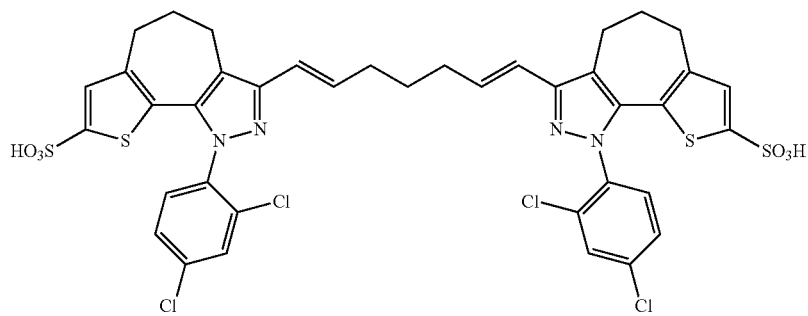
(IDB)
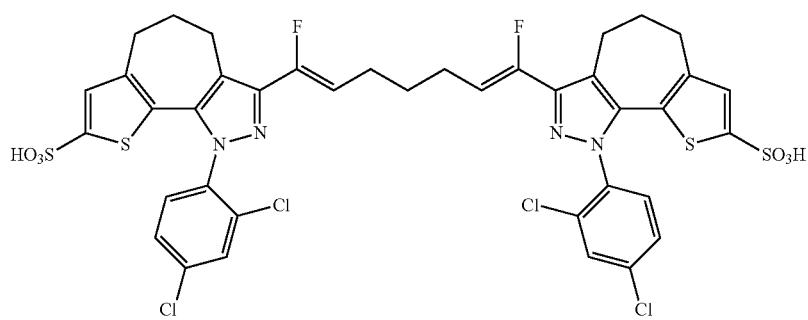
(IDC)
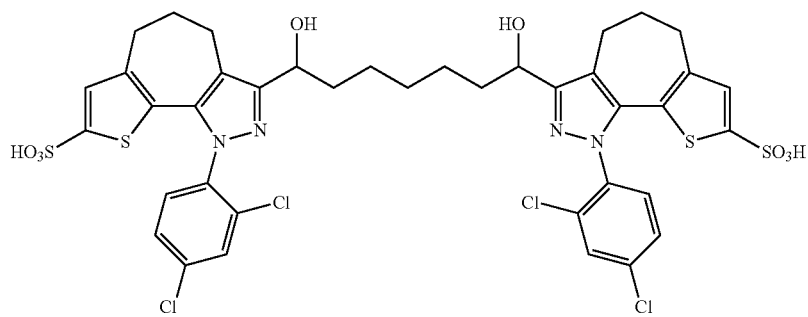
(IDD)

-continued
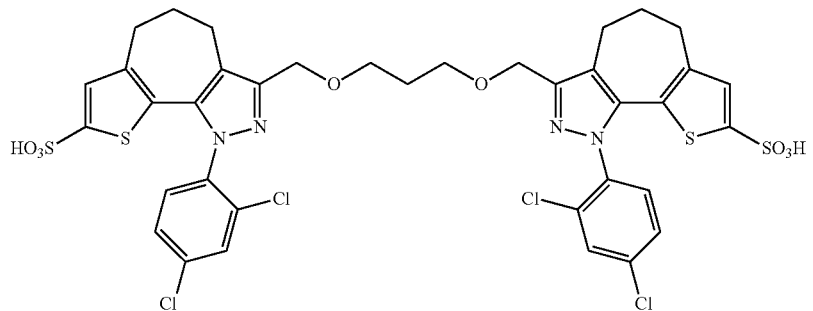
(IDE)
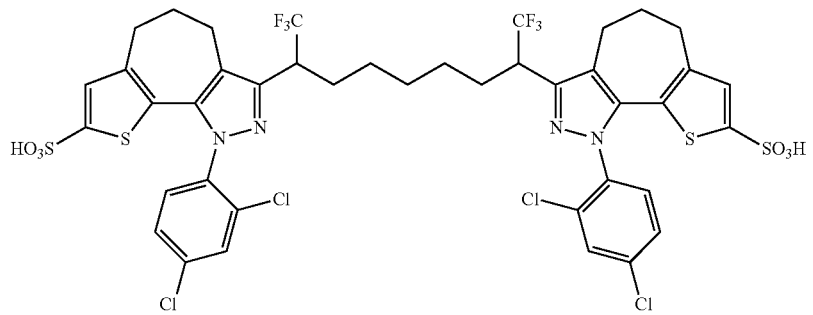
(IDF)
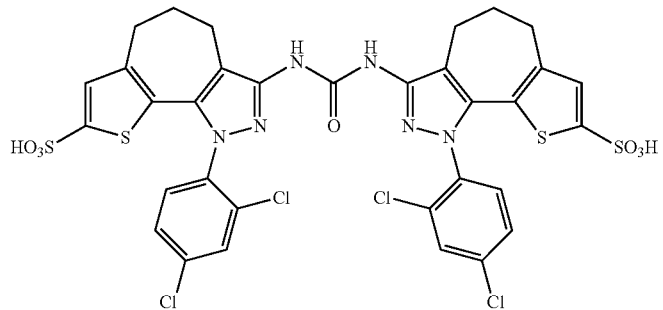
(IDG)
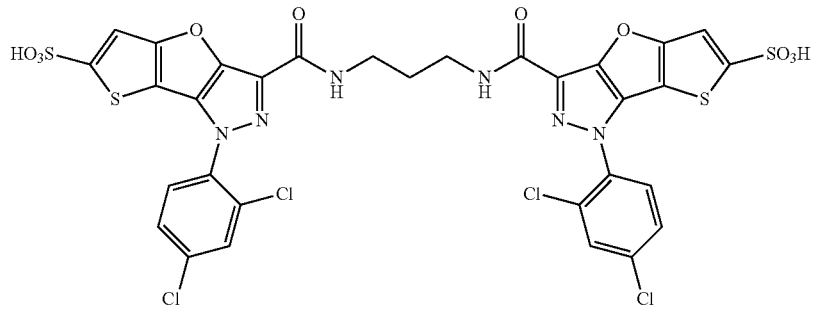
(IEA)
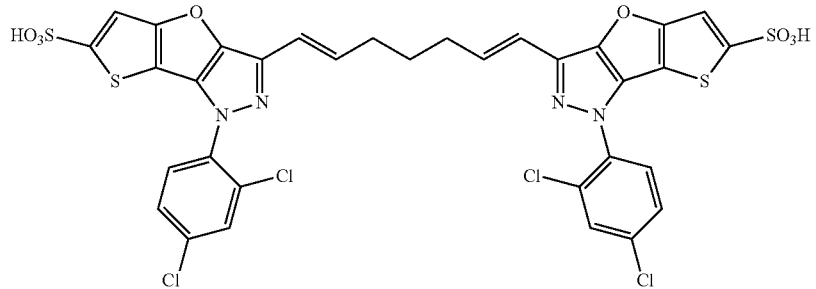
(IEB)

-continued
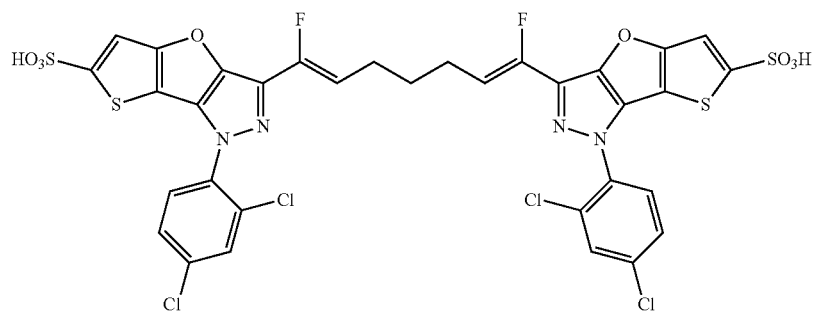
(IEC)
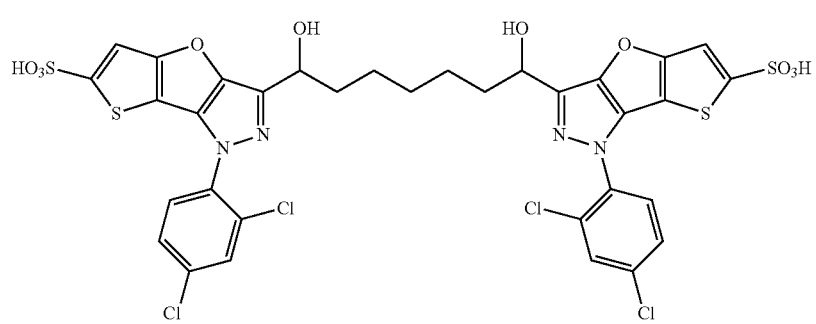
(IED)
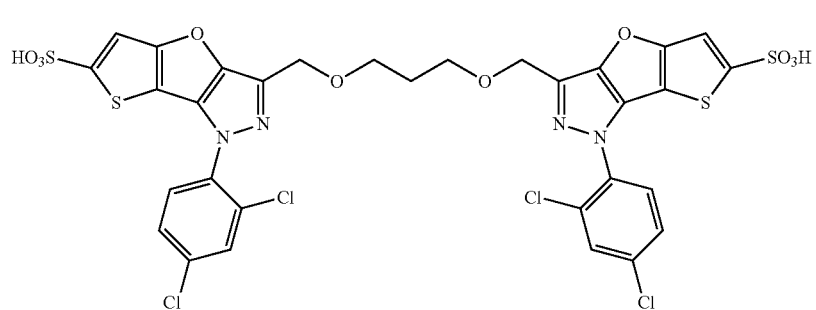
(IEE)
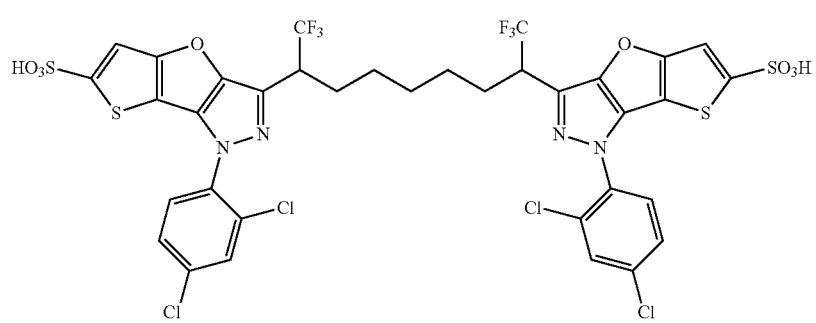
(IEF)
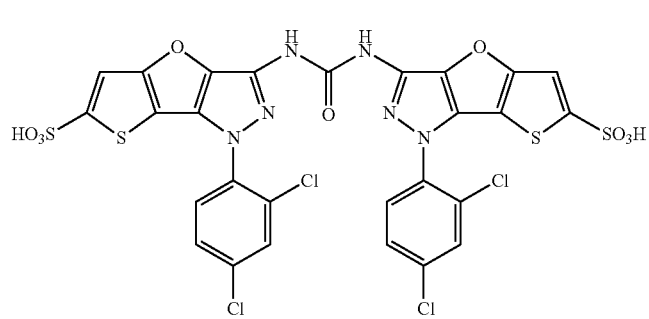
(IEG)

-continued
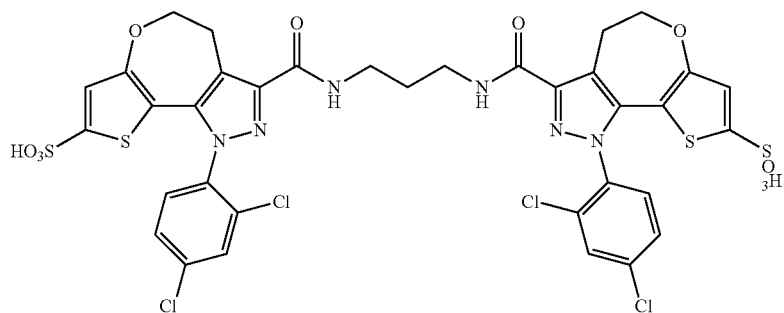
(IFA)
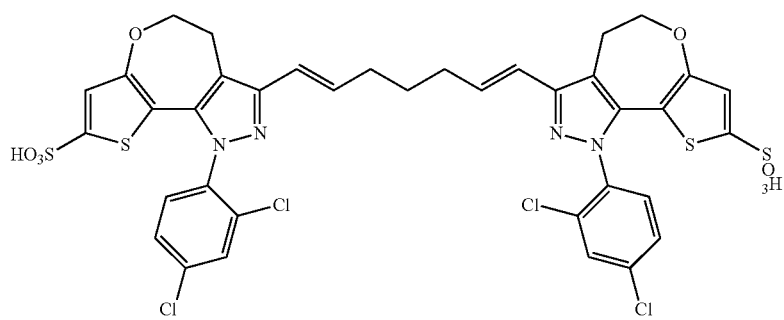
(IFB)
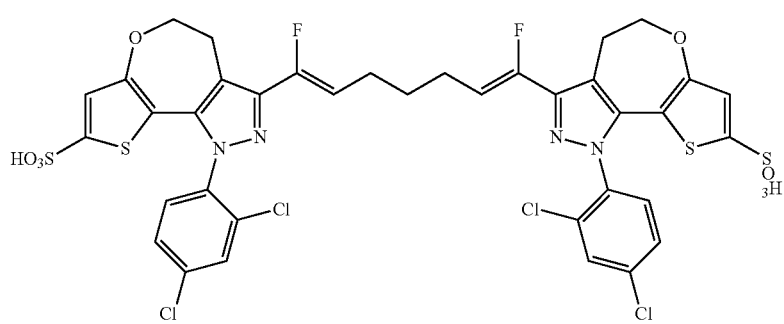
(IFC)
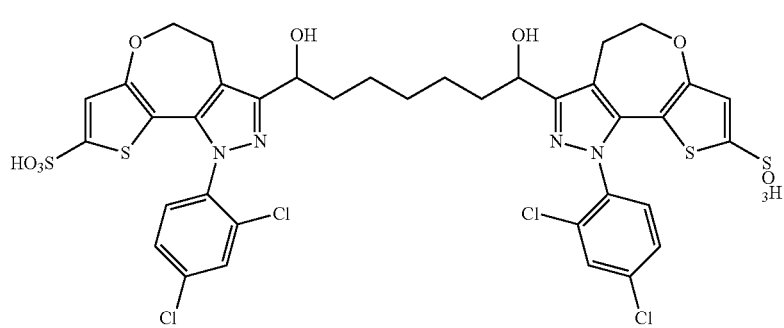
(IFD)
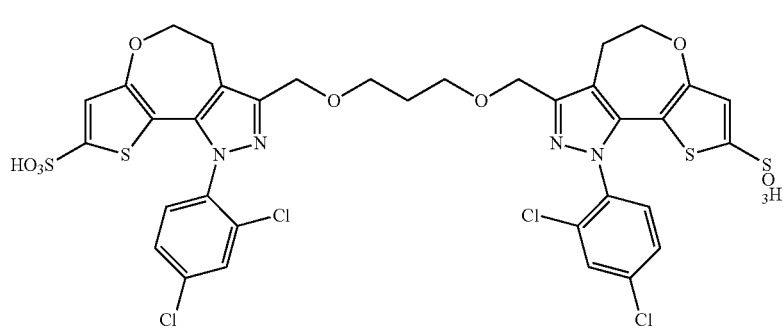
(IFE)

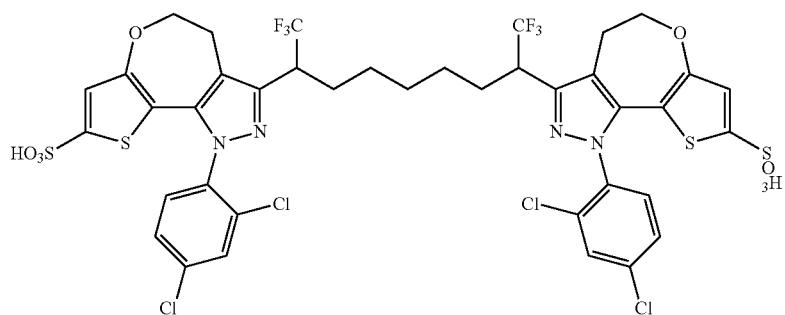
(IFF)
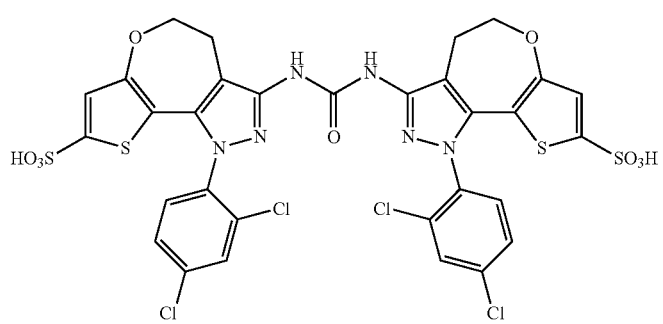
(IFG)
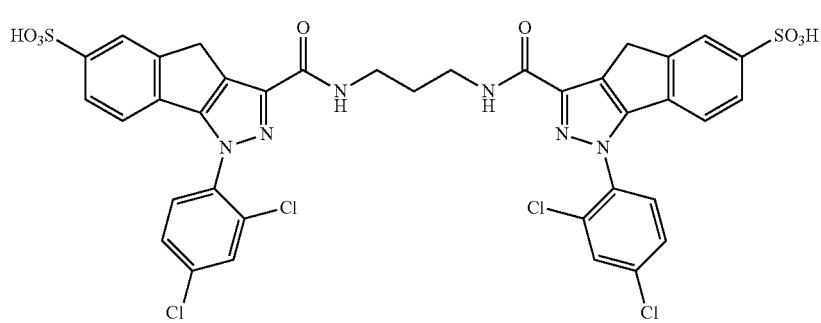
(IGA)
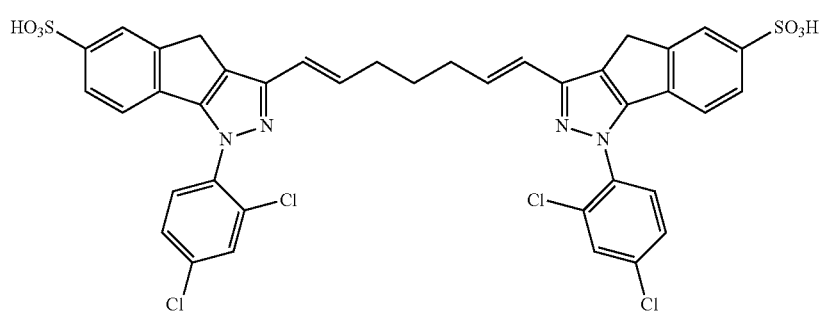
(IGB)
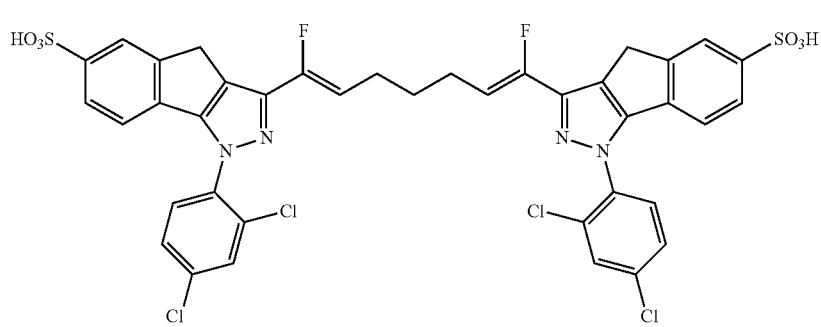
(IGC)

-continued
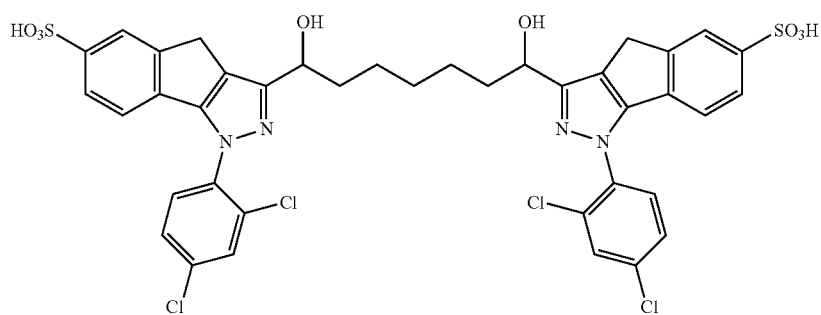
(IGD)
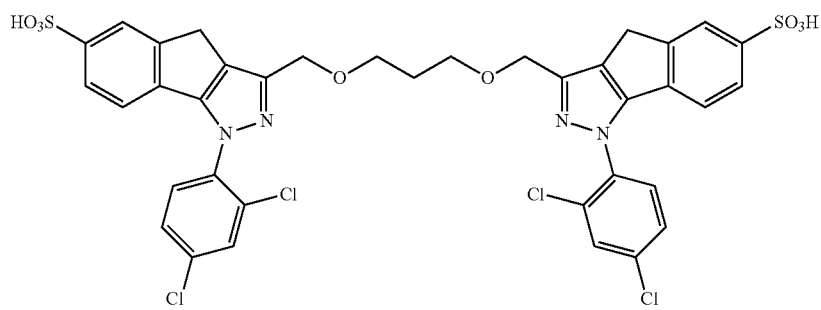
(IGE)
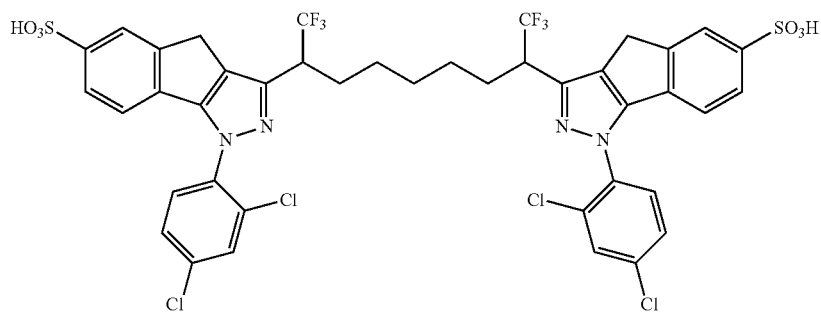
(IGF)
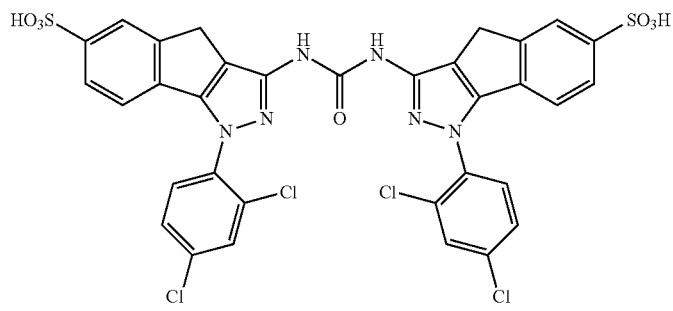
(IGG)
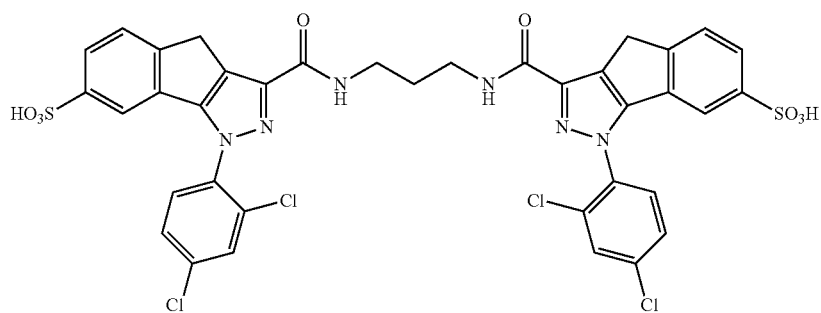
(IHA)

-continued
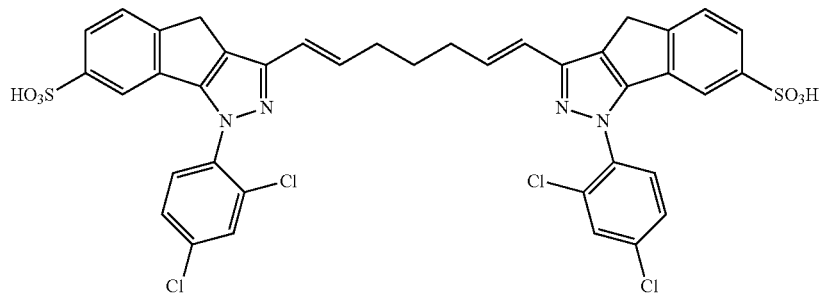
(IHB)
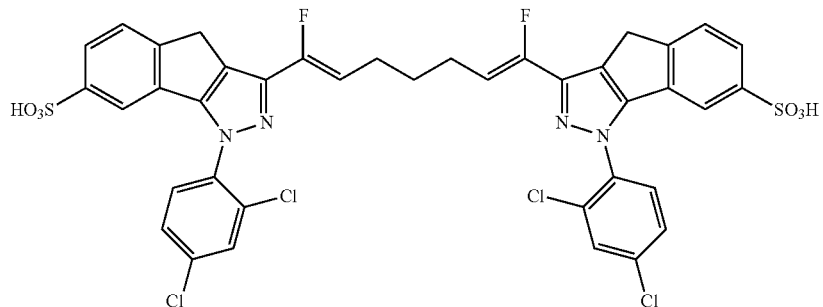
(IHC)
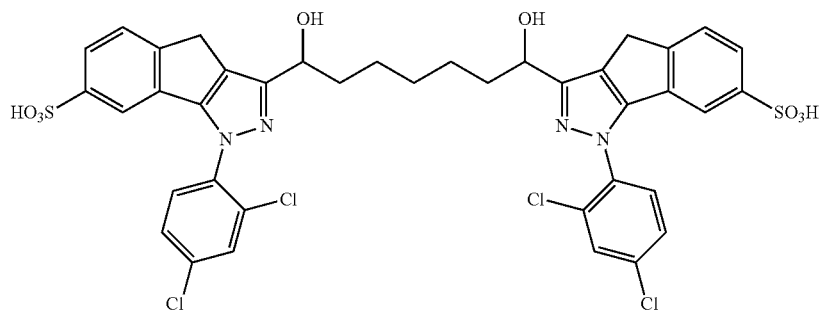
(IHD)
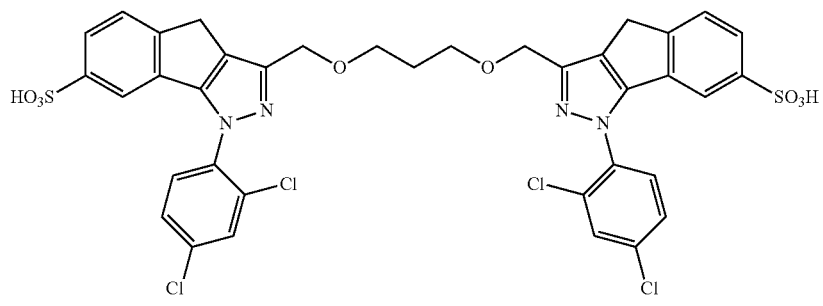
(IHE)
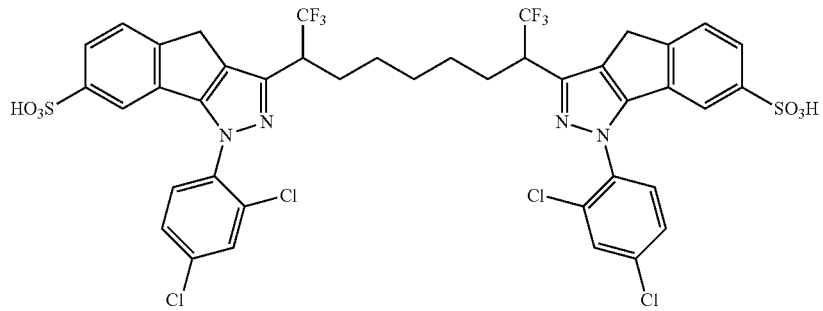
(IHF)

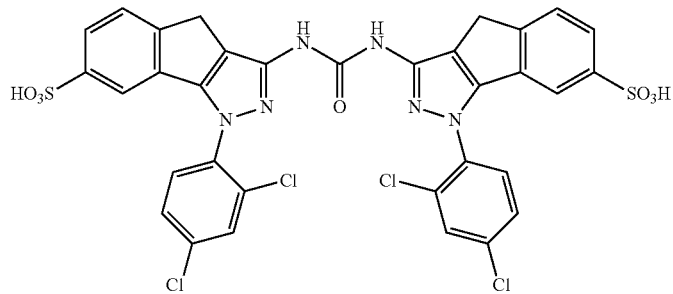
(IHG)
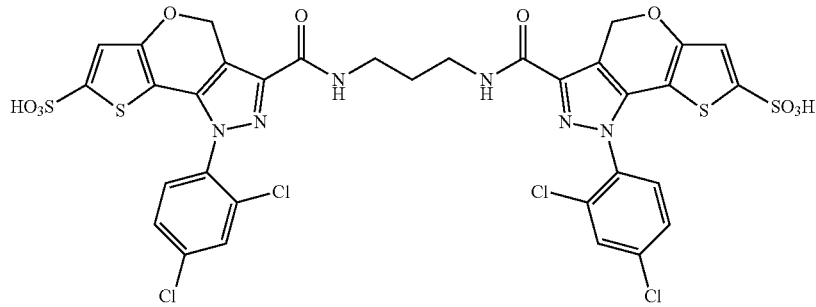
(ILA)
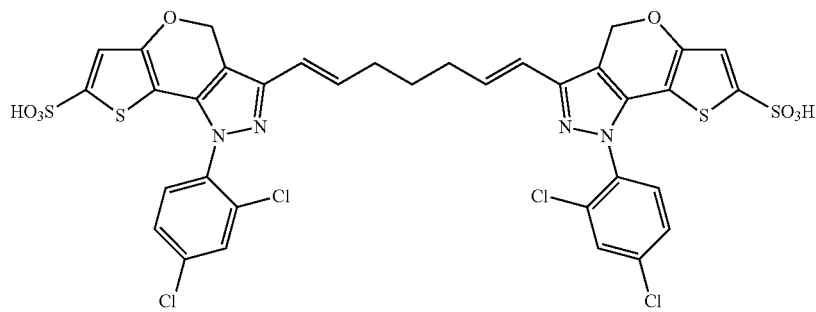
(ILB)
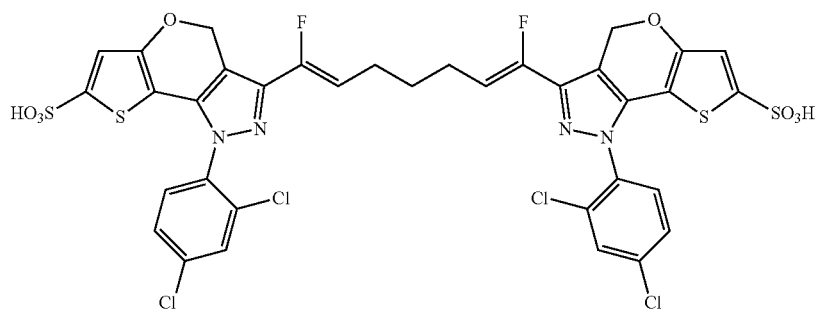
(ILC)
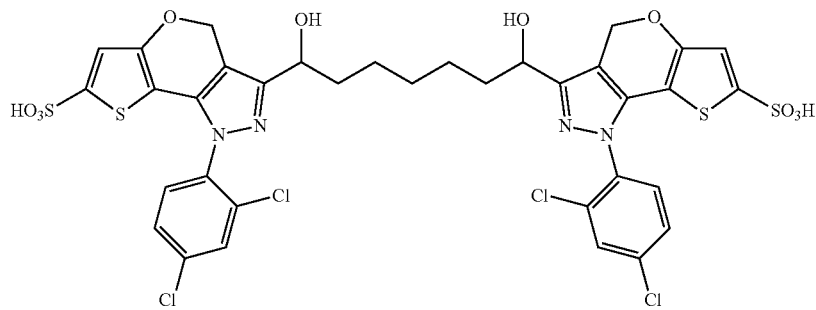
(ILD)

-continued
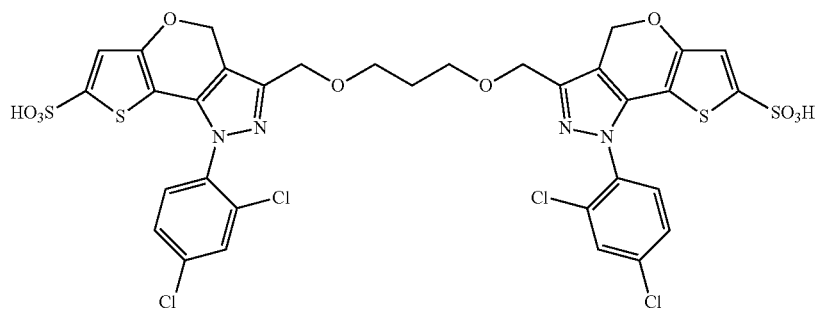 (ILE)
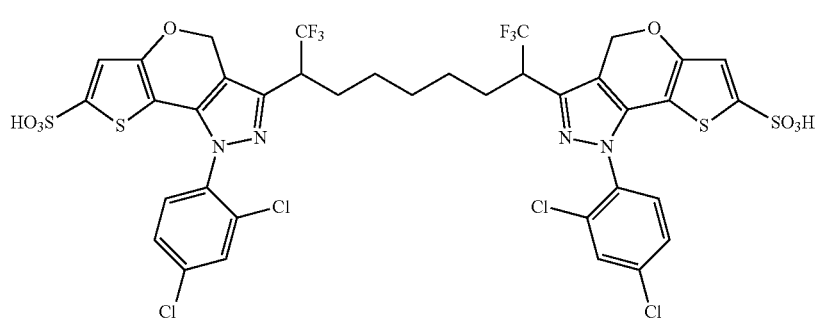 (ILF)
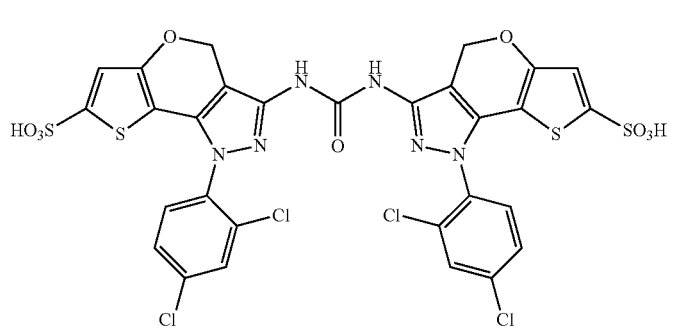 (ILG)
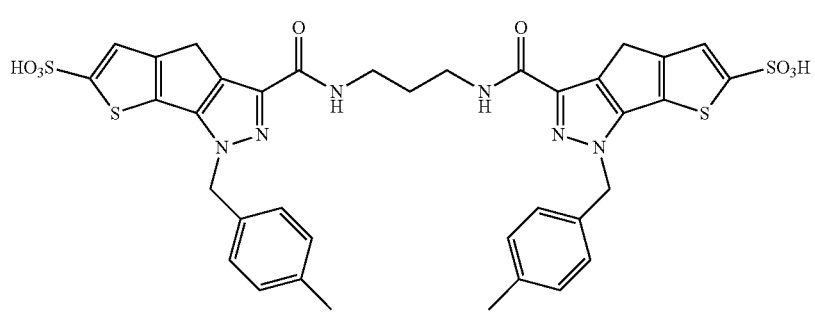 (IIAA)
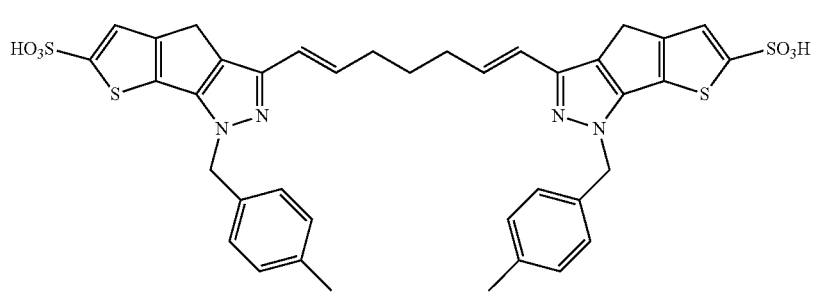 (IIAB)

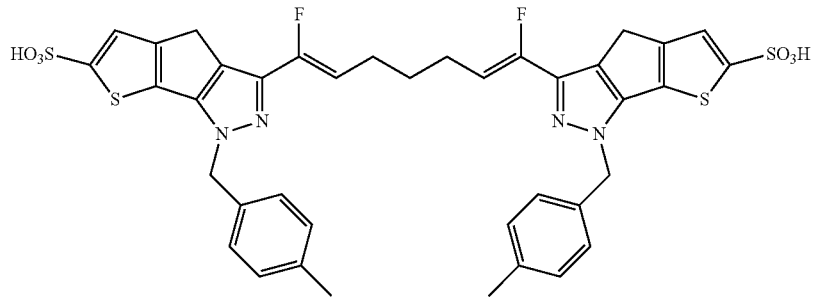
(IIAC)
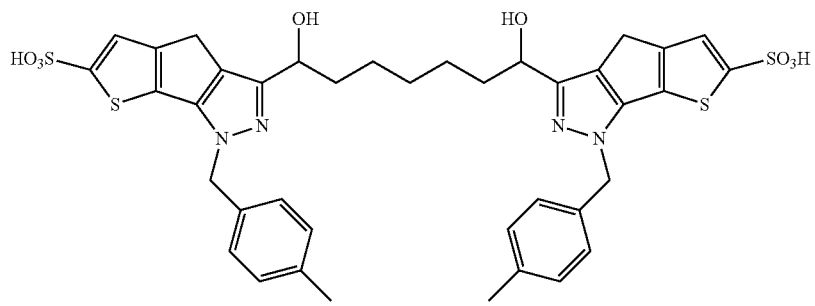
(IIAD)
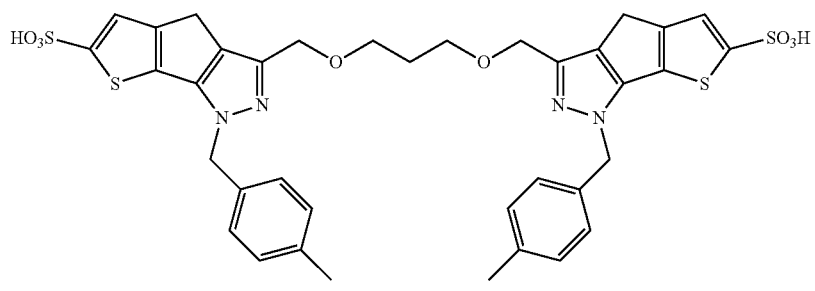
(IIAE)
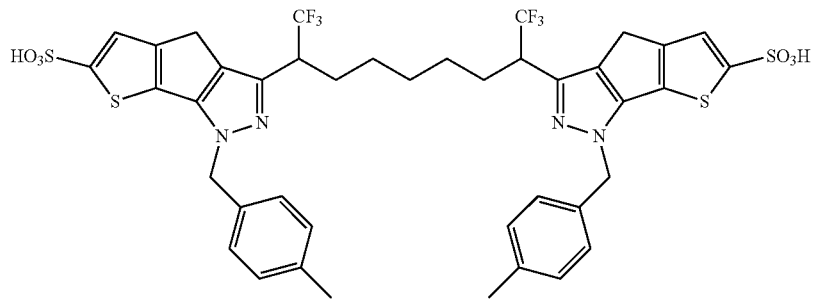
(IIAF)
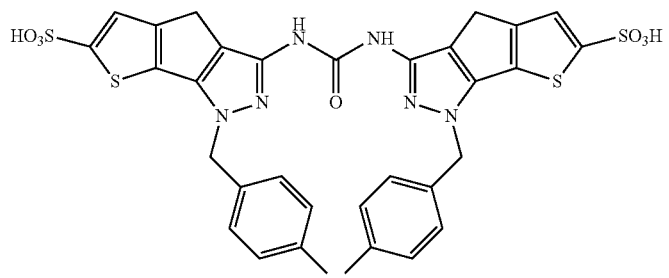
(IIAG)

-continued
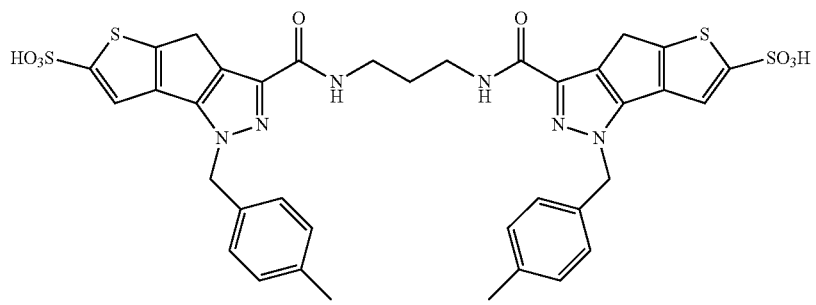
(IIBA)
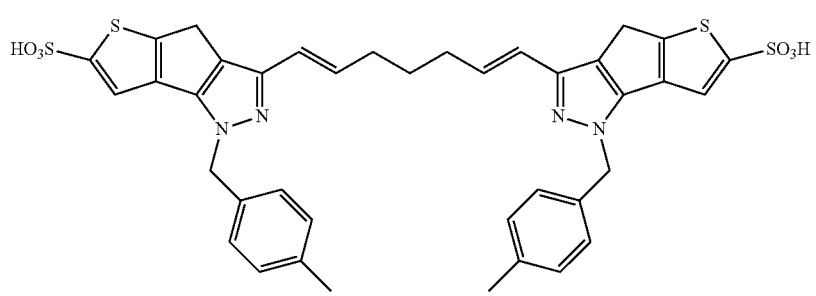
(IIBB)
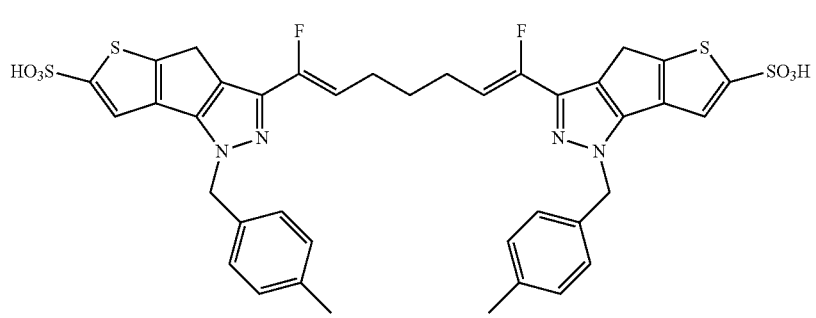
(IIBC)
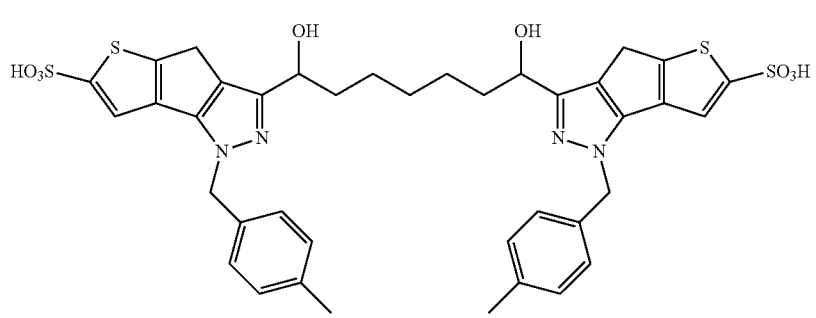
(IIBD)
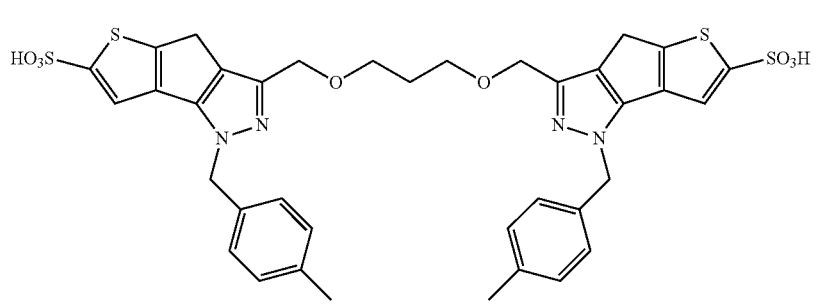
(IIBE)

-continued
(IIBF)
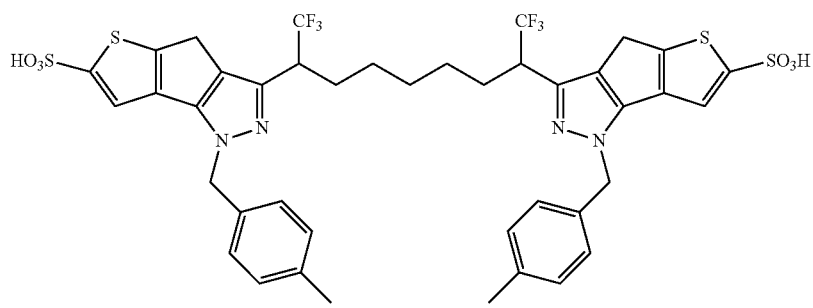
(IIBG)
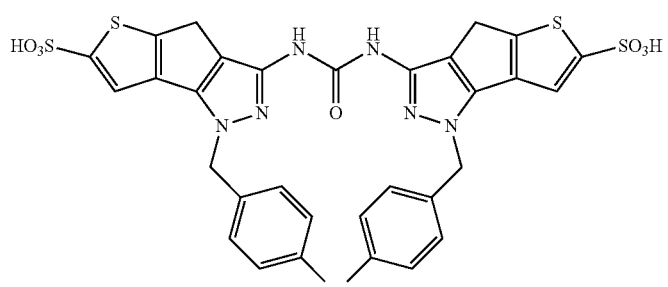
(IICA)
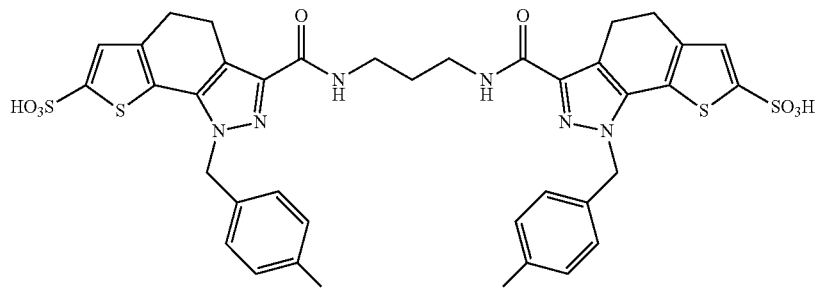
(IICB)
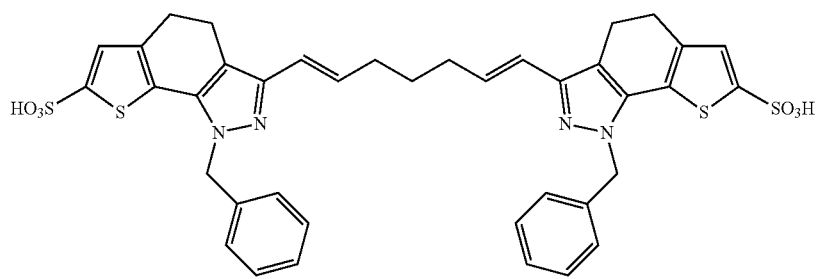
(IICC)
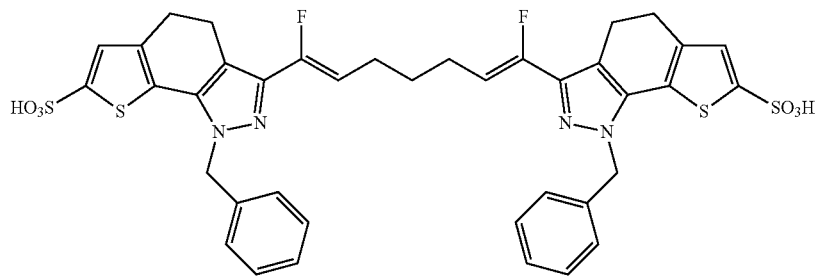

-continued
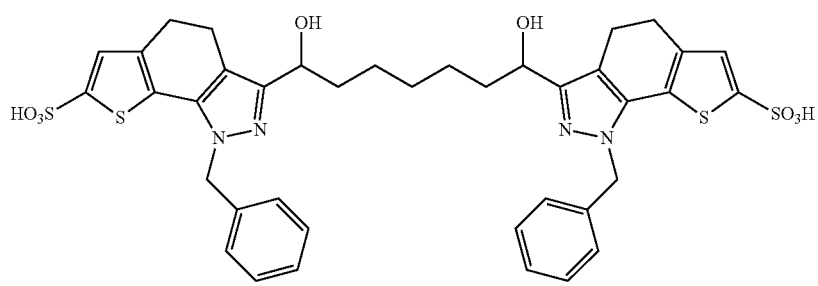
(IICD)
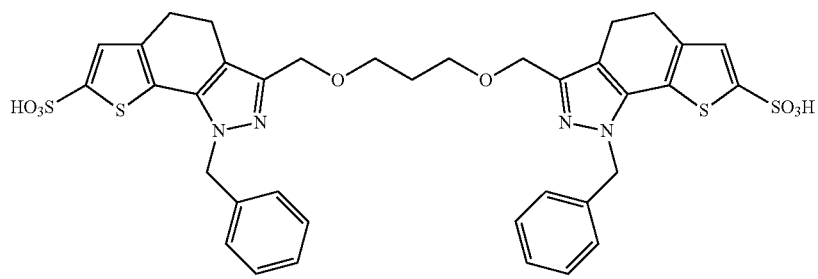
(IICE)
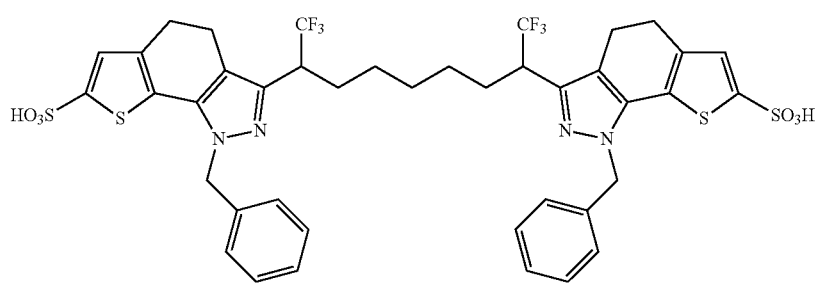
(IICF)
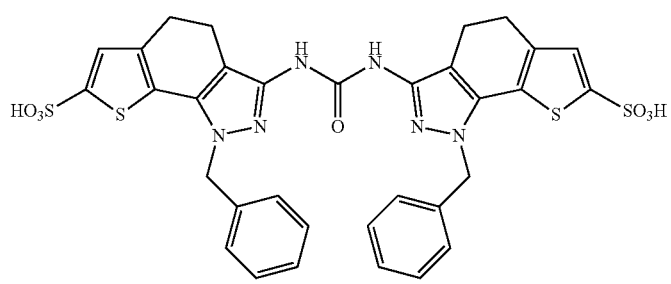
(IICG)
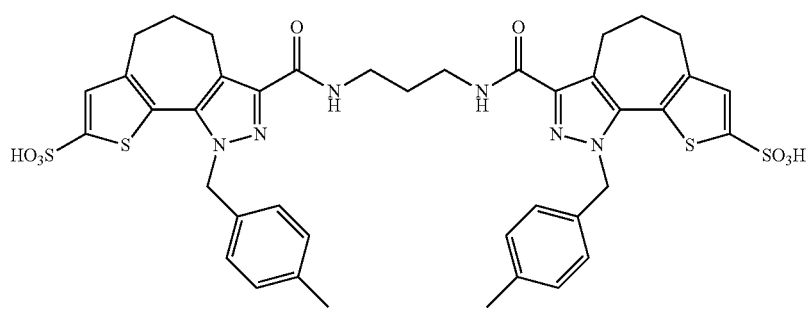
(IIDA)

-continued
(IIDB)
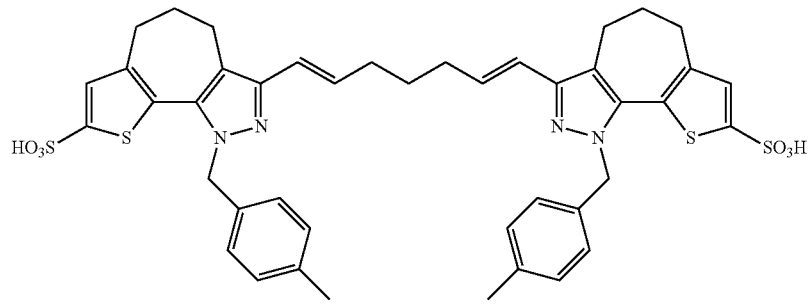
(IIDC)
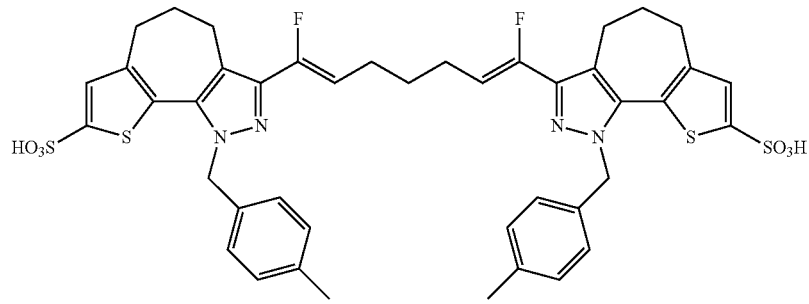
(IIDD)
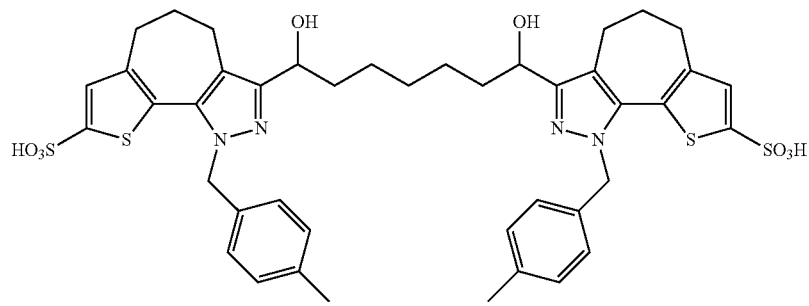
(IIDE)
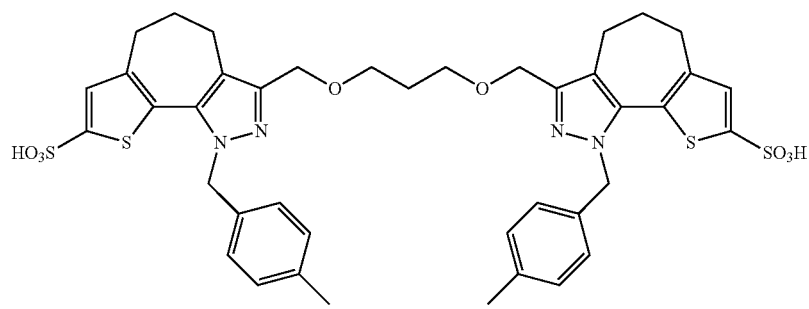
(IIDF)
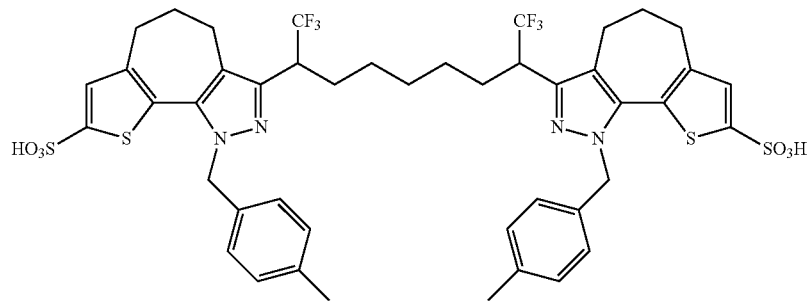

-continued
(IDG)
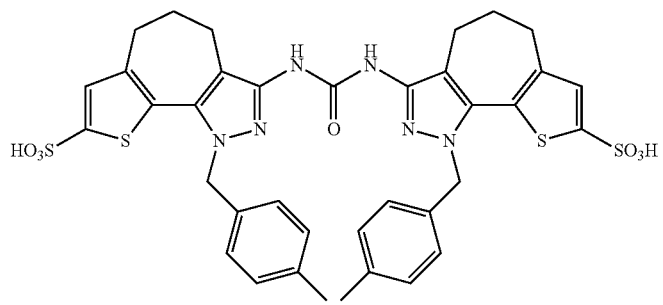
(IIEA)
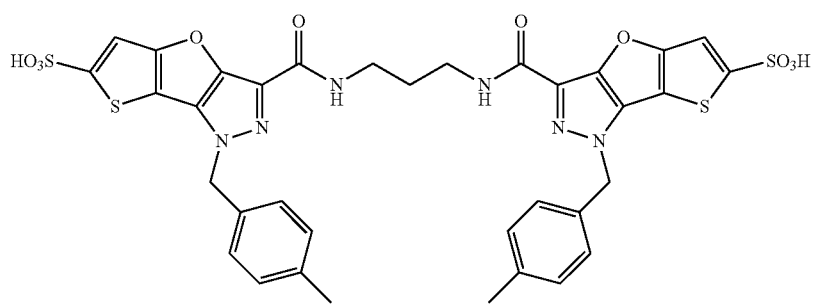
(IIEB)
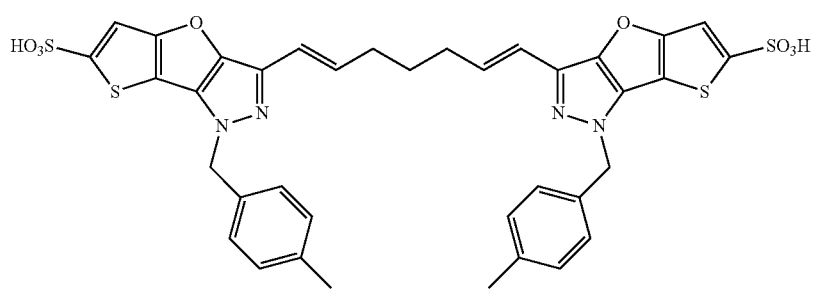
(IIEC)
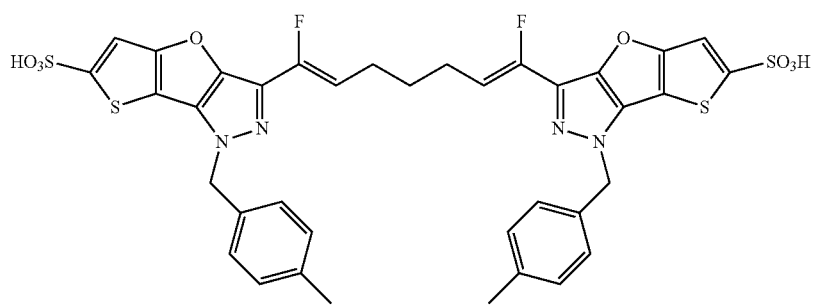
(IIED)
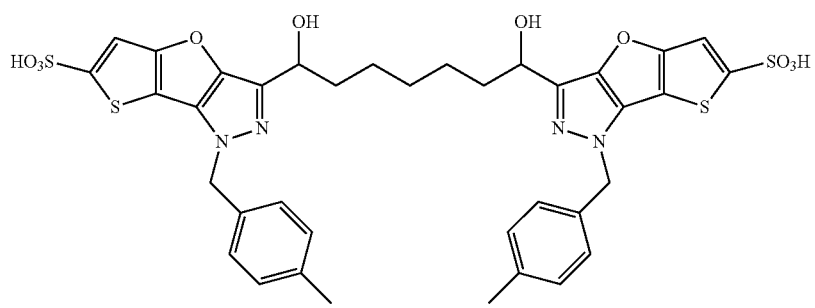

-continued
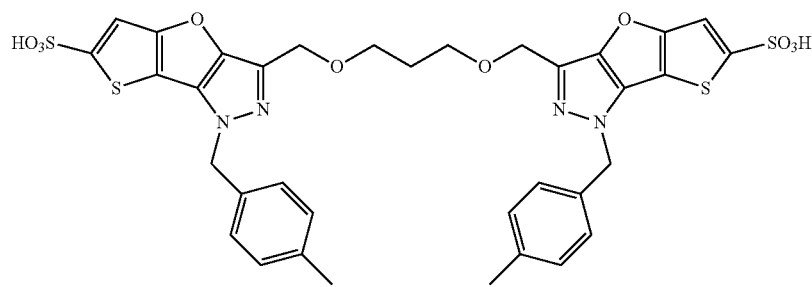
(IIEE)
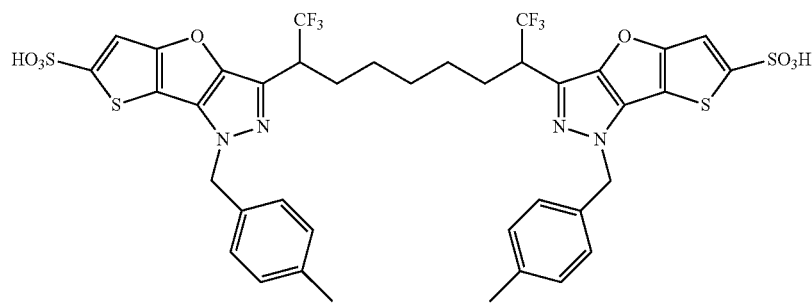
(IIEF)
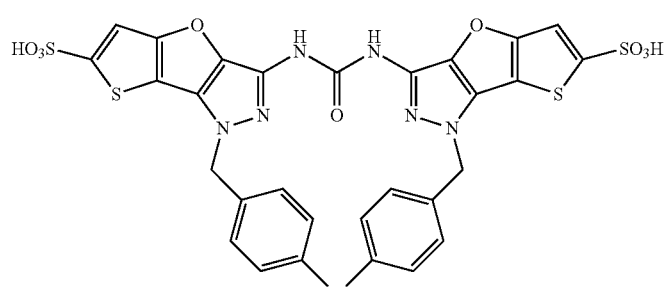
(IIEG)
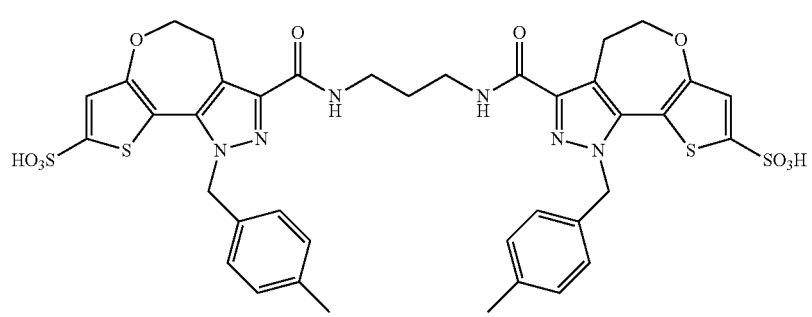
(IIFA)
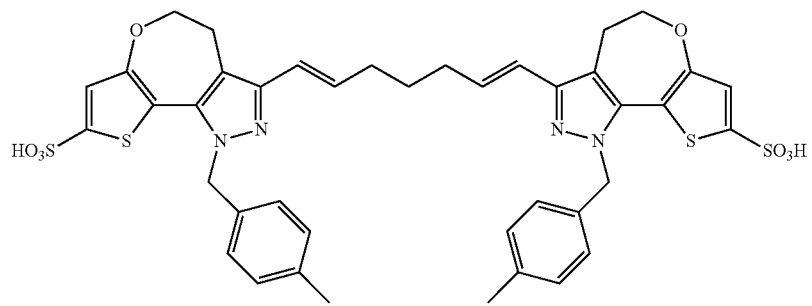
(IIFB)

-continued
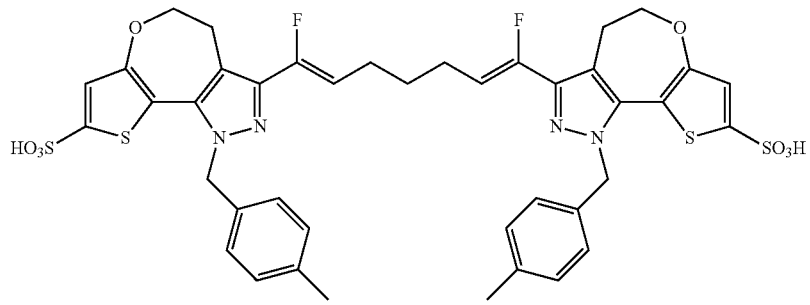
(IIFC)
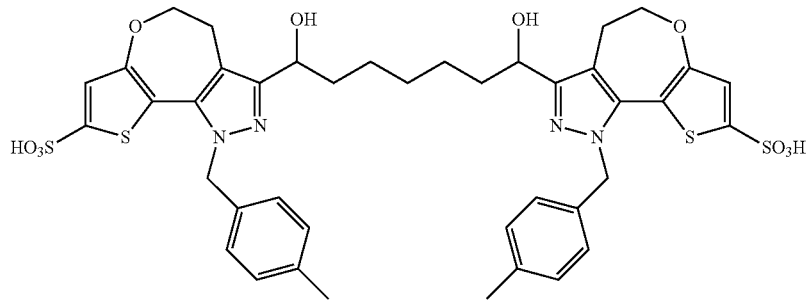
(IIFD)
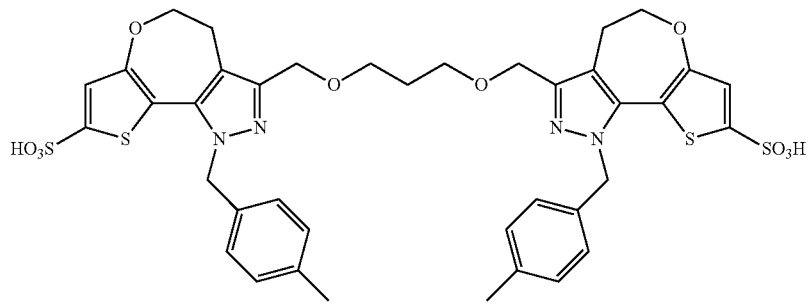
(IIFE)
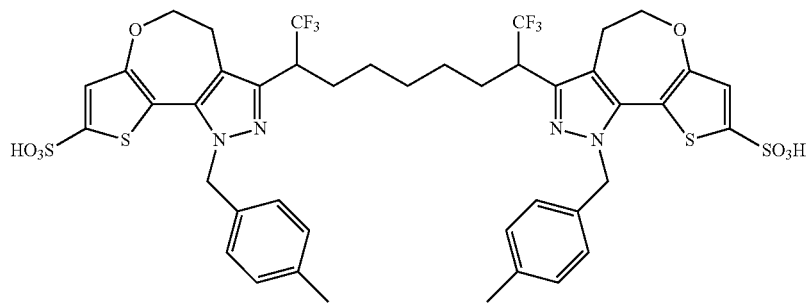
(IIFF)
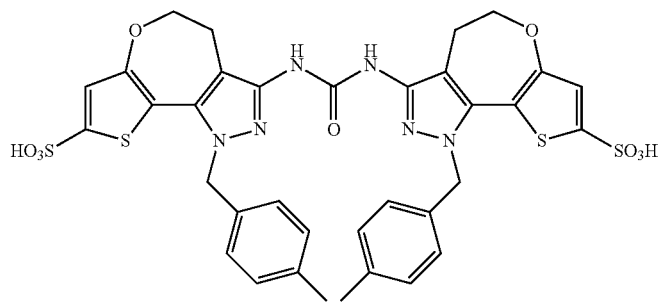
(IIFG)

-continued
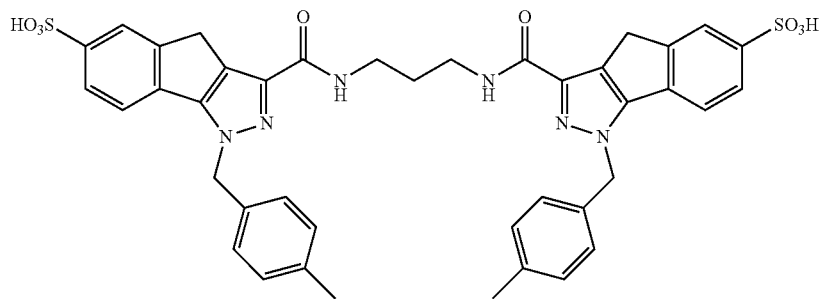
(IIGA)
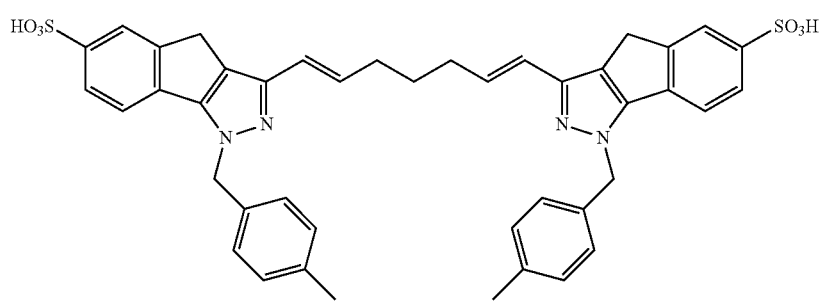
(IIGB)
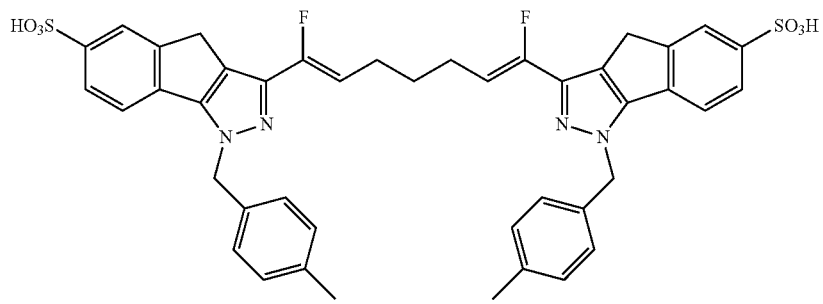
(IIGC)
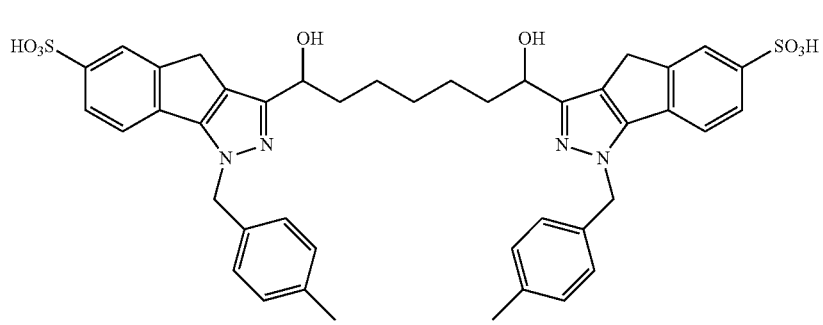
(IIGD)
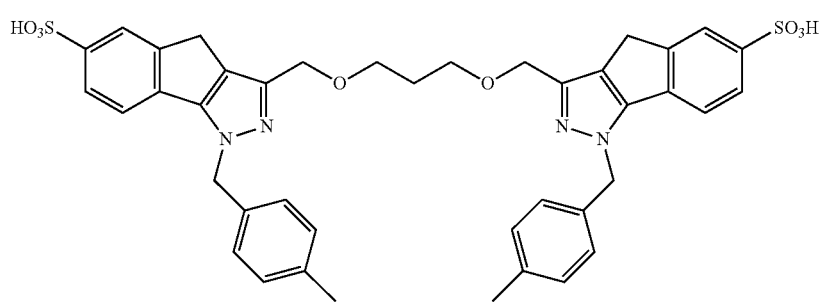
(IIGE)

-continued
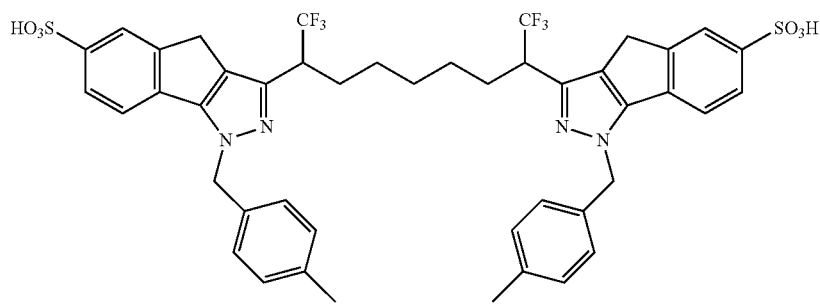
(IIGF)
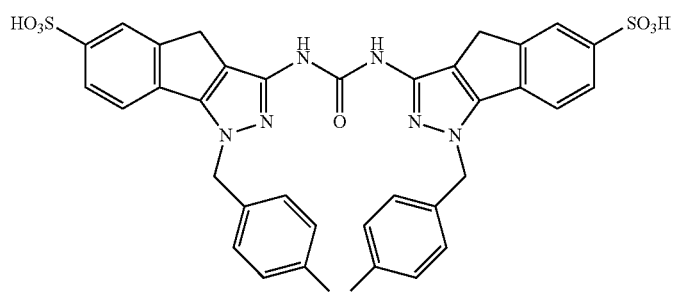
(IIGG)
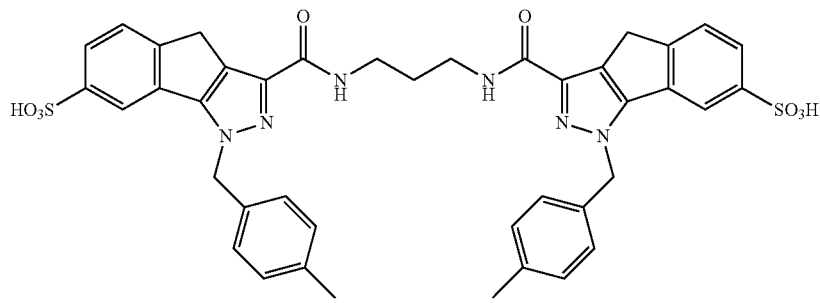
(IIHA)
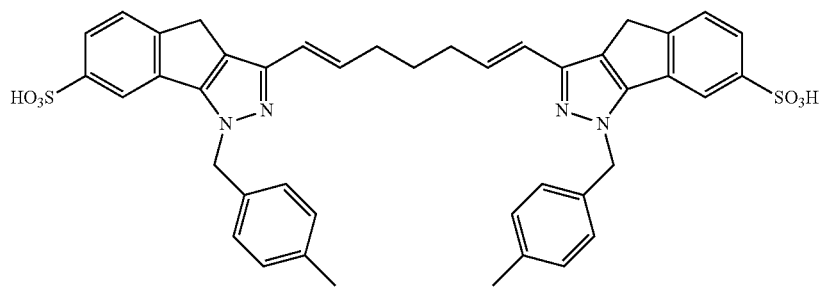
(IIHB)
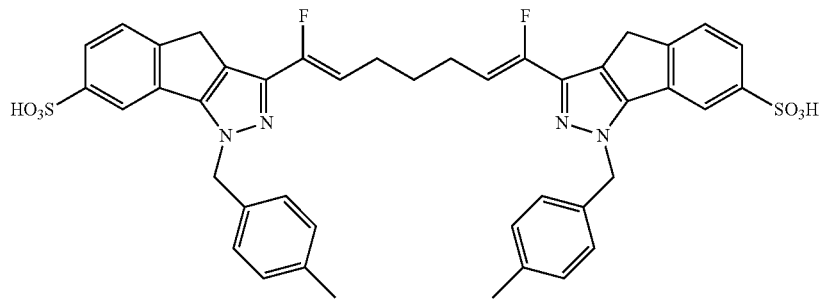
(IIHC)

-continued
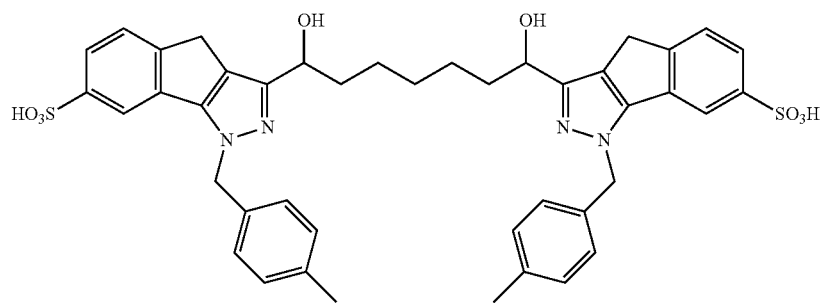
(IIHD)
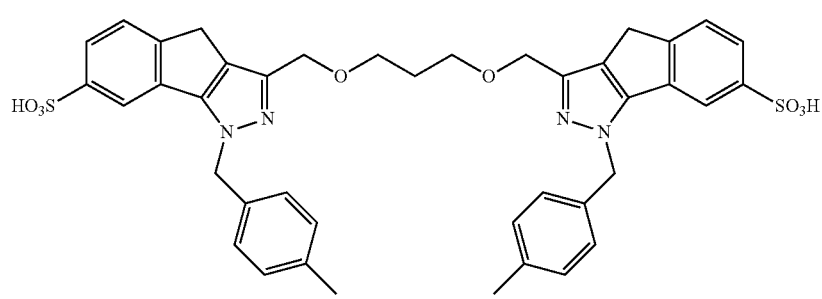
(IIHE)
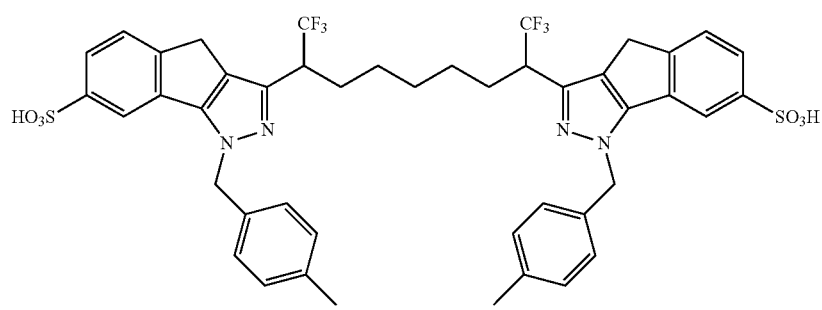
(IIHF)
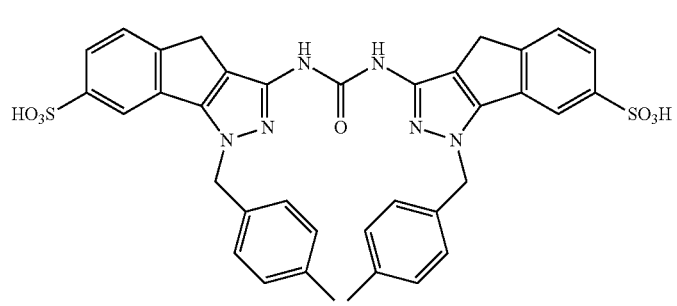
(IIHG)
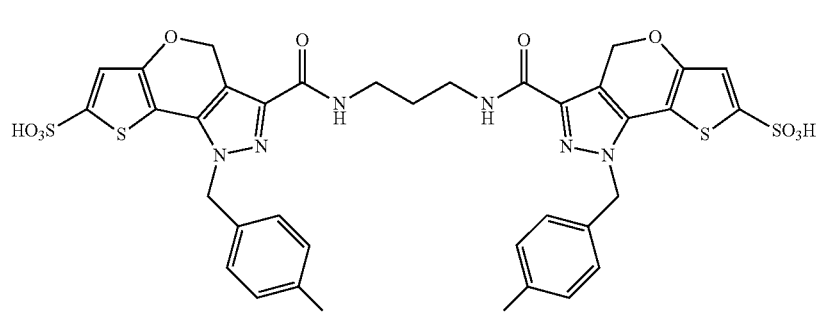
(IILA)

-continued
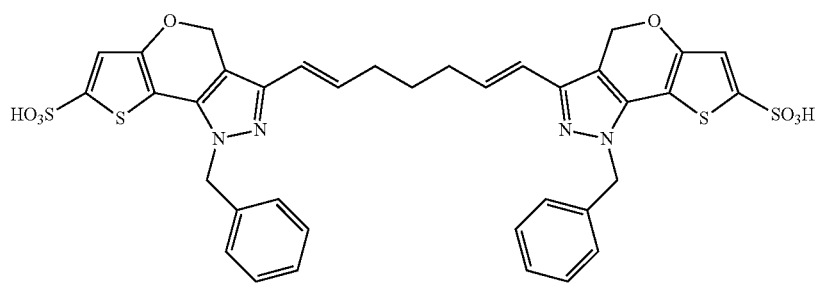
(IILB)
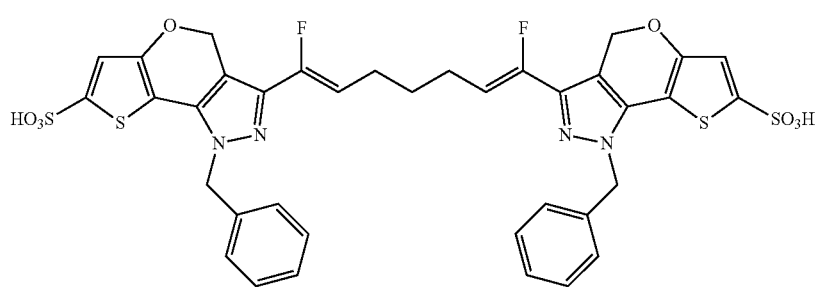
(IILC)
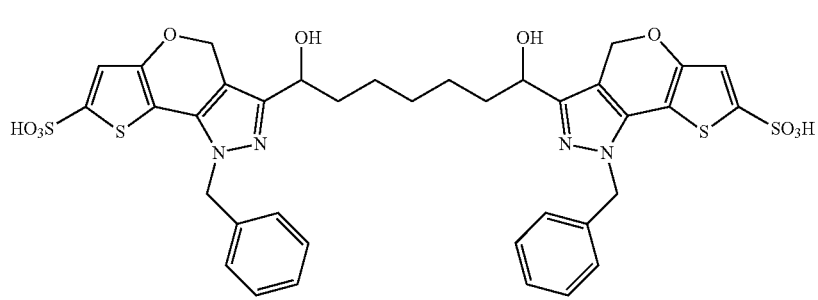
(IILD)
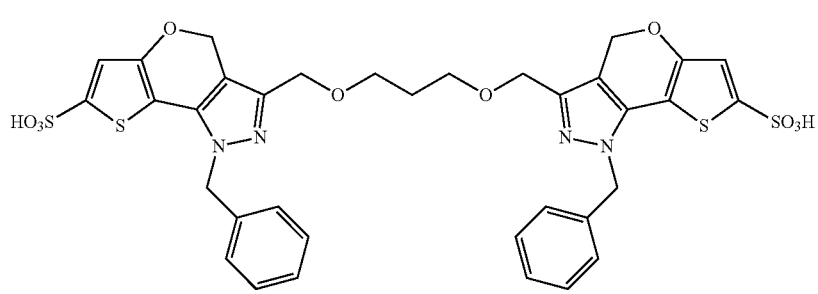
(IILE)
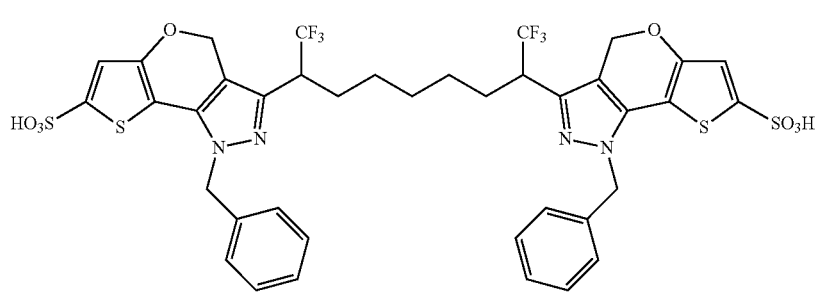
(IILF)

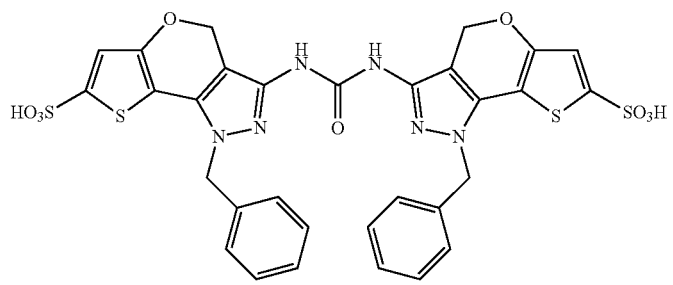
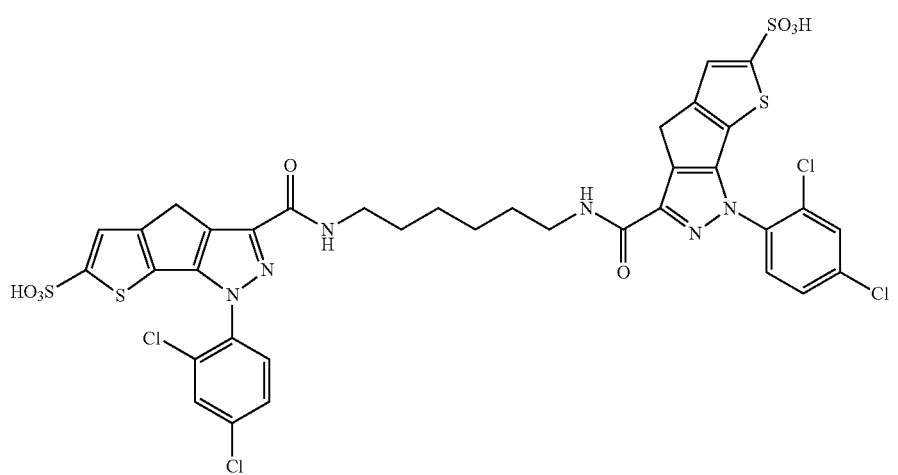
(IILG)
(IIIAA)
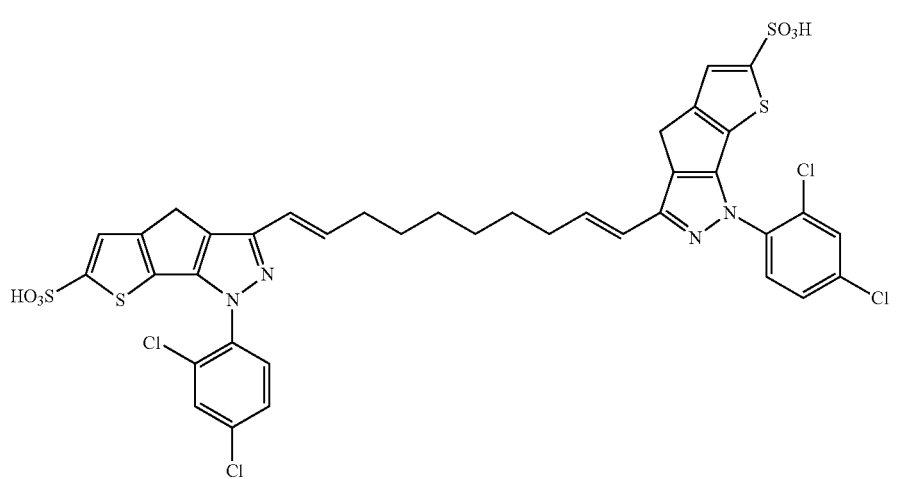
(IIIAB)

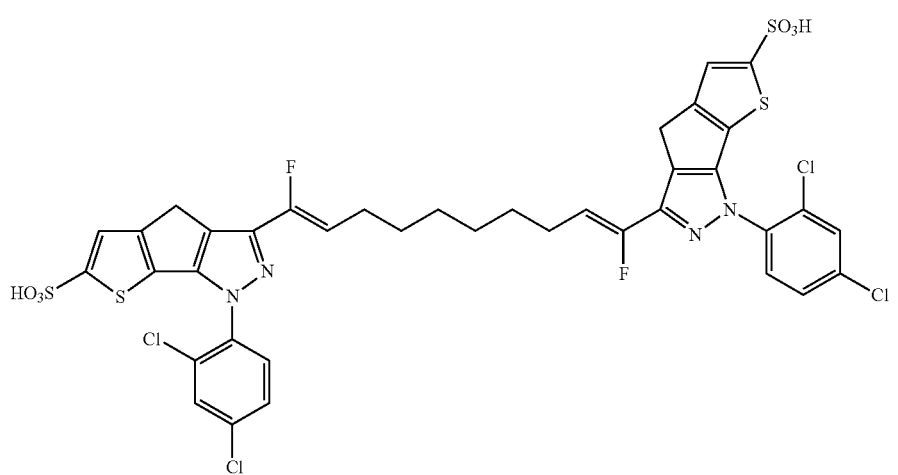
(IIIAC)
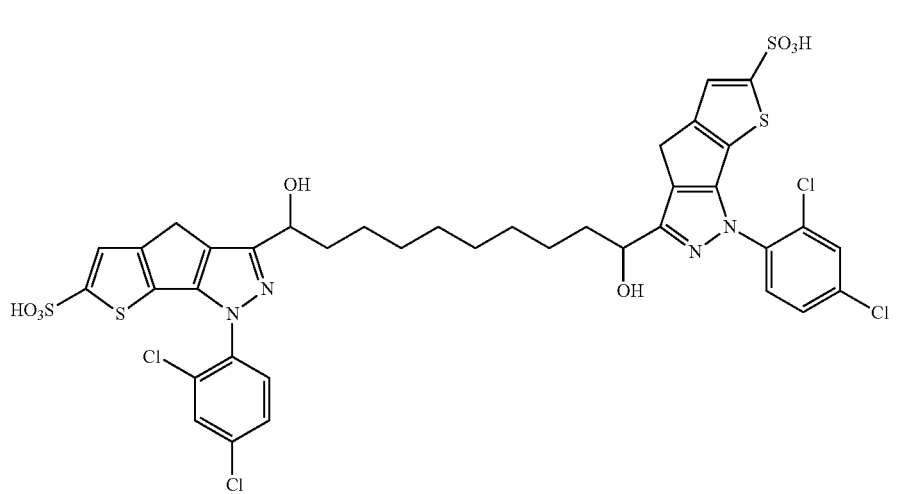
(IIIAD)
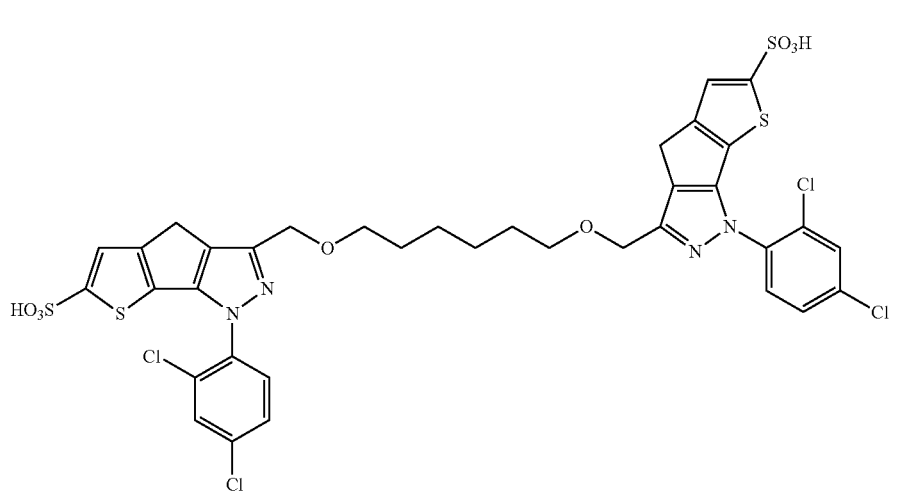
(IIIAE)

-continued
(IIIAF)
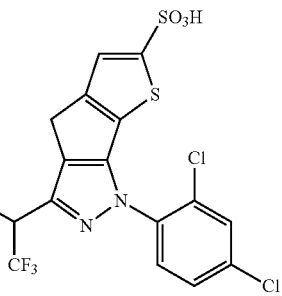
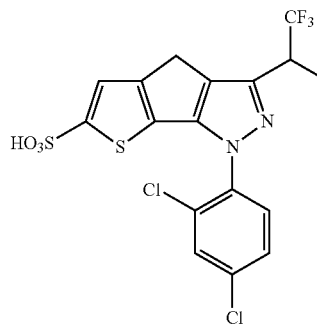
(IIIBA)
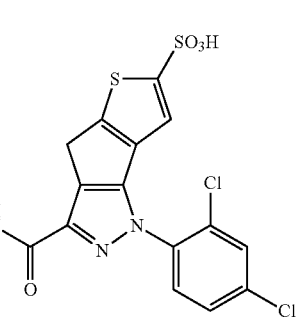
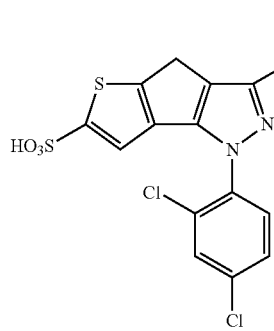
(IIIBB)
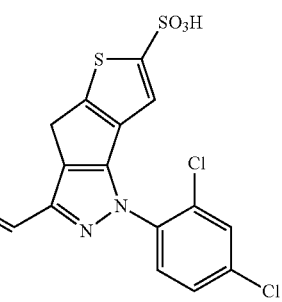
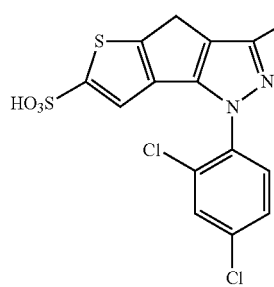

-continued
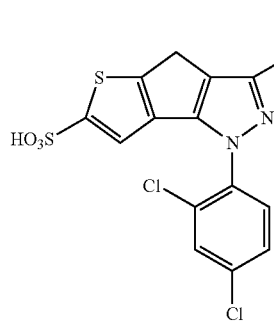
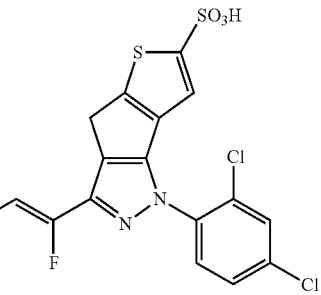
(IIIBC)
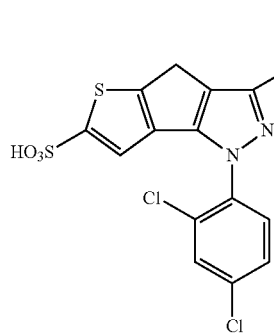
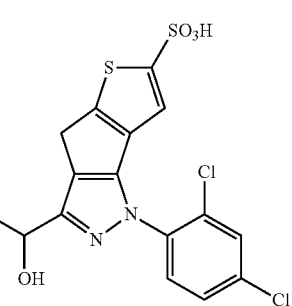
(IIIBD)
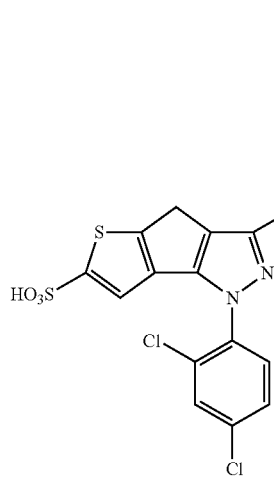
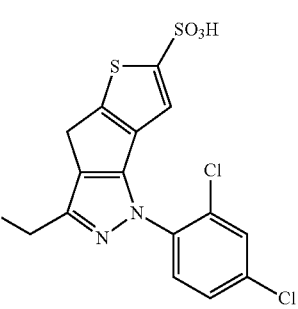
(IIIBE)

(IIIBF)
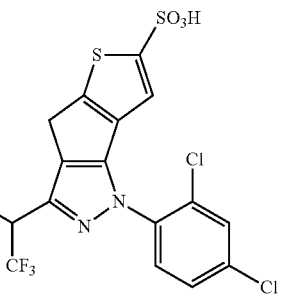
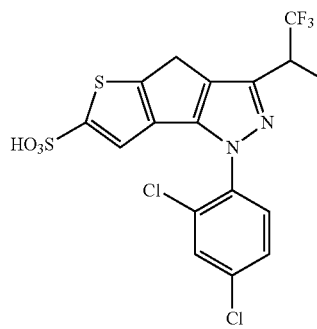
(IIICA)
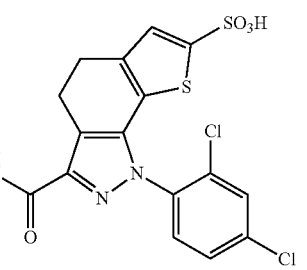
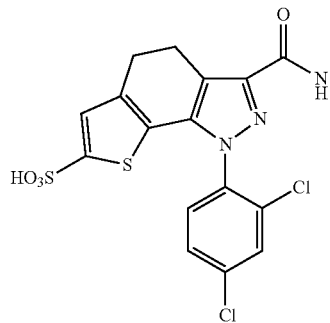
(IIICB)
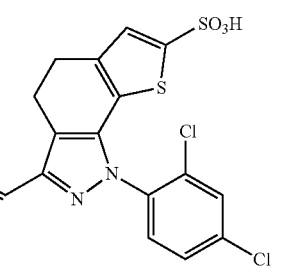
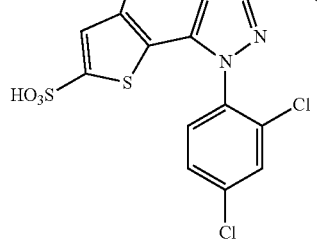

(IIICC)
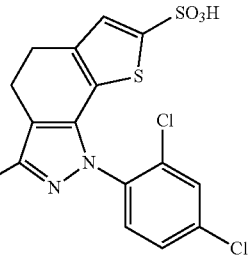
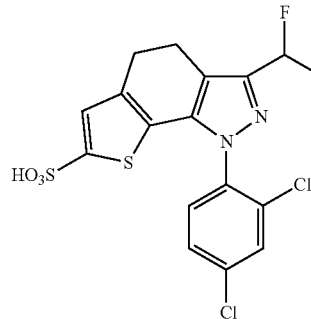
(IIICD)
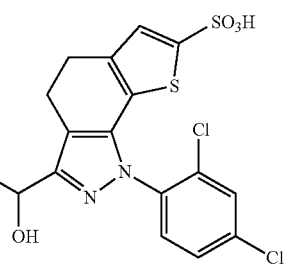
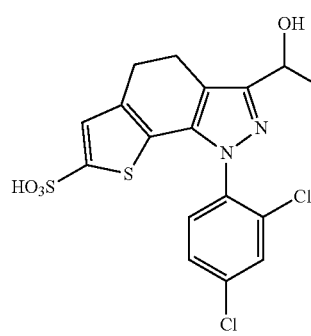
(IIICE)
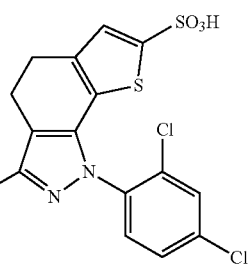
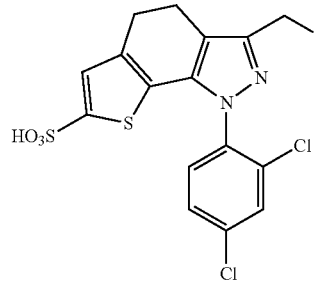

-continued
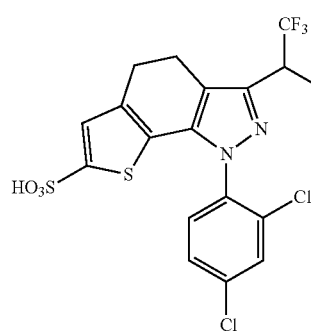
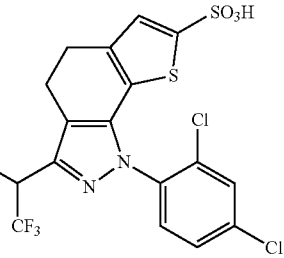
(IIICF)
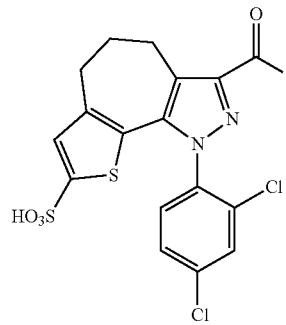
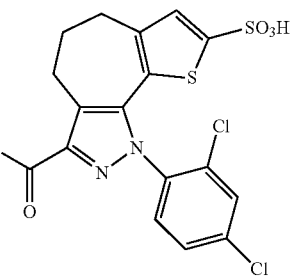
(IIIDA)
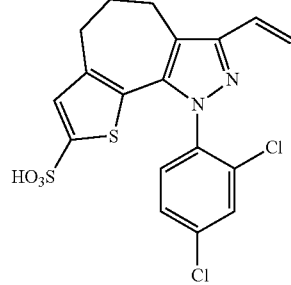
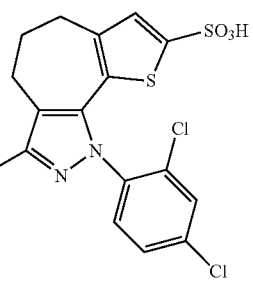
(IIIDB)

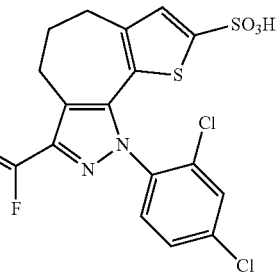
(IIIDC)
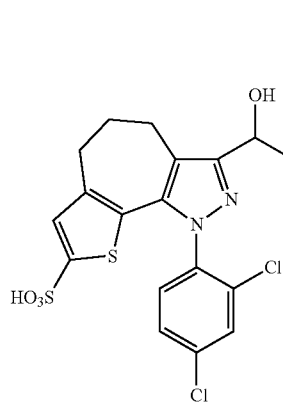
(IIIDD)
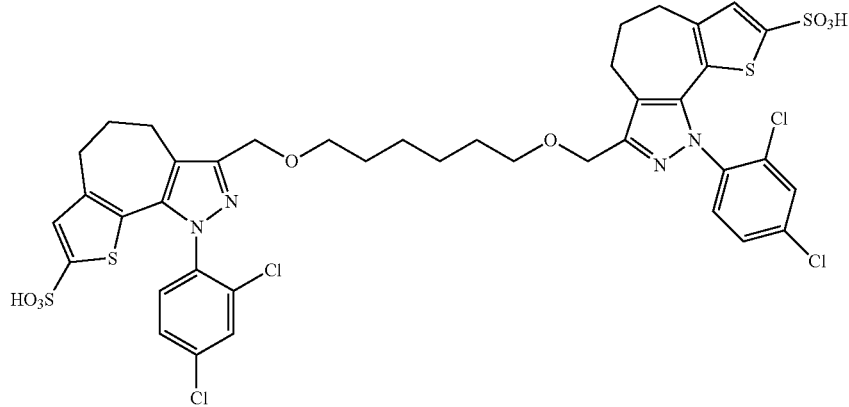
(IIIDE)

(IIIDF)
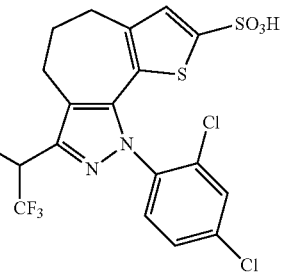
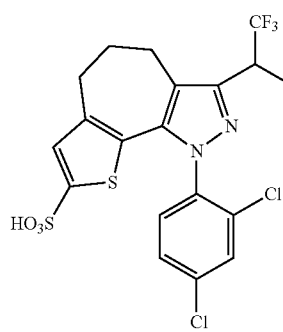
(IIIEA)
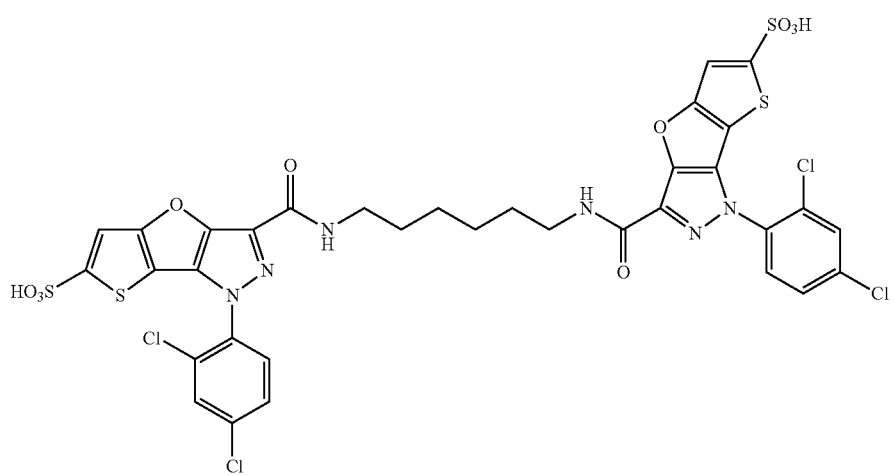
(IIIEB)
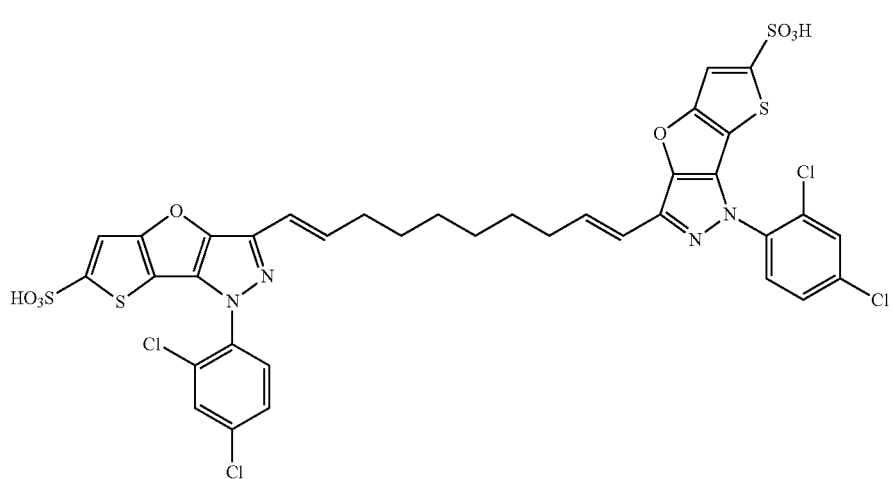

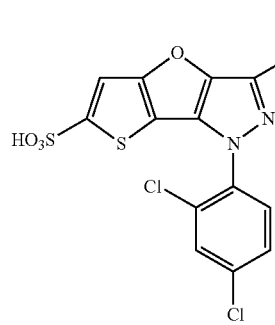 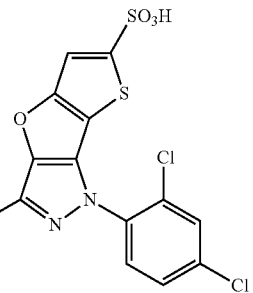
(IIIEC)
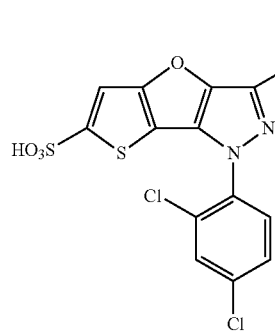 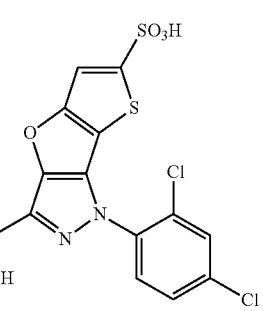
(IIIED)
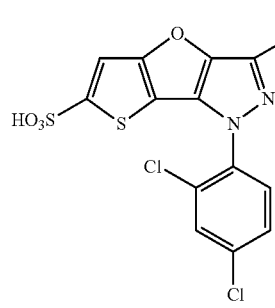 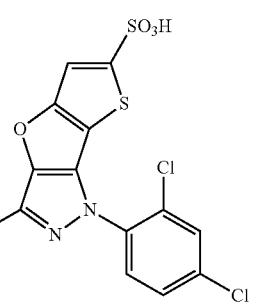
(IIIEE)

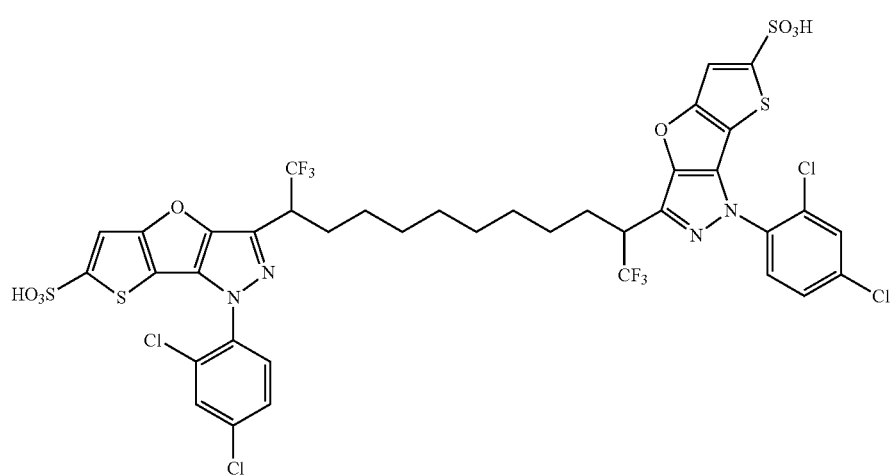
(IIIEF)
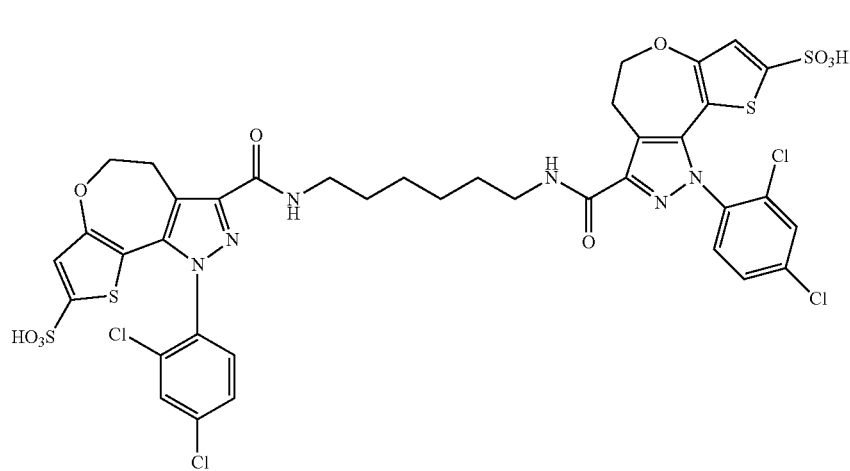
(IIIFA)
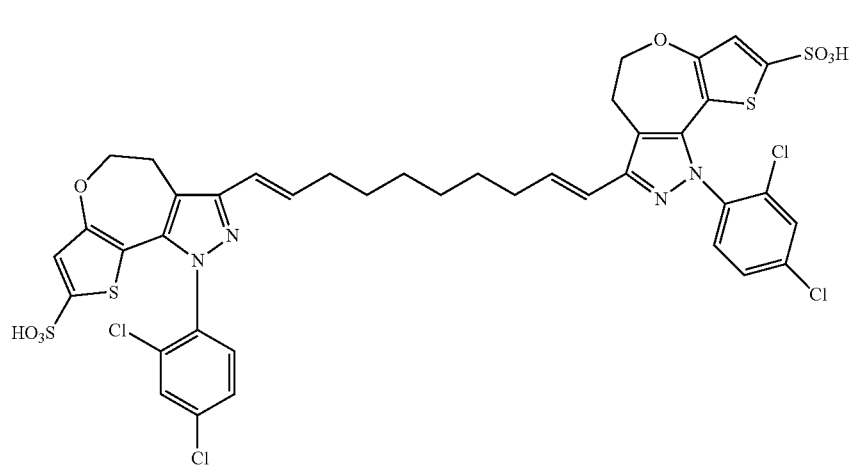
(IIIFB)

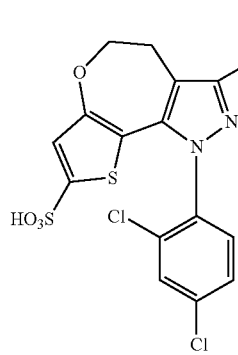
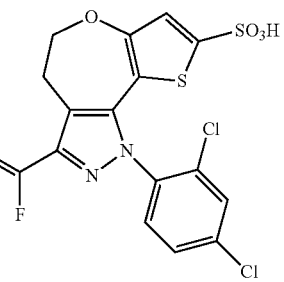
(IIIFC)
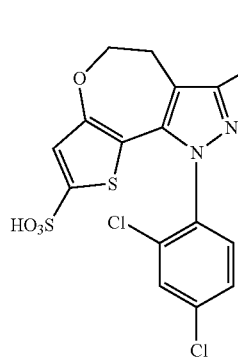
(IIIFD)
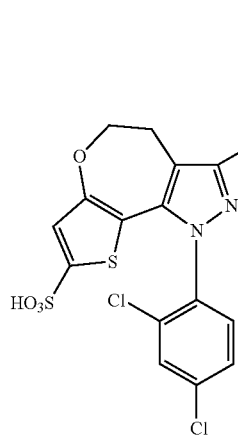
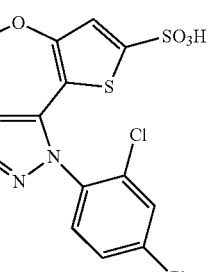
(IIIFE)

(IIIFF)
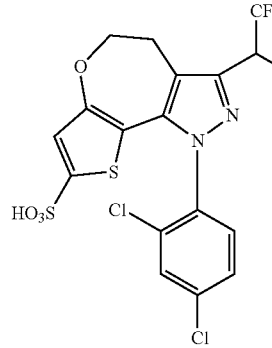
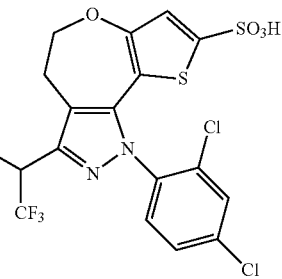
(IIIGA)
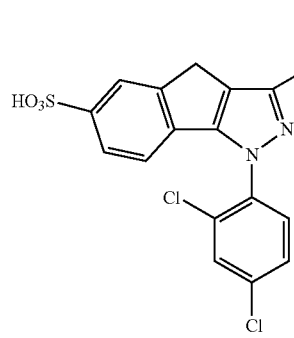
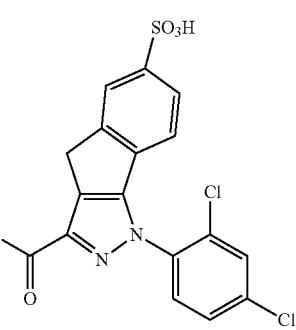
(IIIGB)
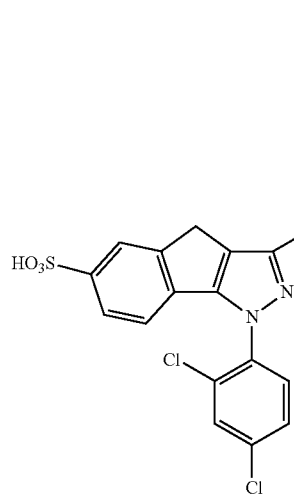
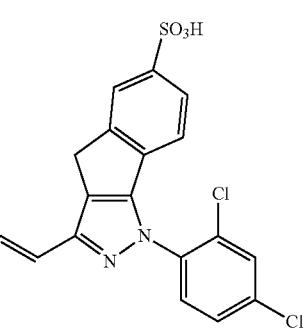

-continued
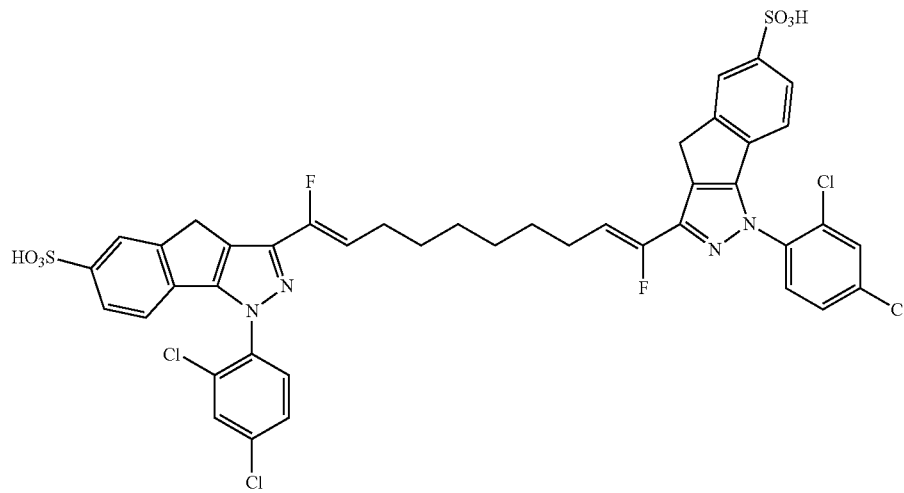
(IIIGC)
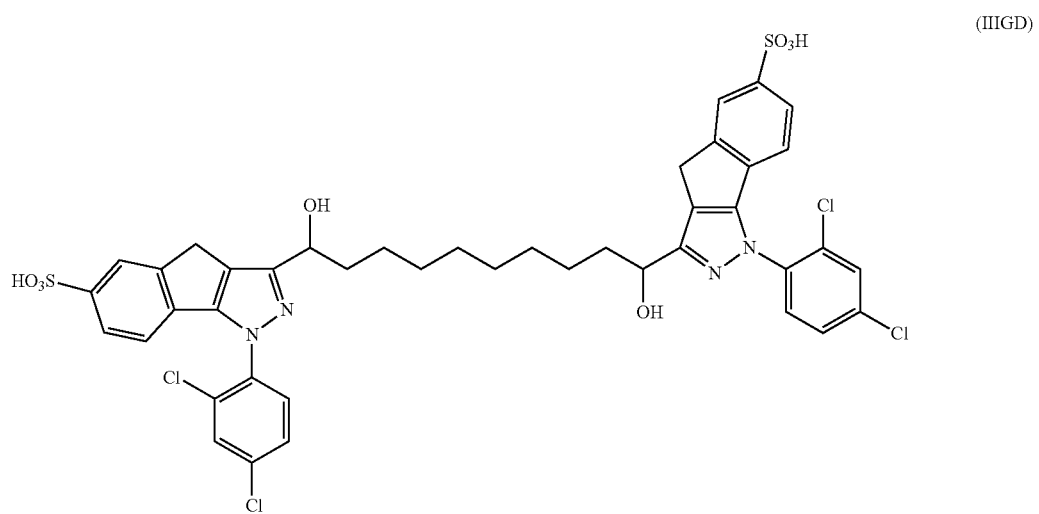
(IIIGD)
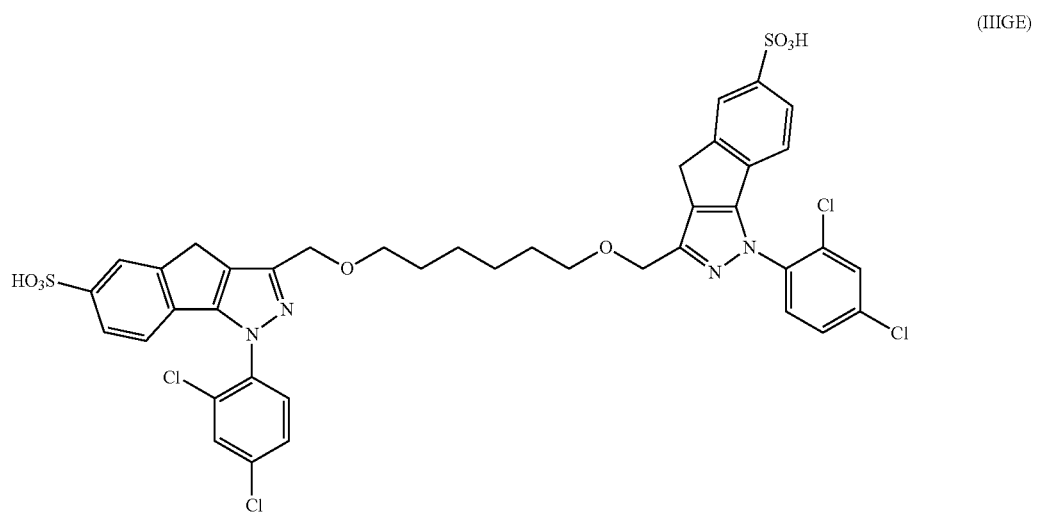
(IIIGE)

(IIIGF)
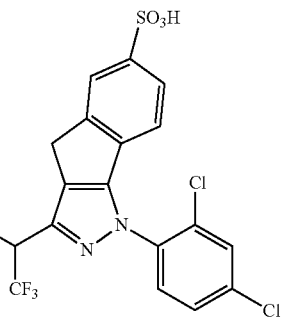
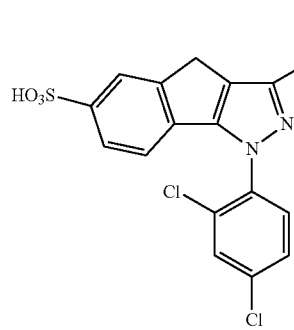
(IIIHA)
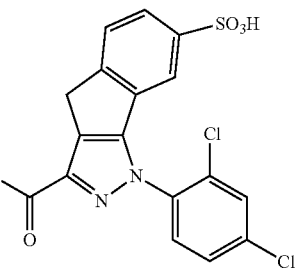
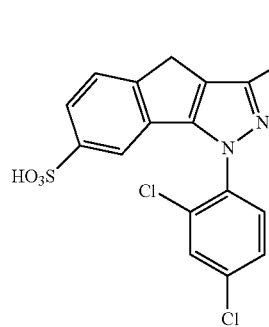
(IIIHB)
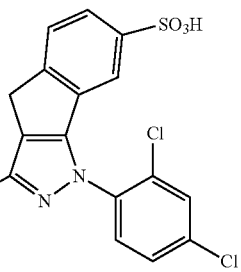
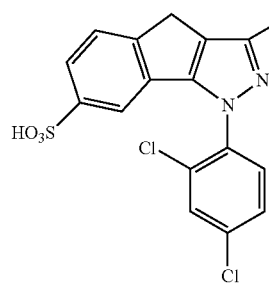

-continued
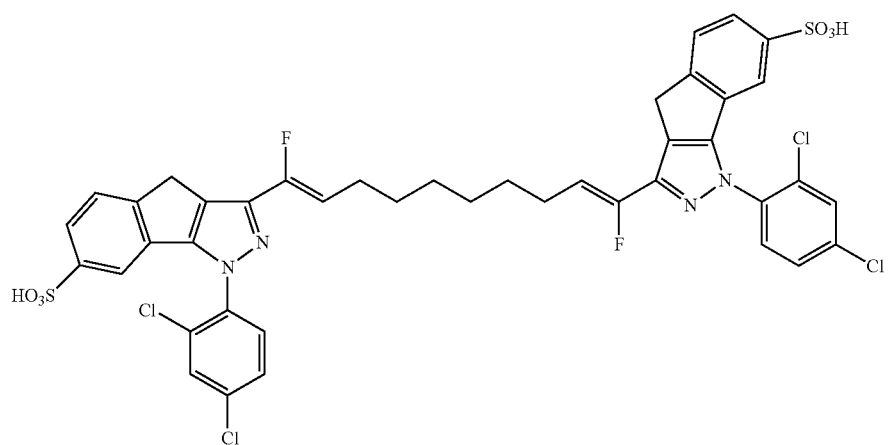
(IIIHC)
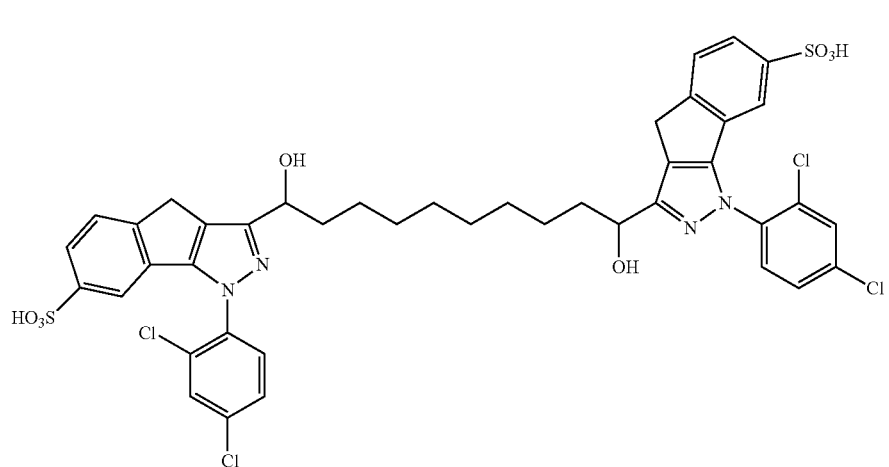
(IIIHD)
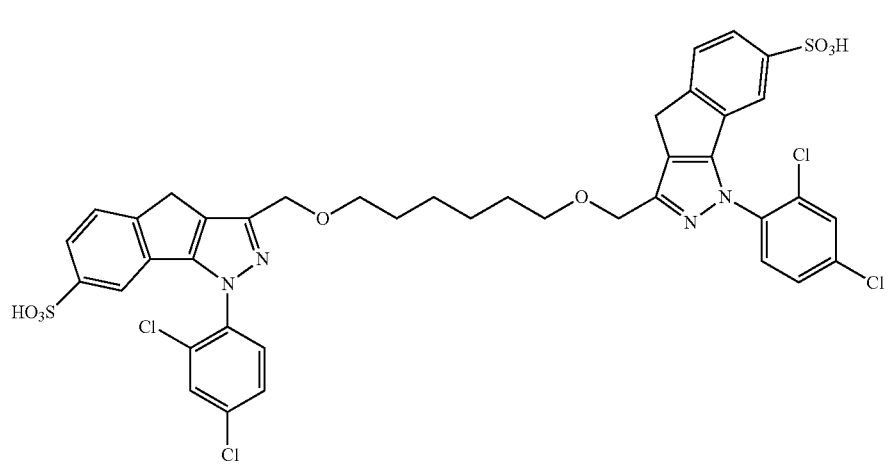
(IIIHE)

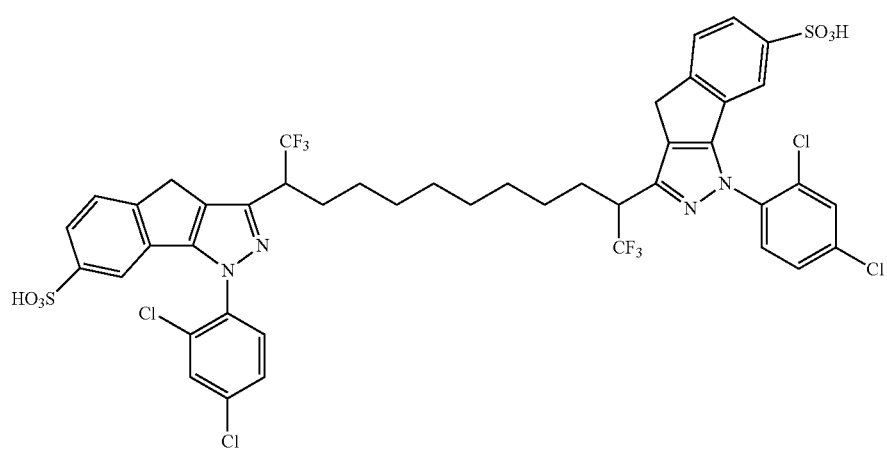
(IIIHF)
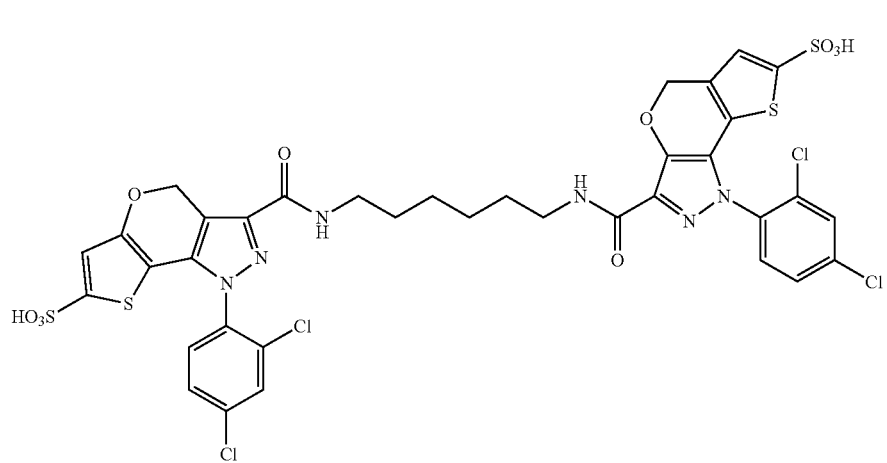
(IIILA)
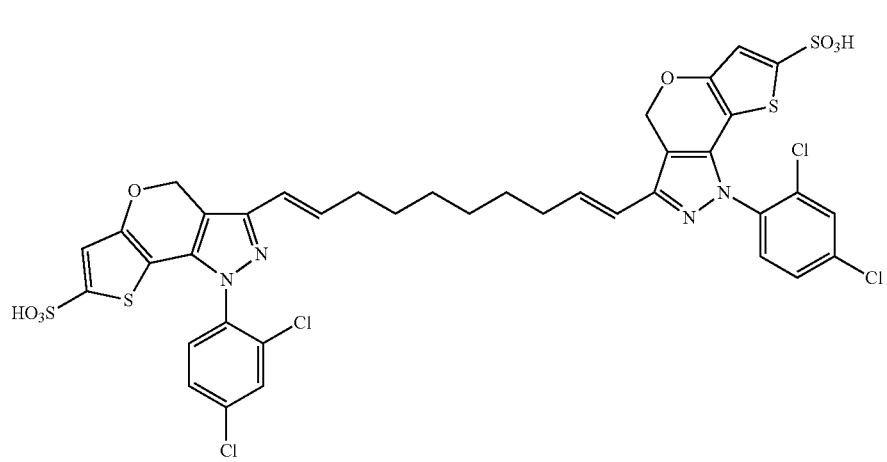
(IIILB)

(IIILC)
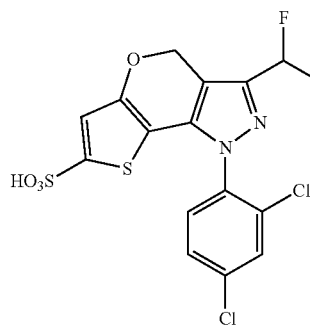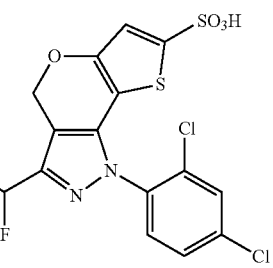
(IIILD)
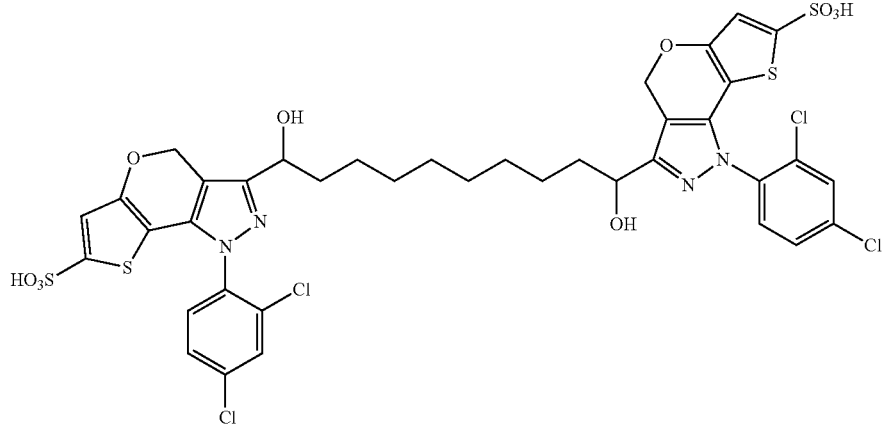
(IIILE)
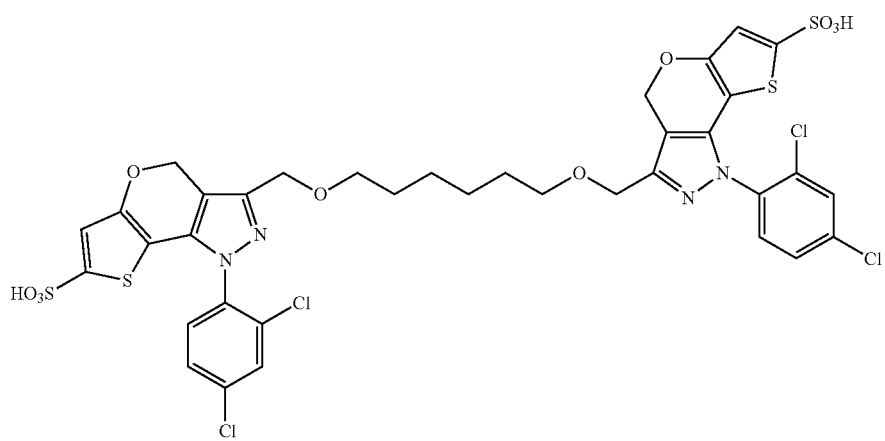

-continued
(IIILF)
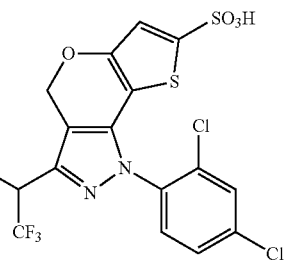
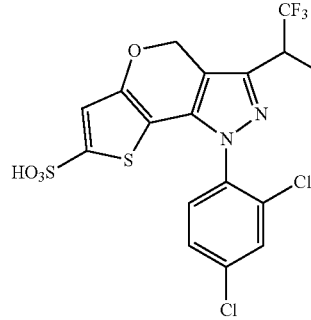
(IVAA)
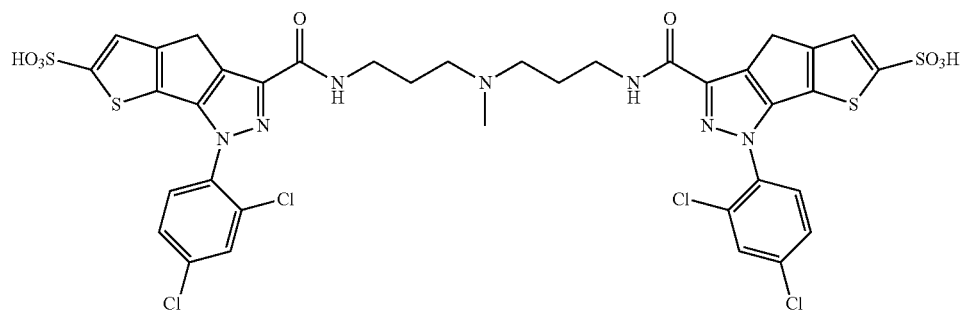
(IVAB)
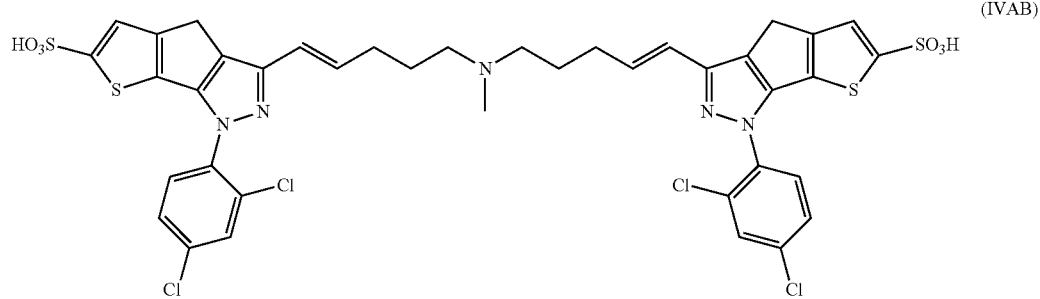
(IVAC)
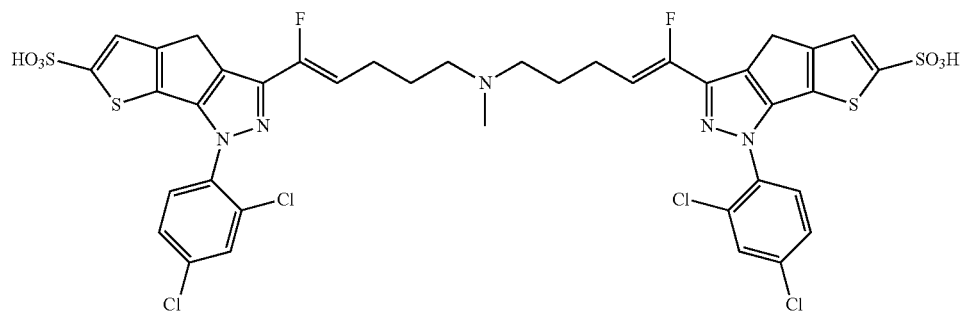

-continued
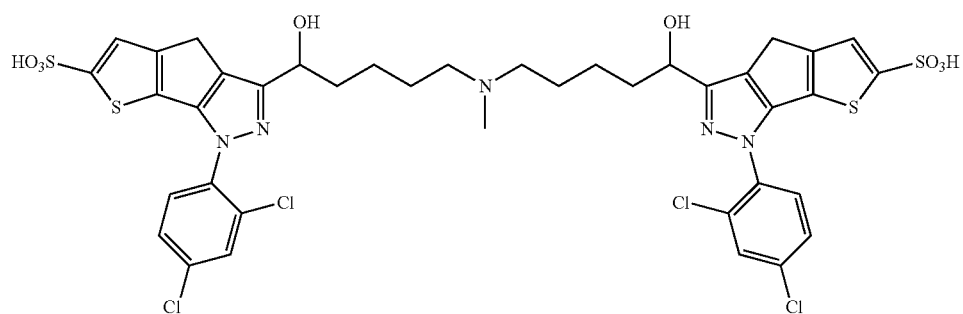
(IVAD)
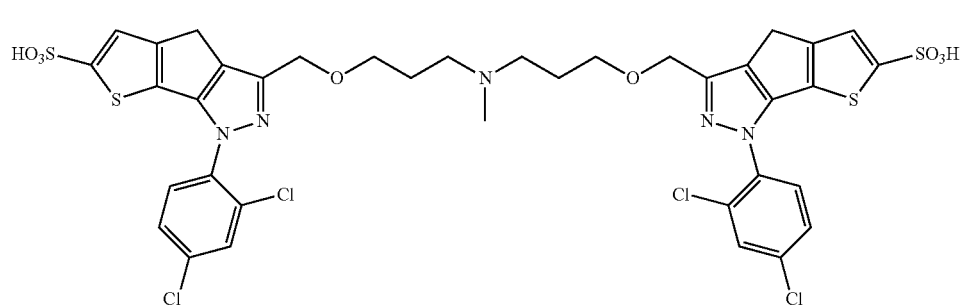
(IVAE)
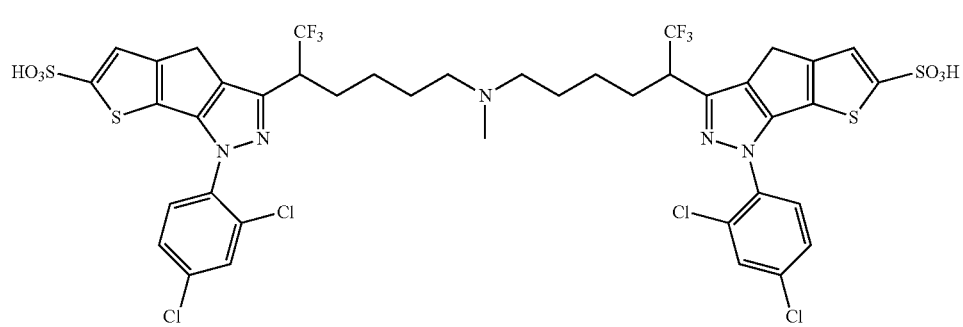
(IVAF)
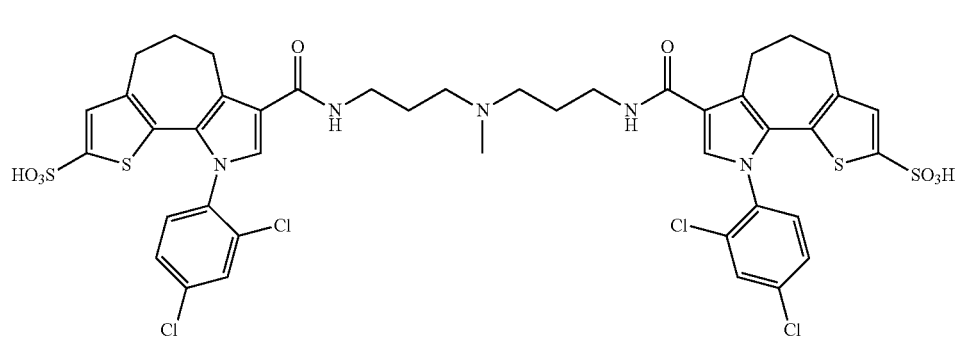
(IVDA)
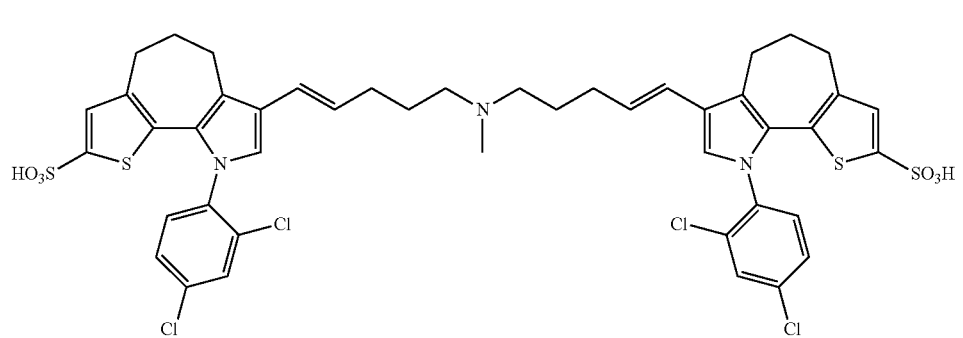
(IVDB)

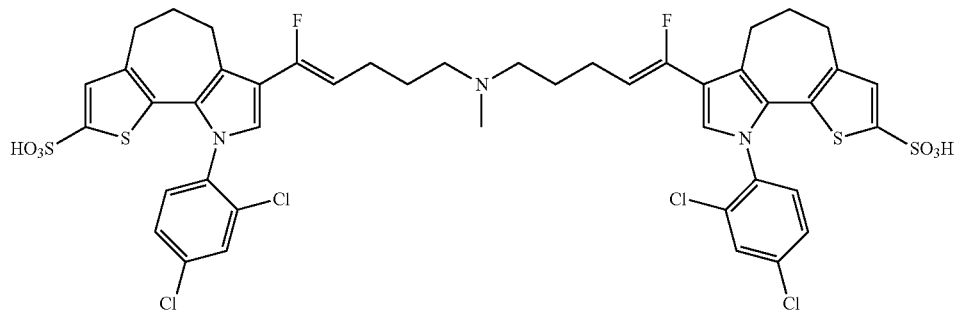
(IVDC)
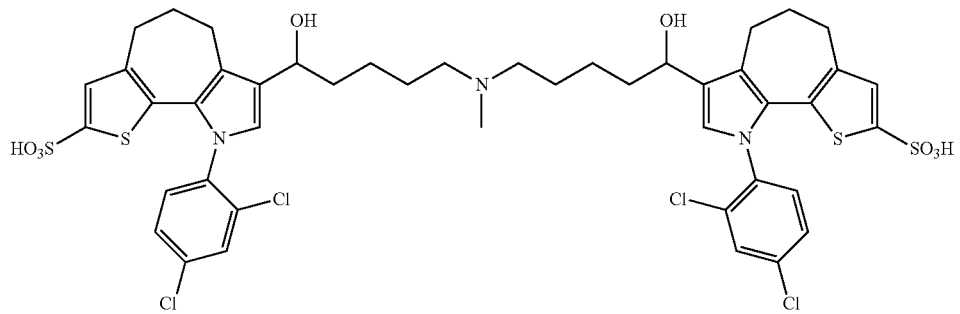
(IVDD)
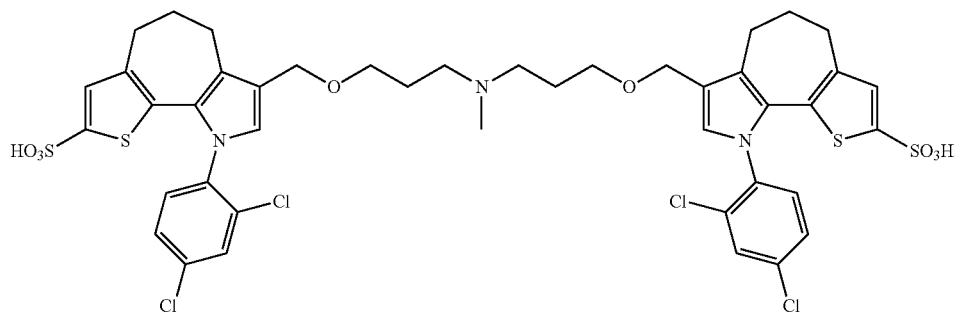
(IVDE)
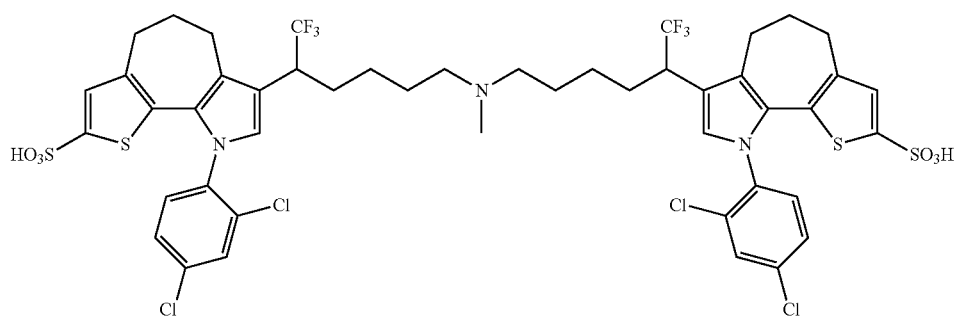
(IVDF)
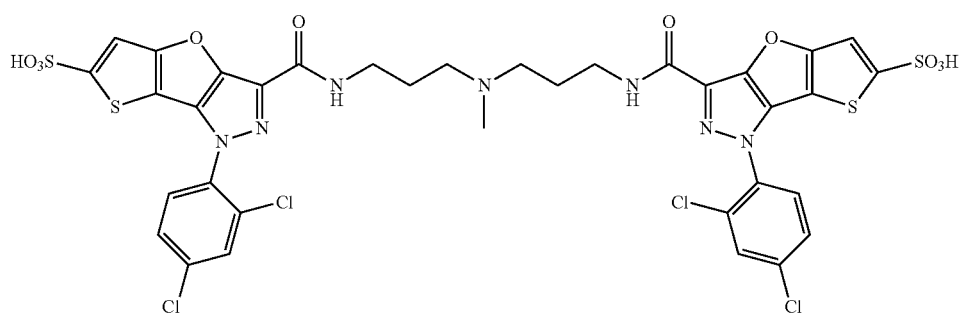
(IVEA)

-continued
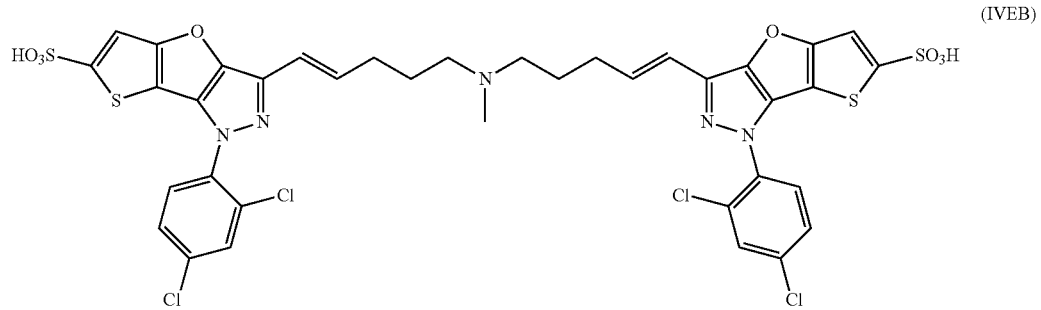
(IVEB)
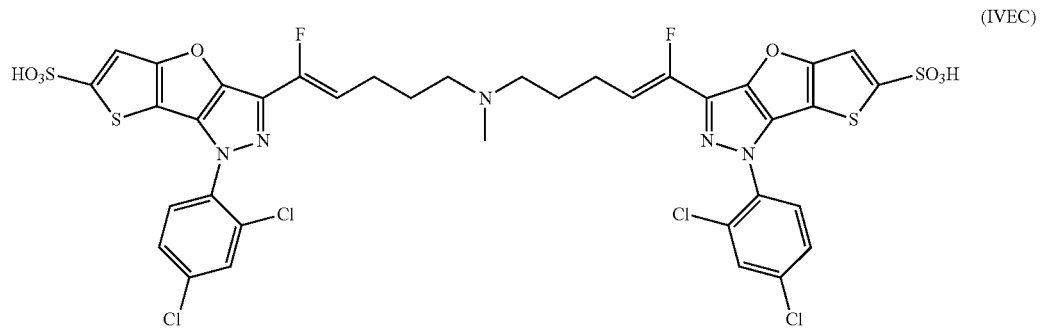
(IVEC)
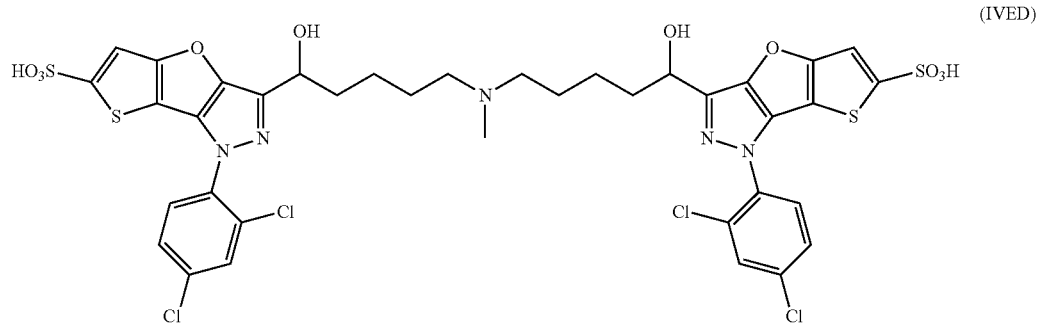
(IVED)
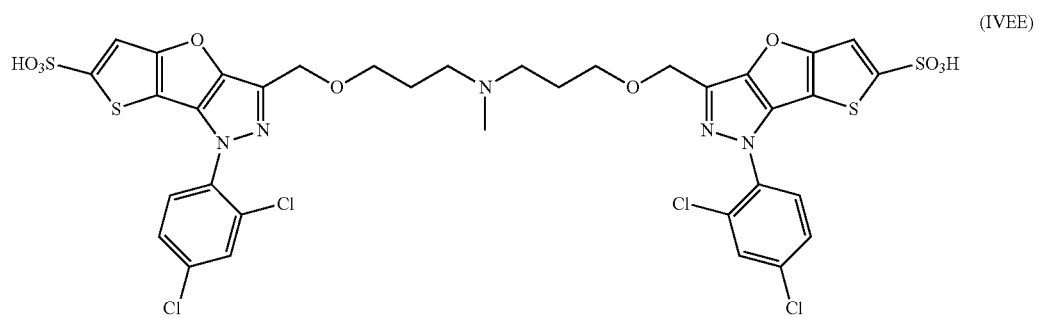
(IVEE)
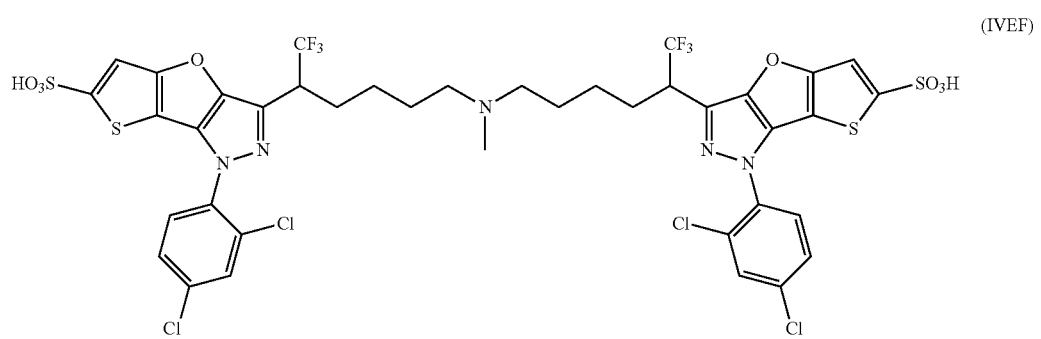
(IVEF)

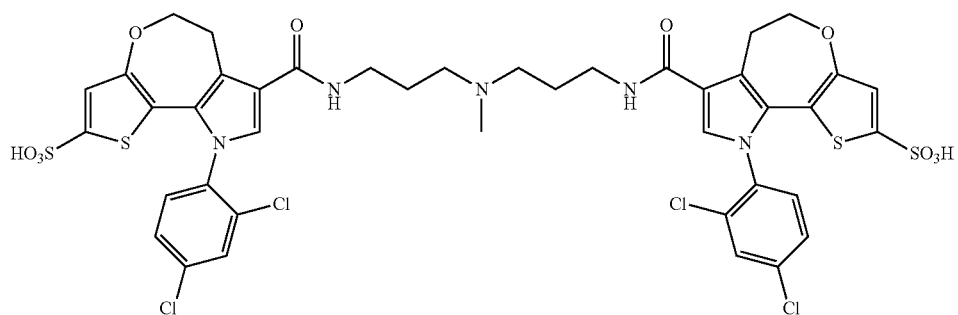
(IVFA)
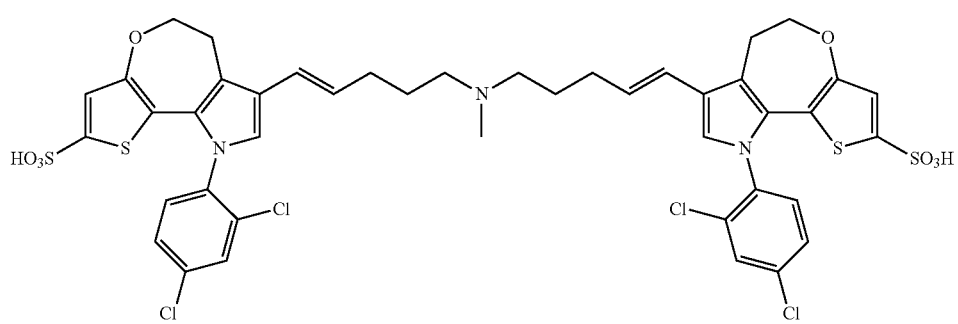
(IVFB)
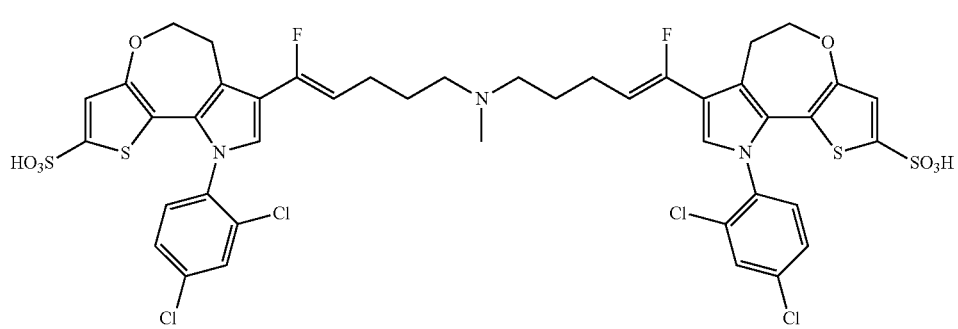
(IVFC)
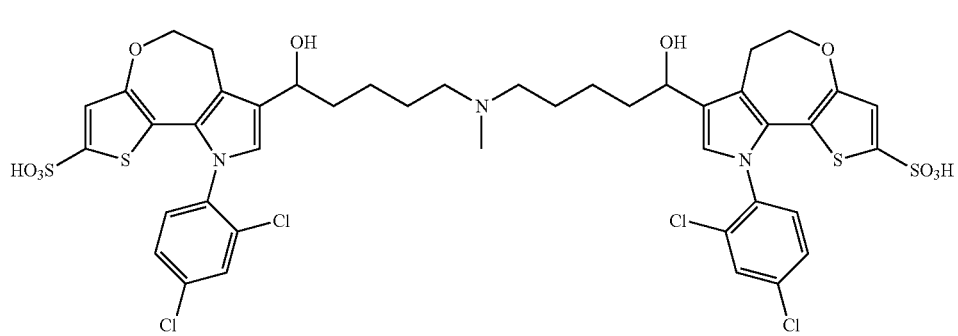
(IVFD)
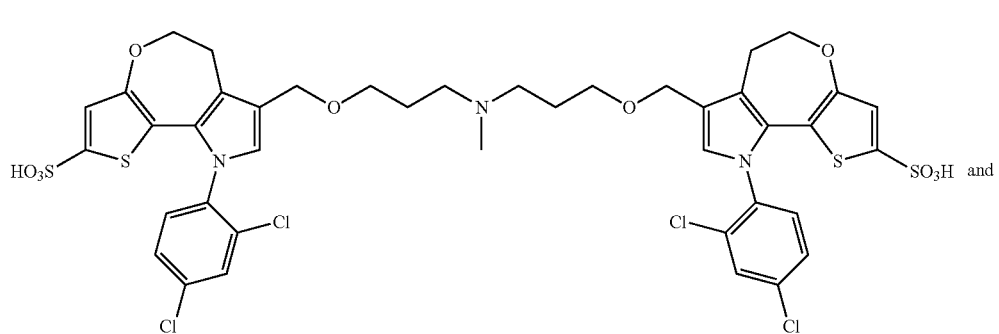
(IVFE) and -continued

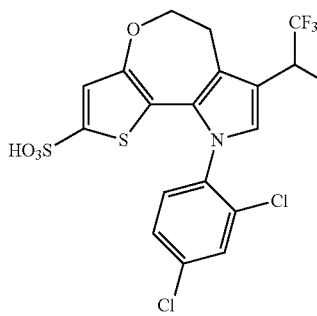
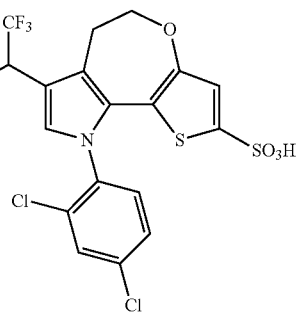

(IVFF)

9. Compounds according to claim 1 wherein the compounds are cis trans isomers, E and Z isomers, optical isomers.

10. Compounds according to claim 1, wherein the compounds are in the form of hydrates and solvates.

11. A process for preparing the compounds of claim 1 starting from the acids of formula (II) and (II-A),

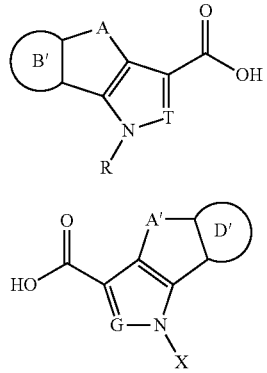

(II)

(II-A)

wherein B' and D', equal to or different from each other, have the meaning of heteroaryl or aryl, said aryl and heteroaryl having as substituents at least one hydrogen atom and optionally one or more G1 groups, equal to or different from each other, comprising:

i) optional activation of the carboxylic group of the acid of formula (II) and of the acid of formula (II-A) to obtain the corresponding reactive derivatives, selected from acyl halides, anhydrides, mixed anhydrides, imidazolides, ester-amide adducts, linear or branched $C_1$-$C_4$ alkyl esters;

ii) synthesis of the compound of formula (I-B):

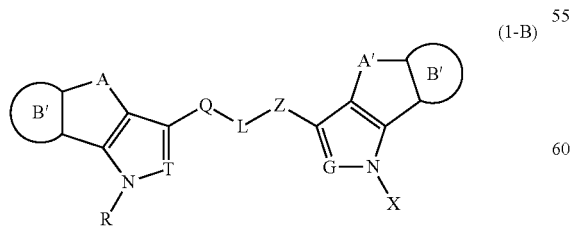

(I-B)

using one of the following synthesis processes:

ii-a) when in (I-B) Q=Z=QA, a two-step synthesis is carried out:

first step: reaction of a reactive derivative of the acid of formula (II) and of the acid of formula (II-A) in an inert organic solvent with an azide of formula $MeN_3$, wherein Me is an alkaline metal, obtaining the acyl azides of formula (III) and of formula (III-A):

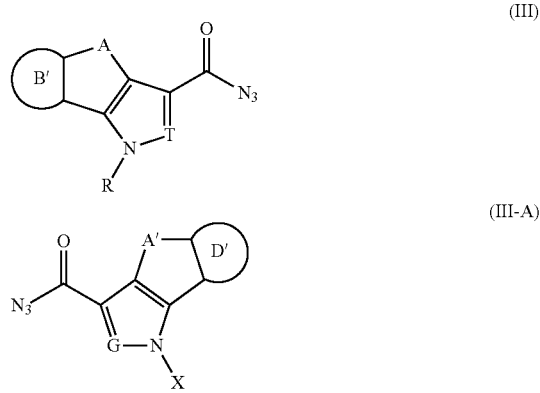

(III)

(III-A)

second step: transposition reaction of the acyl azides of formula (III) and (III-A) by reaction with urea;

ii-b) when Q=QF and Z=QF' a two-step synthesis is carried out:

first step: reduction of the acid of formula (II) and of the acid of formula (II-A), or esters thereof, to the corresponding primary alcohols of formula (IV) and (IV-A), respectively:

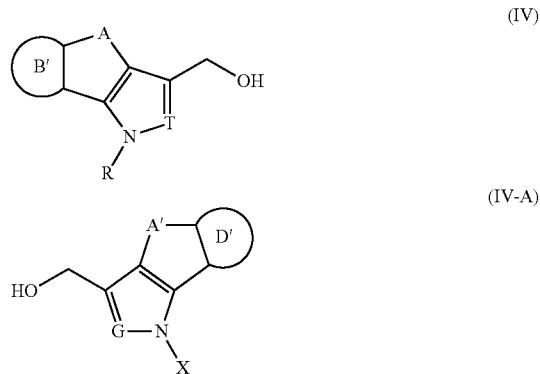

(IV)

(IV-A)

second step: reaction of the primary alcohols of formula (IV) and (IV-A) with an alkyl halide of formula U—Y—U, wherein U is halogen and Y is as defined above;

ii-c) when Q=Z=QB and L=L4, the synthesis is carried out according to one of the following processes:

first process: reaction of an ester of an acid of formula (II) and of an acid of formula (II-A) with trialkylaluminum and with an amine hydrochloride salt until the disappearance of the ester function, followed by the addition to the reaction mixture of the compound of formula BrMg—Y—MgBr, second process: reaction of the acid of formula II) and of the acid of formula (II-A), or of their reactive derivatives with a metallorganic salt of formula $^+$Me-Y-Me$^+$, wherein Me$^+$ is an alkaline metal cation, in an inert organic solvent, third process: reaction of a reactive derivative of the acid of formula (II) and of the acid of formula (II-A) with N,O-dimethylhydroxylamine hydrochloride in the presence of trialkylaluminum, obtaining the Weinreb amides of formula (V) and of formula (V-A), respectively:

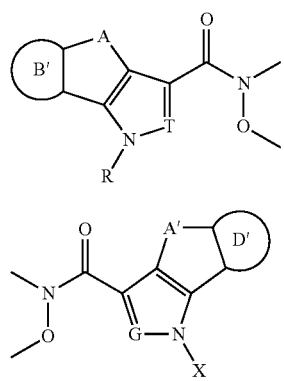

(V)

(V-A)

and following reaction of the amide of formula (V) and of the amide of formula (V-A) with a compound of formula BrMg—Y—MgBr, wherein Y is as defined above;

ii-d) when Q=Z=QB and L=L2, a reactive derivative of the acid of formula (II) and of the acid of formula (II-A) is reacted with a compound of formula (VI):

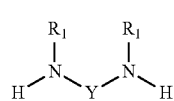

(VI)

wherein R$_1$ and Y are as defined above;

ii-e) when Q=Z=QC, a two-step synthesis is carried out: first step: synthesis of the compound of formula (I) wherein Q and Z have the meaning of QB and L has the meaning of L4, by using one of the processes described in ii-c), second step: reduction of the two carbonyl functions in the compound obtained in the preceding step;

ii-f) when Q=Z=QD a five-step synthesis is carried out: first step: synthesis of primary alcohols by reduction of the acid of formula (II) and of the acid of formula (II-A) according to the process described in the first step of ii-b), second step: conversion of the primary alcohol of the acid of formula (II) and of the acid of formula (II-A) into the corresponding bromine derivatives of formula (VII) and (VII-A) by reaction with a bromination agent:

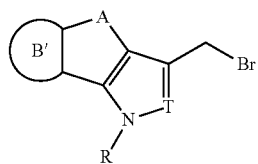

(VII)

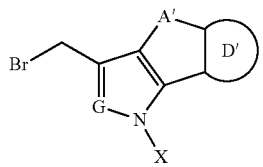

(VII-A)

third step: synthesis of the phosphonium salt of the bromine derivatives by reaction with triphenylphosphine to yield the phosphonium salts of formula (VIII) and (VIII-A):

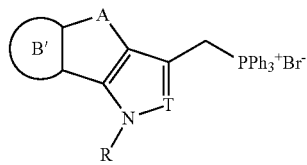

(VIII)

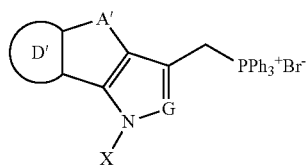

(VIII-A)

wherein Ph has the meaning of phenyl, fourth step: deprotonation of the phosphonium salts of formula (VIII) and (VIII-A) followed by the treatment of the compounds obtained with an aldehyde of formula (IX):

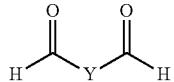

(IX)

wherein Y is as defined above, fifth optional step: separation of isomer E from isomer Z of the compound (I-B) obtained in the fourth step;

ii-g) when Q=QE and Z=QE' a six-step synthesis is carried out:

first step: preparation of the Weinreb amides of formula (V) and (V-A) according to the third process of ii-c), second step: reduction of the Weinreb amides to the corresponding aldehydes of formula (X) and (X-A):

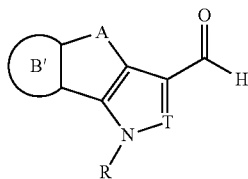
(X)

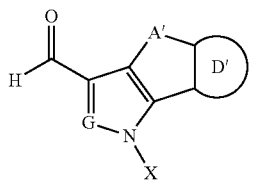
(X-A)

third step: condensation of the aldehydes of formula (X) and (X-A) respectively with diethyl-phosphite to yield, respectively, the compounds of formula (XI) and (XI-A):

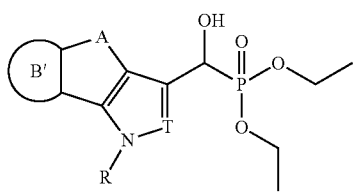
(XI)

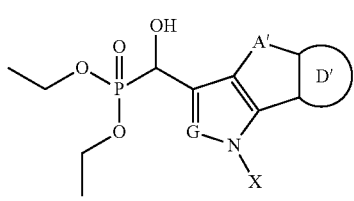
(XI-A)

fourth step: fluorination of the hydroxyl group in the compounds of formula (XI) and (XI-A) to give the corresponding fluoro-derivatives of formula (XII) and (XII-A):

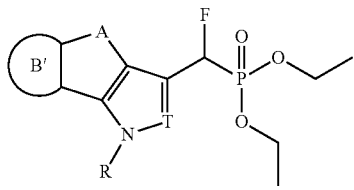
(XII)

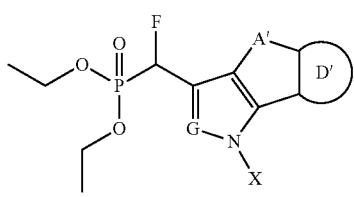
(XII-A)

fifth step: reaction of the fluoro-derivatives respectively of formula (XII) and (XII-A) with an aldehyde of formula (IX), sixth optional step: separation of isomer E from isomer Z of the compound obtained in the fifth step;

ii-h) when Q=Z=QH, a six-step synthesis is carried out: first step: preparation of the Weinreb amides of formula (V) and (V-A) according to the third process of ii-c), second step: reduction of the Weinreb amides (V) and (V-A) to the corresponding aldehydes of formula (X) and (X-A) as described in the second step of ii-g), third step: trifluoromethylation of the aldehydes of formula (X) and (X-A) to yield the alcohols respectively of formula (XIII) and (XIII-A):

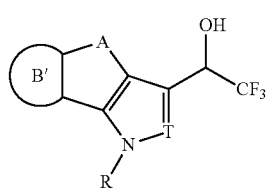
(XIII)

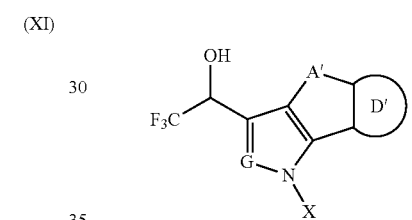
(XIII-A)

fourth step: oxidation of the alcohols of formula (XIII) and (XIII-A) to the corresponding ketones (XIV) and (XIV-A):

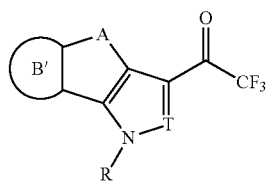
(XIV)

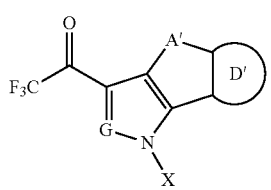
(XIV-A)

fifth step: condensation of the compounds of formula (XIV) and (XIV-A) with a compound of formula $NH_2$-$L_{50}$-$NH_2$, wherein $L_{50}$ is selected between L4 or L5 as defined above, obtaining the compound of formula (XV):

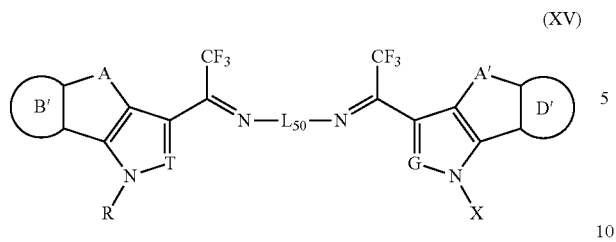
(XV)

wherein A, R, T, G, X, A', B' and D' are as defined above, sixth step: reduction of the double bond in the groups -L-N=CH(CF$_3$)— of the compound of formula (XV);

ii-i) when Q=Z=QB and L=L3, the synthesis is carried out with one of the following alternative processes: first process: reaction of an acid of formula (II) and of an acid of formula (II-A), or esters thereof, with an alcohol of formula (XVI):

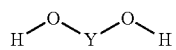
(XVI)

in the presence of strong inorganic acids, second process: reaction of a reactive derivative of an acid of formula (II) and of an acid of formula (II-A) with an alcohol of formula (XVI) in the presence of a weak organic base;

ii-l) when Q=QG and Z=QG' a three-step synthesis is carried out:

first step: reaction of a reactive derivative of the acids respectively of formula (II) and (II-A) with an hydrazine wherein one of the two amine groups is protected by a protecting group GP, obtaining respectively compounds of formula (XVII) and (XVII-A):

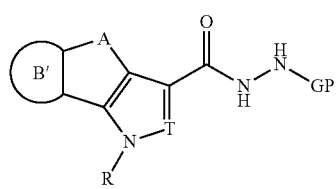
(XVII)

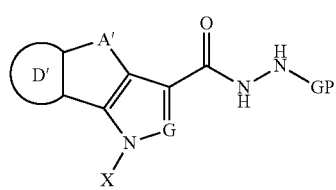
(XVII-A)

second step: deprotection of the amine group linked to GP in the compounds of formula (XVII) and (XVII-A) to yield the compounds of formula (XVIII) and (XVIII-A), respectively:

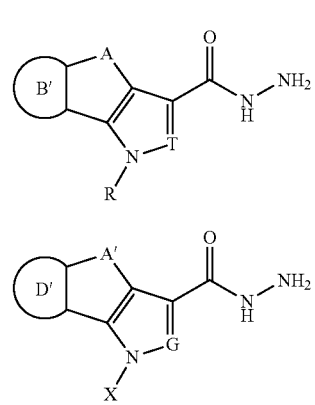
(XVIII)

(XVIII-A)

third step: reaction of the compounds of formula (XVIII) and (XVIII-A) with a compound of formula H-L-H, wherein L is a group selected between L6 and L7 as defined above;

iii) at least one hydrogen atom of the B' and D' rings of the compounds of formula (I-B) obtained according to the processes described sub ii), is substituted with at least one group selected from SO$_3^-$, SO$_3$H, COO$^-$, COOH to yield the compounds of formula (I).

12. A process according to claim 11 wherein the acids of formula (II) and (II-A) are reacted according to step iii) by substituting at least one of the hydrogen atoms of the ring B' of the acid of formula (II) and, respectively, D' of the acid of formula (II-A) with at least one group selected from SO$_3^-$, SO$_3$H, COO$^-$, COOH, obtaining the acids of formula (II-B) and (II-C):

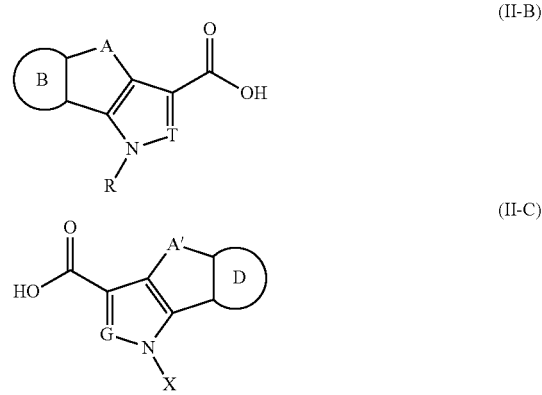
(II-B)

(II-C)

then step (i) and steps sub ii) are sequentially carried out.

13. Compounds of formula (I-B) and pharmaceutically acceptable salts thereof, cis and trans isomers, isomers E and Z, optical isomers, hydrates and solvates

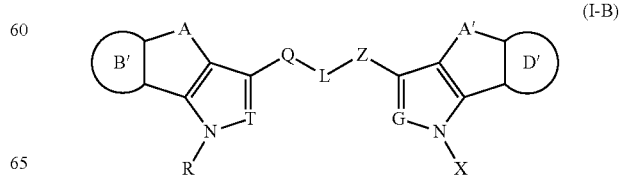
(I-B)

wherein:
A, T, Q, R, L, Z, G, X and A' are as defined in the compounds of formula (I) according to claim 1,
B' and D', equal or different from each other, are selected from aryl and heteroaryl, having as substituents at least one hydrogen atom and, optionally, one or more G1 groups, equal to or different from each other, the following ones being excluded from the compounds of formula (I-B):

R and X, equal to each other, have the following meanings:
$R_{30}$—W with W=$W_b$ wherein $R_{30}$ is a bivalent aliphatic $C_2$-$C_6$ chain, linear or when possible branched, and $W_b$ is as defined above,
phenyl or benzyl, wherein one or more hydrogen atoms of said phenyl or benzyl are optionally substituted with groups selected from halogen, linear or when possible branched $C_1$-$C_6$ alkyl.

each other, selected from: halogen, linear or when possible branched $C_1$-$C_{20}$ alkyl, linear or when possible branched $C_1$-$C_{20}$ alkyl, linear or when possible branched $C_2$-$C_{20}$ alkynyl, cyano, nitro, $SO_2NH_2$, $NH_2$, Q=Z=QA, L=L1;

Q=Z=QB, L=L2 with Y=$Y_{50}$, L2 being as defined above and $Y_{50}$ selected from linear or when possible branched $C_2$-$C_{10}$ alkylene and Y6;

T and G are both nitrogen,

16. Compounds according to claim 1 for use as a medicament.

17. Pharmaceutical compositions comprising the compounds of claim 1.

18. Pharmaceutical compositions according to claim 17 in the form of dispersions, solutions, micellar solutions, liquid crystals, emulsions, microemulsions, powders, micropar- (I-A)

wherein:
t=2, 3,
Z" is a substituent selected from methyl, phenyl or 2,4 dichlorophenyl,
T' is selected between CH=CH and $CH_2$
$T_1$=H, Cl or $OCH_3$
$T_2$=H, Cl
when T'=CH=CH and G'=CH, $T_1$=H, Cl, or $OCH_3$, $T_2$=H, Cl,
when T'=CH=CH and G'=N, $T_1$=$T_2$=H,
when T'=$CH_2$ and G' is selected from N or CH, $T_1$=$T_2$=H.

14. Compounds according to claim 13 wherein B' and D' are equal to each other and are selected from said phenyl and monocyclic heteroaryl having as substituents at least one hydrogen atom and, optionally, one or more Cl groups, equal to or different from each other.

15. Compounds according to claim 13 wherein B' and D', equal to each other, have the meaning of phenyl or monocyclic heteroaryl, wherein the substituents of said phenyl and monocyclic heteroaryl comprise at least one hydrogen atom and, optionally, one or more groups, equal to or different from ticles, nanoparticles, capsules, aerosol, suppositories, tablets, syrups, elixirs, creams, gels, ointments, pastes, plasters, foams.

19. Compounds according to claim 1 for the therapy in mammals and in human beings of angiogenesis and of diseases and disorders wherein angiogenesis is involved.

20. Compounds according to claim 19, wherein angiogenesis is mediated by FGF-2.

21. Compounds according to claim 19 wherein the diseases and disorders wherein angiogenesis is involved are neo-plasias, atherosclerosis, psoriasis, arthritis, rheumatoid arthritis, gastric ulcer, endometriosis, Crohn syndrome, sclerodermia, cancer, solid tumours, eye pathologies, diabetic retinopathy and age-related macular degeneration.

\* \* \* \* \*